(12) United States Patent
Ferber

(10) Patent No.: US 10,975,354 B2
(45) Date of Patent: *Apr. 13, 2021

(54) TRANSDIFFERENTIATED CELL POPULATIONS AND METHODS OF USE THEREOF

(71) Applicants: ORGENESIS LTD., Tel Aviv (IL); TEL HASHOMER MEDICAL RESEARCH INFRASTRUCTURE AND SERVICES LTD., Ramat Gan (IL)

(72) Inventor: Sarah Ferber, Tel Aviv (IL)

(73) Assignees: ORGENESIS LTD., Tel Aviv (IL); TEL HASHOMER MEDICAL RESEARCH INFRASTRUCTURE AND SERVICES LTD., Ramat Gan (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/676,481

(22) Filed: Nov. 7, 2019

(65) Prior Publication Data

US 2020/0140825 A1    May 7, 2020

Related U.S. Application Data

(63) Continuation of application No. PCT/IL2018/050496, filed on May 8, 2018.

(60) Provisional application No. 62/502,796, filed on May 8, 2017, provisional application No. 62/610,300, filed on Dec. 26, 2017.

(51) Int. Cl.
- *C12N 5/071* (2010.01)
- *G01N 33/543* (2006.01)

(52) U.S. Cl.
CPC ..... *C12N 5/0676* (2013.01); *G01N 33/54306* (2013.01); *C12N 2501/11* (2013.01); *C12N 2501/395* (2013.01); *C12N 2501/415* (2013.01); *C12N 2501/998* (2013.01); *C12N 2501/999* (2013.01); *C12N 2506/22* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 4,737,323 A | 4/1988 | Martin et al. |
| 4,837,028 A | 6/1989 | Allen |
| 4,873,316 A | 10/1989 | Meade et al. |
| 4,980,286 A | 12/1990 | Morgan et al. |
| 4,992,417 A | 2/1991 | Katsovannis et al. |
| 5,082,670 A | 1/1992 | Gage et al. |
| 5,328,470 A | 7/1994 | Nabel et al. |
| 5,424,286 A | 6/1995 | Eng |
| 5,427,940 A | 6/1995 | Newgard |
| 5,703,055 A | 12/1997 | Felgner et al. |
| 5,741,673 A | 4/1998 | Montminy et al. |
| 5,849,989 A | 12/1998 | Edlund |
| 5,858,973 A | 1/1999 | Habener et al. |
| 5,942,435 A | 8/1999 | Wheeler |
| 6,114,113 A | 9/2000 | McLaughlin et al. |
| 6,143,293 A | 11/2000 | Weiss et al. |
| 6,242,666 B1 | 6/2001 | Sarvetrick et al. |
| 6,379,962 B1 | 4/2002 | Holy et al. |
| 6,716,824 B1 | 4/2004 | Brunicardi |
| 6,774,120 B1 | 8/2004 | Ferber |
| 7,029,915 B2 | 4/2006 | Yang |
| 7,517,856 B2 | 4/2009 | Cohen et al. |
| 7,524,492 B2 | 4/2009 | Sharma |
| 7,722,894 B2 | 5/2010 | Wang et al. |
| 8,119,405 B2 | 2/2012 | Ferber |
| 8,778,899 B2 | 7/2014 | Ferber |
| 9,359,472 B2 | 6/2016 | Nicholson et al. |
| 2001/0013134 A1 | 8/2001 | Sarvetnick et al. |
| 2002/0001610 A1 | 1/2002 | Cohen et al. |
| 2002/0081725 A1 | 6/2002 | Tsang et al. |
| 2003/0078672 A1 | 4/2003 | Shapiro et al. |
| 2003/0138948 A1 | 7/2003 | Fisk et al. |
| 2003/0219894 A1 | 11/2003 | Seino et al. |
| 2004/0213769 A1 | 10/2004 | Ferber |
| 2005/0003010 A1 | 1/2005 | Cohen et al. |
| 2005/0090465 A1 | 4/2005 | Ferber |
| 2006/0122104 A1 | 6/2006 | Presnell et al. |
| 2006/0205072 A1 | 9/2006 | Uchida et al. |
| 2007/0014772 A1 | 1/2007 | Cohen et al. |
| 2007/0081976 A1 | 4/2007 | Cohen et al. |

(Continued)

FOREIGN PATENT DOCUMENTS

| | | |
|---|---|---|
| EP | 264166 B1 | 8/1996 |
| EP | 1354942 A1 | 10/2003 |

(Continued)

OTHER PUBLICATIONS

Ahlgren et al. "The Morphogenesis of the Pancreatic Mesenchymal is Uncoupled From That of the Pancreatic Epithelium in IPF1/PDX1-Deficient Mice." Dev. 122(1996):1409-1416.

(Continued)

*Primary Examiner* — Daniel C Gamett

(74) *Attorney, Agent, or Firm* — Mark S Cohen; Pearl Cohen; Zedek Latzer Baratz LLP

(57) ABSTRACT

Disclosed herein are methods for manufacturing transdifferentiated populations of non-pancreatic human insulin producing cells, and methods for enriching populations of non-pancreatic β-cells for cells comprising an enriched capacity for transcription factor-induced transdifferentiation into a pancreatic β-cell phenotype and function.

19 Claims, 43 Drawing Sheets

Specification includes a Sequence Listing.

(56) References Cited

U.S. PATENT DOCUMENTS

| | | |
|---|---|---|
| 2007/0111310 A1 | 5/2007 | Cohen et al. |
| 2009/0053249 A1 | 2/2009 | Qi et al. |
| 2009/0239298 A1 | 9/2009 | Gerecht et al. |
| 2010/0145470 A1 | 6/2010 | Cohen et al. |
| 2010/0226976 A1 | 9/2010 | Machluf et al. |
| 2010/0233239 A1 | 9/2010 | Berkland et al. |
| 2010/0247652 A1 | 9/2010 | Ilan et al. |
| 2011/0280842 A1 | 11/2011 | Melton et al. |
| 2012/0210451 A1 | 8/2012 | Shimizu et al. |
| 2014/0147452 A1 | 5/2014 | Izraeli et al. |
| 2015/0017727 A1 | 1/2015 | Ferber |
| 2015/0050247 A1 | 1/2015 | Machluf et al. |
| 2015/0051148 A1 | 2/2015 | Cohen et al. |
| 2015/0352144 A1 | 12/2015 | Cohen et al. |
| 2016/0101133 A1 | 4/2016 | Basu et al. |
| 2016/0130559 A1 | 5/2016 | Ferber |
| 2016/0220616 A1 | 8/2016 | Ferber |
| 2016/0354474 A1 | 12/2016 | Cohen et al. |
| 2017/0096500 A1 | 4/2017 | Cohen et al. |
| 2017/0290954 A1 | 10/2017 | Cohen et al. |

FOREIGN PATENT DOCUMENTS

| | | |
|---|---|---|
| JP | 2011-223993 A | 11/2011 |
| WO | WO 1994/008598 | 4/1994 |
| WO | WO 1995/005463 A1 | 2/1995 |
| WO | WO 1995/035073 A1 | 12/1995 |
| WO | WO 1997/020075 A1 | 6/1997 |
| WO | WO 1997/049728 A1 | 12/1997 |
| WO | WO 2000/072885 A2 | 12/2000 |
| WO | WO 2003/033697 A1 | 4/2003 |
| WO | WO 2003/078636 A1 | 9/2003 |
| WO | WO 2004/098646 A1 | 11/2004 |
| WO | WO 2008/013737 A2 | 1/2008 |
| WO | WO 2009/126927 A2 | 10/2009 |
| WO | WO 2010/022395 A2 | 2/2010 |
| WO | WO 2011/159726 A2 | 12/2011 |
| WO | WO 2013/124855 A1 | 1/2013 |
| WO | WO 2013/021389 A2 | 2/2013 |
| WO | WO 2014/207578 A2 | 12/2014 |
| WO | WO 2016/108237 A1 | 7/2016 |
| WO | WO 2017/118979 A1 | 7/2017 |
| WO | WO 2017/175229 A1 | 10/2017 |
| WO | WO 2018/207179 A1 | 11/2018 |

OTHER PUBLICATIONS

Akbarpour et al. "Insulin B chain 9-23 gene transfer to hepatocytes protects from type 1 diabetes by inducing Ag-specific FoxP3+ Tregs", Sci Transl Med. May 27, 2015;7(289):289ra81.
Alves Cardoso et al. "Gelation and biocompatibility of injectable Alginate-Calcium phosphate gels for bone regeneration" Journal of Biomedical Materials Research Part A. Mar. 2014;102(3):808-17.
Amann et al. "Tightly regulated tac promoter vectors useful for the expression of unfused and fused proteins in *Escherichia coli*" Gene. Sep. 30, 1988;69(2):301-15.
Ambasudhan et al. "Direct reprogramming of adult human fibroblasts to functional neurons under defined conditions", Cell Stem Cell. Aug. 5, 2011;9(2):113-8.
Andersen et al. "3D cell culture in alginate hydrogels" Microarrays. Jun. 2015;4(2)133-61.
Aviv et al. "Exendin-4 promotes liver cell proliferation and enhances the PDX-1-induced liver to pancreas transdifferentiation process" Journal of Biological Chemistry. Nov. 27, 2009;284(48):33509-20.
Baldari et al. 1987 "A novel leader peptide which allows efficient secretion of a fragment of human interleukin 1 fl in *Saccharomyces cerevisine*" EMBO J.;6:229-34.
Banerji et al. "A lymphocyte-specific cellular enhancer is located downstream of the joining region in immunoglobulin heavy chain genes" Cell. Jul. 1, 1983;33(3):729-40.
Banga et al. "In vivo reprogramming of Sox9+ cells in the liver to insulin-secreting ducts", PNAS Sep. 18, 2012, vol. 109, No. 38, pp. 15336-15341.

Ber et al. "Functional, persistent, and extended liver to pancreas trans differentiation" Journal of Biological Chemistry, Aug. 22, 2003;278(34):31950-7.
Bernardo et al. "Pancreatic transcription factors and their role in the birth, life and survival of the pancreatic beta cell", Mol Cell Endocrinol. Nov. 6, 2008;294(1-2):1-9.
Berneman-Zeitouni et al. "The Temporal and Hierarchical Control of Transcription Factors-Induced Liver to Pancreas Transdifferentiation", PLOS One Feb. 1, 2014, vol. 9 | Issue 2, pp. 1-10.
Bhandari et al. "cloning, nucleotide sequence and potential regulatory elements of the glutamine synthetase gene from murine 3t3-11 adipocytes" proc. natl. acad. sci. Aug. 1988, vol. 85, pp. 5789-5793.
Bonal et al. "Genes controlling pancreas ontogeny", Int J Dev Biol. 2008,52(7):823-35.
Bonner-Weir et al. "New Sources of Pancreatic B-Cells" Nat Biotechnol. Jul. 2005;23(7):857-61.
Borowiak "The new generation of beta-cells: replication, stem cell differentiation, and the role of small molecules", Rev Diabet Stud. 2010 Summer;7(2):93-104.
Bretheron-Watt el al. "Insulin Upstream Factor 1 and a Novel Ubiquitous Factor Bind to the Human Islet Amyloid Polypeptide/ Amylin Gene Promoter." Biochem. J. 313.2(1998):495-502.
Brevini et al. "No shortcuts to pig embryonic stem cells", 2010, Theriogenology, vol. 74, pp. 544-550.
Brun et al. "A focus on the role of Pax4 in mature pancreatic islet beta-cell expansion and survival in health and disease", J Mol Endocrinol. Feb. 2008;40(2):37-45.
Byrne et al. "Multiplex gene regulation: a two-tiered approach to transgene regulation in transgenic mice" Proceedings of the National Academy of Sciences. Jul. 1, 1989;86(14):5473-7.
Calame et al. "Transcriptional Controlling Elements in the Immunoglobulin and T Cell Receptor Loci" in Advances in Immunology Jan. 1, 1988 (vol. 43, pp. 235-275). Academic Press.
Camper et al. "Postnatal repression of the alpha-fetoprotein gene is enhancer independent" Genes & development. Apr. 1, 1989;3(4):537-46.
Campos et al. "Divergent Tissue-Specific and Development Expression of Receptors for Glucapon and Glucagon-Like Peptide-1 in the Mouse." Endocrinology. May 1994; 134( 5):2156-64.
Cao et al. "High glucose is necessary for complete maturation of Pdx1-VP16-expressing hepatic cells into functional insulin-producing cells", Diabetes. Dec. 2004;53( 12) :3168-78.
Caplan et al. "Adult Mesenchymal Stem Cells for Tissue Engineering Versus Regenerative Medicine." J. Cell. Physiol. 213{2007):341-347.
Chakrabarti et al. "Transcription factors direct the development and function of pancreatic beta cells", Trends Endocrinol Metab. Mar. 2003;14(2):78-84; Abstract.
Chen et al. "Gene therapy for brain tumors: regression of experimental gliomas by adenovirus-mediated gene transfer in vivo" Proceedings of the National Academy of Sciences. Apr. 12, 1994;91(8):3054-7.
Chiang et al. "The role of the Wnt signaling pathway in incretin hormone production and function" Frontiers in physiology. Jul. 12, 2012;3:273.
Collombat et al. "Opposing actions of Arx and Pax4 in endocrine pancreas development" Genes & development. Oct. 15, 2003;17(20):2591-603.
Collombat et al. "Specifying pancreatic endocrine cell fates" Mechanisms of development. Jul. 1, 2006;123(7):501-12.
Cozar-Castellano et al. "Molecular engineering human hepatocytes into pancreatic beta cells for diabetes therapy" Proceedings of the National Academy of Sciences. May 31, 2005;102(22):7781-2.
D'amour et al. "Efficient differentiation of human embryonic stem cells to definitive endoderm" Nature biotechnology, Dec. 2005;23(12):1534.
Dunbar et al. "Identification of betacellulin as a major peptide growth factor in milk: purification, characterization and molecular cloning of bovine betacellulin" Biochemical Journal. Dec. 15, 1999;344(3):713-21.
Eberhard et al. "The pancreatic β-cell in the islet and organ community" Current opinion in genetics & development. Oct. 1, 2009;19(5):469-75.

(56) References Cited

OTHER PUBLICATIONS

Edlund et al. "Cell-specific expression of the rat insulin gene: evidence for role of two distinct 5'flanking elements" Science. Nov. 22, 1985:230(4728):912-6.
Ferber et al. "Pancreatic and duodenal homeobox gene 1 induces expression of insulin genes in liver and ameliorates streptozotocin-induced hyperglycemia" Nature medicine. May 2000;6(5):568-72.
Ferber et al. "Transdifferentiation and its Implementation" in Autologous Cell Replacement Therapy for Diabetes; May 29, 2014, pp. 1-35.
Figliuzzi et al. "Mesenchymal stem cells help pancreatic islet transplantation to control type 1 diabetes" World journal of stem cells. Apr. 26, 2014;6(2):163.
Freeman et al. "The influence of the sequential delivery of angiogenic factors from affinity-binding alginate scaffolds on vascularization" Biomaterials. Apr. 1, 2009;30(11):2122-31.
Freeman et al. "The effect of sulfation of alginate hydrogels on the specific binding and controlled release of heparin-binding proteins" Biomaterials. Aug. 1, 2008;29(22):3260-8.
Furukawa et al. "Possible involvement of atypical protein kinase C (PKC) in glucose-sensitive expression of the human insulin gene: DNA-binding activity and transcriptional activity of pancreatic and duodenal homeobox gene-1 (PDX-1) are enhanced via calphostin C-sensitive but phorbol 12-myristate 13-acetate (PMA) and Gö6976-insensitive pathway" Endocrine journal. 1999;46(1):43-58.
Gefen-Halevi et al. "NKX6. 1 promotes PDX-1-induced liver to pancreatic β-cells reprogramming" Cellular Reprogramming (Formerly "Cloning and Stem Cells"). Dec. 1, 2010;12(6):655-64.
Gen Bank Accession No. AAA18355.1, May 25, 1994.
Gen Bank Accession No. AAA88820.1, Feb. 20, 1996.
Gen Bank Accession No. AAC41260, Mar. 7, 1998.
Gen Bank Accession No. AF036325, Mar. 7, 1998.
Gen Bank Accession No. U35632.1, Feb. 21, 1996.
Gen Bank Accession No. NM_006193.2, Sep. 6, 2014.
Gen Bank Accession No. AAD02289.1, Mar. 10, 2010.
Gen Bank Accession No. NM_201589.3, Sep. 6, 2014.
Gen Bank Accession No. NP_963883.2 Sep. 6, 2014.
Gen Bank Accession No. NM_020999.3, Sep. 6, 2014.
Gen Bank Accession No. NP_066279.2, Sep. 6, 2014.
Gen Bank Accession No. NM_002500.4, Sep. 6, 2014.
Gen Bank Accession No. NP_002491.2, Sep. 6, 2014.
Gen Bank Accession No. NM_000346.3, Sep. 6, 2014.
Gen Bank Accession No. NP_000337.1, Sep. 6, 2014.
Gen Bank Accession No. X02812.1, Feb. 2, 2011.
Gen Bank Accession No. AJ009860.1, Oct. 19, 2006.
Gerbal-Chaloin et al. "The WNT/β-catenin pathway is a transcriptional regulator of CYP2E1, CYP1A2, and aryl hydrocarbon receptor gene expression in primary human hepatocytes" Molecular pharmacology. Dec. 1, 2014;86(6):624-34.
Göke et al. "Exendin-4 is a high potency agonist and truncated exendin-(9-39)-amide an antagonist at the glucagon-like peptide 1-(7-36)-amide receptor of insulin-secreting beta-cells" Journal of Biological Chemistry. Sep. 15, 1993;268(26):19650-5.
Goodson Jm. "Dental applications" Medical applications of controlled release. 1984;2:115-38.
Gottesman S. "Gene Expression Technology: Methods in Enzymology" Academic Press, San Diego, California. 1990;185:119-29.
Gradwohl et al. "neurogenin3 is required for the development of the four endocrine cell lineages of the pancreas" Proceedings of the National Academy of Sciences. Feb. 15, 2000;97(4):1607-11.
Graf T. "Historical origins of transdifferentiation and reprogramming" Cell stem cell. Dec. 2, 2011;9(6);504-16.
Grapin-Botton A. "Three-dimensional pancreas organogenesis models. Diabetes" Obesity and Metabolism. Sep. 2016;18:33-40.
Greenberger et al. "Corticosteroid suppression of VEGF-A in infantile hemangioma-derived stem cells" New England Journal of Medicine. Mar. 18, 2010:362(11)1005-13.
Gross et al. "Increased susceptibility of islets from diabetes-prone Psammomys obesus to the deleterious effects of chronic glucose exposure" Endocrinology. Dec. 1, 1996;137(12):5610-5.

Ham et al. "Generation of functional insulin-producing cells from neonatal porcine liver-derived cells by PDX1/VP16, BETA2/NeuroD and MafA" PloS one. 2013;8(11).
Hamad et al. "Distinct requirements for Ras oncogenesis in human versus mouse cells" Genes & development. Aug. 15, 2002;16(16):2045-57.
Hamaguchi et al. "Comparison of cytokine effects on mouse pancreatic α-cell and β-cell lines viability, secretory function, and mhc antigen expression" Diabetes. Apr. 1, 1990;39(4):415-25.
Hanna et al. "Direct reprogramming of terminally differentiated mature B lymphocytes to pluripotency" Cell. Apr. 18, 2008;133(2)250-64.
He et al. "A simplified system for generating recombinant adenoviruses" Proceedings of the National Academy of Sciences. Mar. 3, 1998;95(5):2509-14.
Horb et al. "Experimental conversion of liver to pancreas" Current Biology. Jan. 21, 2003;13(2):105-15.
Howard et al. "Intracerebral drug delivery in rats with lesion-induced memory deficits" Journal of neurosurgery. Jul. 1, 1989;71(1):105-12.
Hsu et al. "Molecular cloning of a novel splice variant of the alpha subunit of the mammalian Go protein" Journal of Biological Chemistry. Jul. 5, 1990;265(19):11220-6.
Ieda et al. "Direct reprogramming of fibroblasts into functional cardiomyocytes by defined factors" Cell. Aug. 6, 2010;142(3):375-86.
International Search Report for PCT Application No. PCT/IL2018/050496 dated Aug. 7, 2018.
Ito et al. "Mesenchymal stem cell and islet co-transplantation promotes graft revascularization and function" Transplantation. Jun. 27, 2010;89(12):1438-45.
Iwasaki et al. "The order of expression of transcription factors directs hierarchical specification of hematopoietic lineages" Genes & development. Nov. 1, 2006;20(21):3010-21.
Joliot et al. "Antennapedia homeobox peptide regulates neural morphogenesis" Proceedings of the National Academy of Sciences. Mar. 1, 1991;88(5):1864-8.
Jonsson et al. "Insulin-promoter-factor 1 is required for pancreas development in mice" Nature. Oct. 13, 1994:371(6498):606-9.
Kahn et al. "Islet amyloid: a long-recognized but underappreciated pathological feature of type 2 diabetes" Diabetes. Feb. 1, 1999;48(2):241-53.
Kajimoto et al. "Suppression of transcription factor PDX-1/IPF1/STF-1/IDX-1 causes no decrease in insulin mRNA in MIN6 cells" The Journal of clinical investigation. Oct. 1, 1997;100(7):1840-6.
Kaneto et al. "A crucial role of MafA as a novel therapeutic target for diabetes" Journal of Biological Chemistry. Apr. 15, 2005;280(15):15047-52.
Kaneto et al. "PDX-1/VP16 fusion protein, together with NeuroD or Ngn3, markedly induces insulin gene transcription and ameliorates glucose tolerance" Diabetes, Apr. 1, 2005;54(4):1009-22.
Kang et al. "Bioengineered human vascular networks transplanted into secondary mice reconnect with the host vasculature and re-establish perfusion" Blood, The Journal of the American Society of Hematology. Dec. 15, 2011;118(25):6718-21.
Kataoka et al. "MafA is a glucose-regulated and pancreatic β-cell-specific transcriptional activator for the insulin gene" Journal of Biological Chemistry. Dec. 20, 2002:277(51):49903-10.
Kaufman et al. "Translational efficiency of polycistronic mRNAs and their utilization to express heterologous genes in mammalian cells" The EMBO journal. Jan. 1, 1987;6(1):187-93.
Kessel et al. "Murine developmental control genes" Science. Jul. 27, 1990;249(4967):374-9.
Khaoustov et al. "Induction of three-dimensional assembly of human liver cells by simulated microgravity" In Vitro Cellular & Developmental Biology—Animal. Oct. 1, 1999;35(9):501-9.
Koizumi et al. "Hepatic regeneration and enforced PDX-1 expression accelerate transdifferentiation in liver" Surgery. Aug. 1, 2004;136(2):449-57.
Kojima et al. "NeuroD-betacellulin gene therapy induces islet neogenesis in the liver and reverses diabetes in mice" Nature medicine. May 2003;9(5):596-603.

(56) References Cited

OTHER PUBLICATIONS

Kojima et al. "Combined expression of pancreatic duodenal homeobox 1 and islet factor 1 induces immature enterocytes to produce insulin" Diabetes. May 1, 2002;51(5):1398-408.
Koller et al. "Inactivating the beta 2-microglobulin locus in mouse embryonic stem cells by homologous recombination" Proceedings of the National Academy of Sciences. Nov. 1, 1989;86(22):8932-5.
Koya et al. "Reversal of Streptozotocin-Induced Diabetes in Mice by Cellular Transduction With Recombinant Pancreatic Transcription Factor Pancreatic Duodenal Homeobox-1: A Novel Protein Transduction Domain-Based Therapy" Diabetes. Mar. 1, 2008;57(3):757-69.
Krause et al. "Cultured hepatocytes adopt progenitor characteristics and display bipotent capacity to repopulate the liver" Cell transplantation. Jul. 2014;23(7):805-17.
Kroon et al. "Pancreatic endoderm derived from human embryonic stem cells aenerates glucose-responsive insulin-secreting cells in vivo" Nature biotechnology. Apr. 2008;26(4):443-52.
Kurjan et al. "Structure of a yeast pheromone gene (MF2al2 pha): a putative alpha2 factor precursor contains four tandem copies of mature alpha2factor" Cell. 1982;30:933.
Li et al. "In vitro transdifferentiation of hepatoma cells into functional pancreatic cells" Mechanisms of development. Jun. 1, 2005;122(6):835-47.
Lima et al. "Generation of functional beta-like cells from human exocrine pancreas" PLoS One. 2016;11(5).
Lin et al. "Expression of T cell antigen receptor heterodimers in a lipid-linked form" Science. Aug. 10, 1990;249(4969):677-9.
Lin et al. "Human endothelial colony-forming cells serve as trophic mediators for mesenchymal stem cell engraftment via paracrine signaling" Proceedings of the National Academy of Sciences. Jul. 15, 2014;111(28):10137-42.
Loeffler et al. "Gene transfer into primary and established mammalian cell lines with lipopolyamine-coated DNA" in Recombinant DNA Methodology II Jan. 1, 1995 (pp. 531-549). Academic Press.
Lu et al. "Hepatic progenitor cells of biliary origin with liver repopulation capacity" Nature cell biology. Aug. 2015;17(8):971-83.
Luckow et al. "High level expression of nonfused foreign genes with Autographa californica nuclear polyhedrosis virus expression vectors" Virology. May 1, 1989;170(1):31-9.
Marshak et al. "Purification of the β-cell glucose-sensitive factor that transactivates the insulin gene differentially in normal and transformed islet cells" Proceedings of the National Academy of Sciences. Dec. 24, 1996;93(26):15057-62.
Mauda-Havakuk et al. "Ectopic PDX-1 expression directly reprograms human keratinocytes along pancreatic insulin-producing cells fate" PLoS One. 2011;6(10).
Maxcyte GT® Flow Transfection System at http://www.maxcyte.com/applications/mRNA-CAR.php, 2015.
Meivar-Levy et al. "Pancreatic and duodenal homeobox gene 1 induces hepatic dedifferentiation by suppressing the expression of CCAAT/enhancer-binding protein β" Hepatology. Sep. 2007:46(3):898-905.
Meivar-Levy et al. "New organs from our own tissues: liver-to-pancreas transdifferentiation" Trends in Endocrinology & Metabolism. Dec. 1, 2003;14(10):460-6.
Meivar-Levy et al. "Human liver cells expressing albumin and mesenchymal characteristics give rise to insulin-producing cells" Journal of transplantation. Aug. 24, 2011;2011.
Meivar-Levy et al. "Regenerative medicine: using liver to generate pancreas for treating diabetes" IMAJ-RAMAT GAN-. Jun. 1, 2006;8(6):430.
Meivar-Levy et al. "Adult cell fate reprogramming: converting liver to pancreas" In Cellular Programming and Reprogramming 2010 (pp. 251-283). Humana Press; Abstract.
Melero-Martin et al. "Engineering robust and functional vascular networks in vivo with human adult and cord blood-derived progenitor cells" Circulation research. Jul. 18, 2008;103(2)194-202.

Milewski et al. "Conservation of PDX-1 structure, function, and expression in zebrafish" Endocrinology. Mar. 1, 1998;139(3):1440-9.
Miller et al. "IDX-1: a new homeodomain transcription factor expressed in rat pancreatic islets and duodenum that transactivates the somatostatin gene" The EMBO journal. Mar. 1, 1994;13(5):1145-56.
Minami et al. "Lineage tracing arid characterization of insulin-secreting cells generated from adult pancreatic acinar cells" Proceedings of the National Academy of Sciences. Oct. 18, 2005;102(42)15116-21.
Mitanchez et al. "Regulated expression of mature human insulin in the liver of transgenic mice" FEBS letters. Jan. 16, 1998;421(3):285-9.
Muniappan et al. "Induction of insulin secretion in engineered liver cells by nitric oxide" BMC physiology. Dec. 1, 2007;7(1):11.
Munoz et al. "Conventional pluripotency markers are unspecific for bovine embryonic-derived cell-lines" Theriogenology. Jun. 1, 2008;69(9):1159-64.
Murtaugh et al. "Genes, signals, and lineages in pancreas development" Annual review of cell and developmental biology. Nov. 2003;19(1):71-89.
Muzzin et al. "Hepatic insulin gene expression as treatment for type 1 diabetes mellitus in rats" Molecular Endocrinology. Jun. 1, 1997;11(6):833-7.
Nakajima-Nagata et al. "Pdx-1 enables insulin secretion by regulating synaptotagmin 1 gene expression" Biochemical and biophysical research communications. Jun. 4, 2004;318(3):631-5.
Nasr et al. "Co-transplantation of autologous MSCs delays islet allograft rejection and generates a local immunoprivileged site", Acta Diabetol. Oct. 2015;52(5):917-27.
Nicolau et al. "In viva expression of rat insulin after intravenous administration of the liposome-entrapped gene for rat insulin I" Proceedings of the National Academy of Sciences. Feb. 1, 1983;80(4):1068-72.
Nir et al. "How to make pancreatic βcells—prospects for cell therapy in diabetes" Current opinion in biotechnology. Oct. 1, 2005;16(5):524-9.
Nishimura et al. "Expression of MafA in pancreatic progenitors is detrimental for pancreatic development" Developmental biology. Sep. 1, 2009;333(1)108-20.
Noguchi et al. "Mechanism of PDX-1 protein transduction" Biochemical and biophysical research communications. Jun. 24, 2005;332(1):68-74.
Noguchi et al. "PDX-1 protein containing its own antennapedia-like protein transduction domain can transduce pancreatic duct and islet cells" Diabetes. Jul. 1, 2003;52(7)1732-7.
Offield et al. "PDX-1 is required for pancreatic outgrowth and differentiation of the rostral duodenum" Development. Mar. 1, 1996;122(3):983-95.
Ohneda et al. "The homeodomain of PDX-1 mediates multiple protein-protein interactions in the formation of a transcriptional activation complex on the insulin promoter" Molecular and Cellular Biology. Feb. 1, 2000;20(3):900-11.
Okitsu et al. "Transplantation of reversibly immortalized insulin-secreting human hepatocytes controls diabetes in pancreatectomized pigs" Diabetes. Jan. 1, 2004;53(1):105-12.
Olbrot et al. "Identification of β-cell-specific insulin gene transcription factor RIPE3b1 as mammalian MafA" Proceedings of the National Academy of Sciences. May 14, 2002;99(10):6737-42.
Orr et al. "TGF-β affinity-bound to a macroporous alginate scaffold generates local and peripheral immunotolerant responses and improves allocell transplantation" Acta biomaterialia. Nov. 1, 2016;45:196-209.
Otonkoski et al. "Stem cells in the treatment of diabetes" Annals of medicine. Jan. 1, 2005;37(7):513-20.
Ozcan et al. "Functional expression and analysis of the pancreatic transcription factor PDX-1 in yeast" Biochemical and biophysical research communications. Jul. 19, 2002;295(3):724-9.
Pang et al. "Induction of human neuronal cells by defined transcription factors" Nature. Aug. 2011;476(7359):220-3.

(56) References Cited

OTHER PUBLICATIONS

Paris et al. "Equine embryos and embryonic stem cells: defining reliable markers of pluripotency" Theriogenology. Sep. 1, 2010;74(4):516-24.
Patel et al. "Therapeutic potential mesenchymal stem cells in regenerative medicine" Stem cells international. 2013;2013.
Peers et al. "Insulin expression in pancreatic islet cells relies on cooperative interactions between the helix loop helix factor E47 and the homeobox factor STF-1" Molecular Endocrinology. Dec. 1, 1994;8(12):1798-806.
Pinkert et al. "An albumin enhancer located 10 kb upstream functions along with its promoter to direct efficient, liver-specific expression in transgenic mice" Genes & development. May 1, 1987;1(3):268-76.
Qing-Song et al. "Combined transfection of the three transcriptional factors, PDX-1, NeuroD1, and MafA, causes differentiation of bone marrow mesenchymal stem cells into insulin-producing cells" Experimental diabetes research. Jun. 19, 2012;2012.
Queen et al. "Immunoglobulin gene transcription is activated by downstream sequence elements" Cell. Jul. 1, 1983;33(3):741-8.
Re'em et al. "Simultaneous regeneration of articular cartilage and subchondral bone induced by spatially presented TGF-beta and BMP-4 in a bilayer affinity binding system" Acta biomaterialia. Sep. 1, 2012;8(9):3283-93.
Reniers et al. "Industrialization of a Cell-based Autologous Therapy Targeting Diabetes: Industrialization of a Liver Cell Proliferation Process from Petri Dish to the Xpansion® Multiplate Bioreactor" Cell. 2015;12563:029.
Rheinwald et al. "Epidermal growth factor and the multiplication of cultured human epidermal keratinocytes" Nature. Feb. 3, 1977;265(5593):421-4.
Rojas et al. "Islet Cell Development" The Islets of Langerhans. Mar. 10, 2010;654:59; Abstract.
Ross Mf. "protein power: researchers trigger insulin production in diabetic mice" eurekalert, https://www.eurekalert.org/pub_releases/2008-01/uof-ppr010808.php.
Sakai et al. "Rapid fabricating technique for multi-layered human hepatic cell sheets by forceful contraction of the fibroblast monolayer" PloS one. 2013;8(7).
Sakurai et al. "Comparison of gene expression efficiency and innate immune response induced by Ad vector and lipoplex" Journal of controlled release. Feb. 26, 2007;117(3):430-7.
Salomaa et al. "Non-insulin-dependent diabetes mellitus and fasting glucose and insulin concentrations are associated with arterial stiffness indexes: the ARIC study" Circulation. Mar. 1, 1995;91(5):1432-43; Abstract.
Sambrook et al. (2001) "Molecular cloning: a laboratory manual" Cold Spring Harb Lab Press Cold Spring Harb NY. 2001;999.
Sapir et al. "Cell-replacement therapy for diabetes: Generating functional insulin-producing tissue from adult human liver cells" Proceedings of the National Academy of Sciences. May 31, 2005;102(22):7964-9.
Saudek et al. "A preliminary trial of the programmable implantable medication system for insulin delivery" New England Journal of Medicine. Aug. 31, 1989;321(9):574-9.
Schmidt et al. "The cytomegalovirus enhancer: a pan-active control element in transgenic mice" Molecular and Cellular Biology. Aug. 1, 1990;10(8):4406-11.
Schultz et al. "Expression and secretion in yeast of a 400-kDa envelope glycoprotein derived from Epstein-Barr virus" Gene. Jan. 1, 1987;54(1):113-23.
Seed B. "An LFA-3 cDNA encodes a phospholipid-linked membrane protein homologous to its receptor CD2" Nature. Oct. 29, 1987;329(6142):840-2.
Seijffers et al. "Increase in PDX-1 levels suppresses insulin gene expression in RIN 1046—38 cells" Endocrinology. Jul. 1, 1999;140(7):3311-7.
Serup et al. "Induction of insulin and islet amyloid polypeptide production in pancreatic islet glucagonoma cells by insulin promoter factor 1" Proceedings of the National Academy of Sciences. Aug. 20, 1996;93(17):9015-20.
Shamblott et al. "Cell therapies for type 1 diabetes mellitus" Expert opinion on biological therapy. Mar. 1, 2004;4(3):269-77.
Shanmukhappa et al. "Hepatic to pancreatic switch defines a role for hemostatic factors in cellular plasticity in mice" Proceedings of the National Academy of Sciences. Jul. 19, 2005;102(29):10182-7.
Shapiro et al. "Novel alginate sponges for cell culture and transplantation" Biomaterials. Apr. 1, 1997;18(8):583-90.
Sheyn et al. "Genetically modified cells in regenerative medicine and tissue engineering" Advanced drug delivery reviews. Jun. 15, 2010;62(7-8):683-98.
Shternhall-Ron et al. "Ectopic PDX-1 expression in liver ameliorates type 1 diabetes" Journal of autoimmunity. Mar. 1, 2007;28(2-3):134-42.
Slack et al. "Transdifferentiation and metaplasia—switching cell types" Current opinion in genetics & development. Oct. 1, 2001;11(5):581-6.
Smith Ge. "Production of human beta interferon in insect cells infected with a baculovirus expression vector" Molecular arid Cellular Biology. 1983:3:2156-65.
Smith et al. "Single-step purification of polypeptides expressed in *Escherichia coli* as fusions with glutathione S-transferase" Gene. Jul. 15, 1988;67(1):31-40.
Song et al. "Islet cell differentiation in liver by combinatorial expression of transcription factors neurogenin-3, BETA2, and RIPE3b1" Biochemical and biophysical research communications. Mar. 9, 2007;354(2):334-9.
Stemple et al. "Isolation of a stem cell for neurons and glia from the mammalian neural crest" Cell. Dec. 11, 1992;71(6):973-85.
Stoffel et al. "Localization of human homeodomain transcription factor insulin promoter factor 1 (IPF1) to chromosome band 13q12. 1" Genomics (San Diego, Calif.). 1995;28(1)125-6.
Stoffers et al. "Homeodomain protein IDX-1: a master regulator of pancreas development and insulin gene expression" Trends in Endocrinology & Metabolism. May 1, 1997;8(4):145-51.
Studier et al. "Gene expression technology: Methods Enzymol" 1990;185:60-89.
Szabo et al. "Direct conversion of human fibroblatsts multilineage blood progenitors" Nature. Nov. 2010;468(7323):521-6.
Takahashi et al. "Induction of pluripotent stem cells from mouse embryonic and adult fibroblast cultures by defined factors" cell. Aug. 25, 2006;126(4):663-76.
Takebe et al. "SR alpha promoter: an efficient and versatile mammalian cDNA expression system composed of the simian virus 40 early promoter and the R-U5 segment of human T-cell leukemia virus type 1 long terminal repeat" Molecular and cellular biology. Jan. 1, 1988;8(1):466-72.
Tang et al. "Role of Pax4 in Pdx1-VP16-mediated liver-to-endocrine pancreas transdifferentiation" Laboratory Investigation. Aug. 2006;86(8);829-41.
Thowfeequ et al. "Transdifferentiation in developmental biology, disease, and in therapy. Developmental dynamics: an official publication of the American Association of Anatomists" Dec. 2007;236(12):3208-17.
Thowfeequ et al. "Reprogramming of liver to pancreas" in Stem Cells in Regenerative Medicine 2009 (pp. 407-418). Humana Press.
Torre et al. "Transcription dynamics in a physiological process: β-catenin signaling directs liver metabolic zonation" The international journal of biochemistry & cell biology. Feb. 1, 2011;43(2):271-8.
Treacy et al. "Adenoviral transduction of mesenchymal stern cells; in vitro responses and in vivo immune responses after cell transplantation" PLoS One. 2012;7(8).
Tréhin et al. "Chances and pitfalls of cell penetrating peptides for cellular drug delivery" European journal of pharmaceutics and biopharmaceutics. Sep. 1, 2004;58(2):209-23.
Tur-Kaspa et al. "Use of electroporation to introduce biologically active foreign genes into primary rat hepatocytes" Molecular and cellular biology. Feb. 1, 1986;6(2):716-8.

(56) References Cited

OTHER PUBLICATIONS

Ungrin et al. "Reproducible, ultra high-throughput formation of multicellular organization from single cell suspension-derived human embryonic stem cell aggregates" PloS one. 2008;3(2).
Van Der Meulen et al. "Maturation of stem cell-derived beta-cells guided by the expression of urocortin 3" The review of diabetic studies: RDS. 2014:11(1):115.
Varda-Bloom et al. "Tissue-specific gene therapy directed to tumor angiogenesis" Gene therapy. Jun. 8, 2001;8(11):819-27.
Verma et al. "Gene therapy: promises, problems and prospects" in Genes and Resistance to Disease 2000 (pp. 147-157). Springer, Berlin, Heidelberg.
Vieau et al. "Mouse insulinoma beta TC3 cells express prodynorphin messenger ribonucleic acid and derived peptides: a unique cellular model for the study of prodynorphin biosynthesis and processing" Endocrinology. Mar. 1, 1995;136(3):1187-96.
Vierbuchen et al. "Direct conversion of fibroblasts to functional neurons by defined factors" Nature. Feb. 2010;463(7284):1035-41.
Wada et al. "Codon usage tabulated from the GenBank genetic sequence data" Nucleic acids research. May 11, 1992;20(Suppl):2111.
Wang et al. "Glucagon-like peptide-1 regulates the beta cell transcription factor, PDX-1, in insulinoma cells" Endocrinology. Oct. 1, 1999;140(10):4904-7.
Wang et al. "Adenovirus transduction is required for the correction of diabetes using Pdx-1 or Neurogenin-3 in the liver" Molecular Therapy. Feb. 1, 2007;15(2):255-63.
Wang et al. "Pdx1 level defines pancreatic gene expression pattern and cell lineage differentiation" Journal of Biological Chemistry. Jul. 6, 2001;276(27):25279-86.
Wang et al. "Stoichiometry of Gata4, Mef2c, and Tbx5 influences the efficiency and quality of induced cardiac myocyte reprogramming" Circulation research. Jan. 16, 2015;116(2)237-44.
Watada et al. "Involvement of the homeodomain-containing transcription factor PDX-1 in islet amyloid polypeptide gene transcription" Biochemical and biophysical research communications. Dec. 24, 1996;229(3):746-51.
Weintraub et al. "Anti-sense RNA as a molecular tool for] genetic analysis" Trends in Genetics. Jan. 1, 1985;1:22-5.
Werth et al. "Hepatic expression of glutamine synthetase in rats is controlled by STAT5 and TCF transcription factors" Hepatology. Oct. 2006;44(4):967-75.
Winoto et al. A novel, inducible and T cell-specific enhancer located at the 3' end of the T cell receptor alpha locus. The EMBO journal. Mar. 1, 1989;8(3):729-33.
Wu et al. "Receptor-mediated in vitro gene transformation by a soluble DNA carrier system" Journal of Biological Chemistry. Apr. 5, 1987;262(10);4429-32.
Xu et al. Mesenchymal stem cells differentially mediate regulatory T cells and conventional effector T cells to protect fully allogeneic islet grafts in mice. Diabetologia. Apr. 1, 2012:55(4):1091-102.
Yamada et al. "In vitro transdifferentiation of mature hepatocytes into insulin-producing cells" Endocrine journal. Dec. 2006;53(6):789.
Yamanaka S. "Induction of pluripotent stem cells from mouse fibroblasts by four transcription factors" Cell proliferation. Feb. 2008;41:51-6.
Yang et al. "In vitro trans-differentiation of adult hepatic stem cells into pancreatic endocrine hormone-producing cells" Proceedings of the National Academy of Sciences. Jun. 11, 2002;99(12):8078-83.
Yechoor et al. "Minireview: β-cell replacement therapy for diabetes in the 21st century: manipulation of cell fate by directed differentiation" Molecular endocrinology. Aug. 1, 2010;24(8):1501-11.
Yeung et al. "Human Mesenchymal Stem Cells Protect Human Islets from Pro-Inflammatory Cytokines" PLoS One. 2012:7(5).
Young et al. "β-catenin/Tcf activation partially mimics the transforming activity of Wnt-1 in Rat-1 fibroblasts" Differentiation. Oct. 1, 2003;71(8):477-85.
Zalzman et al. "Differentiation of human liver-derived, insulin-producing cells toward the β-cell phenotype" Diabetes. Sep. 1, 2005;54(9):2568-75.
Zhou et al. "In vivo reprogramming of adult pancreatic exocrine cells to β-cells" nature. Oct. 2008;455(7213):627-32.
Zhu et al. "Human pancreatic beta-like cells converted from fibroblasts" Nature communications. Jan. 6, 2016;7(1):1-3.

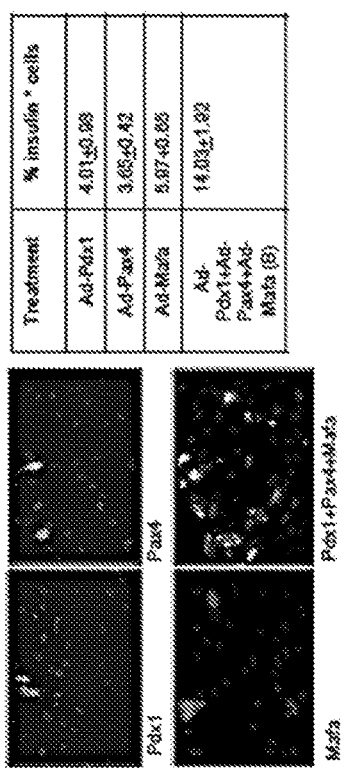
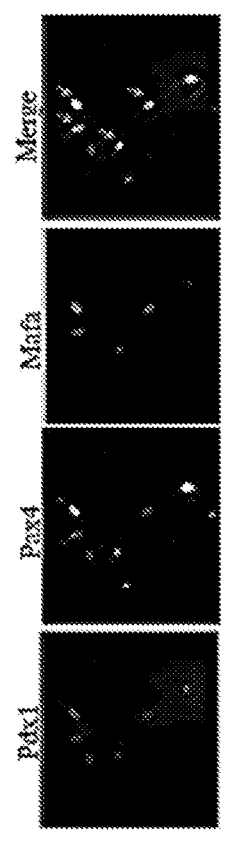
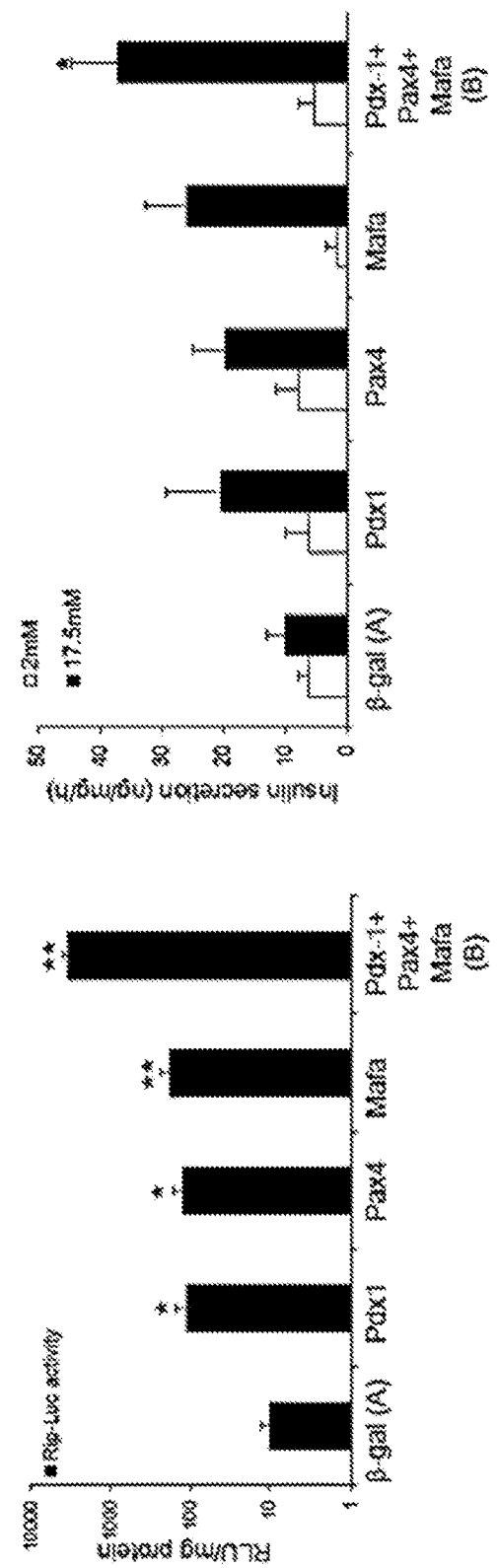
Figure 1A
Figure 1B
Figure 1C
Figure 1D

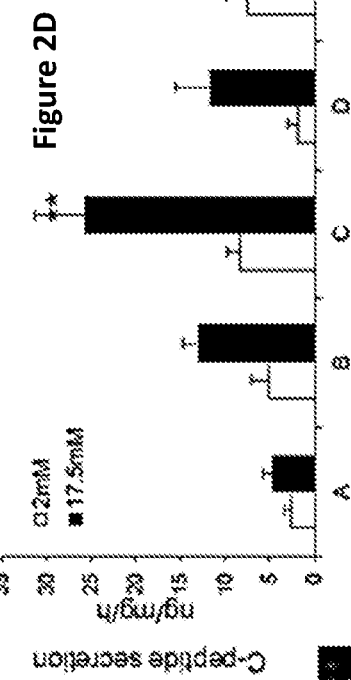
Figure 2A
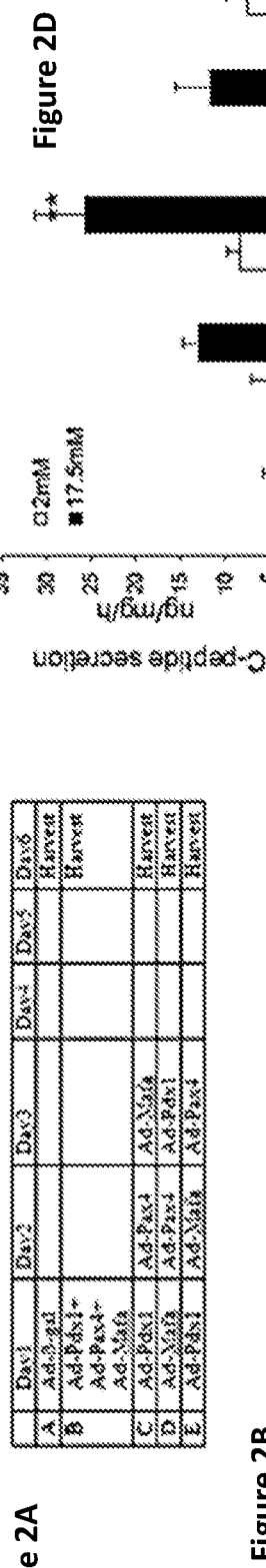
Figure 2B
Figure 2C
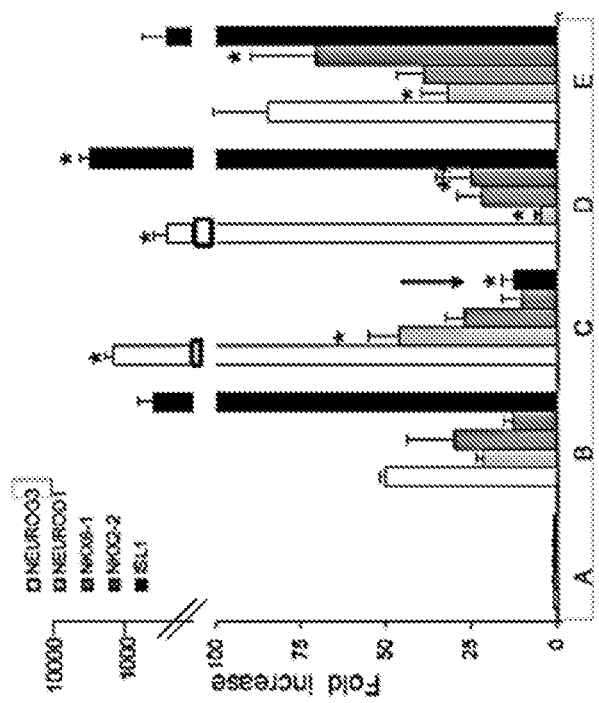
Figure 2D
Figure 2E
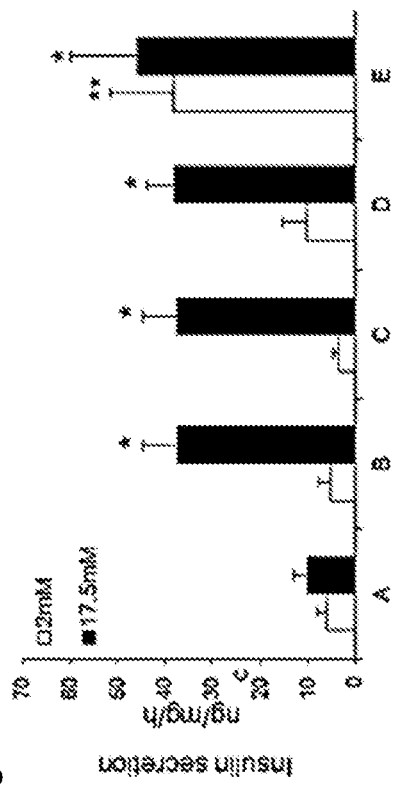

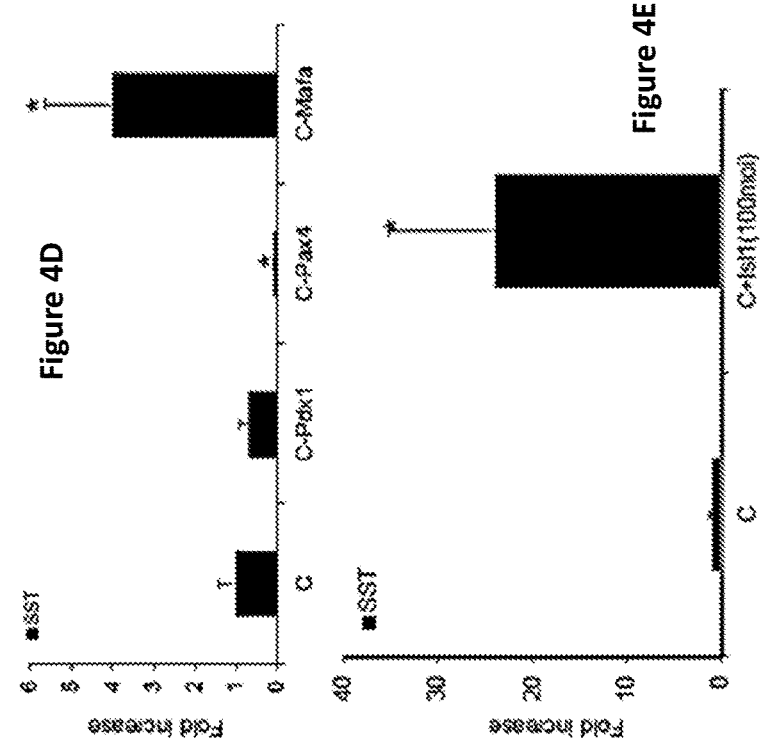
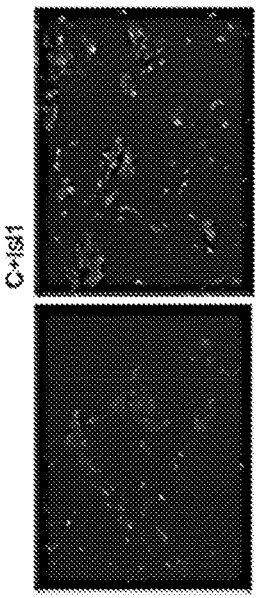
Figure 4A
Figure 4B
Figure 4C
Figure 4D
Figure 4E
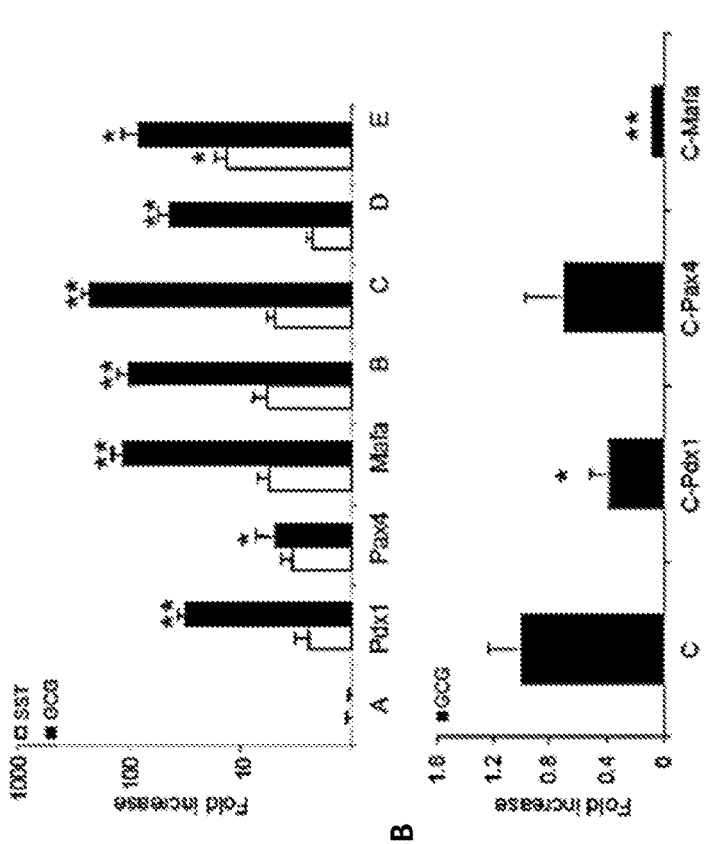
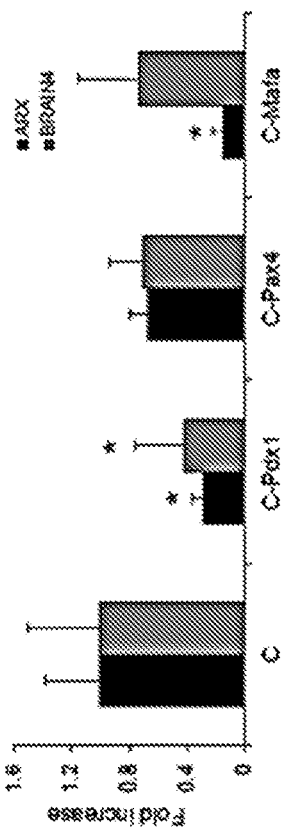
Figure 4F

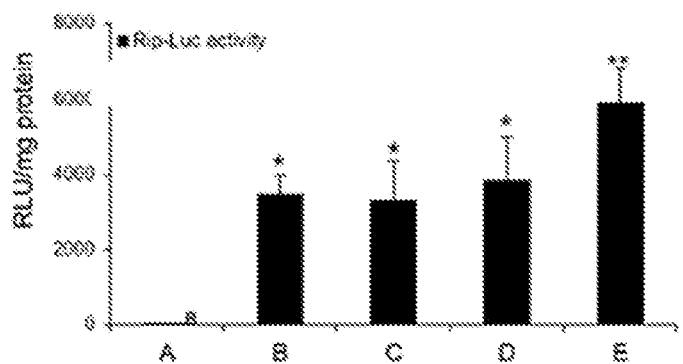
Figure 5
Figure 6A
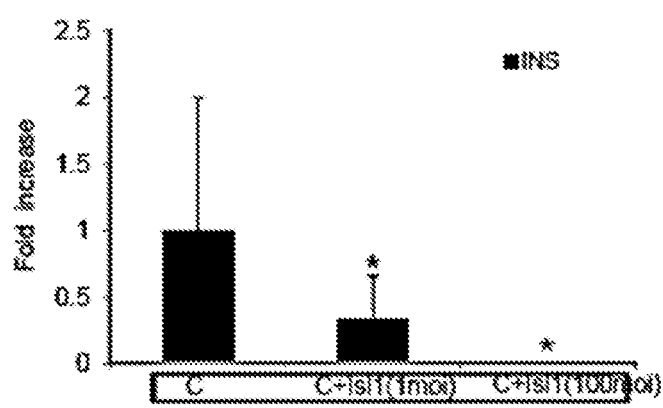
Figure 6B
Figure 6C
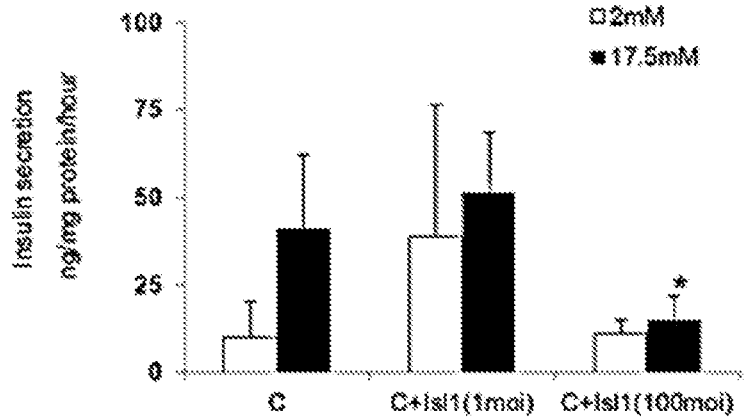
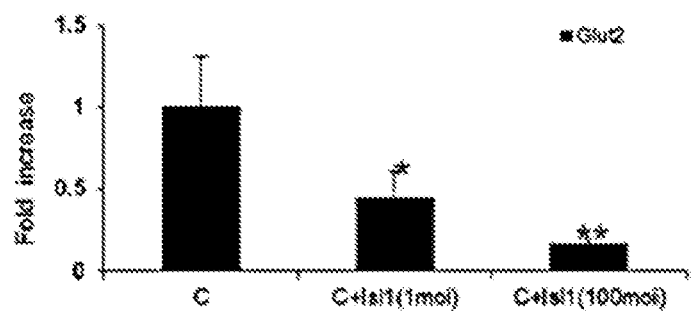

Figure 12A
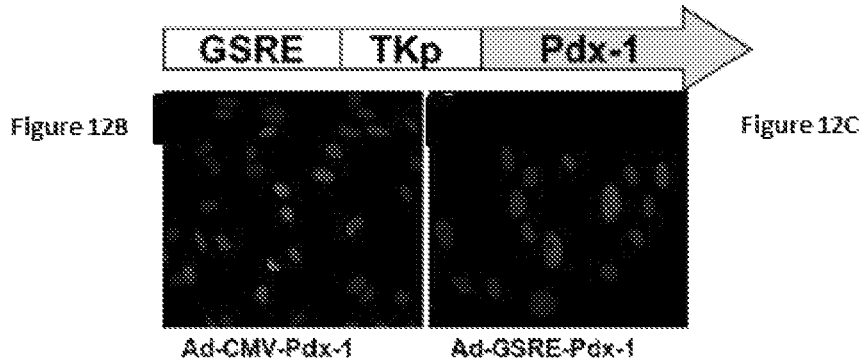
Figure 12B  Figure 12C
Figure 12D
Figure 12E  Figure 12F
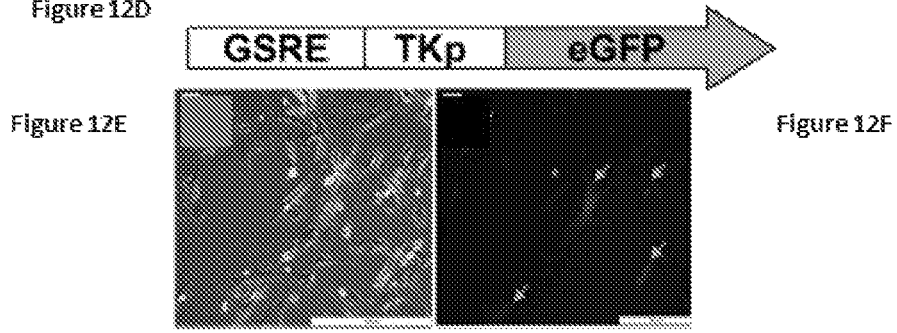
Figure 13A  Figure 13B
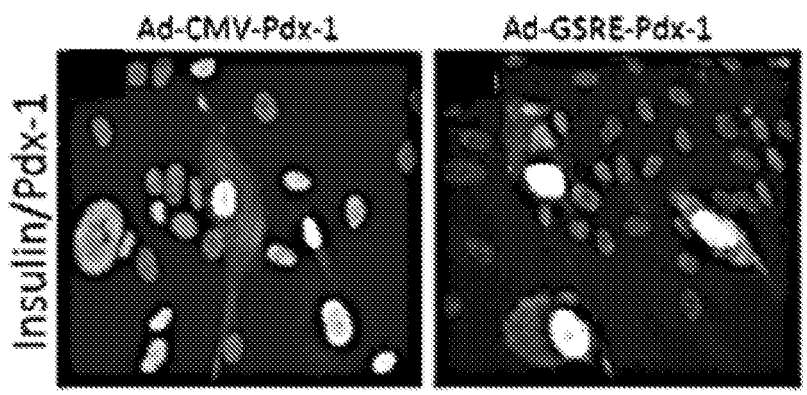
Figure 13C
|  | INS+ | Pdx-1+ | INS+/Pdx-1+ |
|---|---|---|---|
| Ad-CMV-Pdx-1 | 0.6% | 60% | 1% |
| Ad-GSRE-Pdx-1 | 4% | 16% | 25% |

Figure 21A
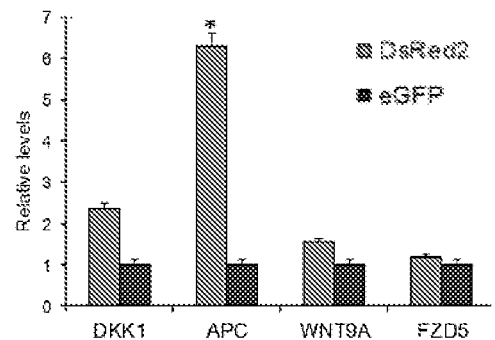
Figure 21B
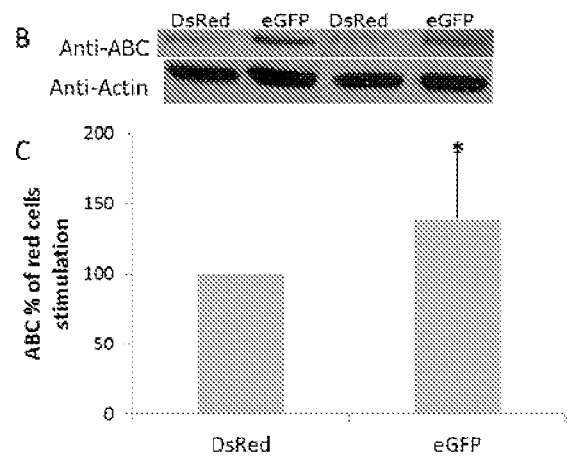
Figure 21C
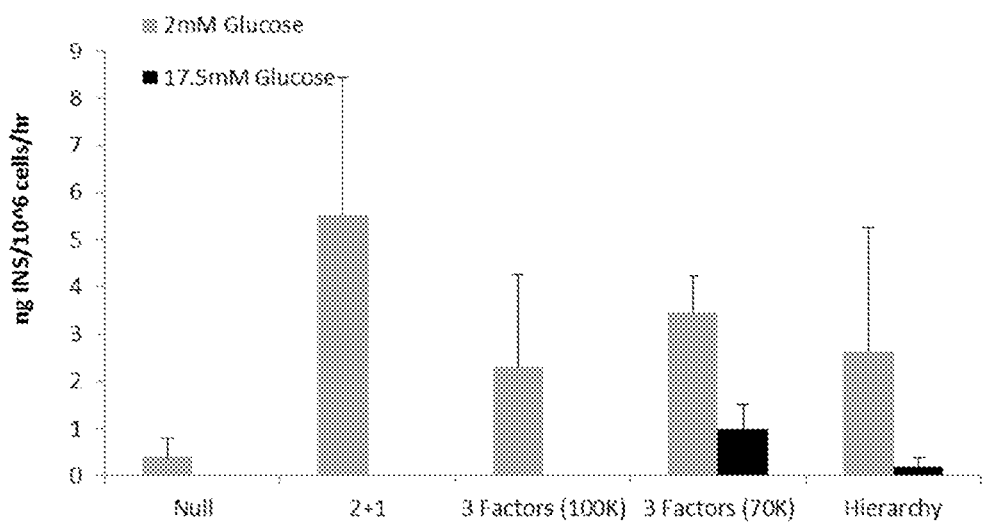
Figure 22A

| Run | Seeding density (cell/cm²) | Harvest density (cell/cm²) | Culture duration (days) |
|---|---|---|---|
| ORG-009 | 4,000 | 17,500 | 8 |
| ORG-014 | 4,000 | 22,780 | 7 |
| ORG-017 | 3,972 | 19,412 | 9 |

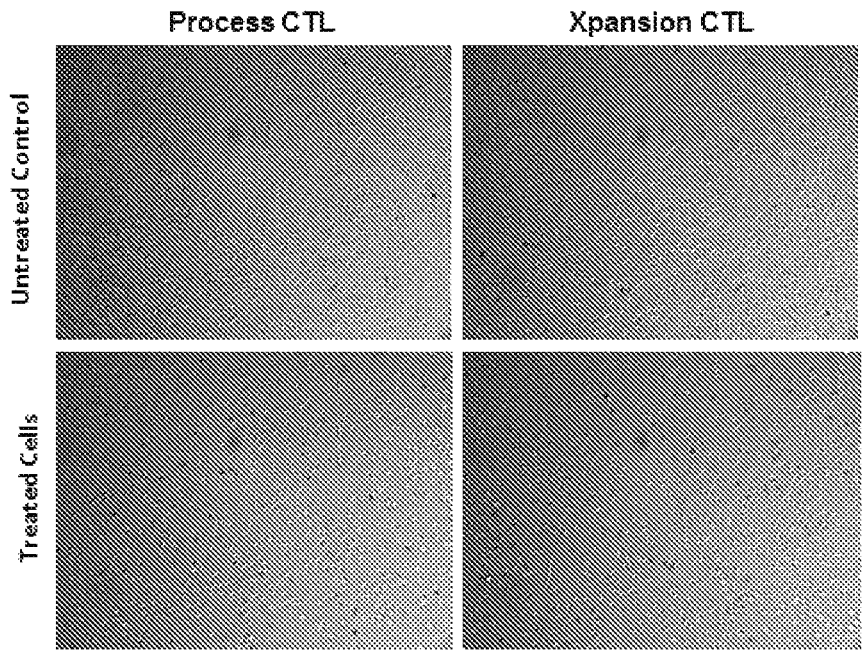
Figure 30A — Process CTL (Untreated Control)
Figure 30B — Xpansion CTL (Untreated Control)
Figure 30C — Process CTL (Treated Cells)
Figure 30D — Xpansion CTL (Treated Cells)
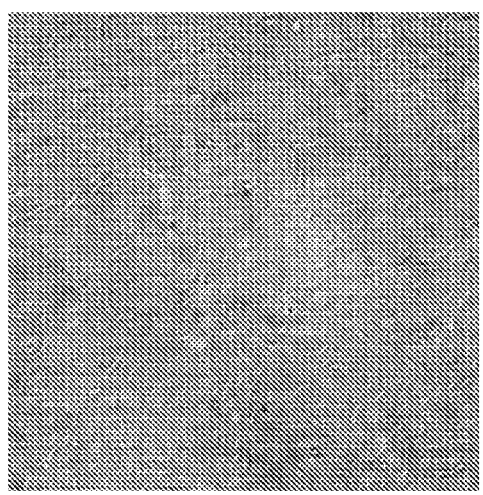
Figure 31A — Plate 3
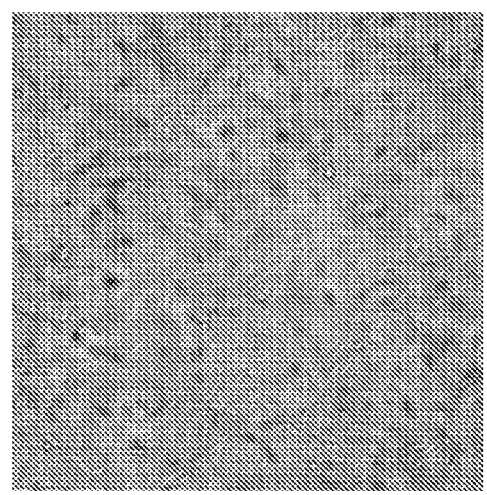
Figure 31B — Plate 5

Figure 32A
Process CTL
Xpansion CTL
Figure 32B
Untreated Control
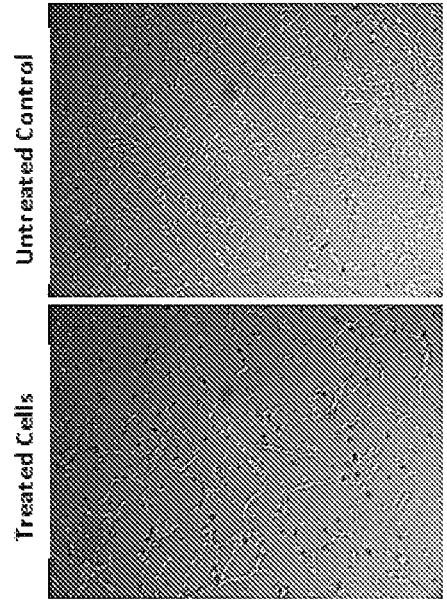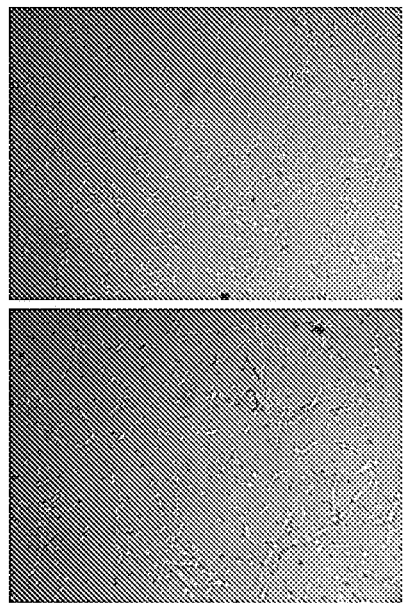
Treated Cells
Figure 32C
Figure 32D
Xpansion 10
Plate 3
Plate 5
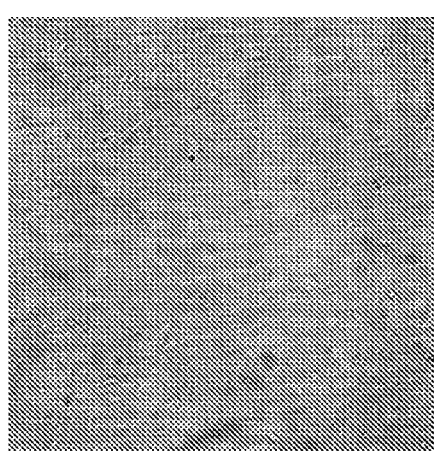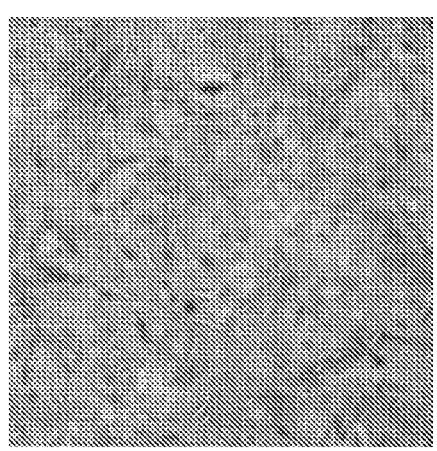
Figure 33A
Figure 33B

| One file | % CD105 | % CD73 | % CD90 | % CD44 | % Negative markers |
|---|---|---|---|---|---|
| P12 | 99,32 | 99,85 | 99,55 | 99,77 | 0,93 |
| P13 | 98,75 | 99,71 | 99,67 | 99,70 | 0,73 |
| P14 | 96,77 | 98,60 | 99,50 | 99,64 | 0,58 |
| P16_AdV infection | 89,77 | 99,41 | 99,22 | 99,91 | 0,44 |

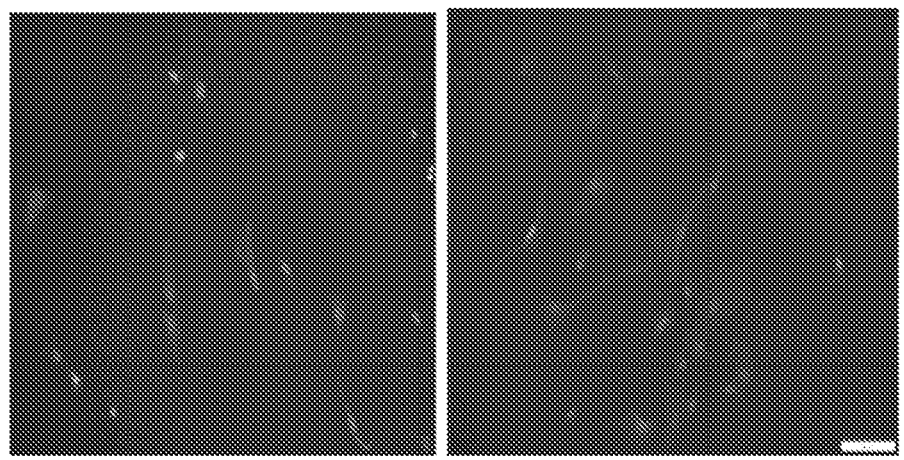
Figure 38E
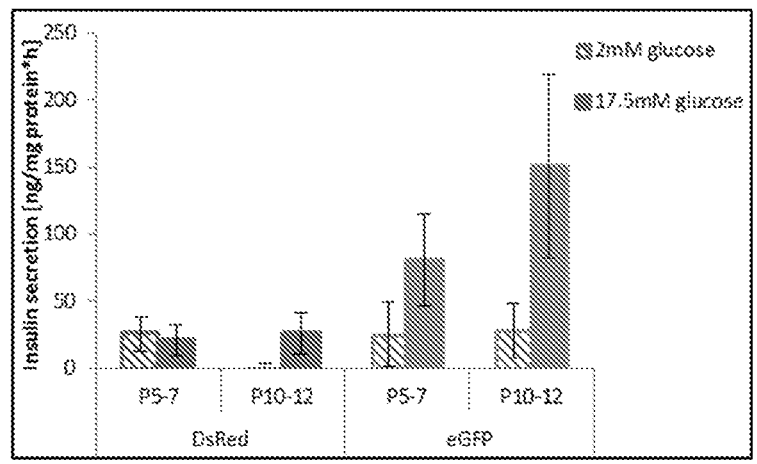
Figure 38F
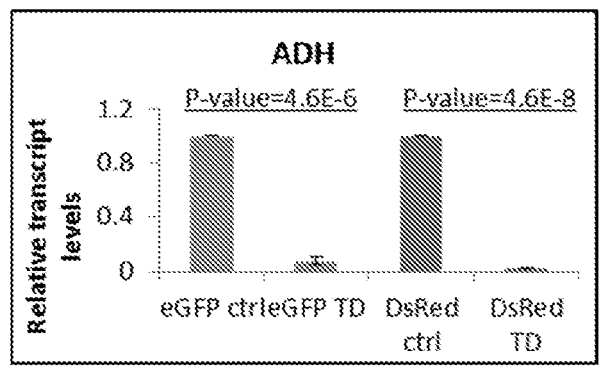 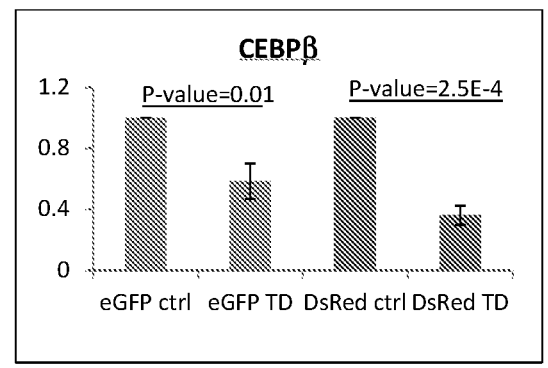
Figure 39A
Figure 39B

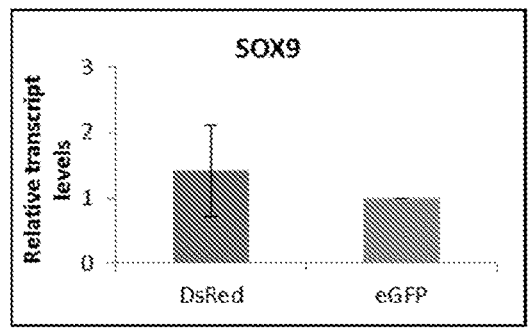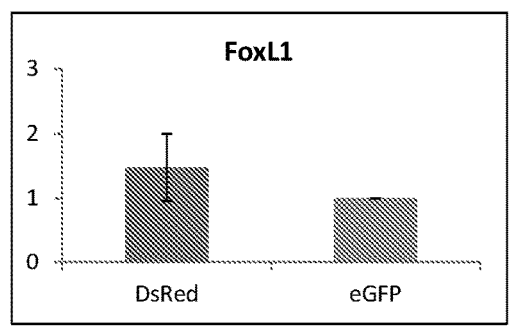
Figure 39C
Figure 39D
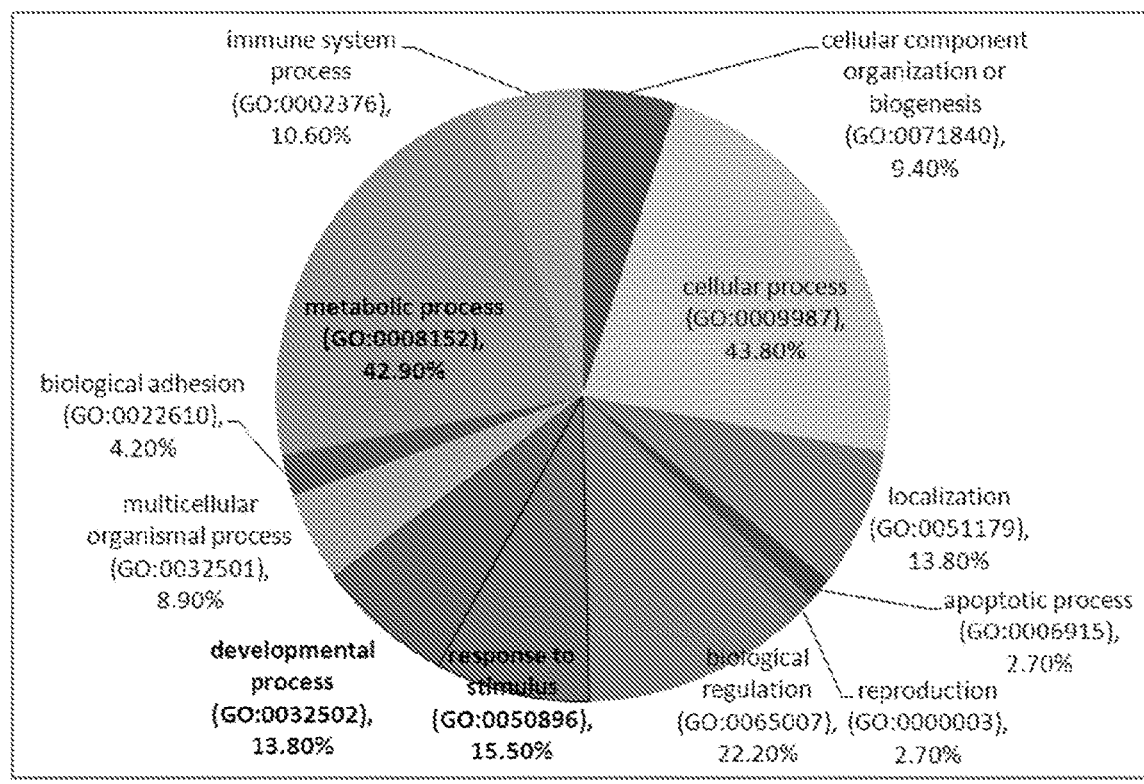
Figure 40A

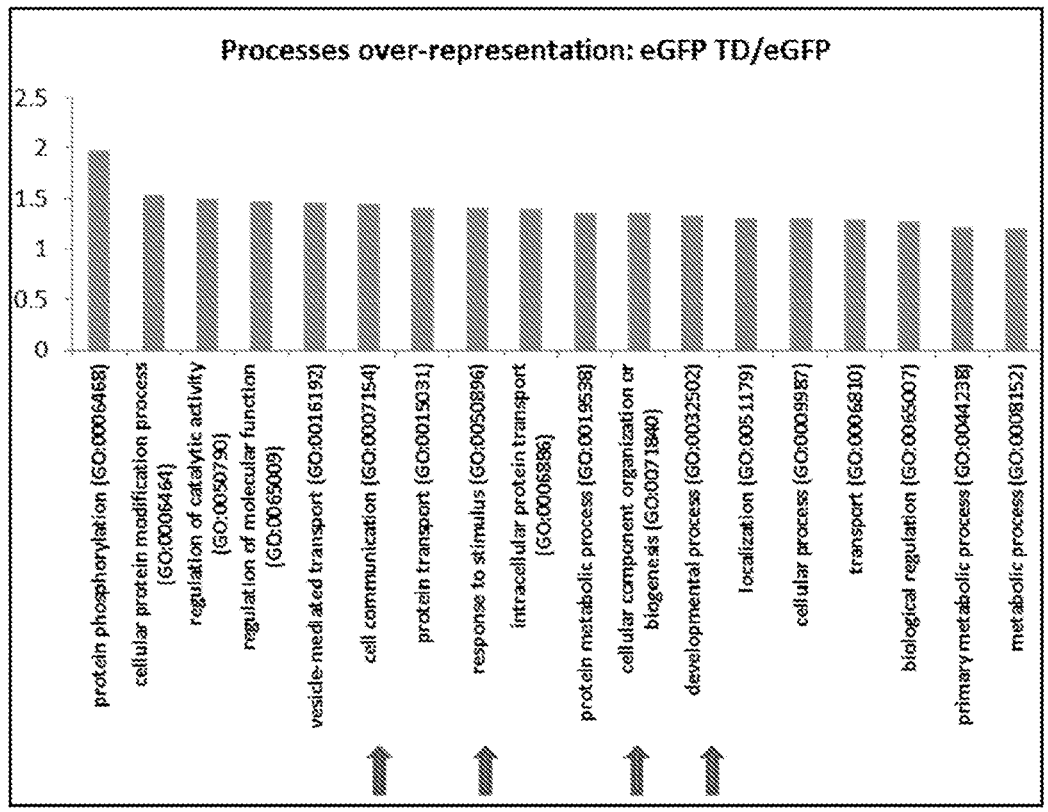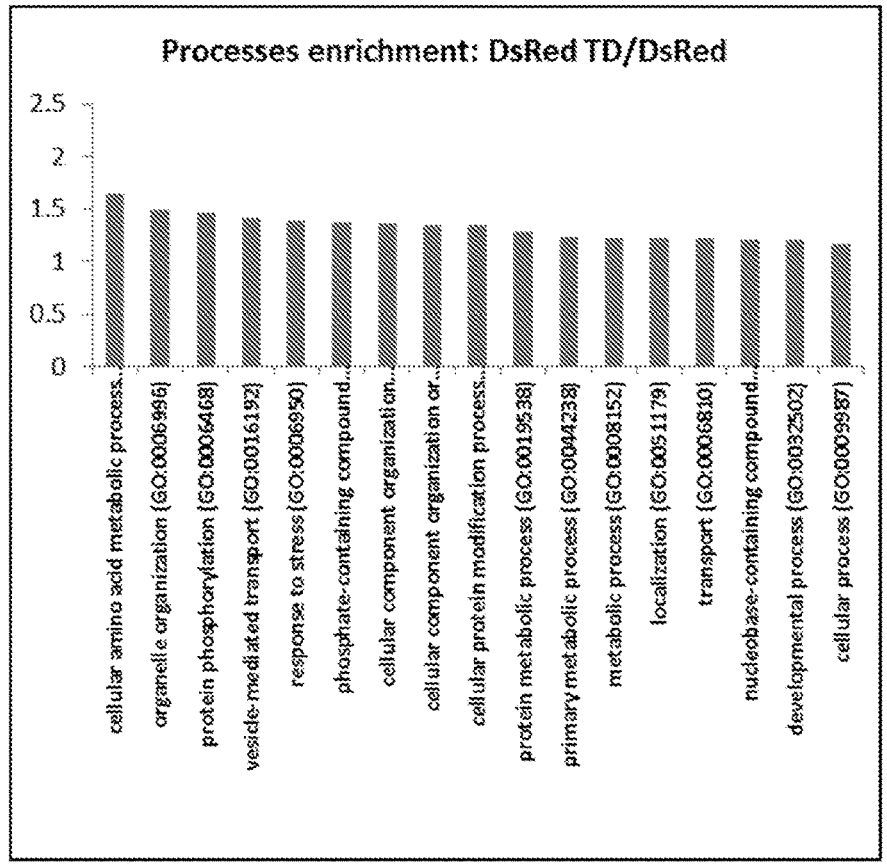
Figure 40B

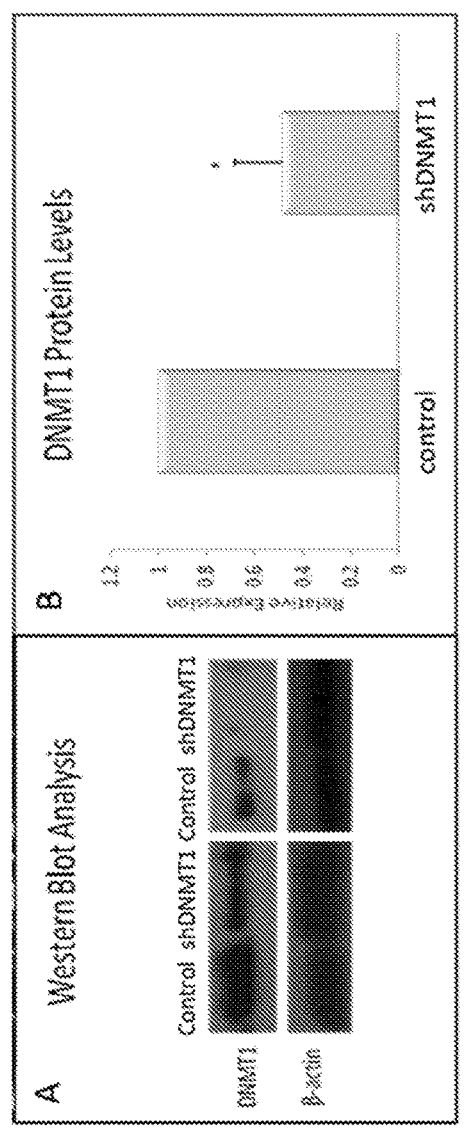
Figure 47A
Figure 47B
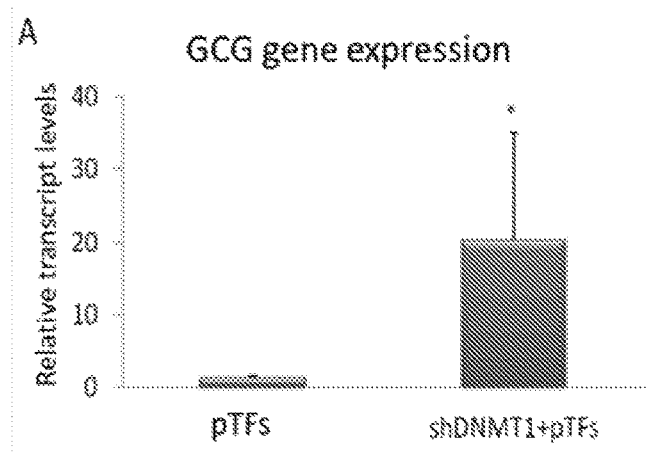
Figure 48A

TRANSDIFFERENTIATED CELL POPULATIONS AND METHODS OF USE THEREOF

CROSS-REFERENCE TO RELATED APPLICATION

This application is a National Phase Application of PCT International Application No. PCT/IL2018/050496, International Filing Date May 8, 2018, claiming the benefit of U.S. Provisional Application No. 62/610,300, filed Dec. 26, 2017 and U.S. Provisional Application No. 62/502,796, filed May 8, 2017, which are hereby incorporated by reference.

FIELD OF THE DISCLOSURE

The invention relates to methods for manufacturing transdifferentiated populations of non-pancreatic human insulin producing cells, and methods for enriching populations of non-pancreatic β-cells for cells comprising an enriched capacity for transcription factor-induced transdifferentiation into a pancreatic β-cell phenotype and function.

BACKGROUND

Ectopic expression of pancreatic transcription factors (pTFs) induces direct reprogramming of adult liver cells into pancreatic-like, glucose-regulated insulin producing cells (IPCs). In primary cultures of human liver cells this process involves two distinct steps: suppression of the hepatic repertoire in all the pTFs expressing cells, and the activation of the pancreatic phenotype and function only in <15% of the cells. In-vivo, in mice, transdifferentiation into pancreatic-like cells is generally restricted to a small group of cells located around the central veins, although additional populations of liver cells were suggested to undergo the process.

Liver cells display a remarkable phenomenon of functional heterogeneity, or metabolic zonation. Heterogeneity of liver cells' function is related to the cells' proximity to the central and portal veins (pericentral and periportal cells, respectively). A major role for the canonical wnt/β-catenin signaling pathway has been demonstrated in mediating this functional heterogeneity. In the normal adult liver, wnt/β-catenin signaling is primarily active in hepatocytes in the pericentral region. In mouse and rat, wnt signaling is instrumental in liver repopulation following injury or partial hepatectomy. Similarly, wnt signaling is responsible for maintenance of a self-renewing niche of pericentral liver cells that can differentiate into- and replace about 40% of the hepatocytes along the liver lobule during homeostatic renewal in mice.

Wnt family glycoproteins signal at the cell surface via at least two receptors: Frizzled (FZD) and lipoprotein-related protein receptor (LRP). A key transducer of canonical wnt signaling is β-catenin. Following binding of WNT proteins to their receptors, β-catenin translocates into the nucleus, where it forms a complex with DNA binding transcription factors to activate target genes.

Cells' differentiation fate can be reprogrammed by overexpression of selected transcription factors, usually a subset of those required for normal development of the relevant cell type. Recent examples include the conversion of fibroblasts to cardiomyocytes, neurons, and hepatocytes. Up to date, the limited efficiency of direct reprogramming is a major obstacle to using autologous organs in regenerative medicine.

As a first step it is clear that there remains a critical need to establish methods for manufacturing, detecting, and enriching transdifferentiated non-pancreatic cells insulin producing cells having pancreatic phenotype and function. There is a need for enriching transdifferentiated non-pancreatic cells having β-cell phenotype and function prior to their use in the treatment of diabetes. The methods disclosed herein comprise manufacturing, detecting and enriching populations of transdifferentiated adult human liver cells to produce an enriched population of non-β pancreatic cells that secrete insulin and have a β-cell phenotype and function. These enriched populations of transdifferentiated cells may be used in transplant therapies, obviating the need for the numerous self-injections of insulin, now required for the treatment of diabetes.

SUMMARY OF DISCLOSURE

In one aspect, provided herein is a method of manufacturing a transdifferentiated population of human non-pancreatic β-like insulin producing cells, the method comprising the steps of: obtaining non-pancreatic human tissue; processing said tissue to recover primary human cells; propagating and expanding said human cells; pre-incubating said expanded cells with a Wnt-pathway agonist; transdifferentiating said pre-incubated cells; and harvesting said transdifferentiated cells; and wherein said method comprises a step of adding a soluble factor either prior to or concurrent with the step of transdifferentiating said pre-incubated cells, thereby manufacturing said population of transdifferentiated human non-β cells insulin producing cells.

In a related aspect, said soluble factor comprises a histone deacetylase inhibitor (HDACi), an inhibitor of DNA methylation, a TGF-β inhibitor, a Rho kinase inhibitor (ROCK), a thyroid hormone, a TGF-β/Activin inhibitor, or a reagent that converts α-pancreatic cells to β-pancreatic cells, or any combination thereof. In a related aspect, the HDACi comprises suberanilohydroxamic acid (SAHA), sodium butyrate, romidepsin, chidamide, panobinostat, or belinostat, or any combination thereof. In a related aspect, the inhibitor of DNA methylation comprises 5-Aza-2-deoxycitidine (5-AZA). In a related aspect, the TGF-β inhibitor comprises SB431542 (SB). In a related aspect, the Rho kinase inhibitor comprises Y27632 (Y2). In a related aspect, the thyroid hormone comprises T3. In a related aspect, the TGF-β/Activin inhibitor comprises Alk5i II. In a related aspect. In a related aspect, the reagent that converts α-pancreatic cells to β-pancreatic cells comprises GABA.

In a related aspect, the HDACi, the inhibitor of DNA methylation, the TGF-β inhibitor, and the Rho kinase inhibitor (ROCK) are added prior to the step of transdifferentiating said expanded cells. In a related aspect, the thyroid hormone, the TGF-β/Activin inhibitor, the pancreatic transcription factor, and the reagent that converts α-pancreatic cells to β-pancreatic cells comprises GABA are added concurrent with the step of transdifferentiating said expanded cells.

In a related aspect, transdifferentiating further comprises: (a) contacting said expanded cells with a PDX-1 polypeptide or a nucleic acid encoding a PDX-1 polypeptide under conditions to allow uptake of said polypeptide or nucleic acid, and contacting the cells with a NeuroD1 polypeptide, or a nucleic acid encoding a NeuroD1 polypeptide under conditions to allow uptake of said polypeptide or nucleic acid at a first timepoint;
(b) contacting the cells of step with a MafA polypeptide or a nucleic acid encoding a MafA polypeptide under conditions to allow uptake of said polypeptide or nucleic acid at a second timepoint. In a related aspect, the second timepoint is at least 48 or 72 hours after the first timepoint.

In a related aspect, transdifferentiating step (d) further comprises contacting the expanded cells with a Wnt-pathway agonist. In a related aspect, a Wnt-pathway agonist comprises Lithium (Li), Wnt9, Wnt3A, or a GSK3b antagonist.

In a related aspect, provided herein is a method of manufacturing a population of human non-pancreatic β-cells comprising an enriched capacity for transcription factor induced transdifferentiation into a pancreatic β-cell phenotype and function, said method comprising the steps of (a) obtaining a population of primary human non-pancreatic β-cells; (b) propagating and expanding said human cells; (c) pre-incubating the expanded cells of step (b) with a Wnt-pathway agonist; (d) incubating said cells, said incubating comprising adding an at least one soluble factor to said cell population; and (e) collecting said cells; thereby manufacturing said population of cells comprising an enriched capacity for transcription factor induced transdifferentiation into a pancreatic β-cell phenotype and function.

In a related aspect, said soluble factor comprises a histone deacetylase inhibitor (HDACi), an inhibitor of DNA methylation, a TGF-β inhibitor, a Rho kinase inhibitor (ROCK), a thyroid hormone, a TGF-β/Activin inhibitor, or a reagent that converts α-pancreatic cells to β-pancreatic cells, or any combination thereof. In a related aspect, the HDACi comprises suberanilohydroxamic acid (SAHA), sodium butyrate, romidepsin, chidamide, panobinostat, or belinostat, or any combination thereof. In a related aspect, the inhibitor of DNA methylation comprises 5-Aza-2-deoxycitidine (5-AZA). In a related aspect, the TGF-β inhibitor comprises SB431542 (SB). In a related aspect, the Rho kinase inhibitor comprises Y27632 (Y2). In a related aspect, the thyroid hormone comprises T3. In a related aspect, the TGF-β/Activin inhibitor comprises Alk5i II. In a related aspect, the reagent that converts α-pancreatic cells to β-pancreatic cells comprises GABA.

In a related aspect, provided herein is a method for enriching a population of non-pancreatic β-cells for cells comprising an enriched capacity for transcription factor induced transdifferentiation into a pancreatic β-cell phenotype and function, said method comprising the steps of: (a) obtaining a population of primary human non-pancreatic β-cells; (b) identifying cells within the population of (a) having increased expression of at least one gene of the group comprising a solute carrier family 2, facilitated glucose transporter member 3 (GLUT-3); a vesicle-associated membrane protein 2 (VAMP2); a syntaxin-1A (Stx1a); a tyrosine-protein kinase transmembrane receptor ROR2 (ROR2); Frizzled-4 (FZD4); a pituitary homeobox 2 (PITX2); and a Proto-oncogene Wnt-1 (WNT1); or any combination thereof, wherein said increased expression is compared within the non-pancreatic β-cell population; and (c) selecting said cells having increased expression of at least one gene recited in (b), wherein said selected cells comprise a population of cells enriched for the capacity for transcription factor induced transdifferentiation to a pancreatic β-cell like phenotype and function.

In a related aspect, said identifying further comprises identifying cells with increased expression of at least one gene selected from the group comprising a vesicle-associated membrane protein 4 (VAMP4); a thrombospondin-1; a discoidin, CUB and LCCL domain-containing protein 2 (THBS1); an integrin alpha-6 (ITGA6); a homer protein homolog 1 (HOMER1); a lysosome-associated membrane glycoprotein 3 (LAMP3); a bone morphogenetic protein receptor type-2(BMPR2); or any combination thereof. In another related aspect, said identifying further comprises identifying cells with decreased expression of at least one gene selected from the group comprising a multidrug resistance protein 1 (ABCB1), an integrin alpha-4 (ITGA4), and a phosphatidylcholine translocator ABCB4 ABCB4); or any combination thereof.

In a related aspect, said non-pancreatic β-cells are adult human liver cells.

In a related aspect, said identifying comprises incubating cells with a labeled antibody that binds the protein product of said at least one gene. In another related aspect, said selecting comprises selecting cells bound to said labeled antibody. In another related aspect, said identifying comprises incubating cells with a labeled ligand that binds the protein product of said at least one gene. In another related aspect, said selecting comprises selecting cells bound to said labeled ligand.

In a related aspect, wherein following transcription factor induced transdifferentiation of said pre-selected cells, said transdifferentiated selected cell population expresses increased endogenous Nkx6.1 compared with a control transdifferentiated non-pre-selected population of cells. In another related aspect, wherein following transcription factor induced transdifferentiation of said selected cells, said transdifferentiated selected cell population comprises increased insulin content compared with a control transdifferentiated non-selected population of cells. In another related aspect, wherein following transcription factor induced transdifferentiation of said selected cells, said transdifferentiated selected cell population comprises increased glucagon content compared with a control transdifferentiated non-selected population of cells. In another related aspect, wherein following transcription factor induced transdifferentiation of said selected cells, said transdifferentiated selected cell population comprises increased glucose-regulated insulin secretion and C-peptide secretion compared with a control transdifferentiated non-selected population of cells.

BRIEF DESCRIPTION OF THE DRAWINGS

The subject matter regarded as transdifferentiated non-beta pancreatic cells having the phenotype and function of pancreatic cells, methods of producing, detecting, and selecting the same is particularly pointed out and distinctly claimed in the concluding portion of the specification. The transdifferentiated non-beta pancreatic cells having the phenotype and function of pancreatic cells, however, both as to organization and method of operation, together with objects, features, and advantages thereof, may best be understood by reference to the following detailed description when read with the accompanying drawings in which:

FIGS. 1A-1D show that ectopic co-expression of pancreatic transcription factors (pTFs) PDX-1, Pax4, and MafA in human liver cells in vitro promotes (pro)insulin secretion, compared to that induced by each of the pTFs alone. (FIG. 1A) Immunofluorescence (IF) staining shows expression of pTFs: PDX-1 (left panel), Pax4 (middle left panel), MafA (middle right panel) and a merge of the 3 pTFs (right panel), with arrows indicating cells expressing all three pTFs. (FIG. 1B) Luciferase assay insulin promoter activation by the indicated pTFs; 3-gal was used as a control. Results are expressed as Relative Light Unit (RLU)/mg protein. Each data point represents the mean±SE of at least two independent experiments, *p<0.05, **p<0.01 in comparison to control virus treated cells, (n>4). (FIG. 1C) Immunofluorescence staining shows insulin-positive cells after ectopic expression of the indicated pTFs. Original magnification ×20. Quantification of IF staining in table (right). The percent of insulin-positive cells was calculated by counting at least 500 positive cells from at least two independent experiments. (FIG. 1D) Insulin secretion after incubation with the indicated concentrations of glucose was detected by radioimmunoassay. *p<0.05, n>12 in five independent experiments. The significance represents the differences between triple infection and all other treatments.

FIGS. 2A-2E show the effects of concerted and sequential expression of pTFs PDX-1, Pax4, and MafA on pancreatic β-cell maturation. (FIG. 2A) A schematic demonstrating the order of infection of pTFs (treatments B-E) or control virus (Ad-CMV-β-gal, treatment A). (FIG. 2B) Immunofluorescence staining for insulin: treatment B (left panel), treatment C (middle panel), treatment D (right panel). Original magnification is at ×20. Quantification of staining (percent) is indicated below each image. The percent of insulin positive cells were calculated by counting at least 1000 positive cells from at least two independent experiments. (FIG. 2C) Insulin and (FIG. 2D) C-peptide secretion after incubation with the indicated concentration of glucose was measured by radioimmunoassay. Infection treatments are indicated on the X-axis and explained in FIG. 2A. *p<0.05, **p<0.01, compared to control virus treated cells; n>12 in 5 independent experiments. (FIG. 2E) Expression levels of the indicated endogenous pancreas-specific transcription factors after the indicated treatments (X-axis) were measured by RT-PCR. CT values are normalized to β-actin gene expression within the same cDNA sample. Results are presented as relative levels of the mean+SE of the relative expression versus control virus treated cells, *p<0.05 n>8 in 4 independent experiments. The arrow points the specific decrease in Isl-1 expression level under treatment C.

(FIG. 3A) Insulin promoter activation was measured by luciferase assay after the indicated infection treatments. Results are expressed as Relative Light Unit (RLU)/mg protein. Each data point represents the mean±SE of at least two independent experiments, *P<0.05, **P<0.01, compared to control virus treated cells, (n>4). (FIG. 3B) Analysis of glucose transporter 2 (GLUT2) expression levels by RT-PCR was performed after the indicated infection treatments. CT values are normalized to β-actin gene expression within the same cDNA sample. Results are presented as relative levels of the mean+SE compared to control virus treated cells. *P<0.05, compared to control virus treated cells n>8 in 4 independent experiments. (FIG. 3C) Expression levels of prohormone convertase 2 (PC2; PCSK2) were determined by RT-PCR after the indicated infection treatments. CT values are normalized to β-actin gene expression within the same cDNA sample. Results are presented as relative levels of the mean+SE compared to control virus treated cells **P<0.01, n>8 in 4 independent experiments.

FIGS. 4A-4F shows the individual role of pTFs in promoting the differentiation of cells to produce glucagon (α-cells) and somatostatin (δ-cells) using hierarchical order of infection (treatment C) and exclusion of each pTF. Expression levels of pancreatic hormones glucagon (GCG) (FIGS. 4A and 4B) and somatostatin (SST) (FIGS. 4A and 4D) were determined by RT-PCR after the indicated infection treatments. (FIG. 4C) Expression levels of cell-specific transcription factors ARX and BRAIN4 were also measured by RT-PCR for the indicated infection treatments. (FIG. 4E) Expression levels of somatostatin (SST) were determined by RT-PCR after additional infection with Isl1 (100 MOI). CT values (for FIGS. 4A, 4B, 4C, and 4D) are normalized to β-actin gene expression within the same cDNA sample. Results are presented as relative levels of the mean+SE compared to control virus treated cells (FIG. 4A) or to "hierarchy sequential infection" treated liver cells (FIGS. 4B-4E). *P<0.05, **P<0.1, n>6 in 3 independent experiments. (FIG. 4F) Immunofluorescence staining for somatostatin after treatment C infection (left panel), and after treatment C infection with additional Isl1 infection (right panel). Original magnification ×20. (FIG. 4F) Immunofluorescence staining for somatostatin and insulin showing that the sequential administration of transcription factors in a direct hierarchical manner results in increased maturation of the transdifferentiated cells along the beta-like-pancreatic lineage.

FIG. 5 shows a bar graph demonstrating transdifferentiation efficiency, indicating hierarchical sequential order of infection (treatment C) is most efficient. Insulin promoter activation was measured by luciferase assay after the indicated infection treatments. Results are expressed as Relative Light Unit (RLU)/mg protein. Each data point represents the mean±SE of at least two independent experiments, *P<0.05, **P<0.01, compared to control virus treated cells, (n>4).

FIGS. 6A-6C shows three graphs showing the effects of Isl1 expression on β-cell maturation of transdifferentiated liver cells after infection by "hierarchical" sequential order (treatment C). (FIG. 6A) Expression levels of insulin were measured by RT-PCR. CT values are normalized to β-actin gene expression within the same cDNA sample. Results are presented as relative levels of the mean+SE compared to control virus treated cells. *P<0.05, n>6 in 3 independent experiments. (FIG. 6B) Insulin secretion was measured by radioimmunoassay. **P<0.01, n>6 and compared to the direct "hierarchical" sequential infection order (C), n>6 in 3 independent experiments. (FIG. 6C) Expression level of glucose transporter 2 (GLUT2) was measured by RT-PCR.

(FIGS. 8C and 8D) analysis of GS expression in human (FIG. 8C) and mice (FIG. 8D) livers indicating the expression of GS at the 1-2 cell layers adjacent to the central veins. Original magnification ×400.

(FIG. 10A) A schematic presentation of the lentivirus vectors. (FIG. 10B) Adult human liver cells at passages 3-10 were infected with the dual lentivirus system. Liver cells were imaged 10 days after infection for DsRed2 (red) or eGFP (green) fluorescence. (FIG. 10C) The cells were sorted by a fluorescence-activated cell sorter (FACS; Aria cell sorter; Becton Dickinson, San Jose, Calif.) with a fluorescein isothiocyanate filter (530/30 nm) for eGFP and a Pe-Texas Red filter (610/20 nm) for DsRed2. (FIGS. 10D and 10E). The separated cells were cultured separately for several passages (original magnification ×10).

FIGS. 12A-12F shows that the GSRE targets subpopulation of human liver cells in vitro. (FIGS. 12A and 12D) Schematic presentations of Ad-GSRE-TK-PDX-1 or GFP recombinant adenoviruses. Liver cells were infected with Ad-GSRE-TK-Pdx-1 (FIG. 12C) or with Ad-CMV-Pdx-1 (FIG. 12B). Immunofluorescent analysis of PDX-1 expression indicated that 13±2% of the human liver cells infected by Ad-GSRE-TK-Pdx-1 (FIG. 12C) while 70±12% of Ad-CMV-Pdx-1-treated cells (FIG. 12B) expressed the ectopic nuclear factor (rabbit anti-Pdx-1, generous gift from C. Wright, pink; FIGS. 12B and 12C, respectively). Similar results were obtained using Ad-GSRE-TK-eGFP; ~15% of the cells were positive to eGFP (FIGS. 12E and 12F). Ad-CMV-eGFP infection resulted in about 75-80% eGFP positive cells within 3-4 days (data not presented).

FIGS. 13A-13C show that the GSRE targets transdifferentiation-prone cells. Liver cells were infected with Ad-GSRE-TK-Pdx-1 (FIG. 13B) or with Ad-CMV-Pdx-1 (FIG. 13A) for 5 days. (FIGS. 13A and 13B), immunofluorescent analysis of co-staining of insulin (Guinea pig anti-insulin, Dako, green) and (Pdx-1 rabbit anti-Pdx-1, generous gift from C. Wright, pink). (FIG. 13C) Statistical analysis of activation of insulin in the treated cells; Ad-GSRE-TK-Pdx-1 activated insulin production in 50%, whereas Ad-CMV-Pdx-1 only in 5% of the Pdx-1-positive cells. Blue-DAPI, nuclear staining; original magnification ×20.

(FIG. 15A) at the molecular level, insulin and glucagon gene expression was studied by Quantitative real-time PCR compared to the control-treated cells. Cultured pancreatic human islet cells (Passage 3) were used as a positive control. (FIGS. 15B and 15C) At the functional level, glucose-regulated insulin secretion was analyzed by static incubations at low glucose concentrations followed by high glucose concentrations (2 mM and 17.5 mM glucose in Krebs-Ringer buffer (KRB), respectively). Insulin (FIG. 15B) and C-peptide (FIG. 15C) secretion were measured using the human insulin radioimmunoassay kit (DPC; n≥8 from 3 different experiments) or human C-peptide radioimmunoassay kit (Linco n≥8 from 3 different experiments. *P<0.01 compared to the DsRed2+ cells, using Student's t-test analysis.

(FIG. 17A) Transdifferentiated eGFP+ (eGFP) cells secrete more processed human insulin (C-peptide) into the blood stream than transdifferentiated DsRed+ (DsRed), 2-8 weeks after implantation. (FIG. 17B) Explants excised from mice 2 weeks after implantation suggest enhanced production of insulin (green) and glucagon (red) in eGFP cells compared to DsRed cells.

FIGS. 21A-21C show eGFP+ cells express lower levels of APC and higher levels of active β-catenin than DsRed2+ cells. (FIG. 21A) APC and DKK1 expression is markedly increased in DsRed2+ cells. This may further suggest that these cells express higher levels of Wnt signaling pathway repressors compared with the eGFP+ cells. n≥6 from 2 different experiments *p<0.01 in DsRed2+ compared to eGFP+ cells, using Student's t-test analysis. (FIG. 21B) Western blot analysis using a specific antibody for activated β-catenin (anti-ABC clone 8E7, Millipore, 1:2000) in eGFP and DsRed2 positive cell extracts. β-actin (SC-1616, Santa Cruz, 1:1000) was used as a normalizing protein. (FIG. 21C) Quantification of the β-catenin protein levels was performed using ImageJ 1.29× software. Activated β-actin (SC-1616, Santa Cruz, 1:1000) was used as a normalizing protein.

FIGS. 22A-22C show insulin secretion measured on day 6 of the experiment following incubation with 2 mM glucose (low concentration) or 17.5 mM glucose (high concentration). Results are presented as Nano grams insulin per million cells per hour (ng INS/$10^6$/hr) for primary liver cells obtained from human donors (FIG. 22A Muhammad, FIG. 22B Pedro, and FIG. 22C Leon).

FIGS. 30A-30D show micrographs of cell densities at day 6 at the time of second infection, including an image of untreated control cells.

FIGS. 31A-31B show micrographs of cell densities at day 6 at the time of second infection from plates 3 (FIG. 31A) and 5 (FIG. 31B) of the Xpansion-10 multi-system bioreactor.

FIGS. 32A-32D show micrographs of cell densities at day 8 at the time of the final harvest, including an image of untreated control cells.

FIGS. 33A-33B show micrographs of cell densities at day 8 at the time of final harvest from plates 3 (FIG. 33A) and 5 (FIG. 33B) of the Xpansion-10 multi-system bioreactor.

FIG. 34A shows a representative FACS plot of several mesenchymal stem cells (MSC) markers, gated on live cells. Markers shown include CD90, CD73, CD105, and CD44. The Negative cocktail includes hematopoietic markers. FIG. 34B shows the frequency of the MSC markers at different cell passages, P12 ($12^{th}$ passage), P13 ($13^{th}$ passage), P14 ($14^{th}$ passage), and in infected cells (P16_AdV infection).

(FIG. 35A) Insulin secretion was measured by ELISA, in response to 17.5 mM glucose stimulation. (FIGS. 35B and 35C). Expression levels of pancreatic genes were measured by Real-Time PCR, and normalized to actin. Results are representative of two donors.

FIGS. 38A-38F show liver cells originating from the pericentral population (eGFP) transdifferentiate into IPCs more efficiently than non-pericentral (DsRed) cells. (FIGS. 38A-38D) eGFP cells exhibit higher reprogramming efficiency, as measured by increase in endocrine pancreatic-lineage gene expression (FIGS. 38A-38C) insulin production (FIG. 38D) and glucose regulated secretion (FIG. 38F), compared to DsRed+ cells derived from the same donor. Representative staining of two independent experiments are presented (FIG. 38E), the collated average % of insulin positive cells in eGFP+ cells separated from 7 different donors is 64.1±7.9%, compared to about 5-14% in the unseparated cells (23). Transcript levels of indicated genes are presented as average and SE of increase above control-virus treated cells, normalized to β-actin levels. PDX1 transcript is the endogenous human PDX1 expression, identified with primers that do not bind the ectopic rat PDX1. N=4-8 independent repeats. * P-value<0.05. (FIG. 38F) Increased reprogramming efficiency of eGFP population is heritable. Efficiency of reprogramming was measured by glucose-regulated insulin secretion at the indicated passage numbers. Results are average and SE of 3-5 independent experiments.

FIGS. 39A-39D show Hepatic dedifferentiation and hepatic progenitor genes expression are equivalent in pre-disposed and recalcitrant cells. (FIGS. 39A-39B) Hepatic genes expression following TD (FIGS. 39C-39D) Hepatic progenitor cells genes. Results are average and SE of specified transcripts normalized to beta-actin in four different donors.

FIGS. 40A-40F show distinct pathways are altered in eGFP in DsRed cells upon reprogramming. Global gene expression analysis was performed in eGFP and DsRed populations from three donors, prior- and post-pTFs treatment. Pathways and biological processes enrichment were analyzed by Panther tool (http://pantherdb.org/). (FIG. 40A) Differentially expressed genes in untreated eGFP and DsRed cells presented by biological processes. (FIG. 40B) Statistical over-representation of biological processes in genes that were altered upon reprogramming of eGFP (left, green) or DsRed (right, red) cells. The graphs represent the ratio of observed number of genes in each process above the number of genes that would be expected in a random list of the same size. (FIGS. 40C-40F) Alterations to levels of pancreas differentiation-associated wnt genes upon pTFs treatment are unique to eGFP cells. N=3-6. * P-value<0.05;  P-value<0.005; * P-value<0.0005; N.S: not significant.

(FIG. 41A) Efficient reprogramming of liver to pancreas relies on active WNT signaling. WNT signaling was activated by Wnt3A, or, alternatively, blocked by DKK, concomitantly to ectopic pTFs expression (TD) in human liver cultures. Glucose stimulated Insulin secretion was measured five days later. Results are average and standard error (SE) of 3-6 repeats from 3 different donors. * P-value<0.05;  P-value<0.005; * P-value<0.0005. (FIGS. 41B-41D) WNT signaling was induced in eGFP cells by addition of lithium (Li) (FIG. 41B-41C) or a recombinant adenovirus that encodes the expression of constitutively active β-catenin (S37A) (FIG. 41D). Efficiency of reprogramming was measured by the activation of pancreatic genes expression and relative insulin secretion induced by high glucose concentrations (17.5 mM). (FIGS. 41E-41G) activation of WNT signaling in DsRed cells (transdifferentiation-resistant cells) by either Li (FIGS. 41E-41F) or S37A (FIG. 41G) does not increase reprogramming efficiency. Transcript levels of indicated genes are presented as average and SE of increase above cells treated with pTFs alone, normalized to β-actin levels. N=3-4 independent repeats in different donors. * P-value<0.05; ** P-value<0.005

(FIG. 43A) Schematic representation of the experiments setup. (FIG. 43B) Pancreatic genes' expression levels following reprogramming in the presence of S37A (10MOI) preceded by DKK treatment. N=3-4 different donors. Transcript levels are presented as average and SE of increase above cells treated with pTFs only, normalized to β-actin levels. * P-value<0.05; ** P-value<0.005.

FIGS. 47A and 47B show the Effects of shDNMT1 on Protein Levels. DNMT1 knock-down (DNMT1 KD) was performed using sh-DNMT1, which reduced DNMT1 expression and protein production in treated cells (TD cells treated with pTFs and sh DNMT1 lentivirus) compared to control cells (TD cells that were only treated with pTFs). FIG. 47A shows a Western blot analysis of two representative cell lines, indicating reduced DNMT1 protein levels two weeks post infection. The intensities of the protein bands were quantified (using ImageJ Software), and FIG. 47B shows protein level quantification of DNMT1 enzyme two weeks post lentiviral infection. N=4, p<0.0006.

FIGS. 48A-48D show DNMT1 knock-down (KD) Effect on Expression of Genes in the Transdifferentiated (TD) Cells. DNMT1 knock down (DNMT1 KD) was performed using sh-DNMT1 (Example 24) and then cells were subjected to the transdifferentiation protocol alongside control cells that were treated with pTFs alone. RNA levels of four genes were measured in DNMT1 KD and control cells: (FIG. 48A) Glucagon (GCG), (FIG. 48B) Nkx6.1, (FIG. 48C) PC1/3, and (FIG. 48D) SULTIC4. Higher expression levels of these genes were observed in the DNMT KD cells compared to the control cells treated with pTFs alone, for all the tested genes. N=4, P<0.05. shDNMT1—short hairpin DNMT1, pTFs—pancreatic transcription factors. As can be seen in FIGS. 48A-48D, the expression levels of the pancreatic genes GCG (FIG. 48A), Nkx6.1 (FIG. 48B), and PC1/3 (FIG. 48C), as well as SULTIC4 (FIG. 48D) remained higher in the DNMT1 KD cells infected with pTFs, compared to the control group that was infected with pTFs alone. These results indicate that while DNMT1 expression remains low, the new acquired pancreatic phenotype stably persists even 28 days post infection.

Figure 3A:
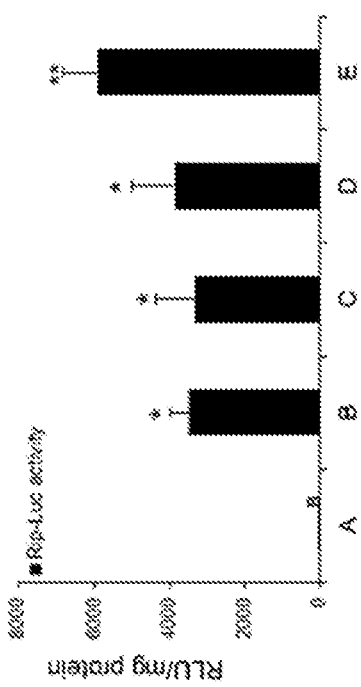
FIGS. 3A-3C show three graphs demonstrating transdifferentiation efficiency, indicating hierarchical sequential order of infection (treatment C) is most efficient.

It will be appreciated that for simplicity and clarity of illustration, elements shown in the figures have not necessarily been drawn to scale. For example, the dimensions of some of the elements may be exaggerated relative to other

DETAILED DESCRIPTION

In the following detailed description, numerous specific details are set forth in order to provide a thorough understanding of methods of manufacturing a transdifferentiated population of non-pancreatic human insulin producing cells, and methods of detecting and enriching a population of cells for increased capacity for transcription factor transdifferentiation to a β-cell line phenotype and function. In other instances, well-known methods, procedures, and components have not been described in detail so as not to obscure the methods for manufacturing a transdifferentiated population of non-pancreatic human insulin producing cells, and methods for detecting and enriching a population of human insulin producing non-pancreatic cells having pancreatic cell phenotype and functions.

Transcription factors (TFs) have been shown to induce transdifferentiation in numerous cell lineages. A skilled artisan would appreciate that the term "transdifferentiation" may encompass the process by which a first cell type loses identifying characteristics and changes its phenotype to that of a second cell type without going through a stage in which the cells have embryonic characteristics. In some embodiments, the first and second cells are from different tissues or cell lineages. In one embodiment, transdifferentiation involves converting a mature or differentiated cell to a different mature or differentiated cell. Specifically, lineage-specific transcription factors (TFs) have been suggested to display instructive roles in converting adult cells to endocrine pancreatic cells, neurons, hematopoietic cells and cardiomyocyte lineages, suggesting that transdifferentiation processes occur in a wide spectrum of milieus. In all transdifferentiation protocols, the ectopic TFs serve as a short-term trigger to a potential wide, functional and irreversible developmental process. Numerous studies suggested that ectopic expression of individual TFs activate a desired alternate repertoire and function, in a process involved with the activation of additional relevant otherwise silent TFs. However, the time course, the relative levels and the hierarchy, or order, of the induced TFs, remains unknown. A skilled artisan would appreciate that, in some embodiments, "transdifferentiation", "cell reprogramming" and "reprogramming" may be used interchangeably, having all the same meanings and qualities.

By exploiting the relative insufficiency of the endogenous transcription factor (TFs) induction by introducing individual ectopic TFs, disclosed herein are methods of transdifferentiation as a sequential and temporally controlled process that is affected by a hierarchical network of TFs.

In some embodiments, methods of transdifferentiation of a cell population described herein comprises incubation with a Wnt-pathway agonist and a soluble factor providing epigenetic changes to the cells DNA. In some embodiments, Wnt-signaling is necessary for transdifferentiation of non-pancreatic β-cells to cell having a pancreatic β-cell phenotype and function. In some embodiments, a combination of Wnt-signaling and epigenetic modification is necessary for transdifferentiation of non-pancreatic β-cells to cell having a pancreatic β-cell phenotype and function.

In some embodiments, activation of a Wnt-signaling pathway in a cell improves transdifferentiation efficiency of non-pancreatic β-cells to cell having a pancreatic β-cell phenotype and function. In some embodiments, a combination of activation of a Wnt-signaling pathway in a cell and epigenetic modification of DNA within the cell improves transdifferentiation efficiency of non-pancreatic β-cells to cell having a pancreatic β-cell phenotype and function.

In some embodiments, activation of a Wnt-signaling pathway in cells converts cells resistant to transdifferentiation to cells having the capacity for transcription factor induced transdifferentiation into cells having a pancreatic β-cell phenotype and function.

The population of enriched cells and methods of use disclosed herein is based on the finding of an additional role for Wnt in the human liver, in controlling direct reprogramming into beta-like cells. Active Wnt pathway appears to play dual roles in reprogramming: (1) marking reprogramming predisposition to endocrine pancreas; and (2) controlling the efficiency of the process in predisposed cells.

Disclosed herein are methods of detecting and enriching a population of adult human liver cells transdifferentiated to produce human insulin producing cells having β-cell phenotype and function.

The methods described herein show substantially enriched populations of transdifferentiated non-pancreatic cells producing insulin and having β-cell phenotype and function. Disclosed herein is a population of cells that possess increased transdifferentiation capacity. These cells are characterized by (1) potential cell membrane markers, (2) possessing the capacity to activate glutamine synthetase regulatory element (GSRE), and (3) by being uniquely equipped with active Wnt-signaling.

In some embodiments non-pancreatic beta cells are selected from a group comprising epithelial cells, endothelial cells, keratinocytes, fibroblasts, muscle cells, hepatocytes, liver cells, blood cells, stem or progenitor cells, embryonic heart muscle cells, liver stem cells, neural stem cells, mesenchymal stem cells, hematopoietic stem or progenitor cells, pancreatic alpha cells, or any combination thereof. In some embodiments, the cell is totipotent or pluripotent. In some embodiments, the cell is an induced pluripotent stem cells. In some embodiments, stem or progenitor cells are obtained from bone marrow, umbilical cord blood, peripheral blood, fetal liver, adipose tissue, or any combination thereof.

In some embodiments, the source of a cell population disclosed here is a human source. In another embodiment, the source of a cell population disclosed herein is an autologous human source relative to a subject in need of insulin therapy. In another embodiment, the source of a cell population disclosed herein is an allogeneic human source relative to a subject in need of insulin therapy.

In certain embodiments, the cell is a mesenchymal stem cell (MSC), also known as a mesenchymal stromal cell, derived from, liver tissue, adipose tissue, bone marrow, skin, placenta, umbilical cord, Wharton's jelly or cord blood. By "umbilical cord blood" or "cord blood" is meant to refer to blood obtained from a neonate or fetus, most preferably a neonate and preferably refers to blood which is obtained from the umbilical cord or the placenta of newborns. These cells can be obtained according to any conventional method known in the art. MSC are defined by expression of certain cell surface markers including, but not limited to, CD105, CD73 and CD90, and the ability to differentiate into multiple lineages including osteoblasts, adipocytes and chondroblasts. MSC can be obtained from tissues by conventional isolation techniques such as plastic adherence, separation using monoclonal antibodies such as STRO-1 or through epithelial cells undergoing an epithelial-mesenchymal transition (EMT).

A skilled artisan would appreciate that the term "adipose tissue-derived mesenchymal stem cells" may encompass undifferentiated adult stem cells isolated from adipose tissue and may also be term "adipose stem cells", having all the same qualities and meanings. These cells can be obtained according to any conventional method known in the art.

A skilled artisan would appreciate that the term, "placental-derived mesenchymal stem cells" may encompass undifferentiated adult stem cells isolated from placenta and may be referred to herein as "placental stem cells", having all the same meanings and qualities.

In some embodiments, the cells are human adult liver cells. In some embodiments, liver cells comprise hepatocytes. In some embodiments, the cells can be transdifferentiated along the pancreatic lineage to mature pancreatic cells with pancreatic function.

Thus, methods disclosed herein solve the problem of previous transdifferentiation or reprogramming protocols that often have restricted efficiency. For example, although ectopic expression of key pancreatic transcription factors results in expression in each host cell, only up to 15% of the cells are successfully transdifferentiated to exhibit pancreatic function.

In some embodiments, a method for isolating cells predisposed to transdifferentiation is by sorting out cells that activate GFP expression operatively linked to the glutamine synthetase regulatory element, or a fragment thereof, thereby isolating those cells that can activate GSRE. The cells may be sorted by FACS and can be propagated in culture, separately from the rest of the cells, for rapid expansion of the cells with enriched transdifferentiation capacity.

In some embodiments, a method for detecting and enriching a population of non-pancreatic human insulin producing cells, comprises the steps of: (a) identifying cells having increased expression of at least one gene of the group comprising a solute carrier family 2, facilitated glucose transporter member 3 (GLUT-3); a vesicle-associated membrane protein 2 (VAMP2); a syntaxin-1A (Stx1a); a tyrosine-protein kinase transmembrane receptor ROR2 (ROR2); Frizzled-4 (FZD4); a pituitary homeobox 2 (PITX2); and a Proto-oncogene Wnt-1 (WNT1); or any combination thereof, wherein said expression is compared with cells not transdifferentiated and wherein said identified cells are non-pancreatic insulin producing cells; and (b) selecting said cells having increased expression, wherein said selected cells comprise a population of cells enriched for non-pancreatic human insulin producing cells having pancreatic phenotype and function.

One skilled in the art would appreciate that the term "increased expression of at least one gene" encompasses increases in an mRNA transcript and variants thereof transcribed from the gene, as well as increases in a polypeptide and variants thereof encoded by the gene and the mRNA transcript.

The population of cells with enriched capacity for transdifferentiation is only a small proportion of the cells that make up the tissue in vivo. For example, in a given tissue or population of cells, the population of cells with enriched capacity for transdifferentiation is only about less than 1%, 2%, 3%, 4%, 5%, about 10%, about 15%, of the entire population of cells in a given tissue. Therefore, methods are disclosed herein for the isolation of said cells with increased transdifferentiation capacity from cells that do not have increased transdifferentiation capacity. Accordingly, the enriched non-pancreatic β-cells, disclosed herein have the advantage of a cell population with a greater proportion of cells that have increased transdifferentiation capacity to increase the efficiency of transdifferentiation to provide transdifferentiated cells for treatment of various diseases or disorders.

It will be obvious to those skilled in the art that various changes and modifications may be made to the methods described herein within the spirit and scope of the non-pancreatic β-cells transdifferentiation human insulin producing cell product, and methods of making a using said product.

Cell Populations Predisposed for Transdifferentiation

Figure 45:
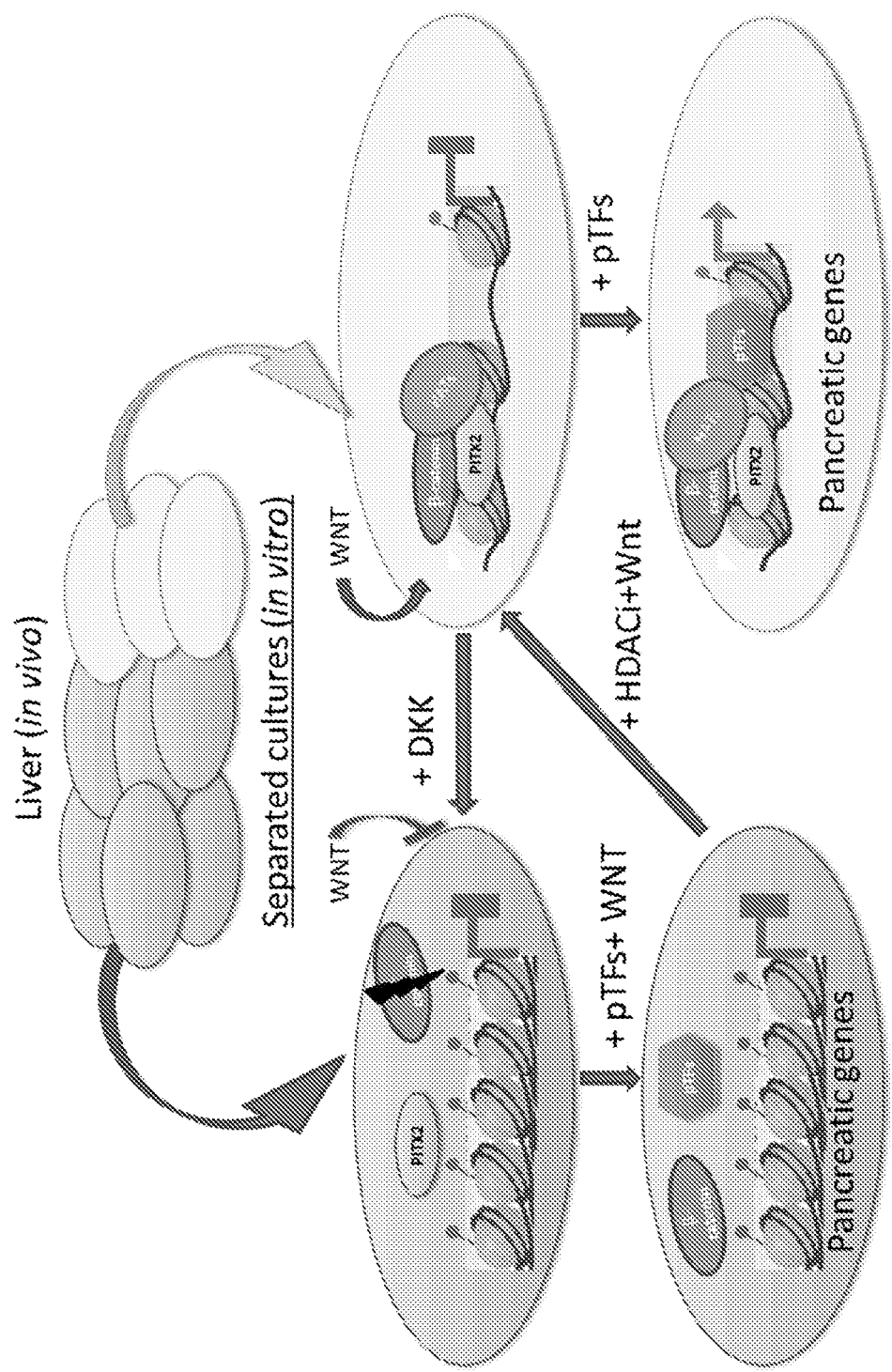
FIG. 45 shows a model for epigenetic and molecular control of reprogramming. The original human liver cells derived cultures are consistently heterogeneous with regard to WNT signaling. Continuous WNT signaling leads to β-catenin and histone acetyl transferases (or other chromatin modifying enzymes) recruitment, dictating permissive chromatin structure (marked here by green dots). Upon addition of pTFs, pancreatic genes transcribed. Lack or disruption of WNT activity results in chromatin closure (red dots), preventing any access for the ectopic pTFs or WNT pathway mediators (exemplified here by PITX2), and the subsequent transcription of pancreatic genes. Opening chromatin by HDAC inhibitors (HDACi) enables WNT and pTFs to induce liver cells reprogramming.

The disclosure presented herein provides liver derived cell populations that are predisposed for transdifferentiation. The cell populations may be useful in the methods of producing pancreatic beta cells described herein. Cells that are predisposed for transdifferentiation of the disclosure presented herein may also be referred to as being transdifferentiation-prone or as having increased or enriched transdifferentiation capacity. By "increased transdifferentiation capacity" is meant that when the cell population of the disclosure presented herein is subjected to a differentiation protocol (i.e. introduction of a pancreatic transcription factor), greater than 15%, greater than 20%, greater than 30%, greater than 40%, greater than 50%, greater than 60%, greater than 70% or greater than 80% of the cells may differentiate to an alternate cell type. In one embodiment, a population of endothelial cells, epithelial cells, mesenchymal cells, fibroblasts, or liver cells with increased transdifferentiation capacity may be differentiated to mature pancreatic cells or mature neural cells (transdifferentiation). A schematic drawing showing the predisposed and non-predisposed subpopulations within the liver is presented in FIG. 45.

In another embodiment, cell populations that are predisposed for transdifferentiation have the capability of activating the glutamine synthetase response element (GSRE). For example, in the cell populations of the disclosure presented herein, at least 2%, at least 3%, at least 4%, at least 5%, at least 10%, at least 15%, at least 20%, at least 30%, at least 40%, at least 50%, at least 60%, at least 70%, at least 80% or at least 90% of the cells in the population are capable of activating GSRE. In one embodiment, at least 30% of the cells in the population are capable of activating GSRE. Glutamine synthetase is an enzyme predominantly expressed in the brain, kidneys and liver, and plays an essential role in the metabolism of nitrogen by catalyzing the condensation of glutamate and ammonia to form glutamine. Glutamine synthetase is, for example, uniquely expressed in pericentral liver cells and astrocytes in the brain. Data presented herein indicate that cells that demonstrate activation of GSRE provide a unique selective parameter for the isolation of cells predisposed for transdifferentiation. In another embodiment, a predisposed population of cells comprises pericentral liver cells.

Activation of GSRE can be measured by methods known to one of ordinary skill in the art. For example, a recombinant adenovirus can be generated containing the glutamine synthetase response element operatively linked to a promoter and a reporter gene, such as a fluorescent protein. This recombinant adenovirus with the GSRE-reporter can be introduced into a heterogeneous mixture of cells containing some proportion of cells that are predisposed for transdifferentiation. Those cells that are competent for activation of the GSRE will express the reporter gene, which can be detected by methods known in the art, thereby identifying cells predisposed for transdifferentiation.

Figure 14:
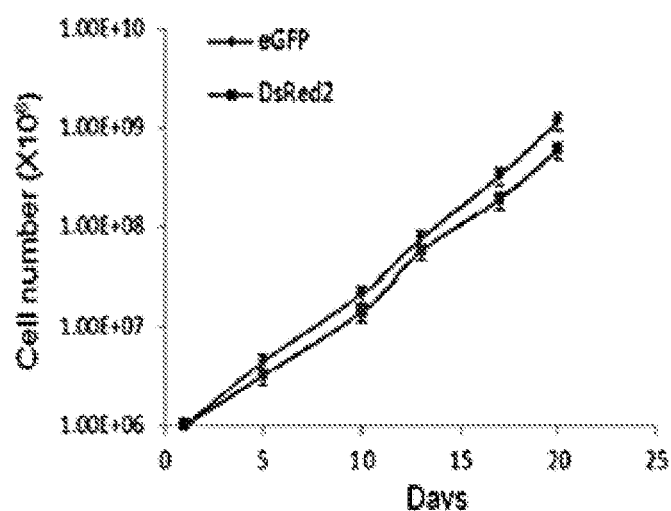
FIG. 14 shows in vitro lineage tracing for GSRE activating human cells. A schematic presentation of the lentivirus vectors.
Figure 16:
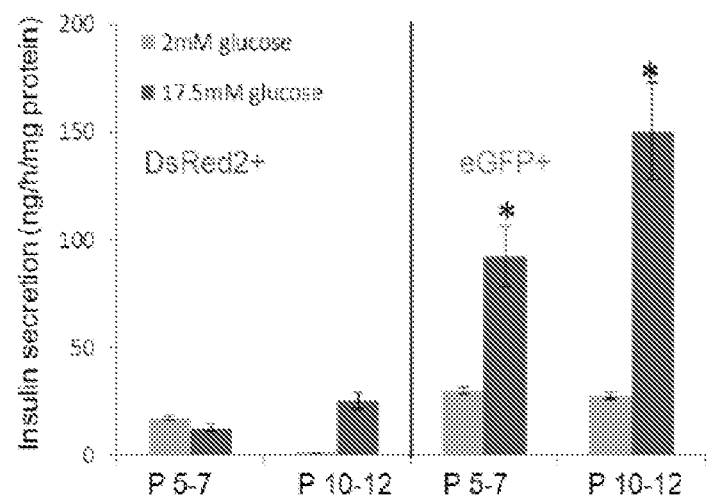
FIG. 16 shows higher transdifferentiation efficiency in eGFP+ population is stable with increasing passages in culture. The two groups proliferated separately after sorting and were similarly treated with pTFs (Ad-Pdx-1+Ad-Pax-4+Ad-MafA and soluble factors) after a few passages (5-7 passages post sorting) or a higher number of passages (10-12 passages post sorting). Regulated insulin secretion was analyzed by static incubations at low followed by high glucose concentrations (2 mM and 17.5 mM glucose in KRB, respectively). Insulin secretion is measured using the human insulin radioimmunoassay kit (DPC; n≥6 from 2 different experiments). No statistical significant differences were detected between the low and high number of passages in both populations of cells, suggesting a persistent tendency of eGFP tagged cells to undergo pTFs induced transdifferentiation along the 3-cell lineage and function.

A heterogeneous population of cells, in which those cells predisposed for transdifferentiation are unknown, can be contacted with an adenoviral vector that contains the GSRE operatively linked to a minimal TK promoter and eGFP. The cells that activate the GSRE will express GFP and can be identified by various methods known in the art to detect GFP expression. For example, separation of the GSRE-activated cells which are predisposed for transdifferentiation from the cells that are not predisposed for transdifferentiation can be achieved through FACs apparatus, sorter and techniques known to those ordinarily skilled in the art (FIG. 14). The separated cells that are predisposed for transdifferentiation can then be propagated or expanded in vitro. Results described herein demonstrate that passaging of the cells predisposed for transdifferentiation for 5-12 passages or more retain their transdifferentiation capacity. For example, isolated liver cells predisposed for transdifferentiation continue to produce and secrete insulin in a glucose-dependent manner even after 12 passages in culture (FIG. 16).

In another embodiment, cell populations that are predisposed for transdifferentiation also have active Wnt signaling pathways. Wnt signaling pathways play a significant role in stem cell pluripotency and cell fate during development, as well as body axis patterning, cell proliferation, and cell migration. Wnt signaling pathways are activated by the binding of a Wnt-protein ligand to a Frizzled (Fz) family receptor (a G-coupled protein receptor), optionally activating a co-receptor protein, and the subsequent activation of a cytoplasmic protein called Dishevelled (Dsh). In the canonical Wnt pathway, co-receptor LRP-5/6 is also activated and beta-catenin accumulates in the cytoplasm and is eventually translocated into the nucleus to act as a transcriptional coactivator of TCF/LEF transcription factors. Without Wnt signaling, a destruction complex that includes proteins such as adenomatosis polyposis coli (APC), Axin, protein phosphatase 2A (PP2A), glycogen synthase kinase 3 (GSK3) and casein kinase 1α (CK1α) targets β-catenin for ubiquitination and its subsequent degradation by the proteasome. However, activation of the Frizzled receptor by Wnt binding causes disruption of the destruction complex, thereby allowing β-catenin to accumulate.

Wnt signaling can also occur through noncanonical pathways that utilize different co-receptor proteins and activate different downstream effectors to, for example, regulate of the cytoskeleton, stimulate of calcium release from the endoplasmic reticulum, activate mTOR pathways, and regulate myogenesis.

One of ordinary skill in the art could readily use methods known in the art to determine the activation of Wnt signaling pathways. For example, cells that express Wnt3a, decreased levels of DKK1 or DKK3, decreased levels of APC, increased activated beta-catenin levels, or STAT5 binding elements have active Wnt signaling pathways. DKK1, DKK3, and APC are known inhibitors of Wnt signaling pathways. Other signaling effectors that indicate active Wnt signaling pathways are readily known in the art.

In one embodiment, methods disclosed further comprise treating the primary adult human liver cell population with lithium, wherein said treated population is enriched in cells predisposed to transdifferentiation. In another embodiment, methods disclosed further comprise treating the primary adult human liver cell population with lithium, wherein said cells predisposed to transdifferentiation within the population have an increased predisposition following treatment with lithium. Thus, an enriched population of cells predisposed to transdifferentiation may be established by treating a primary adult population of cells with lithium.

In one embodiment, a primary adult population of cells is treated with 10 mM of lithium. In another embodiment, a primary adult population of cells is treated with 1 mM of lithium. In one embodiment, a primary adult population of cells is treated with between 1-10 mM of lithium. In one embodiment, a primary adult population of cells is treated with 2 mM of lithium. In one embodiment, a primary adult population of cells is treated with 3 mM of lithium. In one embodiment, a primary adult population of cells is treated with 4 mM of lithium. In one embodiment, a primary adult population of cells is treated with 5 mM of lithium. In one embodiment, a primary adult population of cells is treated with 6 mM of lithium. In one embodiment, a primary adult population of cells is treated with 7 mM of lithium. In one embodiment, a primary adult population of cells is treated with 8 mM of lithium. In one embodiment, a primary adult population of cells is treated with 9 mM of lithium. In one embodiment, a primary adult population of cells is treated with about 10-20 mM of lithium. In one embodiment, a primary adult population of cells is treated with 15 mM of lithium. In one embodiment, a primary adult population of cells is treated with 20 mM of lithium. In one embodiment, a primary adult population of cells is treated with 10-50 mM of lithium. In one embodiment, a primary adult population of cells is treated with 10-100 mM of lithium.

In another embodiment, cells were treated prior to the time of transdifferentiation (the first timepoint). In another embodiment, cells were treated 12 hours prior to transdifferentiation (the first timepoint). In another embodiment, cells were treated 24 hours prior to transdifferentiation (the first timepoint). In another embodiment, cells were treated 36 hours prior to transdifferentiation (the first timepoint). In another embodiment, cells were treated 40 hours prior to transdifferentiation (the first timepoint). In another embodiment, cells were treated 48 hours prior to transdifferentiation (the first timepoint). In another embodiment, cells were treated 60 hours prior to transdifferentiation (the first timepoint). In another embodiment, cells were treated 72 hours prior to transdifferentiation (the first timepoint). In yet another embodiment, cells were treated at the time of transdifferentiation (the first timepoint).

In some embodiments, a timepoint comprises a point in time. In another embodiment, a timepoint comprises a time period shorter than 1 minute. In another embodiment, a timepoint comprises a time period shorter than 5 minutes. In another embodiment, a timepoint comprises a time period shorter than 30 minutes. A skilled artisan would appreciate that the terms "timepoint", "time point" and "time period" may be used interchangeably having all the same qualities and meanings In one embodiment, the cell populations used in methods disclosed herein are predisposed for transdifferentiation to the pancreatic lineage, wherein the transdifferentiated cells exhibit pancreatic phenotype and function. For example, the transdifferentiated cells exhibit mature pancreatic beta cell phenotype and function, which includes, but is not limited to, expression, production, and/or secretion of pancreatic hormones. Pancreatic hormones can include, but are not limited to, insulin, somatostatin, glucagon, or islet amyloid polypeptide (IAPP). Insulin can be hepatic insulin or serum insulin. In one embodiment, the insulin is a fully process form of insulin capable of promoting glucose utilization, and carbohydrate, fat and protein metabolism. For example, the cells predisposed for transdifferentiation may encompass about 15% of all the cells in a heterogeneous in vitro primary human liver cell culture. When the cells ectopically express pTFs, greater than 5%, 10%, 15%, 20%, 25%, 30%, 40%, 50% of the cells in culture produce insulin or secrete C-peptide.

Figure 8A:
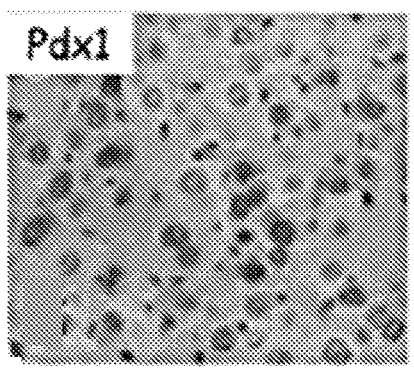
FIGS. 8A-8D shows PDX-1-induced insulin producing cells' (IPCs) activation in mice in vivo is restricted to cells adjacent to the central veins that are characterized by glutamine synthetase (GS) expression. Immunohistochemical analysis of Pdx-1 (FIG. 8A) and insulin (FIG. 8B) 14 days after Ad-CMV-PDX-1 administration. Arrows indicate positive cells, mostly located at the proximity of central veins (cv).
Figure 8B:
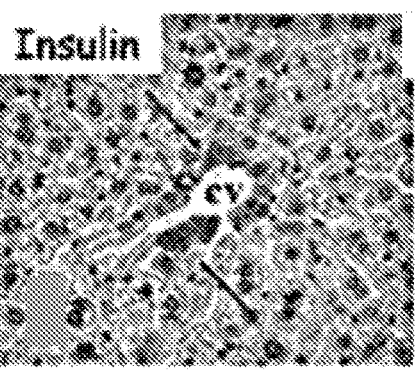

In one embodiment, cell populations that are predisposed for transdifferentiation are located in close proximity to the central veins of the liver, or are pericentral liver cells. As shown herein, although over 40-50% of liver cells that ectopically express pancreatic transcription factors, such as PDX-1, only a subset of cells produced insulin upon pTF expression. These insulin-producing cells (IPCs) were primarily located close to the ventral veins, as shown by FIG. 8B. These cells are also characterized by expression of glutamine synthetase and active Wnt signaling.

In another embodiment, the cell populations used in methods disclosed herein is predisposed for transdifferentiation to the neural lineage, wherein the transdifferentiated cells express neural markers, exhibit neural phenotype, or exhibit neural function. The transdifferentiated cells can be neurons or glial cells.

In another embodiment, cells with increased predisposition for transdifferentiation may be identified through specific cell surface markers. For example, cells with increased levels of HOMER1, LAMP3 or BMPR2 indicate cells with increased transdifferentiation capacity when compared to cells without predisposition for transdifferentiation. Cells with decreased levels of ABCB1, ITGA4, ABCB4, or PRNP indicate cells with increased transdifferentiation capacity when compared to cells without predisposition for transdifferentiation. Any combination of the cell surface markers described can be used to distinguish a cell population predisposed to transdifferentiation from a cell population that is not predisposed to transdifferentiation. Antibodies to these cell surface markers are commercially available. Immunoassay or immunoaffinity techniques known in the art may be utilized to distinguish cells with increased transdifferentiation capacity from those cells without transdifferentiation capacity.

Use of the cell populations of the disclosure presented herein to produce cells that exhibit pancreatic cell phenotypes provide certain advantages over differentiating heterogeneous populations of non-pancreatic cells to produce cells that exhibit pancreatic cell phenotypes. Previous studies that describe expressing a pancreatic transcription factor (pTF) such as PDX-1 in a heterogeneous population of non-pancreatic cells (i.e., liver cells) show that at best, only 15% of the PDX-1-expressing cells are competent for producing insulin. Therefore, only 15% of the cells were successfully differentiated to a mature pancreatic beta cell capable of producing and secreting pancreatic hormones. In contrast, introducing pTFs into the cell populations of the disclosure presented herein results in at least 30%, at least 40%, at least 50%, at least 60%, at least 70%, or at least 80% of the cells are differentiated to a mature pancreatic beta cell phenotype, for example, produce insulin, glucagon, and/or secrete c-peptide. In one embodiment, when the cells of the cell population of the disclosure presented herein express a pancreatic transcription factor, at least 30% of the cells produce insulin or secrete C-peptide.

Methods of Producing Pancreatic Beta-Cells

Disclosed herein are methods for producing cells that exhibit a mature pancreatic beta cell phenotype by contacting mammalian non-pancreatic cells with pancreatic transcription factors, such as PDX-1, Pax-4, NeuroD1, and MafA, at specific time points. In some embodiments, the methods comprise contacting a mammalian non-pancreatic cell with PDX-1 at a first timepoint; contacting the cells from the first step with Pax-4 at a second timepoint; and contacting the cells from the second step with MafA at a third timepoint. In one embodiment, the methods comprise contacting a mammalian non-pancreatic cell with PDX-1 at a first timepoint; contacting the cells from the first step with NeuroD1 at a second timepoint; and contacting the cells from the second step with MafA at a third timepoint. In another embodiment, the methods comprise contacting a mammalian non-pancreatic cell with PDX-1 and a second transcription factor at a first timepoint and contacting the cells from the first step with MafA at a second timepoint. In yet a further embodiment, a second transcription factor is selected from NeuroD1 and Pax4. In another embodiment, the transcription factors provided together with PDX-1 comprise Pax-4, NeuroD1, Ngn3, or Sox-9. In another embodiment, the transcription factors provided together with PDX-1 comprises Pax-4. In another embodiment, the transcription factors provided together with PDX-1 comprises NeuroD1. In another embodiment, the transcription factors provided together with PDX-1 comprises Ngn3. In another embodiment, the transcription factors provided together with PDX-1 comprises Sox-9.

In other embodiments, the methods comprise contacting a mammalian non-pancreatic cell with PDX-1 at a first timepoint; contacting the cells from the first step with Ngn3, or Beta2, or Pax4, at a second timepoint; and contacting the cells from the second step with MafA at a third timepoint. In other embodiments, the methods comprise contacting a mammalian non-pancreatic cell with PDX-1 at a first timepoint; contacting the cells from the first step with Sox9 at a second timepoint; and contacting the cells from the second step with MafA at a third timepoint. In another embodiment, the methods comprise contacting a mammalian non-pancreatic cell with PDX-1 and a second transcription factor at a first timepoint and contacting the cells from the first step with MafA at a second timepoint, wherein a second transcription factor is selected from NeuroD1, Ngn3, Beta 2, Sox9, and Pax4.

In another embodiment, the methods comprise contacting a mammalian non-pancreatic cell with PDX-1 and NeuroD1 at a first timepoint, and contacting the cells from the first step with MafA at a second timepoint. In another embodiment, the methods comprise contacting a mammalian non-pancreatic cell with PDX-1 and Pax4 at a first timepoint, and contacting the cells from the first step with MafA at a second timepoint. In another embodiment, the methods comprise contacting a mammalian non-pancreatic cell with PDX-1 and Ngn3 at a first timepoint, and contacting the cells from the first step with MafA at a second timepoint. In another embodiment, the methods comprise contacting a mammalian non-pancreatic cell with PDX-1 and Sox9 at a first timepoint, and contacting the cells from the first step with MafA at a second timepoint.

In another embodiment, the cells are contacted with all three factors (PDX-1; NeuroD1 or Pax4 or Ngn3; and MafA) at the same time but their expression levels are controlled in such a way as to have them expressed within the cell at a first timepoint for PDX-1, a second timepoint for NeuroD1 or Pax4 or Ngn3; and a third timepoint for MafA. The control of expression can be achieved by using appropriate promoters on each gene such that the genes are expressed sequentially, by modifying levels of mRNA, or by other means known in the art.

In one embodiment, the methods described herein further comprise contacting the cells at, before, or after any of the above steps with the transcription factor Sox-9.

In one embodiment, the first and second timepoints are identical resulting in contacting a cell population with two pTFs at a first timepoint, wherein at least one pTF comprises pDX-1, followed by contacting the resultant cell population with a third pTF at a second timepoint, wherein said third pTF is MafA.

In one embodiment, the second timepoint is at least 24 hours after the first timepoint. In an alternative embodiment, the second timepoint is less than 24 hours after the first timepoint. In another embodiment, the second timepoint is about 1 hour after the first timepoint, about 2 hours, about 3 hours, about 4 hours, about 5 hours, about 6 hours, about 7 hours, about 8 hours, about 9 hours, about 10 hours, about 11 hours, or about 12 hours after the first timepoint. In some embodiments, the second timepoint can be at least 24 hours, at least 48 hours, at least 72 hours, and at least 1 week or more after the first timepoint.

In another embodiment, the third timepoint is at least 24 hours after the second timepoint. In an alternative embodiment, the third timepoint is less than 24 hours after the second timepoint. In another embodiment, the third timepoint is at the same time as the second timepoint. In another embodiment, the third timepoint is about 1 hour after the second timepoint, about 2 hours, about 3 hours, about 4 hours, about 5 hours, about 6 hours, about 7 hours, about 8 hours, about 9 hours, about 10 hours, about 11 hours, or about 12 hours after the second timepoint. In other embodiments, the third timepoint can be at least 24 hours, at least 48 hours, at least 72 hours, and at least 1 week or more after the second timepoint.

In one embodiment, the first, second, and third timepoints are concurrent resulting in contacting a cell population with three pTFs at a single timepoint, wherein at least one pTF comprises pDX-1, at least one pTF comprises NeuroD1 or Pax4, and at least one pTF comprises MafA. In another embodiment, the first, second, and third timepoints are concurrent resulting in contacting a cell population with three pTFs at a single timepoint, wherein one pTF consists of pDX-1, one pTF consists of NeuroD1 or Pax4, and one pTF consists of MafA.

In some embodiments, when the "2+1" transdifferentiation method is used, the second timepoint (addition of MAFA) is about 48 hours after the first time point (PDX-1 and NeuroD1). In some embodiments, when the "2+1" transdifferentiation method is used, the second timepoint (addition of MAFA) is about 72 hours after the first time point (PDX-1 and NeuroD1).

In one embodiment, transcription factors comprise polypeptides, or ribonucleic acids or nucleic acids encoding the transcription factor polypeptides. In another embodiment, the transcription factor comprises a polypeptide. In another embodiment, the transcription factor comprises a nucleic acid sequence encoding the transcription factor. In another embodiment, the transcription factor comprises a Deoxyribonucleic acid sequence (DNA) encoding the transcription factor. In still another embodiment, the DNA comprises a cDNA. In another embodiment, the transcription factor comprises a ribonucleic acid sequence (RNA) encoding the transcription factor. In yet another embodiment, the RNA comprises an mRNA.

Transcription factors for use in the disclosure presented herein can be a polypeptide, ribonucleic acid or a nucleic acid. A skilled artisan would appreciate that the term "nucleic acid" may encompass DNA molecules (e.g., cDNA or genomic DNA), RNA molecules (e.g., mRNA, microRNA or other RNA derivatives), analogs of the DNA or RNA generated using nucleotide analogs, and derivatives, fragments and homologs thereof. The nucleic acid molecule can be single-stranded or double-stranded. In one embodiment, the nucleic acid is a DNA. In other embodiments the nucleic acid is mRNA. mRNA is particularly advantageous in the methods disclosed herein, as transient expression of PDX-1 is sufficient to produce pancreatic beta cells. The polypeptide, ribonucleic acid or nucleic acid maybe delivered to the cell by means known in the art including, but not limited to, infection with viral vectors, electroporation and lipofection.

In certain embodiments, transcription factors for use in the methods described herein are selected from the group consisting of PDX-1, Pax-4, NeuroD1, and MafA. In other embodiments, transcription factors for use in the methods described herein are selected from the group consisting of PDX-1, Pax-4, NeuroD1, MafA, Ngn3, and Sox9.

The homeodomain protein PDX-1 (pancreatic and duodenal homeobox gene-1), also known as IDX-1, IPF-1, STF-1, or IUF-1, plays a central role in regulating pancreatic islet development and function. PDX-1 is either directly or indirectly involved in islet-cell-specific expression of various genes such as, for example insulin, glucagon, somatostatin, proinsulin convertase 1/3 (PC1/3), GLUT-2 and glucokinase. Additionally, PDX-1 mediates insulin gene transcription in response to glucose. Suitable sources of nucleic acids encoding PDX-1 include for example the human PDX-1 nucleic acid (and the encoded protein sequences) available as GenBank Accession Nos. U35632 and AAA88820, respectively. In one embodiment, the amino acid sequence of a PDX-1 polypeptide is set forth in SEQ ID NO: 4:

```
                                             (SEQ ID NO: 4)
MNGEEQYYAATQLYKDPCAFQRGPAPEFSASPPACLYMGRQPPPPPPHPF

PGALGALEQGSPPDISPYEVPPLADDPAVAHLHHHLPAQLALPHPPAGPF

PEGAEPGVLEEPNRVQLPFPWMKSTKAHAWKGQWAGGAYAAEPEENKRTR

TAYTRAQLLELEKEFLFNKYISRPRRVELAVMLNLTERHIKIWFQNRRMK

WKKEEDKKRGGGTAVGGGGVAEPEQDCAVTSGEELLALPPPPPPGGAVPP

AAPVAAREGRLPPGLSASPQPSSVAPRRPQEPR.
```

In one embodiment, the nucleic acid sequence of a PDX-1 polynucleotide is set forth in SEQ ID NO: 5:

```
                                             (SEQ ID NO: 5)
ATGAACGGCGAGGAGCAGTACTACGCGGCCACGCAGCTTTACAAGGACCC

ATGCGCGTTCCAGCGAGGCCCGGCGCCGGAGTTCAGCGCCAGCCCCCCTG

CGTGCCTGTACATGGGCCGCCAGCCCCCGCCGCCGCCGCCGCACCCGTTC

CCTGGCGCCCTGGGCGCGCTGGAGCAGGGCAGCCCCCCGGACATCTCCCC

GTACGAGGTGCCCCCCCTCGCCGACGACCCCGCGGTGGCGCACCTTCACC

ACCACCTCCCGGCTCAGCTCGCGCTCCCCCACCCGCCCGCCGGGCCCTTC

CCGGAGGGAGCCGAGCCGGGCGTCCTGGAGGAGCCCAACCGCGTCCAGCT

GCCTTTCCCATGGATGAAGTCTACCAAAGCTCACGCGTGGAAAGGCCAGT

GGGCAGGCGGCGCCTACGCTGCGGAGCCGGAGGAGAACAAGCGGACGCGC

ACGGCCTACACGCGCGCACAGCTGCTAGAGCTGGAGAAGGAGTTCCTATT

CAACAAGTACATCTCACGGCCGCGCCGGGTGGAGCTGGCTGTCATGTTGA

ACTTGACCGAGAGACACATCAAGATCTGGTTCCAAAACCGCCGCATGAAG

TGGAAAAAGGAGGAGGACAAGAAGCGCGGCGGCGGGACAGCTGTCGGGGG
```

-continued
```
TGGCGGGGTCGCGGAGCCTGAGCAGGACTGCGCCGTGACCTCCGGCGAGG

AGCTTCTGGCGCTGCCGCCGCCGCCGCCCCCGGAGGTGCTGTGCCGCCC

GCTGCCCCCGTTGCCGCCCGAGAGGGCCGCCTGCCGCCTGGCCTTAGCGC

GTCGCCACAGCCCTCCAGCGTCGCGCCTCGGCGGCCGCAGGAACCACGAT

GA.
```

Other sources of sequences for PDX-1 include rat PDX nucleic acid and protein sequences as shown in GenBank Accession No. U35632 and AAA18355, respectively, and are incorporated herein by reference in their entirety. An additional source includes zebrafish PDX-1 nucleic acid and protein sequences are shown in GenBank Accession No. AF036325 and AAC41260, respectively, and are incorporated herein by reference in their entirety.

Pax-4, also known as paired box 4, paired box protein 4, paired box gene 4, MODY9 and KPD, is a pancreatic-specific transcription factor that binds to elements within the glucagon, insulin and somatostatin promoters, and is thought to play an important role in the differentiation and development of pancreatic islet beta cells. In some cellular contexts, Pax-4 exhibits repressor activity. Suitable sources of nucleic acids encoding Pax-4 include for example the human Pax-4 nucleic acid (and the encoded protein sequences) available as GenBank Accession Nos. NM_006193.2 and AAD02289.1, respectively.

MafA, also known as V-maf musculoaponeurotic fibrosarcoma oncogene homolog A or RIPE3B1, is a beta-cell-specific and glucose-regulated transcriptional activator for insulin gene expression. MafA may be involved in the function and development of beta cells as well as in the pathogenesis of diabetes. Suitable sources of nucleic acids encoding MafA include for example the human MafA nucleic acid (and the encoded protein sequences) available as GenBank Accession Nos. NM_201589.3 and NP_963883.2, respectively. In one embodiment, the amino acid sequence of a MafA polypeptide is set forth in SEQ ID NO: 8:

```
                                        (SEQ ID NO: 8)
MAAELAMGAELPSSPLAIEYVNDFDLMKFEVKKEPPEAERFCHRLPPGSL

SSTPLSTPCSSVPSSPSFCAPSPGTGGGGAGGGGSSQAGGAPGPPSGG

PGAVGGTSGKPALEDLYWMSGYQHHLNPEALNLTPEDAVEALIGSGHHGA

HHGAHHPAAAAAYEAFRGPGFAGGGGADDMGAGHHHGAHHAAHHHHAAHH

HHHHHHHHGGAGHGGGAGHHVRLEERFSDDQLVSMSVRELNRQLRGFSKE

EVIRLKQKRRTLKNRGYAQSCRFKRVQQRHILESEKCQLQSQVEQLKLEV

GRLAKERDLYKEKYEKLAGRGGPGSAGGAGFPREPSPPQAGPGGAKGTAD

FFL.
```

In another embodiment, the nucleic acid sequence of a MafA polynucleotide is set forth in SEQ ID NO: 9:

```
                                        (SEQ ID NO: 9)
ATGGCCGCGGAGCTGGCGATGGGCGCCGAGCTGCCCAGCAGCCCGCTGGC

CATCGAGTACGTCAACGACTTCGACCTGATGAAGTTCGAGGTGAAGAAGG

AGCCTCCCGAGGCCGAGCGCTTCTGCCACCGCCTGCCGCCAGGCTCGCTG
```

```
TCCTCGACGCCGCTCAGCACGCCCTGCTCCTCCGTGCCCTCCTCGCCCAG

CTTCTGCGCGCCCAGCCCGGGCACCGGCGGCGGCGGCGGCGCGGGGGCG

GCGGCGGCTCGTCTCAGGCCGGGGCGCCCCCGGGCCGCCGAGCGGGGC

CCCGGCGCCGTCGGGGGCACCTCGGGGAAGCCGGCGCTGGAGGATCTGTA

CTGGATGAGCGGCTACCAGCATCACCTCAACCCCGAGGCGCTCAACCTGA

CGCCCGAGGACGCGGTGGAGGCGCTCATCGGCAGCGGCCACCACGGCGCG

CACCACGGCGCGCACCACCCGGCGGCCGCCGCAGCCTACGAGGCTTTCCG

CGGCCCGGGCTTCGCGGGCGGCGGCGGAGCGGACGACATGGGCGCCGGCC

ACCACCACGGCGCGCACCACGCCGCCCACCACCACCACGCCGCCCACCAC

CACCACCACCACCACCACCATGGCGGCGCGGGACACGGCGGTGGCGCGGG

CCACCACGTGCGCCTGGAGGAGCGCTTCTCCGACGACCAGCTGGTGTCCA

TGTCGGTGCGCGAGCTGAACCGGCAGCTCCGCGGCTTCAGCAAGGAGGAG

GTCATCCGGCTCAAGCAGAAGCGGCGCACGCTCAAGAACCGCGGCTACGC

GCAGTCCTGCCGCTTCAAGCGGGTGCAGCAGCGGCACATTCTGGAGAGCG

AGAAGTGCCAACTCCAGAGCCAGGTGGAGCAGCTGAAGCTGGAGGTGGGG

CGCCTGGCCAAAGAGCGGGACCTGTACAAGGAGAAATACGAGAAGCTGGC

GGGCCGGGGCGGCCCCGGGAGCGCGGGCGGGGCCGGTTTCCCGCGGGAGC

CTTCGCCGCCGCAGGCCGGTCCCGGCGGGGCCAAGGGCACGGCCGACTTC

TTCCTGTAG
```

Neurog3, also known as neurogenin 3 or Ngn3, is a basic helix-loop-helix (bHLH) transcription factor required for endocrine development in the pancreas and intestine. Suitable sources of nucleic acids encoding Neurog3 include for example the human Neurog3 nucleic acid (and the encoded protein sequences) available as GenBank Accession Nos. NM_020999.3 and NP_066279.2, respectively.

NeuroD1, also known as Neuro Differentiation 1 or NeuroD, and beta-2 (02) is a Neuro D-type transcription factor. It is a basic helix-loop-helix transcription factor that forms heterodimers with other bHLH proteins and activates transcription of genes that contain a specific DNA sequence known as the E-box. It regulates expression of the insulin gene, and mutations in this gene result in type II diabetes mellitus. Suitable sources of nucleic acids encoding NeuroD1 include for example the human NeuroD1 nucleic acid (and the encoded protein sequences) available as GenBank Accession Nos. NM_002500.4 and NP_002491.2, respectively.

In one embodiment, the amino acid sequence of a NeuroD1 polypeptide is set forth in SEQ ID NO: 6:

```
                                        (SEQ ID NO: 6)
MTKSYSESGLMGEPQPQGPPSWTDECLSSQDEEHEADKKEDDLETMNAEE

DSLRNGGEEEDEDEDLEEEEEEEEDDDQKPKRRGPKKKKMTKARLERFK

LRRMKANARERNRMHGLNAALDNLRKVVPCYSKTQKLSKIETLRLAKNYI

WALSEILRSGKSPDLVSFVQTLCKGLSQPTTNLVAGCLQLNPRTFLPEQN

QDMPPHLPTASASFPVHPYSYQSPGLPSPPYGTMDSSHVFHVKPPPHAYS
```

-continued

AALEPFFESPLTDCTSPSFDGPLSPPLSINGNFSFKHEPSAEFEKNYAFT

MHYPAATLAGAQSHGSIFSGTAAPRCEIPIDNIMSFDSHSHHERVMSAQL

NAIFHD.

In another embodiment, the nucleic acid sequence of a NeuroD1 polynucleotide is set forth in SEQ ID NO: 7.

(SEQ ID NO: 7)
ATGACCAAATCGTACAGCGAGAGTGGGCTGATGGGCGAGCCTCAGCCCA

AGGTCCTCCAAGCTGGACAGACGAGTGTCTCAGTTCTCAGGACGAGGAGC

ACGAGGCAGACAAGAAGGAGGACGACCTCGAAGCCATGAACGCAGAGGAG

GACTCACTGAGGAACGGGGGAGAGGAGGAGGACGAAGATGAGGACCTGGA

AGAGGAGGAAGAAGAGGAAGAGGAGGATGACGATCAAAAGCCCAAGAGAC

GCGGCCCCAAAAAGAAGAAGATGACTAAGGCTCGCCTGGAGCGTTTTAAA

TTGAGACGCATGAAGGCTAACGCCCGGGAGCGGAACCGCATGCACGGACT

GAACGCGGCGCTAGACAACCTGCGCAAGGTGGTGCCTTGCTATTCTAAGA

CGCAGAAGCTGTCCAAAATCGAGACTCTGCGCTTGGCCAAGAACTACATC

TGGGCTCTGTCGGAGATCTCGCGCTCAGGCAAAAGCCCAGACCTGGTCTC

CTTCGTTCAGACGCTTTGCAAGGGCTTATCCCAACCCACCACCAACCTGG

TTGCGGGCTGCCTGCAACTCAATCCTCGGACTTTTCTGCCTGAGCAGAAC

CAGGACATGCCCCCGCACCTGCCGACGGCCAGCGCTTCCTTCCCTGTACA

CCCCTACTCCTACCAGTCGCCTGGGCTGCCCAGTCCGCCTTACGGTACCA

TGGACAGCTCCCATGTCTTCCACGTTAAGCCTCCGCCGCACGCCTACAGC

GCAGCGCTGGAGCCCTTCTTTGAAAGCCCTCTGACTGATTGCACCAGCCC

TTCCTTTGATGGACCCCTCAGCCCGCCGCTCAGCATCAATGGCAACTTCT

CTTTCAAACACGAACCGTCCGCCGAGTTTGAGAAAAATTATGCCTTTACC

ATGCACTATCCTGCAGCGACACTGGCAGGGGCCCAAAGCCACGGATCAAT

CTTCTCAGGCACCGCTGCCCCTCGCTGCGAGATCCCCATAGACAATATTA

TGTCCTTCGATAGCCATTCACATCATGAGCGAGTCATGAGTGCCCAGCTC

AATGCCATATTTCATGATTAG.

Sox9 is a transcription factor that is involved in embryonic development. Sox9 has been particularly investigated for its importance in bone and skeletal development. SOX-9 recognizes the sequence CCTTGAG along with other members of the HMG-box class DNA-binding proteins. In the context of the disclosure presented herein, the use of Sox9 may be involved in maintaining the pancreatic progenitor cell mass, either before or after induction of transdifferentiation. Suitable sources of nucleic acids encoding Sox9 include for example the human Sox9 nucleic acid (and the encoded protein sequences) available as GenBank Accession Nos. NM_000346.3 and NP_000337.1, respectively.

Homology is, in one embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence of greater than 60%. In another embodiment, "homology" refers to identity to a sequence of greater than 70%. In another embodiment, the identity is greater than 75%, greater than 78%, greater than 80%, greater than 82%, greater than 83%, greater than 85%, greater than 87%, greater than 88%, greater than 90%, greater than 92%, greater than 93%, greater than 95%, greater than 96%, greater than 97%, greater than 98%, or greater than 99%. In another embodiment, the identity is 100%.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the disclosure presented herein.

The cell can be any cell that is capable of producing pancreatic hormones, e.g., bone marrow muscle, spleen, kidney, blood, skin, pancreas, or liver. In one embodiment, the cell is a non-pancreatic cell. In another embodiment, the cell is a non-pancreatic β-cell. In one embodiment, the cells are capable of functioning as a pancreatic islet, i.e., store, process and secrete pancreatic hormones. In another embodiment, secretion is glucose regulated.

In another embodiment, glucose regulated insulin secretion comprises at least 0.001 µg insulin/$10^6$ cells/hour in response to high glucose concentrations. In another embodiment, glucose regulated insulin secretion comprises at least 0.002 µg insulin/$10^6$ cells/hour in response to high glucose concentrations. In another embodiment, glucose regulated insulin secretion comprises at least 0.003 µg insulin/$10^6$ cells/hour in response to high glucose concentrations. In another embodiment, glucose regulated insulin secretion comprises at least 0.005 µg insulin/$10^6$ cells/hour in response to high glucose concentrations. In another embodiment, glucose regulated insulin secretion comprises at least 0.007 µg insulin/$10^6$ cells/hour in response to high glucose concentrations. In another embodiment, glucose regulated insulin secretion comprises at least 0.01 µg insulin/$10^6$ cells/hour in response to high glucose concentrations. In another embodiment, glucose regulated insulin secretion comprises at least 0.5 µg insulin/$10^6$ cells/hour in response to high glucose concentrations. In another embodiment, glucose regulated insulin secretion comprises at least 1 µg insulin/$10^6$ cells/hour in response to high glucose concentrations. In another embodiment, glucose regulated insulin secretion comprises at least 5 µg insulin/$10^6$ cells/hour in response to high glucose concentrations. In another embodiment, glucose regulated insulin secretion comprises at least 10 µg insulin/$10^6$ cells/hour in response to high glucose concentrations. In another embodiment, glucose regulated insulin secretion comprises at least 50 µg insulin/$10^6$ cells/hour in response to high glucose concentrations. In another embodiment, glucose regulated insulin secretion comprises at least 100 µg insulin/$10^6$ cells/hour in response to high glucose concentrations. In another embodiment, glucose regulated insulin secretion comprises at least 500 µg insulin/$10^6$ cells/hour in response to high glucose concentrations. In another embodiment, glucose regulated insulin secretion comprises at least 1 ng insulin/$10^6$ cells/hour in response to high glucose concentrations. In another embodiment, glucose regulated insulin secretion comprises at least 5 ng insulin/$10^6$ cells/hour in response to high glucose concentrations. In another embodiment, glucose regulated insulin secretion comprises at least 10 ng insulin/$10^6$ cells/hour in response to high glucose concentrations. In another embodiment, glucose regulated insulin secretion comprises at least 50 ng insulin/$10^6$ cells/hour in response to high glucose concentrations. In another embodiment, glucose regulated insulin secretion comprises at least 100 ng insulin/$10^6$ cells/hour in response to high glucose concentrations. In another embodiment, glucose regulated insulin secretion comprises at least 500 ng insulin/$10^6$ cells/hour in response to high glucose concentrations. In another embodiment, glucose regulated insulin secretion comprises at least 1 µg insulin/$10^6$ cells/hour in response to high glucose concentrations. In another embodiment, glucose regulated insulin secretion comprises at least 5 µg insulin/$10^6$ cells/hour in response to high glucose concentrations. In another embodiment, glucose regulated insulin secretion comprises at least 10 µg insulin/$10^6$ cells/hour in response to high glucose concentrations. In another embodiment, glucose regulated insulin secretion comprises at least 50 µg insulin/$10^6$ cells/hour in response to high glucose concentrations. In another embodiment, glucose regulated insulin secretion comprises at least 100 µg insulin/$10^6$ cells/hour in response to high glucose concentrations.

In another embodiment, the pancreatic hormone comprises insulin, which may be secreted upon an extracellular trigger. In another embodiment, the cell is a liver cell. In additional embodiments, the cell is totipotent or pluripotent. In alternative embodiments the cell is a hematopoietic stem cell, embryonic stem cell or preferably a hepatic stem cell. In other embodiments, the cell is an induced pluripotent stem cells.

In one embodiment, the source of a cell population disclosed here in is a human source. In another embodiment, the source of a cell population disclosed here in is an autologous human source relative to a subject in need of insulin therapy. In another embodiment, the source of a cell population disclosed here in is an allogeneic human source relative to a subject in need of insulin therapy.

The cell population that is exposed to, i.e., contacted with, the compounds (i.e. PDX-1, Pax-4, MafA, NeuroD1 and/or Sox-9 polypeptides or nucleic acid encoding PDX-1, Pax-4, MafA, NeuroD1 and/or Sox-9 polypeptides) can be any number of cells, i.e., one or more cells, and can be provided in vitro, in vivo, or ex vivo. The cell population that is contacted with the transcription factors can be expanded in vitro prior to being contacted with the transcription factors. The cell population produced exhibits a mature pancreatic beta cell phenotype. These cells can be expanded in vitro by methods known in the art prior to transdifferentiation and maturation along the □-cell lineage, and prior to administration or delivery to a patient or subject in need thereof.

The subject is, in one embodiment, a mammal. The mammal can be, e.g., a human, non-human primate, mouse, rat, dog, cat, horse, or cow.

In some embodiments, the transcription factor is a polypeptide, such as PDX-1, Pax-4, MafA, NeuroD1 or Sox-9, or combination thereof and is delivered to a cell by methods known in the art. For example, the transcription factor polypeptide is provided directly to the cells or delivered via a microparticle or nanoparticle, e.g., a liposomal carrier.

In some embodiments, the transcription factor is a nucleic acid. For example, the nucleic acid encodes a PDX-1, Pax-4, MafA, NeuroD1 or Sox-9 polypeptide. The nucleic acid encoding the transcription factor, or a combination of such nucleic acids, can be delivered to a cell by any means known in the art. In some embodiments, the nucleic acid is incorporated in an expression vector or a viral vector. In one embodiment, the viral vector is an adenovirus vector. In another embodiment, an adenoviral vector is a first generation adenoviral (FGAD) vector. In another embodiment, an FGAD is unable in integrate into the genome of a cell. In another embodiment, a FGAD comprises an E1-deleted recombinant adenoviral vector. In another embodiment, a FGAD provide transient expression of encoded polypeptides.

The expression or viral vector can be introduced to the cell by any of the following: transfection, electroporation, infection, or transduction. In other embodiments the nucleic acid is mRNA and it is delivered for example by electroporation. In one embodiment, methods of electroporation comprise flow electroporation technology. For example, in another embodiment, methods of electroporation comprise use of a MaxCyte electroporation system (MaxCyte Inc. Georgia USA).

In certain embodiments, the manufactured population of human insulin producing cells comprises a reduction of liver phenotypic markers. In one embodiment, there is a reduction of expression of albumin, alpha-1 anti-trypsin, or a combination thereof. In another embodiment, less than 5% of the cell population expressing endogenous PDX-1 expresses albumin and alpha-1 anti-trypsin. In another embodiment, less than 10%, 9%, 8%, 7%, 6%, 4%, 3%, 2%, or 1% of the cell population expressing endogenous PDX-1 expresses albumin and alpha-1 anti-trypsin.

Methods of Transdifferentiation

The disclosure presented herein also provides methods for utilizing the cell populations with increased transdifferentiation capacity to produce cells that exhibit a mature differentiated cell type, where the differentiated cell has a different phenotype from the starting cell population. For example, a population of cells with increased transdifferentiation capacity (i.e. epithelial cells, fibroblasts or liver cells) can be differentiated to cells along the pancreatic or neural lineage to exhibit mature differentiated pancreatic or neural cell phenotypes. Any means known in the art for differentiating cells to pancreatic or neural lineage can be utilized.

In one embodiment, the cell population predisposed for transdifferentiation may be differentiated along the neural lineage through the expression of neural transcription factors. Suitable neural transcription factors are known in the art. In other embodiments, the cell population of the disclosure presented herein may be differentiated to mature neural cells through contacting the cells with various cytokines, growth factors, or other agents known in the art to differentiate cells to the neural lineage. The differentiated neural cells may express neural markers, exhibit a neural phenotype (i.e., neural gene expression profile), or exhibit neural function. The differentiated cells can be neurons or glial cells.

In another embodiment, the cell population predisposed for transdifferentiation may be differentiated along the pancreatic lineage through the expression of pancreatic transcription factors. The pancreatic transcription factors are, for example, PDX-1, Pax-4, MafA, NeuroD1, or a combination thereof. Methods for producing pancreatic beta cells are described in U.S. Pat. No. 6,774,120 and U.S. Publication No. 2005/0090465, the contents of which are incorporated by reference in their entireties.

In another embodiment, the cell population predisposed for transdifferentiation may be differentiated along the pancreatic lineage through the methods described herein.

Pancreatic Beta-cell Phenotypes

The methods provided herein produce cells with a mature pancreatic beta cell phenotype or function. A skilled artisan would appreciate that the term "pancreatic beta cell phenotype or function" may encompass cells that display one or more characteristics typical of pancreatic beta cells, i.e. pancreatic hormone production, processing, storage in secretory granules, hormone secretion, activation of pancreatic gene promoters, or characteristic beta cell gene expression profile. Hormone secretion includes nutritionally and/or hormonally regulated secretion. In one embodiment, the cells produced exhibit at least one pancreatic beta cell phenotype or function, as described herein.

The pancreatic hormone can be for example, insulin, glucagon, somatostatin or islet amyloid polypeptide (IAPP). Insulin can be hepatic insulin or serum insulin. In another embodiment the pancreatic hormone is hepatic insulin. In an alternative embodiment the pancreatic hormone is serum insulin (i.e., a fully processed form of insulin capable of promoting, e.g., glucose utilization, carbohydrate, fat and protein metabolism).

In some embodiments the pancreatic hormone is in the "prohormone" form. In other embodiments the pancreatic hormone is in the fully processed biologically active form of the hormone. In other embodiments the pancreatic hormone is under regulatory control i.e., secretion of the hormone is under nutritional and hormonal control similar to endogenously produced pancreatic hormones. For example, in one embodiment disclosed herein, the hormone is under the regulatory control of glucose.

The pancreatic beta cell phenotype can be determined for example by measuring pancreatic hormone production, i.e., insulin, somatostatin or glucagon protein mRNA or protein expression. Hormone production can be determined by methods known in the art, i.e. immunoassay, Western blot, receptor binding assays or functionally by the ability to ameliorate hyperglycemia upon implantation in a diabetic host. Insulin secretion can also be measured by, for example, C-peptide processing and secretion. In another embodiment, high-sensitivity assays may be utilized to measure insulin secretion. In another embodiment, high-sensitivity assays comprise an enzyme-linked immunosorbent assay (ELISA), a mesoscale discovery assay (MSD), or an Enzyme-Linked ImmunoSpot assay (ELISpot), or an assay known in the art.

In some embodiments, the cells may be directed to produce and secrete insulin using the methods specified herein. The ability of a cell to produce insulin can be assayed by a variety of methods known to those of ordinary skill in the art. For example, insulin mRNA can be detected by RT-PCR or insulin may be detected by antibodies raised against insulin. In addition, other indicators of pancreatic differentiation include the expression of the genes Isl-1, Pdx-1, Pax-4, Pax-6, and Glut-2. Other phenotypic markers for the identification of islet cells are disclosed in U.S. 2003/0138948, incorporated herein in its entirety.

The pancreatic beta cell phenotype can be determined for example by promoter activation of pancreas-specific genes. Pancreas-specific promoters of particular interest include the promoters for insulin and pancreatic transcription factors, i.e. endogenous PDX-1. Promoter activation can be determined by methods known in the art, for example by luciferase assay, EMSA, or detection of downstream gene expression.

In some embodiments, the pancreatic beta-cell phenotype can also be determined by induction of a pancreatic gene expression profile. A skilled artisan would appreciate that the term "pancreatic gene expression profile" may encompass a profile to include expression of one or more genes that are normally transcriptionally silent in non-endocrine tissues, i.e., a pancreatic transcription factor, pancreatic enzymes or pancreatic hormones. Pancreatic enzymes are, for example, PCSK2 (PC2 or prohormone convertase), PC1/3 (prohormone convertase 1/3), glucokinase, glucose transporter 2 (GLUT-2). Pancreatic-specific transcription factors include, for example, Nkx2.2, Nkx6.1, Pax-4, Pax-6, MafA, NeuroD1, NeuroG3, Ngn3, beta-2, ARX, BRAIN4 and Isl-1.

Induction of the pancreatic gene expression profile can be detected using techniques well known to one of ordinary skill in the art. For example, pancreatic hormone RNA sequences can be detected in, e.g., Northern blot hybridization analyses, amplification-based detection methods such as reverse-transcription based polymerase chain reaction or systemic detection by microarray chip analysis. Alternatively, expression can be also measured at the protein level, i.e., by measuring the levels of polypeptides encoded by the gene. In a specific embodiment PC1/3 gene or protein expression can be determined by its activity in processing prohormones to their active mature form. Such methods are well known in the art and include, e.g., immunoassays based on antibodies to proteins encoded by the genes, or HPLC of the processed prohormones.

In some embodiments, the cells exhibiting a mature beta-cell phenotype generated by the methods described herein may repress at least one gene or the gene expression profile of the original cell. For example, a liver cell that is induced to exhibit a mature beta-cell phenotype may repress at least one liver-specific gene. One skilled in the art could readily determine the liver-specific gene expression of the original cell and the produced cells using methods known in the art, i.e. measuring the levels of mRNA or polypeptides encoded by the genes. Upon comparison, a decrease in the liver-specific gene expression would indicate that transdifferentiation has occurred.

In certain embodiments, the transdifferentiated cells disclosed herein comprise a reduction of liver phenotypic markers. In one embodiment, there is a reduction of expression of albumin, alpha-1 anti-trypsin, or a combination thereof. In another embodiment, less than 5% of the cell population expressing endogenous PDX-1 expresses albumin and alpha-1 anti-trypsin. In another embodiment, less than 10%, 9%, 8%, 7%, 6%, 4%, 3%, 2%, or 1% of the transdifferentiated cells expressing endogenous PDX-1 expresses albumin and alpha-1 anti-trypsin.

Methods of Detecting and Enriching a Population of Non-Pancreatic Human Insulin Producing Cells Having Pancreatic Beta-Cell Phenotype And Function In some embodiments, disclosed herein are methods for enriching a population of non-pancreatic human insulin producing cells having pancreatic β-cell phenotype and function, said method comprising the steps of: (a) identifying transdifferentiated cells having increased expression of at least one gene of the group comprising a solute carrier family 2, facilitated glucose transporter member 3 (GLUT-3); a vesicle-associated membrane protein 2 (VAMP2); a syntaxin-1A (Stx1a); a tyrosine-protein kinase transmembrane receptor ROR2 (ROR2); Frizzled-4 (FZD4); a pituitary homeobox 2 (PITX2); and a Proto-oncogene Wnt-1 (WNT1); or any combination thereof, wherein said expression is compared with cells not transdifferentiated and wherein said identified cells are non-pancreatic insulin producing cells having pancreatic β-cell phenotype and function; and (b) selecting said cells having increased expression, wherein said selected cells comprise a population of cells enriched for non-pancreatic human insulin producing cells having pancreatic β-cell phenotype and function.

In some embodiments, an enriched population of non-pancreatic human insulin producing cells having pancreatic β-cell phenotype and function comprises a population wherein greater than 15%, greater than 20%, greater than 30%, greater than 40%, greater than 50%, greater than 60%, greater than 70% or greater than 80% of the cells comprise a β-cell phenotype and function.

In some embodiments, transdifferentiation comprises liver to pancreatic β-cell transdifferentiation. One skilled in the art would appreciate that transdifferentiation of liver to pancreatic β-cells may in some embodiments be termed "transdifferentiation to non-pancreatic β-cell phenotype and function". The skilled artisan would appreciate that transdifferentiated non-pancreatic cells having β-cell phenotype and function may encompass those cells comprising pancreatic β-cell phenotype and function, for example glucose regulated insulin secretion. In some embodiments, non-pancreatic cells having β-cell phenotype and function further comprise cells with reduced liver phenotype and function, for example reduced α-trypsin production. In some embodiments, non-pancreatic cells having β-cell phenotype and function further comprise cells with reduced pancreatic α-cell phenotype and function, for example reduced glucagon production. In some embodiments, non-pancreatic cells having β-cell phenotype and function further comprise cells with reduced pancreatic δ-cell phenotype and function, for example reduced somatostatin production.

In some embodiments, identifying non-pancreatic insulin producing transdifferentiated cells comprises identifying cells having increased expression of a biomarker for active wnt signaling. In some embodiments, identifying non-pancreatic insulin producing transdifferentiated cells comprises identifying cells having increased expression of a biomarker for an active glutamine synthetase regulatory element (GSRE).

In some embodiments, said identifying further comprises identifying cells with increased expression of at least one gene selected from the group comprising a vesicle-associated membrane protein 4 (VAMP4); a thrombospondin-1; a discoidin, CUB and LCCL domain-containing protein 2 (THBS1); an integrin alpha-6 (ITGA6); a homer protein homolog 1 (*HOMER*1); a lysosome-associated membrane glycoprotein 3 (LAMP3); a bone morphogenetic protein receptor type-2(BMPR2); or any combination thereof, wherein said expression is compared with cells not transdifferentiated.

In some embodiments, said identifying further comprises identifying cells with decreased expression of at least one gene selected from the group comprising a multidrug resistance protein 1 (ABCB1), an integrin alpha-4 (ITGA4), and a phosphatidylcholine translocator ABCB4 ABCB4); or any combination thereof, wherein said expression is compared with cells not transdifferentiated.

A skilled artisan would appreciate that genes and in turn the proteins they produce, having increased or decreased expression following transdifferentiation may be termed "biomarkers".

In some embodiments, cells are identified using PCR technologies well known in the art to identify an mRNA molecule or portion thereof or a variant transcribed from a gene with increased expression. A skilled artisan would appreciate that primers may be designed to specific mRNA molecules or portions thereof, and commercially synthesized for use identify expression levels of the mRNAs or portions thereof or variants thereof. PCR technology may be used to determine expression level for genes and their associated mRNAs including but not limited to GLUT-3, VAMP2, Stx1a, ROR2, FZD4, PITX2, WNT1, VAMP4, THBS1, ITGA6, HOMER1, LAMP3, BMPR2, ABCB1, ITGA4, and ABVB4.

In some embodiments, cells are identified using antibodies that bind to a polypeptide or a portion thereof localized to the plasma membrane. A skilled artisan would appreciate that antibodies that bind to proteins or portions thereof are commercially available and may be used to identify polypeptides or portions thereof that reside on the cell surface. For example, polypeptides having increased expression and localized to the plasma membrane following transdifferentiation methods disclosed herein include but are not limited to a solute carrier family 2, facilitated glucose transporter member 3 (GLUT-3); a vesicle-associated membrane protein 2 (VAMP2); a syntaxin-1A (Stx1a); a tyrosine-protein kinase transmembrane receptor ROR2 (ROR2); and Frizzled-4 (FZD4).

In some embodiments, cells are identified using ligands that bind to a polypeptide or a portion thereof localized to the plasma membrane. A skilled artisan would appreciate that ligands that bind to proteins or portions thereof are commercially available and may be used to identify polypeptides or portions thereof that reside on the cell surface. For example, polypeptides having increased expression and localized to the plasma membrane following transdifferentiation methods disclosed herein include but are not limited to a solute carrier family 2, facilitated glucose transporter member 3 (GLUT-3); a vesicle-associated membrane protein 2 (VAMP2); a syntaxin-1A (Stx1a); a tyrosine-protein kinase transmembrane receptor ROR2 (ROR2); and Frizzled-4 (FZD4).

In some embodiments, polypeptides having increased expression are localized to the plasma membrane. Polypeptide that may be increase in transdifferentiated cells disclosed herein include but are not limited to a solute carrier family 2, facilitated glucose transporter member 3 (GLUT-3); a vesicle-associated membrane protein 2 (VAMP2); a syntaxin-1A (Stx1a); a tyrosine-protein kinase transmembrane receptor ROR2 (ROR2); and. Frizzled-4 (FZD4). In some embodiments, following transdifferentiation, cells having increased expression and localized to the plasma membrane further include but are not limited to a vesicle-associated membrane protein 4 (VAMP4); a thrombospondin-1; a discoidin, CUB and LCCL domain-containing protein 2 (THBS1); an integrin alpha-6 (ITGA6); a bone morphogenetic protein receptor type-2 (BMPR2).

In some embodiments, cells are identified based on a product produced by the protein or the secretion of the protein to the media. In some embodiments, following transdifferentiation as disclosed herein, polypeptides having increased expression include but are not limited to a pituitary homeobox 2 (PITX2) polypeptide, a proto-oncogene wnt-1 (WNT1), a homer protein homolog 1 (HOMER1), and a lysosomal-associated membrane glycoprotein 3 (LAMP3). In some embodiments, regulatory proteins may be identified by downstream products using antibodies or ligands.

A skilled artisan would appreciate that methods to label an antibody or a ligand, for example fluorescent labeling, are well known in the art. By labeling an antibody or a ligand that specifically binds to a subpopulation of adult human liver cells, for example those cells having a β-pancreatic cell phenotype and function following transdifferentiation may be identified.

In some embodiments, following identifying cells, cells having increased expression of mRNA and/or polypeptide biomarkers or the products thereof are selected. A skilled artisan would appreciate that labeled cells may be specifically isolated using sorting technologies well known in the art, for example but not limited to using Fluorescence-activated cell sorting (FACS), which is a specialized type of flow cytometry. In some embodiment, isolating a specific subpopulation of cells following transdifferentiation comprises selecting cells having increased expression of biomarkers, wherein the increased expression indicates that the cells comprise a β-cell phenotype and function.

In some embodiments, FACS provides a method for sterilely sorting a heterogeneous mixture of biological cells into two or more containers, one cell at a time, based upon the specific light scattering and fluorescent characteristics of each cell. It is a useful scientific instrument as it provides fast, objective and quantitative recording of fluorescent signals from individual cells as well as physical separation of cells of particular interest.

In some embodiments, FACS is used to select cells with increased expression of genes following transdifferentiation. In some embodiments, selecting comprises the increased expression of a single gene product. In some embodiments, selecting comprises increased expression of multiple gene products. In some embodiments, selecting comprises concurrently selecting for increased expression of multiple gene products. In some embodiments, selecting comprises selecting for increased expression of multiple gene products performed in reiterative cycles, first selecting for a single gene product having increased expression, and then reselecting from the population of isolated cells based on a different single gene product having increased expression. In some embodiments, the isolated cells from multiple rounds of identifying and isolating are pooled to form the enriched population of non-pancreatic human insulin secreting cells.

In some embodiments, increased expression of a biomarker comprises at least a 2-fold increase, compared with cells not transdifferentiated. In some embodiments, increased expression of a biomarker comprises at least a 4-fold increase, compared with cells not transdifferentiated. In some embodiments, increased expression of a biomarker comprises at least a 6-fold increase, compared with cells not transdifferentiated. In some embodiments, increased expression of a biomarker comprises at least a 8-fold increase, compared with cells not transdifferentiated. In some embodiments, increased expression of a biomarker comprises at least a 10-fold increase, compared with cells not transdifferentiated.

In some embodiments, decreased expression of a biomarker comprises at least a 2-fold decrease, compared with cells not transdifferentiated.

In some embodiments, the non-pancreatic cells are transdifferentiated adult human liver cells. In some embodiments, the non-pancreatic cells are transdifferentiated adult human liver cells transdifferentiated using the methods described herein.

In some embodiments, the pancreatic β-cell phenotype and function comprises mature pancreatic beta cell phenotype and function, which includes, but is not limited to, expression, production, and/or secretion of pancreatic hormones. Pancreatic hormones can include, but are not limited to, insulin, somatostatin, glucagon, or islet amyloid polypeptide (IAPP). Insulin can be hepatic insulin or serum insulin. In one embodiment, the insulin is a fully process form of insulin capable of promoting glucose utilization, and carbohydrate, fat and protein metabolism. In some embodiments, the enriched cell population has decreased phenotypes and function for liver cells. In some embodiments, greater than 5%, 10%, 15%, 20%, 25%, 30%, 40%, 50%, 60%, 70%, 80%, or greater than 80% of the enriched cells produce insulin or secrete C-peptide.

In some embodiment, the enriched population of non-pancreatic insulin producing cells comprises a population of cells wherein at least 20% of the cells produce insulin or secretes C-peptide. In some embodiment, the enriched population of non-pancreatic insulin producing cells comprises a population of cells wherein at least 30% of the cells produce insulin or secrete C-peptide. In some embodiment, the enriched population of non-pancreatic insulin producing cells comprises a population of cells wherein at least 40% of the cells produce insulin or secrete C-peptide. In some embodiment, the enriched population of non-pancreatic insulin producing cells comprises a population of cells wherein at least 50% of the cells produce insulin or secrete C-peptide. In some embodiment, the enriched population of non-pancreatic insulin producing cells comprises a population of cells wherein at least 60% of the cells produce insulin or secrete C-peptide. In some embodiment, the enriched population of non-pancreatic insulin producing cells comprises a population of cells wherein at least 70% of the cells produce insulin or secrete C-peptide. In some embodiment, the enriched population of non-pancreatic insulin producing cells comprises a population of cells wherein at least 80% of the cells produce insulin or secrete C-peptide. In some embodiment, the enriched population of non-pancreatic insulin producing cells comprises a population of cells wherein more than 80% of the cells produce insulin or secrete C-peptide.

In some embodiments, said enriched population of non-pancreatic human insulin producing cells comprise increased insulin content compared with said control cells non-transdifferentiated cells. In some embodiments, said pancreatic β-cell phenotype and function comprises increased glucose-regulated insulin secretion and concurrent decreased somatostatin (SST) production, or decreased glucagon (GCG) production, or a combination thereof, compared with non-transdifferentiated cells.

In some embodiments, the enriched population of non-pancreatic human insulin producing cells expresses increased endogenous Nkx6.1 compared with control non-transdifferentiated adult human liver cells.

In some embodiments, said transdifferentiation comprises liver to pancreatic β-cell transdifferentiation. In some embodiments, said enriched population comprises adult human liver cells transdifferentiated using a method disclosed herein.

In some embodiments, based on the β-cell phenotype and function biomarkers and insulin production and glucose regulated secretion further selection of the cells may not be necessary. Therefore, it is critical to be able to distinguish these characteristics. In some embodiments, a method for detecting non-pancreatic human insulin producing cells having pancreatic β-cell phenotype and function following transdifferentiation is disclosed herein, said method comprising a step of: identifying transdifferentiated cells having increased expression of at least one gene of the group comprising a solute carrier family 2, facilitated glucose transporter member 3 (GLUT-3); a vesicle-associated membrane protein 2 (VAMP2); a syntaxin-1A (Stx1a); a tyrosine-protein kinase transmembrane receptor ROR2 (ROR2); Frizzled-4 (FZD4); a pituitary homeobox 2 (PITX2); and a Proto-oncogene Wnt-1 (WNT1); or any combination thereof, wherein said expression is compared with cells not transdifferentiated and wherein said identified cells are non-pancreatic insulin producing cells having pancreatic β-cell phenotype and function.

As described above, in some embodiments, a method for detecting non-pancreatic human insulin producing cells further comprises identifying further comprises identifying cells with increased expression of at least one gene selected from the group comprising a vesicle-associated membrane protein 4 (VAMP4); a thrombospondin-1; a discoidin, CUB and LCCL domain-containing protein 2 (THBS1); an integrin alpha-6 (ITGA6); a homer protein homolog 1 (*HOMER*1); a lysosome-associated membrane glycoprotein 3 (LAMP3); a bone morphogenetic protein receptor type-2 (BMPR2); or any combination thereof, wherein said expression is compared with cells not transdifferentiated.

As described above, in some embodiments, a method for detecting non-pancreatic human insulin producing cells further comprises identifying cells with decreased expression of at least one gene selected from the group comprising a multidrug resistance protein 1 (ABCB1), an integrin alpha-4 (ITGA4), and a phosphatidylcholine translocator ABCB4 ABCB4); or any combination thereof, wherein said expression is compared with cells not transdifferentiated.

Methods of Treating a Pancreatic Disorder

The disclosure presented herein discloses methods for use in treating, i.e., preventing or delaying the onset or alleviating a symptom of a pancreatic disorder in a subject. For example, the pancreatic disorder is a degenerative pancreatic disorder. The methods disclosed herein are particularly useful for those pancreatic disorders that are caused by or result in a loss of pancreatic cells, e.g., islet beta cells, or a loss in pancreatic cell function.

Common degenerative pancreatic disorders include, but are not limited to: diabetes (e.g., type I, type II, or gestational) and pancreatic cancer. Other pancreatic disorders or pancreas-related disorders that may be treated by using the methods disclosed herein are, for example, hyperglycemia, pancreatitis, pancreatic pseudocysts or pancreatic trauma caused by injury. Additionally, individuals whom have had a pancreatectomy are also suitable to treatment by the disclosed methods Diabetes is a metabolic disorder found in three forms: type 1, type 2 and gestational. Type 1, or IDDM, is an autoimmune disease; the immune system destroys the pancreas' insulin-producing beta cells, reducing or eliminating the pancreas' ability to produce insulin. Type 1 diabetes patients must take daily insulin supplements to sustain life. Symptoms typically develop quickly and include increased thirst and urination, chronic hunger, weight loss, blurred vision and fatigue. Type 2 diabetes is the most common, found in 90 percent to 95 percent of diabetes sufferers. It is associated with older age, obesity, family history, previous gestational diabetes, physical inactivity and ethnicity. Gestational diabetes occurs only in pregnancy. Women who develop gestational diabetes have a 20 percent to 50 percent chance of developing type 2 diabetes within five to 10 years.

A subject suffering from or at risk of developing diabetes is identified by methods known in the art such as determining blood glucose levels. For example, a blood glucose value above 140 mg/dL on at least two occasions after an overnight fast means a person has diabetes. A person not suffering from or at risk of developing diabetes is characterized as having fasting sugar levels between 70-110 mg/dL.

Symptoms of diabetes include fatigue, nausea, frequent urination, excessive thirst, weight loss, blurred vision, frequent infections and slow healing of wounds or sores, blood pressure consistently at or above 140/90, HDL cholesterol less than 35 mg/dL or triglycerides greater than 250 mg/dL, hyperglycemia, hypoglycemia, insulin deficiency or resistance. Diabetic or pre-diabetic patients to which the compounds are administered are identified using diagnostic methods know in the art.

Hyperglycemia is a pancreas-related disorder in which an excessive amount of glucose circulates in the blood plasma. This is generally a glucose level higher than (200 mg/dl). A subject with hyperglycemia may or may not have diabetes.

Pancreatic cancer is the fourth most common cancer in the U.S., mainly occurs in people over the age of 60, and has the lowest five-year survival rate of any cancer. Adenocarcinoma, the most common type of pancreatic cancer, occurs in the lining of the pancreatic duct; cystadenocarcinoma and acinar cell carcinoma are rarer. However, benign tumors also grow within the pancreas; these include insulinoma—a tumor that secretes insulin, gastrinoma—which secretes higher-than-normal levels of gastrin, and glucagonoma—a tumor that secretes glucagon.

Pancreatic cancer has no known causes, but several risks, including diabetes, cigarette smoking and chronic pancreatitis. Symptoms may include upper abdominal pain, poor appetite, jaundice, weight loss, indigestion, nausea or vomiting, diarrhea, fatigue, itching or enlarged abdominal organs. Diagnosis is made using ultrasound, computed tomography scan, magnetic resonance imaging, ERCP, percutaneous transhepatic cholangiography, pancreas biopsy or blood tests. Treatment may involve surgery, radiation therapy or chemotherapy, medication for pain or itching, oral enzymes preparations or insulin treatment.

Pancreatitis is the inflammation and autodigestion of the pancreas. In autodigestion, the pancreas is destroyed by its own enzymes, which cause inflammation. Acute pancreatitis typically involves only a single incidence, after which the pancreas will return to normal. Chronic pancreatitis, however, involves permanent damage to the pancreas and pancreatic function and can lead to fibrosis. Alternately, it may resolve after several attacks. Pancreatitis is most frequently caused by gallstones blocking the pancreatic duct or by alcohol abuse, which can cause the small pancreatic ductules to be blocked. Other causes include abdominal trauma or surgery, infections, kidney failure, lupus, cystic fibrosis, a tumor or a scorpion's venomous sting.

Symptoms frequently associated with pancreatitis include abdominal pain, possibly radiating to the back or chest, nausea or vomiting, rapid pulse, fever, upper abdominal swelling, ascites, lowered blood pressure or mild jaundice. Symptoms may be attributed to other maladies before being identified as associated with pancreatitis.

Recombinant Expression Vectors and Host Cells

Another embodiment disclosed herein, pertains to vectors. In one embodiment, a vector used in methods disclosed herein comprises an expression vector. In another embodiment, an expression vector comprises a nucleic acid encoding a PDX-1, Pax-4, NeuroD1 or MafA protein, or other pancreatic transcription factor, such as Ngn3, or derivatives, fragments, analogs, homologs or combinations thereof. In some embodiments, the expression vector comprises a single nucleic acid encoding any of the following transcription factors: PDX-1, Pax-4, NeuroD1, Ngn3, MafA, or Sox-9 or derivatives or fragments thereof. In some embodiments, the expression vector comprises two nucleic acids encoding any combination of the following transcription factors: PDX-1, Pax-4, NeuroD1, Ngn3, MafA, or Sox-9 or derivatives or fragments thereof. In a yet another embodiment, the expression vector comprises nucleic acids encoding PDX-1 and NeuroD1. In a still another embodiment, the expression vector comprises nucleic acids encoding PDX-1 and Pax4. In another embodiment, the expression vector comprises nucleic acids encoding MafA.

In some embodiments, methods described herein utilize co-expression of multiple genes. In some embodiments, co-expression comprises expression of individual genes from multiple vectors at the same time. In some embodiments, co-expression comprises expression of individual genes from multiple vectors at the same time. In some embodiments, co-expression comprises expression of multiple individual genes from a single multi-cistronic vector. In some embodiments, co-expression comprises a combination of (1) expression of an individual gene from a vector or expression of multiple individual genes each expressed from a vector expressing the individual gene, and (2) expression of at least two genes from a single multi-cistronic vector.

A skilled artisan would appreciate that the use of multi-cistronic vectors is well known in the art, and as such, methods described herein use known techniques for making and using mutli-cistronic vectors. Unlike promoters which will create unique mRNA transcripts for each gene that is expressed, multi-cistronic vectors simultaneously express two or more separate proteins from the same mRNA.

In some embodiments, methods for co-expression include but are not limited to: co-transfection of two or more plasmids, the use of multiple or bidirectional promoters, or the creation of bicistronic or multicistronic vectors. In some embodiments, a multi-cistronic vector comprises a bi-cistronic vector.

Translation in eukaryotes usually begins at the 5' cap so that only a single translation event occurs for each mRNA. However, some bicistronic vectors take advantage of an element called an Internal Ribosome Entry Site (IRES) to allow for initiation of translation from an internal region of the mRNA. In some embodiments, a multi-cistronic vector described herein, comprises an IRES element.

A skilled artisan would appreciate that the term "vector" encompasses a nucleic acid molecule capable of transporting another nucleic acid to which it has been linked. One type of vector is a "plasmid", which encompasses a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. A skilled artisan would appreciate that the terms "plasmid" and "vector" may be used interchangeably having all the same qualities and meanings. In one embodiment, the term "plasmid" is the most commonly used form of vector. However, the disclosure presented herein is intended to include such other forms of expression vectors, such as viral vectors (e.g., replication defective retroviruses, lentivirus, adenoviruses and adeno-associated viruses), which serve equivalent functions. Additionally, some viral vectors are capable of targeting a particular cells type either specifically or non-specifically.

The recombinant expression vectors disclosed herein comprise a nucleic acid disclosed herein, in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, a skilled artisan would appreciate that the term "operably linked" may encompass nucleotide sequences of interest linked to the regulatory sequence(s) in a manner that allows for expression of the nucleotide sequence (e.g., in an in vitro transcription/translation system or in a host cell when the vector is introduced into the host cell). A skilled artisan would appreciate that term "regulatory sequence" may encompass promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors disclosed here may be introduced into host cells to thereby produce proteins or peptides, including fusion proteins or peptides, encoded by nucleic acids as described herein (e.g., PDX-1, Pax-4, MafA, NeuroD1 or Sox-9 proteins, or mutant forms or fusion proteins thereof, etc.).

In some embodiments, a vector comprises a nucleic acid encoding a PDX-1 pTF. In some embodiments, a vector comprises a nucleic acid encoding a functional PDX-1 pTF. In some embodiments, a multicistronic vector comprises a nucleic acid encoding a PDX-1 pTF and a nucleic acid encoding a NeuroD1 pTF. In some embodiments, a vector comprises a nucleic acid encoding a functional PDX-1 pTF and a nucleic acid encoding a functional NeuroD1 pTF. In some embodiment, a multicistronic vector comprises a nucleic acid encoding a PDX-1 pTF and a nucleic acid encoding a Pax4 pTF. In some embodiments, a vector comprises a nucleic acid encoding a functional PDX-1 pTF and a nucleic acid encoding a functional Pax4 pTF. In some embodiment, a multicistronic vector comprises a nucleic acid encoding a PDX-1 pTF, a NeuroD1 pTF, and a nucleic acid encoding a Pax4 pTF. In some embodiments, a vector comprises a nucleic acid encoding a functional PDX-1 pTF, a functional NeuroD1 pTF, and a nucleic acid encoding a functional Pax4 pTF. In some embodiment, a multicistronic vector comprises a nucleic acid encoding a NeuroD1 pTF and a nucleic acid encoding a Pax4 pTF. In some embodiments, a vector comprises a nucleic acid encoding a functional a functional NeuroD1 pTF and a nucleic acid encoding a functional Pax4 pTF. In some embodiment, a multicistronic vector comprises a nucleic acid encoding a MafA pTF and a nucleic acid encoding a Pax4 pTF. In some embodiments, a vector comprises a nucleic acid encoding a functional a functional MafA pTF and a nucleic acid encoding a functional Pax4 pTF.

For example, an expression vector comprises one nucleic acid encoding a transcription factor operably linked to a promoter. In expression vectors comprising two nucleic acids encoding transcription factors, each nucleic acid may be operably linked to a promoter. The promoter operably linked to each nucleic acid may be different or the same. Alternatively, the two nucleic acids may be operably linked to a single promoter. Promoters useful for the expression vectors disclosed here could be any promoter known in the art. The ordinarily skilled artisan could readily determine suitable promoters for the host cell in which the nucleic acid is to be expressed, the level of expression of protein desired, or the timing of expression, etc. The promoter may be a constitutive promoter, an inducible promoter, or a cell-type specific promoter.

The recombinant expression vectors disclosed here can be designed for expression of PDX-1 in prokaryotic or eukaryotic cells. For example, PDX-1, Pax-4, MafA, NeuroD1, and/or Sox-9 can be expressed in bacterial cells such as E. coli, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion E. coli expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in E. coli is to express the protein in host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences disclosed here can be carried out by standard DNA synthesis techniques.

In another embodiment, the PDX-1, Pax-4, MafA, NeuroD1, or Sox-9 expression vector is a yeast expression vector. Examples of vectors for expression in yeast S. cerevisiae include pYepSec1 (Baldari, et al., (1987) EMBO J 6:229-234), pMFa (Kujan and Herskowitz, (1982) Cell 30:933-943), pJRY88 (Schultz et al., (1987) Gene 54:113-123), pYES2 (Invitrogen Corporation, San Diego, Calif.), and picZ (Invitrogen Corp, San Diego, Calif.).

Alternatively, PDX-1, Pax-4, MafA, NeuroD1 or Sox-9 can be expressed in insect cells using baculovirus expression vectors. Baculovirus vectors available for expression of proteins in cultured insect cells (e.g., SF9 cells) include the pAc series (Smith et al. (1983) Mol Cell Biol 3:2156-2165) and the pVL series (Lucklow and Summers (1989) Virology 170:31-39).

In yet another embodiment, a nucleic acid disclosed here is expressed in mammalian cells using a mammalian expression vector. Examples of mammalian expression vectors include pCDM8 (Seed (1987) Nature 329:840) and pMT2PC (Kaufman et al. (1987) EMBO J 6: 187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev 1:268-277), lymphoid-specific promoters (Calame and Eaton (1988) Adv Immunol 43:235-275), in particular promoters of T cell receptors (Winoto and Baltimore (1989) EMBO J 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) PNAS 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally regulated promoters are also encompassed, e.g., the murine hox promoters (Kessel and Gruss (1990) Science 249:374-379) and the alpha-fetoprotein promoter (Campes and Tilghman (1989) Genes Dev 3:537-546).

The disclosure herein, further provides a recombinant expression vector comprising a DNA molecule disclosed here cloned into the expression vector in an antisense orientation. That is, the DNA molecule is operatively linked to a regulatory sequence in a manner that allows for expression (by transcription of the DNA molecule) of an RNA molecule that is antisense to PDX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another embodiment disclosed herein pertains to host cells into which a recombinant expression vector disclosed here has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. Additionally, host cells could be modulated once expressing PDX-1, Pax-4, MafA, NeuroD1 or Sox-9 or a combination thereof, and may either maintain or loose original characteristics.

A host cell can be any prokaryotic or eukaryotic cell. For example, PDX-1, Pax-4, MafA, NeuroD1 or Sox-9 protein can be expressed in bacterial cells such as E. coli, insect cells, yeast or mammalian cells (such as Chinese hamster ovary cells (CHO) or COS cells). Alternatively, a host cell can be a premature mammalian cell, i.e., pluripotent stem cell. A host cell can also be derived from other human tissue. Other suitable host cells are known to those skilled in the art.

Vector DNA may be introduced into prokaryotic or eukaryotic cells via conventional transformation, transduction, infection or transfection techniques. A skilled artisan would appreciate that the terms "transformation" "transduction", "infection" and "transfection" may encompass a variety of art-recognized techniques for introducing foreign nucleic acid (e.g., DNA) into a host cell, including calcium phosphate or calcium chloride co-precipitation, DEAE-dextran-mediated transfection, lipofection, or electroporation. In addition, transfection can be mediated by a transfection agent. A skilled artisan would appreciate that the term "transfection agent" may encompass any compound that mediates incorporation of DNA in the host cell, e.g., liposome. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

Transfection may be "stable" (i.e. integration of the foreign DNA into the host genome) or "transient" (i.e., DNA is episomally expressed in the host cells) or mRNA is electroporated into cells).

For stable transfection of mammalian cells, it is known that, depending upon the expression vector and transfection technique used, only a small fraction of cells may integrate the foreign DNA into their genome the remainder of the DNA remains episomal In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding PDX-1 or can be introduced on a separate vector. Cells stably transfected with the introduced nucleic acid can be identified by drug selection (e.g., cells that have incorporated the selectable marker gene will survive, while the other cells die). In another embodiment the cells modulated by PDX-1 or the transfected cells are identified by the induction of expression of an endogenous reporter gene. In a specific embodiment, the promoter is the insulin promoter driving the expression of green fluorescent protein (GFP).

In one embodiment the PDX-1, Pax-4, MafA, NeuroD1, or Sox-9 nucleic acid is present in a viral vector. In one embodiment, the PDX-1 and NeuroD1 nucleic acids are present in the same viral vector. In another embodiment, the PDX-1 and Pax4 nucleic acids are present in the same viral vector. In another embodiment the PDX-1, Pax-4, MafA, NeuroD1, or Sox-9 nucleic acid is encapsulated in a virus. In another embodiment, the PDX-1 and NeuroD1 is encapsulated in a virus (i.e., nucleic acids encoding PDX-1 and NeuroD1 are encapsulated in the same virus particle). In another embodiment, the PDX-1 and Pax4 are encapsulated in a virus (i.e., nucleic acids encoding PDX-1 and Pax4 are encapsulated in the same virus particle). In some embodiments the virus preferably infects pluripotent cells of various tissue types, e.g. hematopoietic stem, cells, neuronal stem cells, hepatic stem cells or embryonic stem cells, preferably the virus is hepatotropic. A skilled artisan would appreciate that the term "hepatotropic" it is meant that the virus has the capacity to preferably target the cells of the liver either specifically or non-specifically. In further embodiments the virus is a modulated hepatitis virus, SV-40, or Epstein-Bar virus. In yet another embodiment, the virus is an adenovirus.

Gene Therapy

In one embodiment, a nucleic acid or nucleic acids encoding a PDX-1, Pax-4, MafA, NeuroD1, or Sox-9 polypeptide or a combination thereof, as disclosed herein, or functional derivatives thereof, are administered by way of gene therapy. Gene therapy refers to therapy that is performed by the administration of a specific nucleic acid to a subject. In one embodiment, the nucleic acid produces its encoded peptide(s), which then serve to exert a therapeutic effect by modulating function of an aforementioned disease or disorder. e.g., diabetes. Any of the methodologies relating to gene therapy available within the art may be used in the practice of the disclosure presented herein. See e.g., Goldspiel, et al., 1993. Clin Pharm 12: 488-505.

In another embodiment, the therapeutic comprises a nucleic acid that is part of an expression vector expressing any one or more of the aforementioned PDX-1, Pax-4, MafA, NeuroD1, and/or Sox-9 polypeptides, or fragments, derivatives or analogs thereof, within a suitable host. In one embodiment, such a nucleic acid possesses a promoter that is operably linked to coding region(s) of a PDX-1, Pax-4, MafA, NeuroD1 and Sox-9 polypeptide. The promoter may be inducible or constitutive, and, optionally, tissue-specific. The promoter may be, e.g., viral or mammalian in origin. In another specific embodiment, a nucleic acid molecule is used in which coding sequences (and any other desired sequences) are flanked by regions that promote homologous recombination at a desired site within the genome, thus providing for intra-chromosomal expression of nucleic acids. See e.g., Koller and Smithies, 1989. Proc Natl Acad Sci USA 86: 8932-8935. In yet another embodiment, the nucleic acid that is delivered remains episomal and induces an endogenous and otherwise silent gene.

Delivery of the therapeutic nucleic acid into a patient may be either direct (i.e., the patient is directly exposed to the nucleic acid or nucleic acid-containing vector) or indirect (i.e., cells are first contacted with the nucleic acid in vitro, then transplanted into the patient). These two approaches are known, respectively, as in vivo or ex vivo gene therapy. In another embodiment, a nucleic acid is directly administered in vivo, where it is expressed to produce the encoded product. This may be accomplished by any of numerous methods known in the art including, but not limited to, constructing said nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun.®; Biolistic, DuPont); coating said nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see, e.g., Wu and Wu, 1987. J Biol Chem 262: 4429-4432), which can be used to "target" cell types that specifically express the receptors of interest, etc.

An additional approach to gene therapy involves transferring a gene or mRNA into cells in in vitro tissue culture by such methods as electroporation, lipofection, calcium phosphate-mediated transfection, viral infection, or the like. Generally, the methodology of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In another embodiment, prior to the in vivo administration of the resulting recombinant cell, the nucleic acid is introduced into a cell by any method known within the art including, but not limited to: transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. Meth Enzymol 217: 599-618. The chosen technique should provide for the stable transfer of the nucleic acid to the cell, such that the nucleic acid is expressible by the cell. In yet another embodiment, said transferred nucleic acid is heritable and expressible by the cell progeny. In an alternative embodiment, the transferred nucleic acid remains episomal and induces the expression of the otherwise silent endogenous nucleic acid.

In one embodiment, the resulting recombinant cells may be delivered to a patient by various methods known within the art including, but not limited to, injection of epithelial cells (e.g., subcutaneously), application of recombinant skin cells as a skin graft onto the patient, and intravenous injection of recombinant blood cells (e.g., hematopoietic stem or progenitor cells) or liver cells. The total number of cells that are envisioned for use depend upon the desired effect, patient state, and the like, and may be determined by one skilled within the art. In one embodiment, at least $10^6$ transdifferentiated cells are needed for use in a method of treating as disclosed herein. In another embodiment, at least $10^7$ transdifferentiated cells, at least $10^8$ transdifferentiated cells, at least $10^9$ transdifferentiated cells, or at least $10^{10}$ transdifferentiated cells are needed for use in a method of treating as disclosed herein. In yet another embodiment, about $1.8 \times 10^9$ transdifferentiated cells are needed for use in a method of treating as disclosed herein.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, Cell 71: 973-985), hematopoietic stem or progenitor cells, e.g., as obtained from bone marrow, umbilical cord blood, peripheral blood, fetal liver, and the like. In a preferred embodiment, the cells utilized for gene therapy are autologous to the patient.

DNA for gene therapy can be administered to patients parenterally, e.g., intravenously, subcutaneously, intramuscularly, and intraperitoneally. DNA or an inducing agent is administered in a pharmaceutically acceptable carrier, i.e., a biologically compatible vehicle that is suitable for administration to an animal e.g., physiological saline. A therapeutically effective amount is an amount that is capable of producing a medically desirable result, e.g., an increase of a pancreatic gene in a treated animal. Such an amount can be determined by one of ordinary skill in the art. As is well known in the medical arts, dosage for any given patient depends upon many factors, including the patient's size, body surface area, age, the particular compound to be administered, sex, time and route of administration, general health, and other drugs being administered concurrently. Dosages may vary, but a preferred dosage for intravenous administration of DNA is approximately $10^6$ to $10^{22}$ copies of the DNA molecule. For example, the DNA is administered at approximately $2 \times 10^{12}$ virions per Kg.

Methods of Manufacturing Human Insulin Producing (IP) cells

Manufacturing of human insulin producing cells may overcome the shortage of tissue available for cell-based therapies, for instance for treating a subject suffering from type I Diabetes Mellitus. The methods of manufacturing human insulin producing cells in sufficient numbers, in some embodiments, provide a cell-based product for use in these and other therapies, as disclosed herein.

Figures 25, 26:
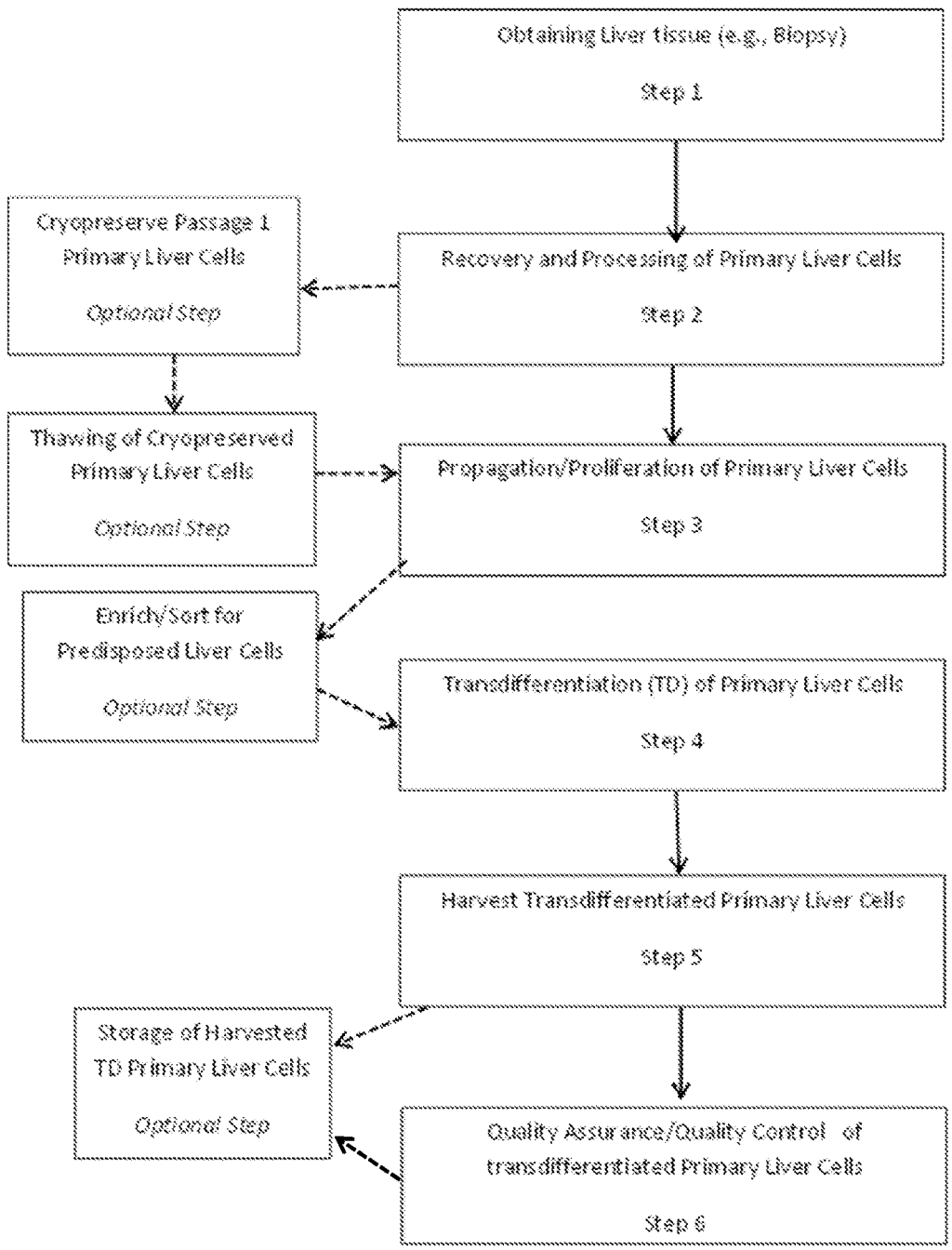
FIG. 25 shows an overview of the autologous insulin-producing (AIP) cell manufacturing process. Steps include: Step 1—Obtaining liver tissue (e.g., a liver biopsy); Step 2—Processing of the tissue to recover primary liver cells; Step 3—Propagating the primary liver cells to predetermined cell number; Step 4—Transdifferentiation of the primary liver cells; Step 5—Harvesting of the primary transdifferentiated liver cells; and Step 6—testing the transdifferentiated cells for quality assurance and quality control (i.e., safety, purity and potency). Optional steps include cryopreserving early passage primary liver cells, where in one embodiment an early passage is passage 1; thawing cryopreserved cells for use at a later date and storage of transdifferentiated cells for use at a later date.
FIG. 26 shows the variability of cell density at harvest from cells manufactured during three individual runs, wherein the starting densities are comparable.

Reference is now made to FIG. 25, which presents a flowchart of a manufacturing process of the human insulin producing cell product, which may in one embodiment be autologous or allogeneic insulin producing cells (AIP). FIG. 25 describes some embodiments of a manufacturing process of human insulin producing cells, wherein the starting material comprises liver tissue. A skilled artisan would recognize that any source of non-pancreatic β-cell tissue could be used in this manufacturing process.

Embodiments for many of the steps presented in FIG. 25 are described in detail throughout this application, and will not be repeated herein, though they should be considered herein. Reference is also made to Example 13, which exemplifies many of these steps. In brief, the manufacturing process may be understood based on the steps presented below.

As indicated at Step 1: Obtaining Liver Tissue. In one embodiment, liver tissue is human liver tissue. In another embodiment, the liver tissue is obtained as part of a biopsy. In another embodiment, liver tissue is obtained by way of any surgical procedure known in the art. In another embodiment, obtaining liver tissue is performed by a skilled medical practitioner. In another embodiment, liver tissue obtained is liver tissue from a healthy individual. In a related embodiment, the healthy individual is an allogeneic donor for a patient in need of a cell-based therapy that provides processed insulin in a glucose regulated manner, for example a type I Diabetes mellitus patient or a patient suffering for pancreatitis. In another embodiment, donor Screening and Donor Testing was performed to ensure that tissue obtained from donors shows no clinical or physical evidence of or risk factors for infectious or malignant diseases were from manufacturing of AIP cells. In yet another embodiment, liver tissue is obtained from a patient in need of a cell-based therapy that provides processed insulin in a glucose regulated manner, for example a type I Diabetes mellitus patient or a patient suffering for pancreatitis. In still another embodiment, liver tissue is autologous with a patient in need of a cell-based therapy that provides processed insulin in a glucose regulated manner, for example a type I Diabetes mellitus patient or a patient suffering for pancreatitis.

Figure 24:
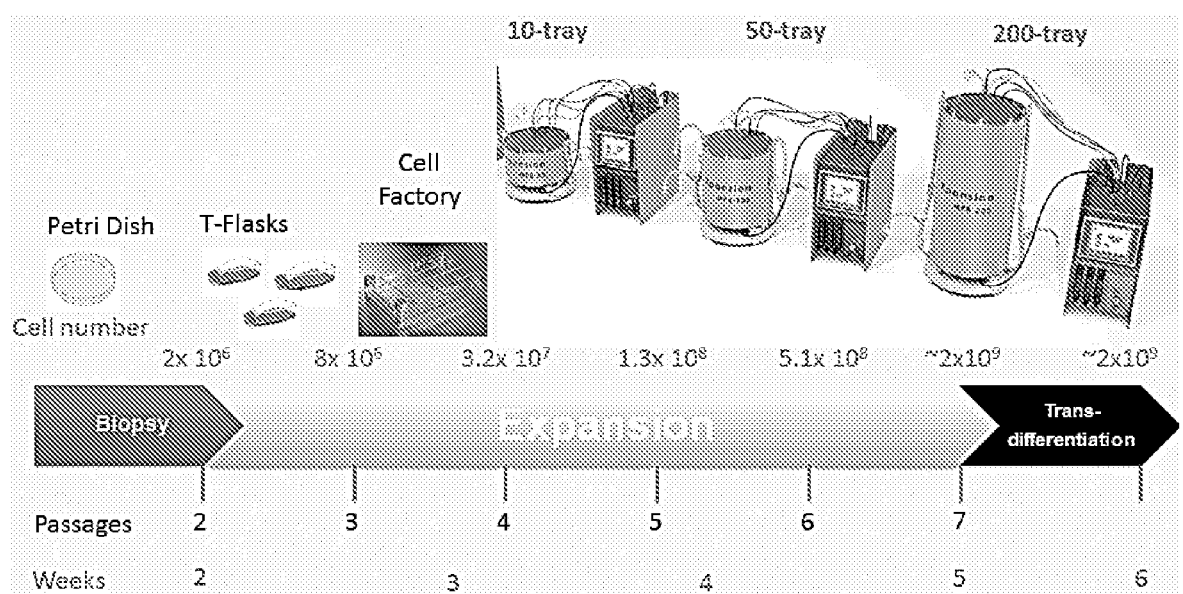
FIG. 24 shows a manufacturing process showing adult human primary liver cells undergoing a 1,000-fold expansion before transdifferentiation and final quality assurance/quality control (QA/QC) testing.

As indicated at Step 2: Recovery and Processing of Primary Liver Cells. Liver tissue is processed using well know techniques in the art for recovery of adherent cells to be used in further processing. In one embodiment, liver tissue is cut into small pieces of about 1-2 mm and gently pipetted up and down in sterile buffer solution. The sample may then be incubated with collagenase to digest the tissue. Following a series of wash steps, in another embodiment, primary liver cells may be plated on pre-treated fibronectin-coated tissue culture tissue dishes. The skilled artisan would know well how to then process (passage) the cells following well-known techniques for propagation of liver cells. Briefly, cells may be grown in a propagation media and through a series of seeding and harvesting cell number is increased. Cells may be split upon reaching 80% confluence and re-plated. FIG. 24 (0-2 weeks) shows a schematic of one embodiment of this recovery and process step representing 2 passages of the primary liver cells.

A skilled artisan would appreciate the need for sufficient cells at, for example the 2 week timepoint, prior to beginning the expansion phase of the protocol (step 3). The skilled artisan would recognize that the 2-week timepoint is one example of a starting point for expanding cells, wherein cells may be ready for expansion be before or after this timepoint. In one embodiment, recovery and processing of primary cells yields at least $1\times10^5$ cells after two passages of the cells. In another embodiment, recovery and processing of primary cells yields at least $1\times10^6$ cells after two passages of the cells. In another embodiment, recovery and processing of primary cells yields at least $2\times10^6$ cells after two passages of the cells. In another embodiment, recovery and processing of primary cells yields at least $5\times10^6$ cells after two passages of the cells. In another embodiment, recovery and processing of primary cells yields at least $1\times10^7$ cells after two passages of the cells. In another embodiment, recovery and processing of primary cells yields between $1\times10^5$-$1\times10^6$ cells after two passages of the cells. In another embodiment, recovery and processing of primary cells yields between $1\times10^6$-$1\times10^7$ cells after two passages of the cells. In another embodiment, enough starting tissue is used to ensure the recovery and processing of primary cells yields enough cells after two passages for an adequate seeding density at Step 3, large-scale expansion of the cells.

In one embodiment, $1^{st}$ passage primary cells are cryopreserved for later use. In another embodiment, early passage primary cells are cryopreserved for later use. In yet another embodiment, $2^{nd}$ passage primary cells are cryopreserved for later use.

As indicated at Step 3: Propagation/Proliferation of Primary Liver Cells

Step 3 represents the large-scale expansion phase of the manufacturing process. A skilled artisan would appreciate the need for sufficient cells at the 5 week timepoint, prior to beginning the transdifferentiation phase of the protocol (step 4), wherein a predetermined number of cells may be envisioned to be needed for treating a patient. In one embodiment, the predetermined number of cells needed prior to transdifferentiation comprises about $1\times10^8$ primary cells. In another embodiment, the predetermined number of cells needed prior to transdifferentiation comprises about $2\times10^8$ primary cells. In one embodiment, the predetermined number of cells needed prior to transdifferentiation comprises about $3\times10^8$ primary cells, $4\times10^8$ primary cells, $5\times10^8$ primary cells, $6\times10^8$ primary cells, $7\times10^8$ primary cells, $8\times10^8$ primary cells, $9\times10^8$ primary cells, $1\times10^9$ primary cells, $2\times10^9$ primary cells, $3\times10^9$ primary cells, $4\times10^9$ primary cells, $5\times10^9$ primary cells, $6\times10^9$ primary cells, $7\times10^9$ primary cells, $8\times10^9$ primary cells, $9\times10^9$ primary cells, or $1\times10^{10}$ primary cells.

In one embodiment, the cell seeding density at the time of expansion comprises $1\times10^3$-$10\times10^3$ cell/cm$^2$. In another embodiment, the cell seeding density at the time of expansion comprises $1\times10^3$-$8\times10^3$ cell/cm$^2$. In another embodiment, the cell seeding density at the time of expansion comprises $1\times10^3$-$5\times10^3$ cell/cm$^2$. In another embodiment, the cell seeding density at the time of expansion comprises $1\times10^3$. In another embodiment, the cell seeding density at the time of expansion comprises $2\times10^3$. In another embodiment, the cell seeding density at the time of expansion comprises $3\times10^3$. In another embodiment, the cell seeding density at the time of expansion comprises $4\times10^3$. In another embodiment, the cell seeding density at the time of expansion comprises $5\times10^3$. In another embodiment, the cell seeding density at the time of expansion comprises $6\times10^3$. In another embodiment, the cell seeding density at the time of expansion comprises $7\times10^3$. In another embodiment, the cell seeding density at the time of expansion comprises $8\times10^3$. In another embodiment, the cell seeding density at the time of expansion comprises $9\times10^3$. In another embodiment, the cell seeding density at the time of expansion comprises $10\times10^3$.

In another embodiment, the range for cells seeding viability at the time of expansion comprises 60-100%. In another embodiment, the range for cells seeding viability at the time of expansion comprises a viability of about 70-99%. In another embodiment, the cell seeding viability at the time of expansion comprises a viability of about 60%. In another embodiment, the cell seeding viability at the time of expansion comprises a viability of about 65%. In another embodiment, the cell seeding viability at the time of expansion comprises a viability of about 70%. In another embodiment, the cell seeding viability at the time of expansion comprises a viability of about 75%. In another embodiment, the cell seeding viability at the time of expansion comprises a viability of about 80%. In another embodiment, the cell seeding viability at the time of expansion comprises a viability of about 85%. In another embodiment, the cell seeding viability at the time of expansion comprises a viability of about 90%. In another embodiment, the cell seeding viability at the time of expansion comprises a viability of about 95%. In another embodiment, the cell seeding viability at the time of expansion comprises a viability of about 99%. In another embodiment, the cell seeding viability at the time of expansion comprises a viability of about 99.9%.

FIG. 24 schematically illustrates one embodiment of this expansion period. In one embodiment, expansion occurs between weeks 2 and 5. The skilled artisan would recognize variability within starting tissue material. Therefore, in another embodiment expansion occurs between weeks 2 and 6. In still another embodiment, expansion occurs between weeks 2 and 7. In another embodiment, expansion occurs between weeks 2 and 4. In yet another embodiment, expansion occurs until the needed number of primary cells has been propagated. For example, in some embodiments a target goal of 1 billion cells was reached by day 30 of culture (data not shown; see for example International Application Publication No. WO 2016/108237, which is incorporated herein in its entirety).

A skilled artisan would appreciate that concurrent with expansion of cells, the population could be enhanced for transdifferentiation. Description of primary adult liver cells enhanced for transdifferentiation and methods for enriching these populations have been disclosed herein, and are exemplified in Examples 3-10 and 13. In one embodiment, selection for GSRE activity is used to enrich a population of adult cells for transdifferentiation. In another embodiment, levels of gene expression are measured for genes known to have either increased or decreased expression, wherein such increases or decreases indicate predisposition to transdifferentiation. In another embodiment, primary adult liver cells may be incubated with lithium prior to transdifferentiation, wherein the incubation enhances predisposition of a population of cells within said population of primary adult liver cells.

In one embodiment, bioreactors are used to expand and propagate primary cells prior to the transdifferentiation step. Bioreactors may be used or cultivation of cells, in which conditions are suitable for high cell concentrations (Data not shown; see for example International Application Publication No. WO 2016/108237, which is incorporated herein in its entirety). In another embodiment, a bioreactor provides a closed system for expansion of cells. In another embodiment, multiple bioreactors are used in a series for cell expansion. In another embodiment, a bioreactor used in the methods disclosed herein is a single use bioreactor. In another embodiment, a bioreactor used is a multi-use bioreactor. In yet another embodiment, a bioreactor comprises a control unit for monitoring and controlling parameters of the process. In another embodiment, parameters for monitoring and controlling comprise Dissolve Oxygen (DO), pH, gases, and temperature.

As indicated at Step 4: Transdifferentiation (TD) of primary Liver Cells.

In one embodiment, transdifferentiation comprises any method of transdifferentiation disclosed herein. For example, transdifferentiation may comprise a hierarchy (1+1+1) protocol or a "2+1" protocol, as disclosed herein.

In one embodiment, the resultant cell population following transdifferentiation comprises transdifferentiated cells having a pancreatic phenotype and function. In another embodiment, the resultant cell population following transdifferentiation comprises transdifferentiated cells having a mature β-cell pancreatic phenotype and function. In another embodiment, the resultant cell population following transdifferentiation comprises transdifferentiated cells having increased insulin content. In another embodiment, the resultant cell population following transdifferentiation comprises transdifferentiated cells able to secrete processed insulin in a glucose-regulated manner. In another embodiment, the resultant cell population following transdifferentiation comprises transdifferentiated cells has increased C-peptide levels.

In another embodiment, the resultant cell population following transdifferentiation comprises transdifferentiated cells having increased endogenous expression of at least one pancreatic gene marker. In another embodiment, endogenous expression is increased for at least two pancreatic gene markers. In another embodiment, endogenous expression is increased for at least three pancreatic gene markers. In another embodiment, endogenous expression is increased for at least four pancreatic gene markers. In a related embodiment, pancreatic gene markers comprise PDX-1, NeuroD, MafA, Nkx6.1, glucagon, somatostatin and Pax4.

In one embodiment, endogenous PDX-1 expression is greater than $10^2$ fold over non-differentiated cells. In another embodiment, endogenous PDX-1 expression is greater than $10^3$ fold over non-differentiated cells. In another embodiment, endogenous PDX-1 expression is greater than $10^4$ fold over non-differentiated cells. In another embodiment, endogenous PDX-1 expression is greater than $10^5$ fold over non-differentiated cells. In another embodiment, endogenous PDX-1 expression is greater than $10^6$ fold over non-differentiated cells.

In another embodiment, endogenous NeuroD1 expression is greater than $10^2$ fold over non-differentiated cells. In another embodiment, endogenous NeuroD1 expression is greater than $10^3$ fold over non-differentiated cells. In another embodiment, endogenous NeuroD1 expression is greater than $10^4$ fold over non-differentiated cells. In another embodiment, endogenous NeuroD1 expression is greater than $10^5$ fold over non-differentiated cells.

In another embodiment, endogenous MafA expression is greater than $10^2$ fold over non-differentiated cells. In another embodiment, endogenous MafA expression is greater than $10^3$ fold over non-differentiated cells. In another embodiment, endogenous MafA expression is greater than $10^4$ fold over non-differentiated cells. In another embodiment, endogenous MafA expression is greater than $10^5$ fold over non-differentiated cells.

In another embodiment, endogenous glucagon expression is greater than 10 fold over non-differentiated cells. In another embodiment, endogenous glucagon expression is greater than $10^2$ fold over non-differentiated cells. In another embodiment, endogenous glucagon expression is greater than $10^3$ fold over non-differentiated cells.

In another embodiment, endogenous expression of PDX-1, NeuroD1, or MafA, or any combination thereof is each greater than 60% over non-differentiated cells. In another embodiment, endogenous expression of PDX-1, NeuroD1, or MafA, or any combination thereof is each greater than 70% over non-differentiated cells. In another embodiment, endogenous expression of PDX-1, NeuroD1, or MafA, or any combination thereof is each greater than 80% over non-differentiated cells In some embodiments, following transdifferentiation, methods may be used, as described above, to enrich the population of cells for non-pancreatic human insulin producing cells having a pancreatic β-cell phenotype and function. In some embodiments, enrichment comprises identifying and selecting for increased gene expression of at least one of GLUT-3, VAMP2, Stx1a, ROR2, FZD4, PITX2, WNT1, VAMP4, THBS1, ITGA6, HOMER1, LAMP3, or BMPR2, or any combination thereof. In some embodiments, enrichment comprises identifying and selecting for decreased gene expression of at least one of ABCB1, ITGA4, or ABVB4, or any combination thereof. In some embodiments, enrichment comprises identifying and selecting for increased gene expression or decreased gene expression, or a combination thereof, as described herein.

In another embodiment, the resultant cell population following transdifferentiation comprises transdifferentiated cells having at least 60% viability. In another embodiment, the resultant cell population following transdifferentiation comprises transdifferentiated cells having at least 70% viability. In another embodiment, the resultant cell population following transdifferentiation comprises transdifferentiated cells having at least 80% viability. In another embodiment, the resultant cell population following transdifferentiation comprises transdifferentiated cells having at least 90% viability.

In another embodiment, the resultant cell population following transdifferentiation comprises transdifferentiated cells showing decreased liver cell markers. In another embodiment, the resultant cell population following transdifferentiation comprises transdifferentiated cells showing decreased albumin or alpha-1 antitrypsin (AAT), or any combination. In another embodiment, the resultant cell population following transdifferentiation comprises transdifferentiated cells comprising less than 1% by FACS albumin or alpha-1 antitrypsin (AAT), or any combination.

In another embodiment, transdifferentiated cells maintain a pancreatic phenotype and function for at least 6 months. In another embodiment, transdifferentiated cells maintain a pancreatic phenotype and function for at least 12 months. In another embodiment, transdifferentiated cells maintain a pancreatic phenotype and function for at least 18 months. In another embodiment, transdifferentiated cells maintain a pancreatic phenotype and function for at least 24 months. In another embodiment, transdifferentiated cells maintain a pancreatic phenotype and function for at least 36 months. In another embodiment, transdifferentiated cells maintain a pancreatic phenotype and function for at least 48 months. In another embodiment, transdifferentiated cells maintain a pancreatic phenotype and function for at least 4 years. In another embodiment, transdifferentiated cells maintain a pancreatic phenotype and function for at least 5 years.

In one embodiment, cell number is maintained during transdifferentiation. In another embodiment, cell number decreases by less than 5% during transdifferentiation. In another embodiment, cell number decreases by less than 10% during transdifferentiation. In another embodiment, cell number decreases by less than 15% during transdifferentiation. In another embodiment, cell number decreases by less than 20% during transdifferentiation. In another embodiment, cell number decreases by less than 25% during transdifferentiation.

As indicated at Step 5: Harvest Transdifferentiated Primary Liver Cells

In one embodiment, transdifferentiated primary liver cells comprising human insulin producing cells are harvested and used for a cell-based therapy. In one embodiment, cell number is maintained during harvesting. In another embodiment, cell number decreases by less than 5% during harvesting. In another embodiment, cell number decreases by less than 10% during harvesting. In another embodiment, cell number decreases by less than 15% during harvesting. In another embodiment, cell number decreases by less than 20% during harvesting. In another embodiment, cell number decreases by less than 25% during harvesting.

In one embodiment, the number of transdifferentiated cells recovered at harvest is about $1\times10^7$-$1\times10^{10}$ cells total. In another embodiment, the number of transdifferentiated cells recovered at harvest is about $1\times10^8$-$1\times10^{10}$ cells total. In another embodiment, the number of transdifferentiated cells recovered at harvest is about $1\times10^7$-$1\times10^9$ cells total. In another embodiment, the number of transdifferentiated cells recovered at harvest is about $1\times10^7$ cells total. In another embodiment, the number of transdifferentiated cells recovered at harvest is about $5\times10^7$ cells total. In another embodiment, the number of transdifferentiated cells recovered at harvest is about $7.5\times10^7$ cells total. In another embodiment, the number of transdifferentiated cells recovered at harvest is about $1\times10^8$ cells total. In another embodiment, the number of transdifferentiated cells recovered at harvest is about $2.5\times10^8$ cells total. In another embodiment, the number of transdifferentiated cells recovered at harvest is about $5\times10^8$ cells total. In another embodiment, the number of transdifferentiated cells recovered at harvest is about $7.5\times10^8$ cells total. In another embodiment, the number of transdifferentiated cells recovered at harvest is about $1\times10^9$ cells total. In another embodiment, the number of transdifferentiated cells recovered at harvest is about $2\times10^8$ cells total. In another embodiment, the number of transdifferentiated cells recovered at harvest is about $3\times10^8$ cells total. In another embodiment, the number of transdifferentiated cells recovered at harvest is about $4\times10^9$ cells total. In another embodiment, the number of transdifferentiated cells recovered at harvest is about $5\times10^9$ cells total. In another embodiment, the number of transdifferentiated cells recovered at harvest is about $6\times10^9$ cells total. In another embodiment, the number of transdifferentiated cells recovered at harvest is about $7\times10^9$ cells total. In another embodiment, the number of transdifferentiated cells recovered at harvest is about $8\times10^9$ cells total. In another embodiment, the number of transdifferentiated cells recovered at harvest is about $9\times10^9$ cells total.

In one embodiment, the density of transdifferentiated cells at harvest is about $1\times10^3$-$1\times10^5$ cells/cm$^2$. In another embodiment, the density of transdifferentiated cells at harvest is about $1\times10^4$-$5\times10^4$ cells/cm$^2$. In another embodiment, the density of transdifferentiated cells at harvest is about $1\times10^4$-$4\times10^4$ cells/cm$^2$. In another embodiment, the density of transdifferentiated cells at harvest is about $1\times10^3$ cells/cm$^2$. In another embodiment, the density of transdifferentiated cells at harvest is about $2\times10^3$ cells/cm$^2$. In another embodiment, the density of transdifferentiated cells at harvest is about $3\times10^3$ cells/cm$^2$. In another embodiment, the density of transdifferentiated cells at harvest is about $4\times10^3$ cells/cm$^2$. In another embodiment, the density of transdifferentiated cells at harvest is about $5\times10^3$ cells/cm$^2$. In another embodiment, the density of transdifferentiated cells at harvest is about $6\times10^3$ cells/cm$^2$. In another embodiment, the density of transdifferentiated cells at harvest is about $7\times10^3$ cells/cm$^2$. In another embodiment, the density of transdifferentiated cells at harvest is about $8\times10^3$ cells/cm$^2$. In another embodiment, the density of transdifferentiated cells at harvest is about $9\times10^3$ cells/cm$^2$. In another embodiment, the density of transdifferentiated cells at harvest is about $1\times10^4$ cells/cm$^2$. In another embodiment, the density of transdifferentiated cells at harvest is about $2\times10^4$ cells/cm$^2$. In another embodiment, the density of transdifferentiated cells at harvest is about $3\times10^4$ cells/cm$^2$. In another embodiment, the density of transdifferentiated cells at harvest is about $4\times10^4$ cells/cm$^2$. In another embodiment, the density of transdifferentiated cells at harvest is about $5\times10^4$ cells/cm$^2$. In another embodiment, the density of transdifferentiated cells at harvest is about $6\times10^4$ cells/cm$^2$. In another embodiment, the density of transdifferentiated cells at harvest is about $7 \times 10^4$ cells/cm$^2$. In another embodiment, the density of transdifferentiated cells at harvest is about $8 \times 10^4$ cells/cm$^2$. In another embodiment, the density of transdifferentiated cells at harvest is about $9 \times 10^4$ cells/cm$^2$.

In another embodiment, the range for cell viability at the time of harvesting comprises 50-100%. In another embodiment, the range for cell viability at the time of harvesting comprises 60-100%. In another embodiment, the range for cell viability at the time of harvesting comprises 50-90%. In another embodiment, the range for cell viability at the time of harvesting comprises a viability of about 60-99%. In another embodiment, the range for cell viability at the time of harvesting comprises a viability of about 60-90%. In another embodiment, the cell viability at the time of harvesting comprises a viability of about 60%. In another embodiment, the cell viability at the time of harvesting comprises a viability of about 65%. In another embodiment, the cell viability at the time of harvesting comprises a viability of about 70%. In another embodiment, the cell viability at the time of harvesting comprises a viability of about 75%. In another embodiment, the cell viability at the time of harvesting comprises a viability of about 80%. In another embodiment, the cell viability at the time of harvesting comprises a viability of about 85%. In another embodiment, the cell viability at the time of harvesting comprises a viability of about 90%. In another embodiment, the cell viability at the time of harvesting comprises a viability of about 95%. In another embodiment, the cell viability at the time of harvesting comprises a viability of about 99%. In another embodiment, the cell viability at the time of harvesting comprises a viability of about 99.9%.

In another embodiment, transdifferentiated primary liver cells comprising human insulin producing cells are harvested and stored for use in a cell-based therapy at a later date. In another embodiment, storage comprises cryopreserving the cells.

As indicated at Step 6: Quality Analysis/Quality Control

Before any use of transdifferentiated cells in a cell-based therapy, the transdifferentiated cells must undergo a quality analysis/quality control assessment. FACS analysis and/or RT-PCR may be used to accurately determine membrane markers and gene expression. Further, analytical methodologies for insulin secretion are well known in the art including ELISA, MSD, ELISpot, HPLC, RP-HPLC. In one embodiment, insulin secretion testing is at low glucose concentrations (about 2 mM) in comparison to high glucose concentrations (about 17.5 mM).

Therapeutics Compositions

The herein-described transdifferentiation-inducing compounds, or ectopic pancreatic transcription factors (i.e., PDX-1, Pax-4, MafA, NeuroD1 or Sox-9 polypeptides, ribonucleic acids or nucleic acids encoding PDX-1, Pax-4, MafA, NeuroD1 or Sox-9 polypeptides) and the cells having a pancreatic beta cell phenotype produced by the methods disclosed here, when used therapeutically, are referred to herein as "Therapeutics". Methods of administration of Therapeutics include, but are not limited to, intradermal, intramuscular, intraperitoneal, intravenous, subcutaneous, intranasal, epidural, and oral routes. The Therapeutics of the disclosure presented herein may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local, e.g. through portal vein delivery to the liver. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant. Various delivery systems are known and can be used to administer a Therapeutic of the disclosure presented herein including, e.g.: (i) encapsulation in liposomes, microparticles, microcapsules; (ii) recombinant cells capable of expressing the Therapeutic; (iii) receptor-mediated endocytosis (See, e.g., Wu and Wu, 1987. J Biol Chem 262:4429-4432); (iv) construction of a Therapeutic nucleic acid as part of a retroviral, adenoviral or other vector, and the like. In one embodiment of the disclosure presented herein, the Therapeutic may be delivered in a vesicle, in particular a liposome. In a liposome, the protein of the disclosure presented herein is combined, in addition to other pharmaceutically acceptable carriers, with amphipathic agents such as lipids that exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028; and 4,737,323, all of which are incorporated herein by reference. In yet another embodiment, the Therapeutic can be delivered in a controlled release system including, e.g.: a delivery pump (See, e.g., Saudek, et al., 1989. New Engl J Med 321:574 and a semi-permeable polymeric material (See, e.g., Howard, et al., 1989. J Neurosurg 71:105). Additionally, the controlled release system can be placed in proximity of the therapeutic target (e.g., the brain), thus requiring only a fraction of the systemic dose. See, e.g., Goodson, In: Medical Applications of Controlled Release 1984. (CRC Press, Boca Raton, Fla.).

In one embodiment of the disclosure presented herein, where the Therapeutic is a nucleic acid encoding a protein, the Therapeutic nucleic acid may be administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., 1991. Proc Natl Acad Sci USA 88:1864-1868), and the like. Alternatively, a nucleic acid Therapeutic can be introduced intracellularly and incorporated within host cell DNA for expression, by homologous recombination or remain episomal.

In one embodiment, the Therapeutic is a cell having pancreatic beta cell phenotype produced by the methods disclosed here and, the Therapeutic is administered intravenously. Specifically, the Therapeutic can be delivered via a portal vein infusion.

A skilled artisan would appreciate that the term "therapeutically effective amount" may encompass total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

Suitable dosage ranges for intravenous administration of the Therapeutics of the disclosure presented herein are generally at least 1 million transdifferentiated cells, at least 2 million transdifferentiated cells, at least 5 million transdifferentiated cells, at least 10 million transdifferentiated cells, at least 25 million transdifferentiated cells, at least 50 million transdifferentiated cells, at least 100 million transdifferentiated cells, at least 200 million transdifferentiated cells, at least 300 million transdifferentiated cells, at least 400 million transdifferentiated cells, at least 500 million transdifferentiated cells, at least 600 million transdifferentiated cells, at least 700 million transdifferentiated cells, at least 800 million transdifferentiated cells, at least 900 million transdifferentiated cells, at least 1 billion transdifferentiated cells, at least 2 billion transdifferentiated cells, at least 3 billion transdifferentiated cells, at least 4 billion transdifferentiated cells, or at least 5 billion transdifferentiated cells. In one embodiment, the dose is 1-2 billion transdifferentiated cells into a 60-75 kg subject. One skilled in the art would appreciate that effective doses may be extrapolated from dose-response curves derived from in vitro or animal model test systems. In another embodiment, the effective dose may be administered intravenously into the liver portal vein.

Cells may also be cultured ex vivo in the presence of therapeutic agents, nucleic acids, or proteins of the disclosure presented herein in order to proliferate or to produce a desired effect on or activity in such cells. Treated cells can then be introduced in vivo via the administration routes described herein for therapeutic purposes.

Pharmaceutical Compositions

The compounds, e.g., PDX-1, Pax-4, MafA, NeuroD1, or Sox-9 polypeptides, nucleic acids encoding PDX-1, Pax-4, MafA, NeuroD1, or Sox-9 polypeptides, or a nucleic acid or compound that increases expression of a nucleic acid that encodes PDX-1, Pax-4, MafA, NeuroD1, or Sox-9 polypeptides (also referred to herein as "active compounds") and derivatives, fragments, analogs and homologs thereof and pancreatic beta cells produced by the methods disclosed here, can be incorporated into pharmaceutical compositions suitable for administration. Such compositions typically comprise the nucleic acid molecule, or protein, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition disclosed here is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms disclosed here are dictated by and directly dependent on the unique characteristics of the active compound and the particular therapeutic effect to be achieved.

The nucleic acid molecules disclosed here can be inserted into vectors and used as gene therapy vectors. Gene therapy vectors can be delivered to a subject by any of a number of routes, e.g., as described in U.S. Pat. No. 5,703,055. Delivery can thus also include, e.g., intravenous injection, local administration (see U.S. Pat. No. 5,328,470) or stereotactic injection (see e.g., Chen et al. (1994) PNAS 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Soluble Factors

In some embodiments, methods disclosed herein comprise manufacturing a transdifferentiated population of non-pancreatic human insulin producing cells, the method comprising the steps of: obtaining non-pancreatic human tissue; processing said tissue to recover primary human cells; propagating and expanding said human cells to a predetermined number of cells; transdifferentiating said expanded cells, wherein said transdifferentiating comprises incubating said expanded cells; and harvesting said transdifferentiated expanded cells, wherein said method comprises a step of adding a soluble factor either prior to or concurrent with the step of transdifferentiating said expanded cells.

In some embodiments, soluble factors comprise epigenetic modifiers.

In some embodiments, methods disclosed herein comprise manufacturing a population of human non-pancreatic β-cells comprising an enriched capacity for transcription factor induced transdifferentiation into a pancreatic β-cell phenotype and function, said method comprising the steps of (a) obtaining a population of primary human non-pancreatic β-cells; (b) propagating and expanding said human cells to a predetermined number of cells; (c) incubating said cells, said incubating comprising adding an at least one soluble factor to said cell population; and (d) collecting said cells; thereby manufacturing said population of cells comprising an enriched capacity for transcription factor induced transdifferentiation into a pancreatic β-cell phenotype and function.

Soluble factors, as described herein, including at Examples 21-23, promote pancreatic differentiation and reprogramming by inducing epigenetic modifications or altering signaling pathways. In some embodiments, the soluble factors suitable for use in the methods described herein include, without limitation, histone deacetylase inhibitors (HDACi), inhibitors of DNA methylation, TGF-β inhibitors, Rho kinase inhibitors (ROCK), thyroid hormones, TGF-β/Activin inhibitors, reagents that convert α-pancreatic cells to β-pancreatic cells, or any combination thereof.

In some embodiments, methods of manufacturing a transdifferentiated population of human non-pancreatic β-like insulin producing cells comprises a step of promoting β-cell transdifferentiation capacity of the cells by incubating them with factors that induce epigenetic alterations. In some embodiments, methods include the use of epigenetic modifiers and Wnt-pathway agonists.

The disclosure presented herein provides methods of manufacturing a transdifferentiated population of non-pancreatic human insulin producing cells, the method comprising the steps of: (a) obtaining non-pancreatic human tissue; (b) processing said tissue to recover primary human cells; (c) propagating and expanding said human cells to a predetermined number of cells; (d) transdifferentiating said expanded cells, wherein said transdifferentiating comprises incubating said expanded cells with histone deacetylase (HDAC) inhibitors (HDACi); and (e) harvesting said transdifferentiated expanded cells.

A skilled artisan would appreciate that chromatin is a complex comprising DNA wrapped around structural proteins. Chromatin undergoes morphological changes that tighten or loosen DNA structure, thus hindering or facilitating ribosomal access to DNA. DNA loci coding genes being transcribed are more loosely packaged. DNA loci coding inactive genes are more tightly packaged. Additionally, epigenetic modifications of structural proteins, as histones, alter local chromatin structure. In some embodiments, histones can be epigenetically modified by methylation, phosphorylation, acetylation, ubiquitylation, and sumoylation. Modifying enzymes involved in histone acetylation are called histone acetyltransferases (HAT), and enzymes removing those acetyl groups are called HDAC. In some embodiments, loosen chromatin organization is termed "non-condensed" or "permissive" chromatin organization. In some embodiments, a tighten chromatin organization is termed "condensed", "compact" or "repressive" chromatin organization.

In some embodiments, an HDACi comprises any compound capable of arresting the activity of HDAC, thus decreasing the removal of acetyl groups from the lysine residues in histones. In some embodiments, HDACi remodel the chromatin structure to a less compact structure. In some embodiments, remodeling the chromatin structure to a less compact structure affects gene expression. In some embodiments, HDACi facilitate the expression of pancreatic genes.

In some embodiments, an HDACi is selected from the group comprising: suberoylanilide hydroxamic acid (SAHA), sodium butyrate, Vorinostat, Entinostat, MS-275, Panobinostat, LBH589, Trichostatin A (TSA), Mocetinostat, MGCD0103, ACY-738, Chidamide, Tucidinostat, TMP195, ACY-241, Citarinostat, PXD101, Belinostat, FK228, Romidepsin, MC1568, Tubastatin A HCl, ITF2357, Givinostat, LAQ824, Dacinostat, CUDC-101, Quisinostat, JNJ-26481585, Pracinostat, SB939, PCI-34051, Droxinostat, Abexinostat, PCI-24781, RGFP966, AR-42, Ricolinostat, ACY-1215, Valproic acid sodium salt, Sodium valproate, Tacedinaline, CI994, CUDC-907, Sodium butyrate (SB), Curcumin, M344, Tubacin, RG2833, RGFP109, Resminostat, Divalproex Sodium, Scriptaid, Sodium phenylbutyrate, Tubastatin A, TMP269, CAY10683, Santacruzamate A, Tasquinimod, BRD73954, Splitomicin, HPOB, LMK-235, Nexturastat A, ITSA1, (−)-Parthenolide, CAY10603, 4SC-202, BG45, PXD-101, Depsipeptide, and FK228. In some embodiments, cells are incubated with 2 or more HDACi.

In some embodiments, methods disclosed herein comprise incubating a population of primary human cells with a HDACi and contacting said cells with pancreatic transcription factors simultaneously. In some embodiments, a population of primary human cells is incubated with a HDACi before being contacted with pancreatic transcription factors. In some embodiments, a population of primary human cells is incubated with a HDACi after being contacted with pancreatic transcription factors.

In some embodiments, methods described herein comprise a step of adding at least one soluble factor comprising addition either prior to incubation with a Wnt-pathway agonist, or addition prior to a transdifferentiation step, concurrent with a transdifferentiation step, or addition follow a transdifferentiation step. In some embodiments, the step of adding an at least one soluble factor to cells may be at the same time as pre-incubation with a Wnt-pathway agonist. In some embodiments, the step of adding an at least one soluble factor to cells comprises multiple additions of the same soluble factor at the same or different time points. In some embodiments, the step of adding an at least one soluble factor to cells comprises multiple additions of different soluble factors at the same or different time points.

In some embodiments, a population of primary human cells is incubated with a HDACi compound and with a Wnt-pathway agonist simultaneously. In some embodiments, a population of primary human cells is incubated with a HDACi and afterwards with a Wnt-pathway agonist. In some embodiments, a population of primary human cells is incubated with a HDACi before being incubated with a Wnt-pathway agonist. In some embodiments, the Wnt-pathway agonist is selected from the group comprising: Lithium (Li), WAY-316606, (hetero)arylpyrimidines, IQ1, QS11, SB-216763, SB-216763, BIO(6-bromoindirubin-β'-oxime), DCA, Wnt9, Wnt3A, and 2-amino-4-[3,4-(methylenedioxy)benzyl-amino]-6-(3-methoxyphenyl)pyrimidine.

In some embodiments, a Wnt-pathway agonist comprises a GSK3b antagonist. In some embodiments, a GSK3b antagonist comprises lithium (Li).

In some embodiments, the Wnt-pathway agonist comprises Li. In some embodiments, a population of primary human cells is incubated with Li for 48 hours prior to being contacted with pancreatic transcription factors. In some embodiments, Li is supplemented to the cell medium in a 0.1-1 mM concentration. In some embodiments, Li is supplemented to the cell medium in a 1-10 mM concentration. In some embodiments, Li is supplemented to the cell medium in a 10-100 mM concentration. In some embodiments, Li is supplemented to the cell medium in a 100-1000 mM concentration. In some embodiments, Li is supplemented to the cell medium in a 1-10 M concentration. In some embodiments, Li is supplemented to the cell medium in a 10 mM concentration. In some embodiments, a population of primary human cells is incubated with Li and with SAHA simultaneously.

In some embodiments, a HDACi compound comprises SAHA. In some embodiments, SAHA is supplemented to the cell medium in a concentration of 0.01-0.1 µM. In some embodiments, SAHA is supplemented to the cell medium in a concentration of 0.1-1 µM. In some embodiments, SAHA is supplemented to the cell medium in a concentration of 1-10 µM. In some embodiments, SAHA is supplemented to the cell medium in a concentration of 10-100 µM. In some embodiments, SAHA is supplemented to the cell medium in a concentration of 100-1000 µM. In some embodiments, SAHA is supplemented to the cell medium in a concentration of 1 mM.

In some embodiments, a population of primary human cells comprises cells resistant to transdifferentiation.

In some embodiments, provided herein is a method of converting cells resistant to transdifferentiation into cells competent for transdifferentiation. In some embodiments, said method comprises incubating cells resistant to transdifferentiation with a HDACi. In some embodiments, said method comprises incubating cells resistant to transdifferentiation with SAHA. In some embodiments, said method comprises incubating cells resistant to transdifferentiation with a Wnt pathway agonist.

In some embodiments, cells resistant to transdifferentiation comprise cells that cannot be transdifferentiated by being contacted with transcription factors. In some embodiments, cells resistant to transdifferentiation comprise cells that cannot be transdifferentiated to insulin producing cells by being contacted with pancreatic transcription factors. In some embodiments, cells resistant to transdifferentiation comprise a population of cells in which less than 20% of the cells are transdifferentiated to insulin producing cells by being contacted with pancreatic transcription factors. In some embodiments, cells resistant to transdifferentiation comprise a population of cells in which less than 10% of the cells are transdifferentiated to insulin producing cells by being contacted with pancreatic transcription factors. In some embodiments, cells resistant to transdifferentiation comprise a population of cells in which less than 5% of the cells are transdifferentiated to insulin producing cells by being contacted with pancreatic transcription factors. In some embodiments, cells resistant to transdifferentiation comprise a population of cells in which less than 1% of the cells are transdifferentiated to insulin producing cells by being contacted with pancreatic transcription factors. In some embodiments, cells resistant to transdifferentiation comprise cells with an inactive Wnt pathway.

In some embodiments, cells competent for transdifferentiation comprise cells that can be transdifferentiated by being contacted with transcription factors. In some embodiments cells competent for transdifferentiation comprise cells with a permissive epigenetic configuration that allows expression of pancreatic genes. In some embodiments cells competent for transdifferentiation comprise cells that can be transdifferentiated to insulin producing cells by being contacted with pancreatic transcription factors. In some embodiments, cells competent for transdifferentiation comprise a population of cells in which at least 20% of the cells are transdifferentiated to insulin producing cells when contacted with pancreatic transcription factors. In some embodiments, cells competent for transdifferentiation comprise a population of cells in which at least 40% of the cells are transdifferentiated to insulin producing cells when contacted with pancreatic transcription factors. In some embodiments, cells competent for transdifferentiation comprise a population of cells in which at least 60% of the cells are transdifferentiated to insulin producing cells when contacted with pancreatic transcription factors. In some embodiments, cells competent for transdifferentiation comprise a population of cells in which at least 80% of the cells are transdifferentiated to insulin producing cells when contacted with pancreatic transcription factors. In some embodiments cells competent for transdifferentiation comprise cells with an activated Wnt pathway.

In some embodiments, the inhibitor of DNA methylation comprises 5-Aza-2-deoxycitidine (5-AZA). In some embodiments, the TGF-β inhibitor comprises SB431542 (SB). In some embodiments, the Rho kinase inhibitor comprises Y27632 (Y2). In some embodiments, the thyroid hormone comprises T3. In some embodiments, the TGF-β/Activin inhibitor comprises Alk5i II. In some embodiments, the pancreatic transcription factor comprises PAX4, PAX6, ILS-1, NGN3, NKX6.1, RFX6, or FOXA2.

In some embodiments, the pancreatic transcription factor comprises PAX4. In some embodiments, the pancreatic transcription factor comprises PAX6. In some embodiments, the pancreatic transcription factor comprises ILS-1. In some embodiments, the pancreatic transcription factor comprises NGN3. In some embodiments, the pancreatic transcription factor comprises NKX6.1. In some embodiments, the pancreatic transcription factor comprises RFX6. In some embodiments, the pancreatic transcription factor comprises FOXA2.

In some embodiments, the reagent that converts α-pancreatic cells to β-pancreatic cells comprises GABA.

Histone deacetylase inhibitors (HDACi), including suberanilohydroxamic acid (SAHA), romidepsin, chidamide, panobinostat, or belinostat, and others suitable for use in the disclosed methods are described herein.

DNA methylation is a common epigenetic mechanism cells use to turn off gene expression and is a process by which methyl groups are added to the DNA molecule. Methylation can change the activity of a DNA segment without changing the sequence. Abnormal methylation has been implicated in various human diseases. DNA methyiation is catalyzed by DNA methyltransferases (DN MeTs) and involves the addition of a methyl group to the 5-carbon of the cytosine ring, which results in 5-methyicytosine or 5-mC. Inhibitors of DNA methylation include 5-Aza-2-deoxycitidine (5-AZA) and 5-azacytosine.

Transforming growth factor-β (TGF-β) regulates cell growth and differentiation, apoptosis, cell motility, extracellular matrix production, angiogenesis, and cellular immunity. SB431542 (SB) inhibits TGF3-induced proliferation of human osteosarcoma cells, enhances growth and integrity of embryonic stem cell-derived endothelial cells, and is a frequently used agent employed in numerous stem cell differentiation protocols. TGFβ receptor signaling may improve the outcome of human islet transplantation, seemingly through increasing β-cell number and function. Other inhibitors of TGF-0 suitable for use in the methods described herein include, without limitation, RepSox, SD 208, A 83-01, LY 364947, D 4476, SB 525334, SB505124, GW 788388, R 268712, and IN 1130.

Rho kinase inhibitors (rho-associated protein kinase inhibitor or ROCK inhibitor) are a series of compounds that target rho kinase (ROCK: Rho-associated coiled coil forming protein serine/threonine kinase). Rho-kinase has various functions, including the regulation of cellular contraction, motility, morphology, polarity, cell division, and gene expression. Pharmacological analyses have revealed that Rho-kinase is involved in a wide range of diseases and is therefore considered to be a potential therapeutic target. Y27632 (Y2) is a rho kinase inhibitor suitable for use in the methods described herein. Other suitable rho kinase inhibitors include, without limitation, Fasudil, Ripasudil, RKI-1447, GSK429286A, and Y-30141.

Thyroid hormones affect protein synthesis and regulate a number of developmental, metabolic, and neural activities throughout the body. The thyroid gland synthesizes 2 hormones. The 2 main hormones secreted by the thyroid gland are thyroxine, which contains 4 atoms of iodine (T4), and triiodothyronine (T3). T3 is a thyroid hormone that affects almost every physiological process in the body, including growth and development, metabolism, body temperature, and heart rate.

TGF-β, a pleiotropic polypeptide described above, regulates multiple biological processes, including embryonic development, adult stem cell differentiation, immune regulation, wound healing, and inflammation. It transduces its signal through the ALK5 ser/thr kinase receptor, and increases transcription of different genes, including PAI-1 and collagens. Activin A is a member of the TGF-0 family of proteins produced by many cell types throughout development. It is a disulfide-linked homodimer (two beta-A chains) that binds to heteromeric complexes of a type I (Act RI-A and Act RI-B) and a type II (Act RII-A and Act RII-B) serine-threonine kinase receptor (Attisano et al.). Activins primarily signal through SMAD2/3 proteins to regulate a variety of functions, including cell proliferation, differentiation, wound healing, apoptosis, and metabolism. Activin A maintains the undifferentiated state of human embryonic stem cells and facilitates differentiation of human embryonic stem cells into definitive endoderm. In embodiments, the TGF-β/Activin inhibitor comprises Alk5i II. Other TGF-β/Activin inhibitors suitable for use in the methods described herein include, without limitation.

Although pancreatic transcription factors (pTF) are not considered soluble factors, cells may be incubated with additional pTF for improved transdifferentiation (TD).

Pancreatic transcription factors (pTF), including Pax4 (Paired box protein Pax-4), and others suitable for use in the disclosed methods including but not limited to FOXA2, NGN3, PAX6, NKX 6.1, ARX anti-sense or knock down, may be used as an additional pTF. Use of the pTF Pax4 is described as a representative example in detail herein. In addition to the uses of pTFs as described in methods disclosed herein, pTF also can be used as a soluble factor in some embodiments. As described herein, pancreatic transcription factors may be encoded by a nucleic acid sequence, wherein a vector comprising said pTF may be brought into contact with a cell to allow uptake of said vector comprising the pTF, for example but not limited to Pax4. In some embodiments, a Pax4 polypeptide may be brought into contact with a cell to allow uptake of said Pax4 pTF.

Pancreatic α- and β-cells are normally very stable: the cells live for a year or more, and when they divide, α-cells make α-cells and β-cells make β-cells. However, various types of damage to the pancreas and other internal organs can cause unexpected changes in cell type.

Pancreatic islet β-cells produce large amounts of γ-aminobutyric acid (GABA), which is co-released with insulin. GABA inhibits glucagon secretion by hyperpolarizing α-cells via type-A GABA receptors ($GABA_ARs$). GABA exerts protective and regenerative effects on islet beta cells and can induce the conversion of α-cells to β-cells.

In some embodiments, a Wnt-pathway agonist pre-incubation occurs 24 hours prior to a step of transdifferentiation. In some embodiments, a Wnt-pathway agonist pre-incubation occurs 48 hours prior to a step of transdifferentiation. In some embodiments, a Wnt-pathway agonist pre-incubation occurs 72 hours prior to a step of transdifferentiation.

In some embodiments, addition of at least one soluble factor occurs 24 hours prior to a step of transdifferentiation. In some embodiments, addition of at least one soluble factor occurs 48 hours prior to a step of transdifferentiation. In some embodiments, addition of at least one soluble factor occurs 72 hours prior to a step of transdifferentiation.

In some embodiments, addition of at least one soluble factor occurs after a step of transdifferentiation.

In one embodiment, transdifferentiation comprises any method of transdifferentiation disclosed herein. For example, transdifferentiation may comprise a hierarchy (1+1+1) protocol or a "2+1" protocol, as disclosed herein.

In some embodiments, methods disclosed herein comprise a step of adding one or more soluble factors either prior to or concurrent with the step of transdifferentiation. In some embodiments, the soluble factor or factors may be added prior to the step of transdifferentiation. In some embodiments, the soluble factor or factors may be added concurrent with transdifferentiation. In some embodiments, when the soluble factor or factors are added concurrent with transdifferentiation they are added at the same time as PDX-1 in the hierarchy (1+1+1) protocol. In some embodiments, when the soluble factor or factors are added concurrent with transdifferentiation they are added at the same time as NeuroD in the hierarchy (1+1+1) protocol. In some embodiments, when the soluble factor or factors are added concurrent with transdifferentiation they are added at the same time as MafA in the hierarchy (1+1+1) protocol. In some embodiments, when the soluble factor or factors are added concurrent with transdifferentiation they are added at the same time as PDX-1 and NeuroD1 in the 2+1 protocol. In some embodiments, when the soluble factor or factors are added concurrent with transdifferentiation they are added at the same time as MafA in the 2+1 protocol.

In some embodiments, an inhibitor of DNA methylation is added prior to transdifferentiation. In some embodiments, the inhibitor of DNA methylation added prior to transdifferentiation comprises 5-Aza-2-deoxycitidine (5-AZA). In some embodiments, 5-AZA is supplemented to the cell medium in a concentration of 0.5 µM. In some embodiments, 5-AZA is supplemented to the cell medium in a concentration of 0.05-0.5 µM. In some embodiments, 5-AZA is supplemented to the cell medium in a concentration of 0.5-5 µM.

In some embodiments, a histone deacetylase inhibitor (HDACi) is added prior to transdifferentiation. In some embodiments, the HDACi added prior to transdifferentiation comprises SAHA. In some embodiments, SAHA is supplemented to the cell medium in a concentration of 0.5 µM. In some embodiments, SAHA is supplemented to the cell medium in a concentration of 0.05-0.5 µM. In some embodiments, SAHA is supplemented to the cell medium in a concentration of 0.5-5 µM.

In some embodiments, a TGF-β inhibitor is added prior to transdifferentiation. In some embodiments, the TGF-β inhibitor added prior to transdifferentiation comprises SB431542 (SB). In some embodiments, SB is supplemented to the cell medium in a concentration of 10 µM. In some embodiments, SB is supplemented to the cell medium in a concentration of 1-10 µM. In some embodiments, SB is supplemented to the cell medium in a concentration of 10-100 µM.

In some embodiments, a Rho kinase inhibitor (ROCK) is added prior to transdifferentiation. In some embodiments, the Rho kinase inhibitor (ROCK) added prior to transdifferentiation comprises Y27632(Y2). In some embodiments, Y2 is supplemented to the cell medium in a concentration of 2 µM. In some embodiments, Y2 is supplemented to the cell medium in a concentration of 0.2-2 µM. In some embodiments, SB is supplemented to the cell medium in a concentration of 2-20 µM.

In some embodiments, a thyroid hormone is added concurrent with transdifferentiation. In some embodiments, the thyroid hormone added concurrent with transdifferentiation comprises T3. In some embodiments, T3 is supplemented to the cell medium in a concentration of 1 µM. In some embodiments, T3 is supplemented to the cell medium in a concentration of 0.1-1 µM. In some embodiments, T3 is supplemented to the cell medium in a concentration of 1-10 µM.

In some embodiments, a TGF-β/Activin inhibitor is added concurrent with transdifferentiation. In some embodiments, the TGF-β/Activin inhibitor added concurrent with transdifferentiation comprises Alk5iII. In some embodiments, Alk5iII is supplemented to the cell medium in a concentration of 10 µM. In some embodiments, Alk5iII is supplemented to the cell medium in a concentration of 1-10 µM. In some embodiments, Alk5iII is supplemented to the cell medium in a concentration of 10-100 µM.

In some embodiments, a pancreatic transcription factor (pTF) is added concurrent with transdifferentiation. In some embodiments, the pTF added concurrent with transdifferentiation comprises Pax4 (Ad-Pax4-Pax4 comprised within a Adenoviral vector). In some embodiments, Pax4 (Ad-Pax4) is supplemented to the cell medium in a concentration of 250 moi. In some embodiments, Pax4 (Ad-Pax4) is supplemented to the cell medium in a concentration of 25-250 moi.

In some embodiments, Pax4 (Ad-Pax4) is supplemented to the cell medium in a concentration of 250-2500 moi.

In some embodiments, a reagent that converts α-pancreatic cells to β-pancreatic cells is added concurrent with transdifferentiation. In some embodiments, the reagent that converts α-pancreatic cells to β-pancreatic cells added concurrent with transdifferentiation comprises GABA. In some embodiments, GABA is supplemented to the cell medium in a concentration of 0.5 µM. In some embodiments, GABA is supplemented to the cell medium in a concentration of 0.05-0.5 µM. In some embodiments, GABA is supplemented to the cell medium in a concentration of 0.5-5 µM.

In an embodiment, transdifferentiating comprises adding a first two pTFs to the cells followed by adding a third pTF to the cells in accordance with the "2+1" protocols described herein. In an embodiment, the first two pTFs comprise Ad-PDX-1 and Ad-NeuroD1. In an embodiment, the third pTF comprises Ad-MAFA. In an embodiment, soluble factors are added to the cells prior to the adding a first two pTFs. In an embodiment, the soluble factors added prior to the adding the first two pTFs comprise 5-AZA, SAHA, SB, and Y2. In an embodiment the soluble factors are added 72 hours prior to the adding the first two pTFs. In an embodiment the soluble factors are added 24 hours prior to the adding the first two pTFs. In an embodiment the soluble factors are added 40 hours prior to the adding the first two pTFs. In an embodiment, soluble factors are added to the cells concurrent with the third pTF. In an embodiment, the soluble factors added to the cells concurrent with the third pTF comprise T3, GABA, Alk5i II, and Ad-PAX4. In an embodiment, the third pTF and the soluble factors added concurrent with the third pTF are added 48 hours after addition of the first two pTFs.

In some embodiments, adding soluble factors concurrently with the transdifferentiating step comprises adding the soluble factors concurrently with all pTFs. In some embodiments wherein transdifferentiating comprises adding pTFs in accordance with a "2+1" protocol, soluble factors are added concurrently with a first two pTFs. In some embodiments wherein transdifferentiating comprises adding pTFs in accordance with a "2+1" protocol described herein, soluble factors are added concurrently with the third pTF. In some embodiments wherein transdifferentiating comprises adding pTFs in accordance with a "2+1" protocol, soluble factors are added concurrently with the first two pTFs and soluble factors are added concurrently with the third pTF.

In some embodiments wherein transdifferentiating comprises adding pTFs in accordance with a "1+1+1" protocol described herein, soluble factors are added concurrently with a first pTF. In some embodiments wherein transdifferentiating comprises adding pTFs in accordance with a "1+1+1" protocol described herein, soluble factors are added concurrently with a second pTF. In some embodiments wherein transdifferentiating comprises adding pTFs in accordance with a "1+1+1" protocol described herein, soluble factors are added concurrently with a third pTF. In some embodiments wherein transdifferentiating comprises adding pTFs in accordance with a "1+1+1" protocol described herein, soluble factors are added concurrently with a first and second pTF. In some embodiments wherein transdifferentiating comprises adding pTFs in accordance with a "1+1+1" protocol described herein, soluble factors are added concurrently with a first and third pTF. In some embodiments wherein transdifferentiating comprises adding pTFs in accordance with a "1+1+1" protocol described herein, soluble factors are added concurrently with a second and third pTF. In some embodiments wherein transdifferentiating comprises adding pTFs in accordance with a "1+1+1" protocol described herein, soluble factors are added concurrently with a first and a second and a third pTF.

It should be understood that the disclosure presented herein is not limited to the particular methodologies, protocols and reagents, and examples described herein. The terminology and examples used herein is for the purpose of describing particular embodiments only, for the intent and purpose of providing guidance to the skilled artisan, and is not intended to limit the scope of the disclosure presented herein.

EXAMPLES

General Methods for Examples 1-13

Human Liver Cells

Adult human liver tissues were obtained from individuals 3-23 years old or older. Liver tissues were used with the approval from the Committee on Clinical Investigations (the institutional review board). The isolation of human liver cells was performed as described (Sapir et al, (2005) Proc Natl Acad Sci USA 102: 7964-7969; Meivar-Levy et al, (2007) Hepatology 46: 898-905). The cells were cultured in Dulbecco's minimal essential medium (1 g/l of glucose) supplemented with 10% fetal calf serum, 100 units/ml penicillin; 100 ng/ml streptomycin; 250 ng/ml amphotericin B (*Biological Industries*, Beit Haemek, Israel), and kept at 37° C. in a humidified atmosphere of 5% $CO_2$ and 95% air.

Viral Infection

The adenoviruses used in this study were as follows: Ad-CMV-Pdx-1 (Sapir et al, 2005 ibid; Meivar-Levy et al, 2007 ibid), Ad-RIP-luciferase (Seijffers et al, (1999) Endocrinology 140: 3311-3317), Ad-CMV-β-Gal, Ad-CMV-MafA (generous gift from Newgard, C. B., Duke University), Ad-CMV-Pax4-IRES-GFP (generous gift from St Onge, L. DeveloGen AG, Gittingen, Germany), and Ad-CMV-Isl1 (generous gift from Kieffer, T. University of British Columbia, Vancouver, Canada). The viral particles were generated by the standard protocol (He et al, (1998) Proc Natl Acad Sci USA 95: 2509-2514).

Liver cells were infected with recombinant adenoviruses for 5-6 days (Table 1) supplemented with EGF (20 ng/ml; Cytolab, Ltd., Israel) and nicotinamide (10 mM; Sigma). The optimal multiplicity of infection (MOI) was determined according to cell survival (<75%) and induction of C-peptide secretion. The MOI of the viruses used were; Ad-CMV-Pdx-1 (1000 MOI), Ad-CMV-Pax4-IRES-GFP (100 MOI), Ad-CMV-MafA (10 MOI) and Ad-CMV-Isl1(100 MOI).

RNA Isolation, RT and RT-PCR Reactions

Total RNA was isolated and cDNA was prepared and amplified, as described previously (Ber et al, (2003) J Biol Chem 278: 31950-31957; Sapir et al, (2005) ibid). Quantitative real-time RT-PCR was performed using ABI Step one plus sequence Detection system (Applied Biosystems, CA, USA), as described previously (Sapir et al, (2005) ibid; Meivar-Levy et al, (2007) ibid; Aviv et al, (2009) J Biol Chem 284: 33509-33520).

C-Peptide and Insulin Secretion Detection

C-peptide and insulin secretion were measured by static incubations of primary cultures of adult liver cells 6 days after the initial exposure to the viral treatment, as described (Sapir et al, (2005) ibid; Meivar-Levy et al, (2007) ibid; Aviv et al, (2009) ibid). The glucose-regulated C-peptide secretion was measured at 2 mM and 17.5 mM glucose, which was determined by dose-dependent analyses to maximally induce insulin secretion from transdifferentiated liver cells, without having adverse effects on treated cells function (Sapir et al, (2005) ibid; Meivar-Levy et al, (2007) ibid; Aviv et al, (2009) ibid). C-peptide secretion was detected by radioimmunoassay using the human C-peptide radioimmunoassay kit (Linco Research, St. Charles, Mo.; <4% cross-reactivity to human proinsulin). Insulin secretion was detected by radioimmunoassay using human insulin radioimmunoassay kit (DPC, Angeles, Calif.; 32% cross-reactivity to human proinsulin). The secretion was normalized to the total cellular protein measured by a Bio-Rad protein assay kit.

Luciferase Assay

Human liver cells were co-infected with Ad-RIP-luciferase (200 moi) and the various adenoviruses (as described below). Six days later, luciferase activity was measured using the Luciferase assay System (Promega) and the LKB 1250 Luminometer (LKB, Finland). The results were normalized to total cellular protein measured by the Bio-Rad Protein Assay kit (Bio-Rad).

Immunofluorescence

Human liver cells treated with the various adenoviruses, were plated on glass cover slides in 12-well culture plates ($2\times10^5$ cells/well). 3-4 days later, the cells were fixed and stained as described (Sapir et al, (2005) ibid; Meivar-Levy et al, (2007) ibid; Aviv et al, (2009) ibid). The antibodies used in this study were: anti-rabbit PDX-1, anti-goat PDX-1 (both 1:1000 a generous gift from C.V. E. Wright), anti-human insulin, anti-human somatostatin (both 1:100, Dako, Glostrup, Denmark), anti-Pax4 (1:100; R&D Systems, Minneapolis, Minn.), anti-MafA (1:160; Santa Cruz Biotechnology, Inc., Santa Cruz, Calif.). The secondary antibodies used were: anti-rabbit IgG Cyanine (cy2) conjugated antibody 1:250, anti-rabbit IgG indocarbocyanine (cy3) conjugated antibody 1:250, anti-goat IgG Cyanine (cy2) conjugated antibody 1:200, anti-goat IgG indocarbocyanine (cy3) conjugated antibody 1:250, and anti-mouse IgG indocarbocyanine (cy3) conjugated antibody 1:250 (all from *Jackson ImmunoResearch*, PA). Finally, the cells were stained with 4', 6-diamidino-2-phenyl-indole (DAPI, Sigma). The slides were imaged and analyzed using a fluorescent microscope (Provis, Olympus).

Purity Assays

A flow cytometry based assay has been developed as the principal purity assay to ensure that more than 90% of the cells during expansion and transdifferentiation have a mesenchymal stem cell (MSC) like phenotype. Cultivated MSCs should stain positive for CD73, CD90, CD105 and CD44 and should be negative for CD45, CD34, CD14 or CD11b, CD19 or CD79a, and HLA-DR surface molecules.

Figure 34A:
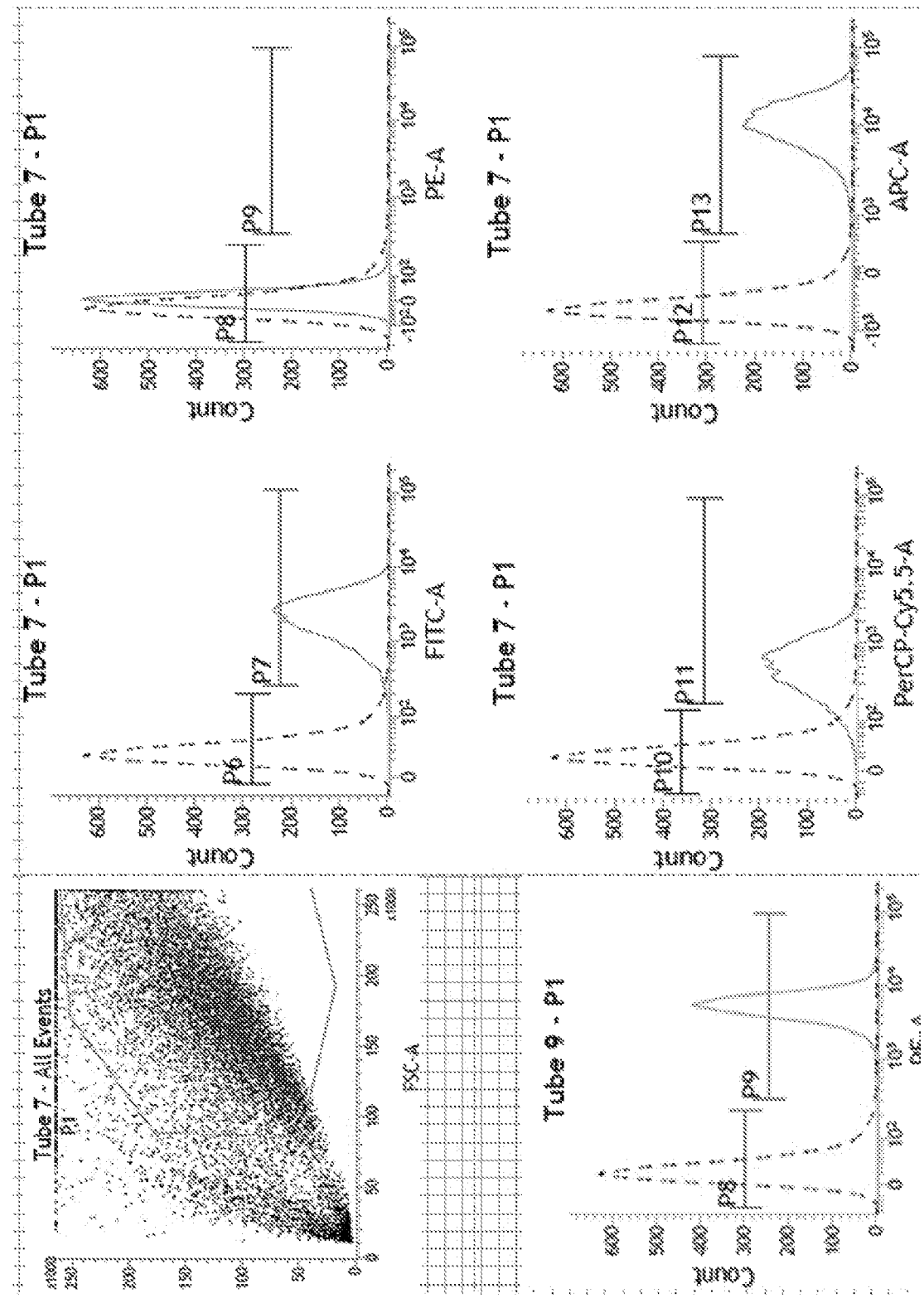
FIGS. 34A-34B show the results of flow cytometry analysis of expanded and transdifferentiated liver cells.
Figures 34B, 35A:
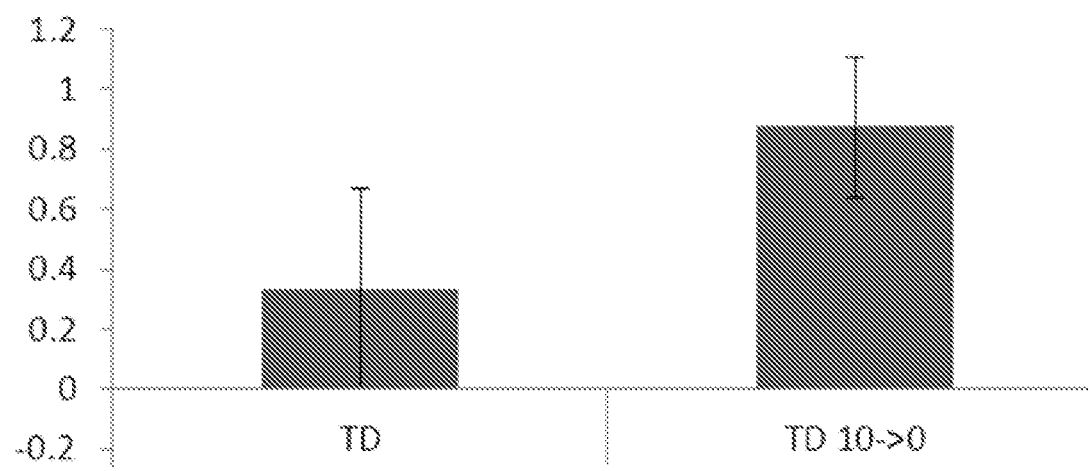
FIGS. 35A-35C shows pre-existing WNT/β-catenin signal disposes cells to efficient transdifferentiation. WNT signaling was induced by Li for 48 hours prior to transdifferentiation, which was then removed (Li day −2) or maintained (Li day −2 onward) throughout the transdifferentiation protocol.

As shown in FIGS. 34A and 34B (below), expanded liver cells and infected cells expressed CD90, CD44, CD105 and CD73 markers at high levels (≥90%) while they did not express lineage negative markers (cocktail of CD34, CD11b, CD45, CD19 and HLA-DR). To note, CD105 expression was slightly decreased in infected cells at P16 compared to non-infected cells at P14. Additional experiments are needed to understand if this decrease is significant and if it decreases with passage numbers or with transdifferentiation. These results demonstrate that MSC markers were stable over time and during transdifferentiation of liver cells. Flow cytometry for MSC markers may be indeed used as a QC test.

Statistical Analysis

Statistical analyses were performed with a 2-sample Student t-test assuming unequal variances.

Example 1: Maturation and Segregation into the Different Hormones Producing Cells of Transdifferentiated Cells is Temporally Controlled in an Hierarchical Manner In this example, the impact of temporally controlling the ectopic pancreatic transcription factors (pTFs) expression was investigated to determine whether increased transdifferentiation efficiency by combined ectopic expression of the three pTFs is also temporally controlled as suggested above (FIGS. 1A-1D). In support of temporal control having a role in pancreas transdifferentiation, the three pTFs Pdx-1, Pax4, and MafA display distinct temporal expression and function during pancreas organogenesis.

The three pTFs PDX-1, Pax4, and MafA were introduced sequentially or in concert to primary cultures of adult human liver cells using recombinant adenoviruses. Adenovirus-mediated ectopic gene expression peaks 17 hours post infection. Therefore, the pTFs were sequentially administered during three consecutive days, allowing the manifestation of their individual effects. Cells were infected according to the schedule as displayed in Table 1.

TABLE 1

| Treatment order | Day 1 | Day 2 | Day 3 | Day 4 | Day 5 | Day 6 |
|---|---|---|---|---|---|---|
| A | Ad-β-gal (control) | | | | | Harvest |
| B | Ad-Pdx-1 + Ad-Pax4 + Ad-MafA | | | | | Harvest |
| C | Ad-Pdx-1 | Ad-Pax4 | Ad-MafA | | | Harvest |
| D | Ad-MafA | Ad-Pax4 | Ad-Pdx-1 | | | Harvest |
| E | Ad-Pdx1 | Ad-MafA | Ad-Pax4 | | | Harvest |

Cells were sequentially infected with one pTF adenoviral construct per day over three days in three different sequences: a direct hierarchical order (treatment C=Pdx-1→Pax4→MafA), in an opposite order (treatment D=MafA→Pax4→Pdx-1), and in a random order (treatment E=Pdx-1→MafA→Pax4). The effect of the sequential pTFs administration on transdifferentiation efficiency and on the β-cell-like maturation was compared to that of the concerted or simultaneous administration of all three pTFs on the first day (treatment B=Pdx-1+Pax4+MafA) and to similar MOI of control virus (treatment A=β-gal) (Table 1 and FIG. 2A). Specifically, cultured adult human liver cells were infected with Ad-CMV-Pdx-1(1000 MOI), Ad-CMV-Pax-4 (100 MOI) and Ad-CMV-MafA (10 MOI) together or in a sequential manner as summarized in FIG. 2A and Table 1 (treatments B-E) or with control virus (Ad-CMV-β-gal, 1000 moi, treatment A), and analyzed for their pancreatic differentiation six days later.

Figure 3C:
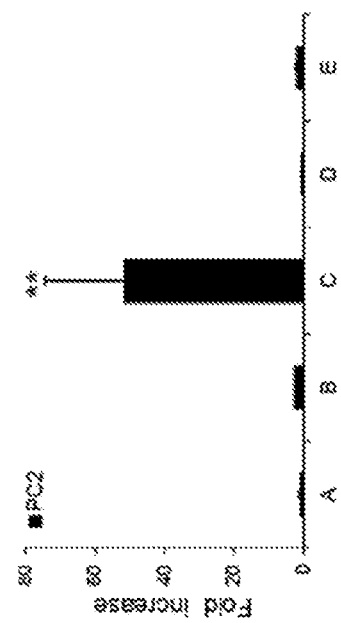
Figure 3B:
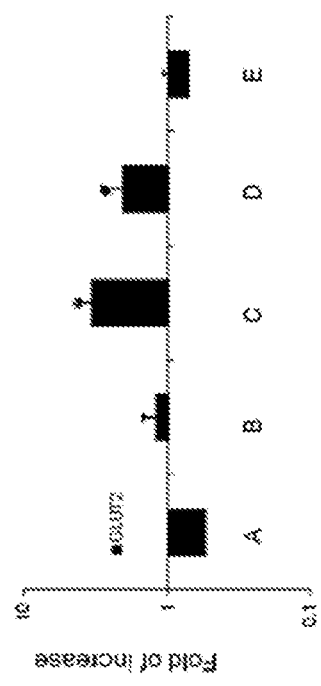

Insulin promoter activity (FIG. 3A), the percent of insulin producing cells (FIG. 2B) and glucose-regulated (pro)insulin secretion (FIG. 2C) were unaffected by the order of the sequentially administered pTFs. Interestingly, the levels of glucose regulated C-peptide secretion and PC2 expression were significantly increased in treatment C (FIG. 2D and FIG. 3C) Interestingly, the sequential pTF administration in the random order (treatment E=Pdx-1-MafA-Pax4) resulted in increased insulin promoter activity but was associated with loss of glucose regulation of insulin secretion and decreased glucose transporter 2 (GLUT-2) expression (FIGS. 2B, 2C and 3B). Loss of glucose sensing ability upon changing the order of Pax4 and MafA administration suggests a potential effect of the sequence of expressed pTFs on β-cell-like maturation but not on the efficiency of the transdifferentiation process.

Example 2: PDX-1, Pax4 and Mafa Hierarchical Administration Induces Glucagon and Somatostatin Expression Transdifferentiation along the endocrine pancreatic lineage results in the activation of expression of numerous pancreatic hormones. The extent with which these hormone expression levels are affected by the temporal manipulation of the pTFs was also investigated. Gene expression of pancreatic hormones glucagon (GCG) (FIGS. 4A and 4B), somatostatin (SST) (FIGS. 4A, 4D, and 4E) or cells specific transcription factors (FIG. 4C) were determined by quantitative real-time PCR analysis after the indicated treatments.

The transcription of both glucagon (GCG) and somatostatin (SST) genes was induced by each of the individually expressed pTFs, mainly by Pdx-1 and MafA and to a lower extent by Pax4 (FIG. 4A). A further increase in glucagon gene transcription occurred only upon the direct hierarchical administration of pTFs (FIG. 5, see treatment C of Table 1). Pdx-1 and MafA exerted their effects on glucagon expression in a process associated with the activation of the □-cell specific transcription factors ARX and BRAIN4 or ARX alone, respectively (FIG. 4C). Somatostatin gene expression that remained unaffected by most treatments (FIGS. 4A and 4D), was increased when the temporal protocol was concluded by ectopic Pax4 expression (E=Pdx-1→MafA→Pax4). This sequential protocol also exhibited a deteriorative effect on glucose-regulated (pro)insulin secretion and was associated by increased Isl1 endogenous expression (FIGS. 2C and 2E). The ablated maturation along the β cell lineage was associated with increased somatostatin gene expression and an increased number of somatostatin positive cells (FIG. 4F). Many of the cells exhibited somatostatin and insulin co-localization (data not shown).

Exclusion of each pTF from the hierarchical administration (treatment C) was also utilized to further investigate the role of the individual pTFs in glucagon and somatostatin expression (FIGS. 1B and 1D). Pax4 exclusion substantially reduced somatostatin gene expression, suggesting its potential role in inducing the transcription of this gene (FIG. 1D). Interestingly, MafA exclusion at the end of the developmental process also substantially increased somatostatin gene expression, suggesting a potential inhibitory effect of MafA on somatostatin gene expression. This effect could be also attributed to MafA's capacity to repress Isl1 expression. To address this hypothesis, the effect of ectopic Isl1 on somatostatin gene expression was analyzed. Indeed, Ad-Isl1 administration on the third day together with MafA (C+Isl1) increased somatostatin gene expression (FIG. 1E), while decreasing insulin gene expression, hormone production and secretion (FIGS. 1A, 1B and FIG. 6A-6C). Under these experimental conditions, 40% of the insulin producing cells stained positive for somatostatin with very few cells expressing somatostatin alone.

These results suggest that part of the maturation of transdifferentiated cells to β-cells is attributed to MafA expression at the late stages of the transdifferentiation process. At this stage, MafA restricts somatostatin expression in a process associated with its capacity to inhibit Isl1 expression.

Figure 7:
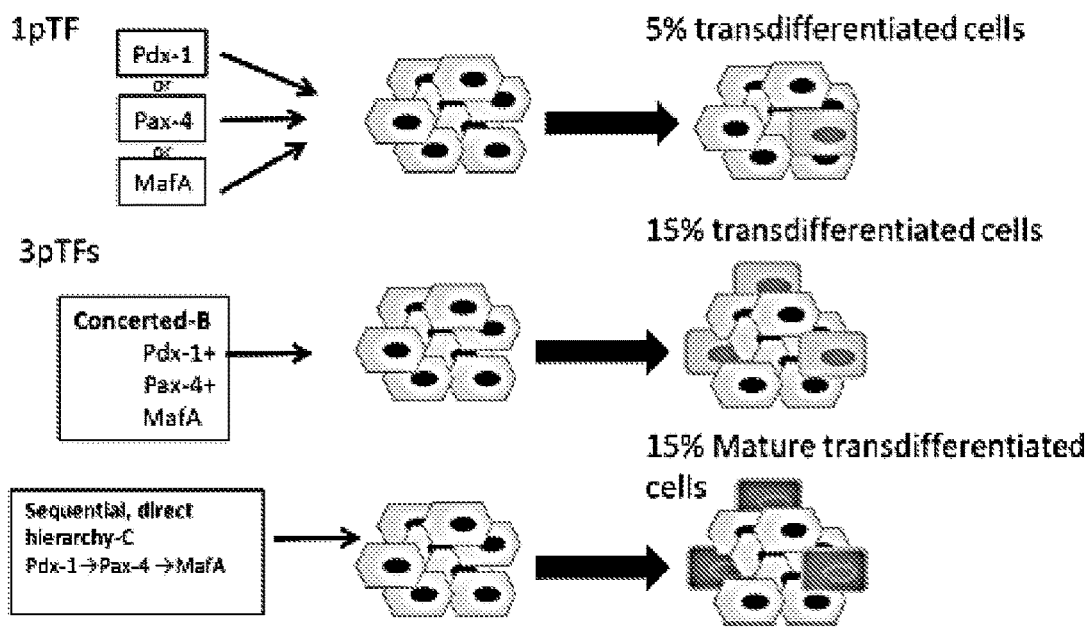
FIG. 7 shows a schematic representation of the proposed mechanism of pancreatic transcription factor-induced transdifferentiation from liver to pancreas. The concerted expression of the three pTFs results in increased number of transdifferentiated liver cells compared to each of the factor's individual effect (Treatment B). The sequential administration of transcription factors in a direct hierarchical manner results in increased maturation of the Transdifferentiated cells along the beta-like-pancreatic lineage (Treatment C).

FIG. 7 shows the proposed mechanism of pancreatic transcription factor induced liver to pancreas transdifferentiation. Each of the pTFs is capable of activating a modest □-cell-like phenotype, in a restricted number of human liver cells. The concerted expression of the pTFs markedly increases liver to endocrine pancreas transdifferentiation. However the newly generated cells are immature and coexpress both insulin and somatostatin. Only sequential administration of the same factors in a direct hierarchical manner both increases transdifferentiation efficiency and also the transdifferentiated cell maturation along the □-cell lineage.

Figure 8C:
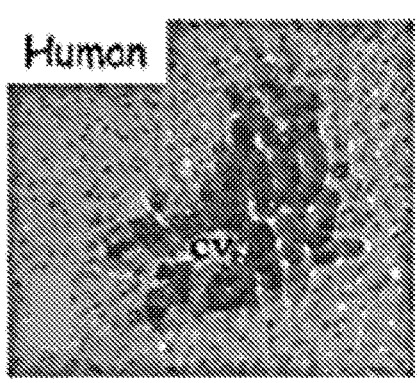
Figure 8D:
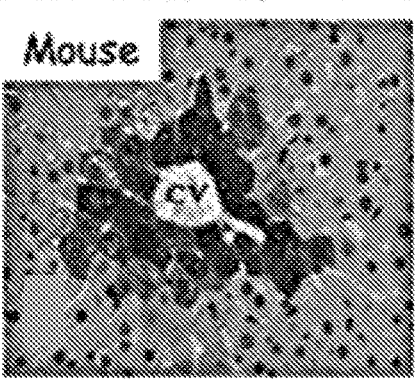

Example 3: Identification of Cell Populations with Transdifferentiation Capacity In Vivo Cell populations with transdifferentiation capacity were identified in vivo in mice. Ectopic expression of the Pdx-1 gene was achieved in mice livers. Despite the uniform expression of the ectopic Pdx-1 gene in about 40-50% of the cells of the liver (FIG. 8A) insulin-producing cells (IPCs) in Pdx-1-treated mice in vivo were primarily located close to central veins (FIG. 8B), which is characterized by active Wnt signaling and the expression of glutamine synthetase (GS) (FIG. 8C). The co-localization of GS expression and insulin activation by Pdx-1 also indicated that those cells that can activate the GSRE have a predisposition for increased transdifferentiation capacity. Therefore, cell populations predisposed for transdifferentiation can also be identified by GSRE activation or active Wnt-signaling pathway.

Example 4: Using Adenoviruses to Identify Human Liver Cells Predisposed for Transdifferentiation This example demonstrates the use of recombinant adenoviruses to identify human liver cells that are predisposed for transdifferentiation. Human liver cells in culture are heterogeneous with regard to the activation of the intracellular Wnt signaling pathway and expression of GS. As GS is uniquely expressed in pericentral liver cells, therefore the capacity to activate GSRE (GS Regulatory Element) can be used as a selective parameter of isolation of relevant cells.

In addition as the GSRE contains also a STAT5 binding element, the predisposition of the cells to transdifferentiation could be mediated by this element. The STAT5 pathway could also be involved in endowing the cells with reprogramming or transdifferentiation predisposition (FIGS. 8A-8D, 9, 10A-10E and 11).

Example 5: GSRE Repetitively Targets β-15% of the Human Liver Cells in Culture

Figure 9:
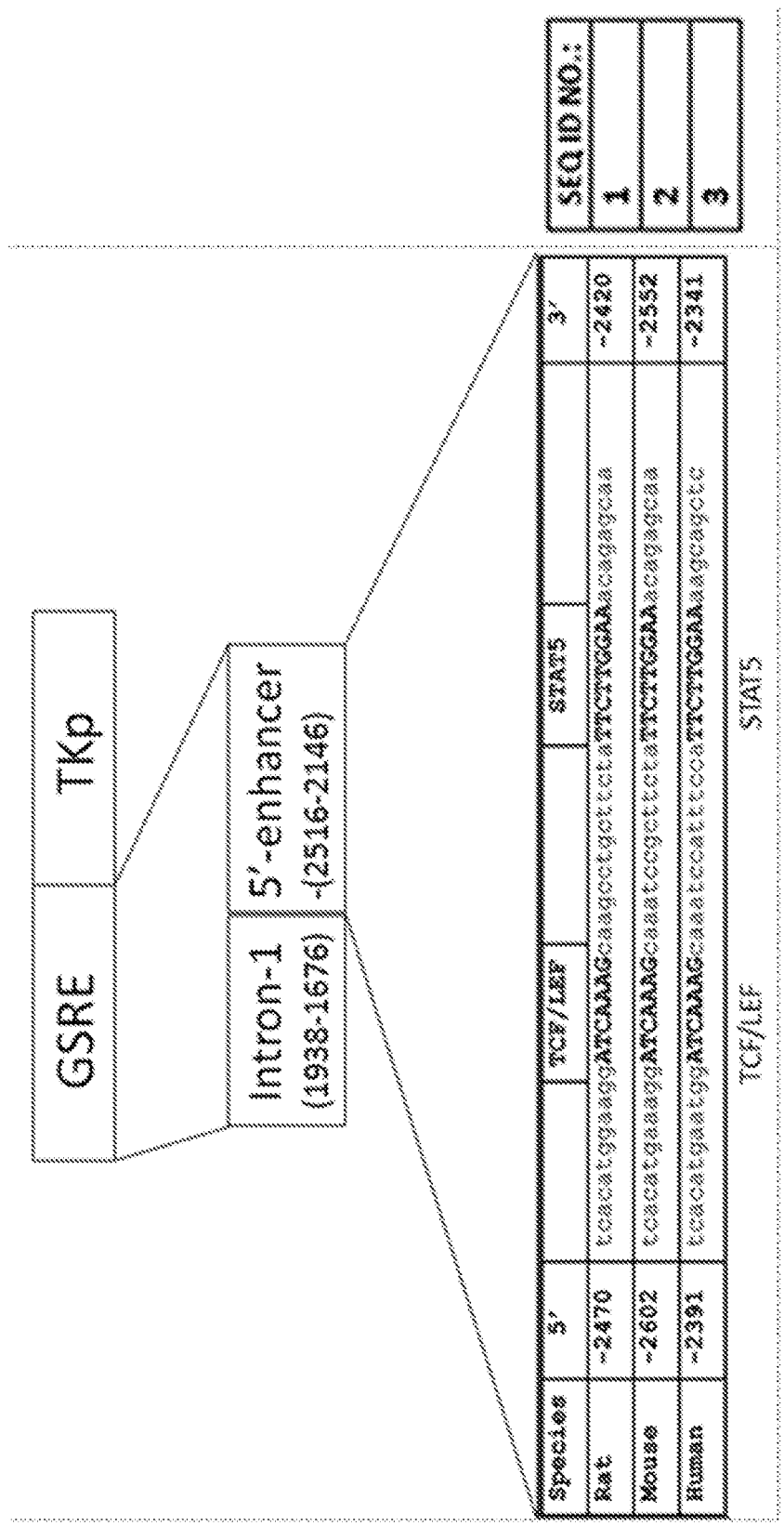
FIG. 9 shows glutamine synthetase response element (GSRE) contains Wnt signaling responding element-TCF-LEF binding site. A schematic presentation of GSRE indicating the presence of TCF-LEF and STAT 5 binding sites. The nucleotide sequences for the GSRE (intron-1 and 5' enhancer are provided in SEQ ID NO: 1 (rat), SEQ ID NO: 2 (mouse), and SEQ ID NO: 3 (human).
Figure 10A:
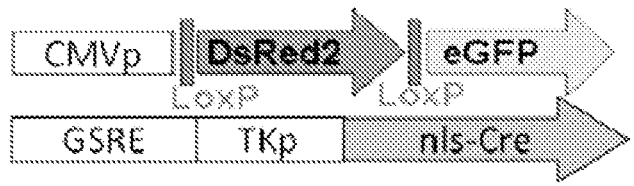
FIGS. 10A-10E show in vitro lineage tracing for GSRE activating human cells.
Figure 10B:
Figure 10C:
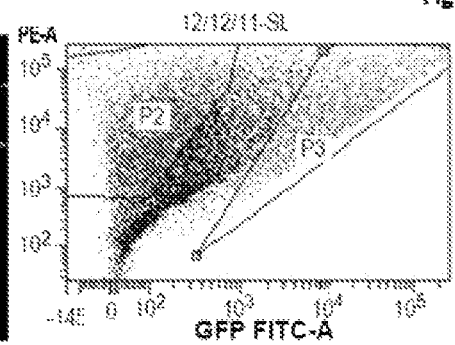
Figure 10D:
Figure 10E:

GSRE includes TCF/LEF and STAT5 binding elements (FIG. 9). Two recombinant adenoviruses that carry the expression of eGFP gene or Pdx-1 genes under the control of GSRE (FIG. 9) operatively linked to a minimal TK promoter have been generated. These adenoviruses drove the expression of either Pdx-1 (FIG. 12A) or eGFP (FIG. 12B). Both proteins were repetitively expressed in about β-15% of the human liver cells in culture suggesting the targeting of a specific population of liver cells.

Example 6: GSRE Driven PDX-1 is More Efficient Than CMV Driven PDX-1 In Activating Insulin Production In Liver Cells Despite the repetitive expression of GSRE driven PDX-1 only about 13±2% of the cells in culture showed transdifferentiation capacity similar or higher than that induced by Ad-CMV-Pdx-1, which drives Pdx-1 expression in 60-80% of the cells in culture (FIGS. 13A-13C). GSRE-activating cells could account for most of the transdifferentiation capacity of the entire adult human liver cells in culture. Insulin production occurred in 25% of Pdx-1 positive cells upon Ad-GSRE-Pdx-1 treatment compared to 1% of the Ad-CMV-Pdx-1 treated cells.

Example 7: Using Lentiviruses To Permanently Label The GSRE+ Cells By EGFP

Permanent lineage tracing was performed using Lentivirus constructs. In vitro lineage tracing for GSRE activity was performed by a modified dual lentivirus system recently used to trace KRT5 in keratinocytes or albumin expression in liver cells. This lentivirus system (FIG. 12A) includes the CMV-loxP-DsRed2-loxP-eGFP (R/G) reporter and an additional lentiviral vector carrying the expression of Cre recombinase under the control of GSRE and a minimal TK promoter (generously contributed by Prof. Gaunitz, Germany, FIG. 10A). Thus, GSRE-activating cells are irreversibly marked by eGFP (eGFP+), while the rest of the doubly infected cells are marked by DsRed2 (DsRed2+). Ten to fourteen percent of the cells became eGFP+ within less than 10 days (FIG. 8B). The cells were separated by a cell sorter (FIGS. 8A-8E) and separately propagated (FIG. 14). Cultures of eGFP+ (GSRE activators) and DsRed2+ cells were generated from 10 different human donors (ages 3-60).

Figures 15A, 15B, 15C:
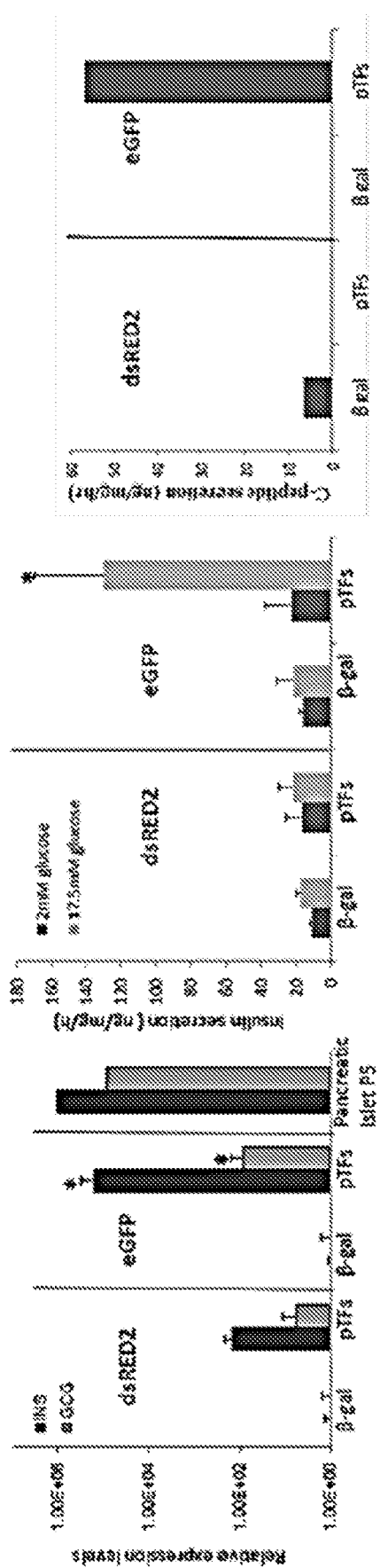
FIGS. 15A-15C shows eGFP+ cells respond more efficiently than DsRed2+ cells to pTFs-induced transdifferentiation. The two groups were similarly treated with soluble factors and pTFs: Ad-Pdx-1+Ad-Pax-4+ad-MafA or a control virus (Ad-β-gal) for 6 days. β-cell-like characteristics and function were compared in the separated groups.

Example 8: EGFP+ Cells Consistently Exhibited Superior Transdifferentiation Capacity Human liver cells separated by lineage tracing according to GSRE activity efficiently propagated (FIG. 14) and were similarly efficiently infected by recombinant adenoviruses. eGFP+ cells consistently exhibited superior transdifferentiation capacity (FIG. 15A-15C) manifested by insulin and glucagon gene expression that was comparable to that of human pancreatic islets in culture (FIG. 15A), glucose regulated insulin secretion (FIG. 15B) and glucose regulated C-peptide secretion (FIG. 15C). These capacities were consistent and did not diminished upon extensive cell proliferation (FIG. 16).

Example 9: Transdifferentiated eGFP+ Cells Exhibited Increased Production of Pancreatic Hormones In Vivo In order to corroborate TD-eGFP+ superior transdifferentiation capacity in vivo, TD-eGFP+ and TD-DsRed+ cells were implanted in immune deficient mice. TD-eGFP+ cells showed long-lasting increased production of pancreatic hormones over TD-DsRed+ in vivo.

Methods:

SCID-Beige mice (8-9 weeks old, 22-25 gr) were implanted with $4\times10^6$ of either TD-eGFP+ or TD-DsRed+ cells subcutaneously, as described in Greenberger et al., (2010) N Engl J Med 362:1005-1013. Implants were collected 2 weeks post implantation, fix and stained according to standard methods using anti-insulin (DAKO) and anti-Glucagon (DAKO) antibodies.

Human serum insulin secretion was measured in mice implanted with TD cells according to the following method: Following a 6 hr fast, mice were injected i.p. with glucose in saline at 2 mg/g glucose/body weight. Serum was collected 30 min later and human C-peptide levels were analyzed as described in Sapir et al. (2005) Proc Natl Acad Sci USA 102:7964-7969. The Ultrasensitive Human C-Peptide ELISA kit (Mercodia, Uppsala) used has 3% cross reactivity with proinsulin but no cross reactivity with mouse C-peptide and mouse insulin.

Figure 17A:
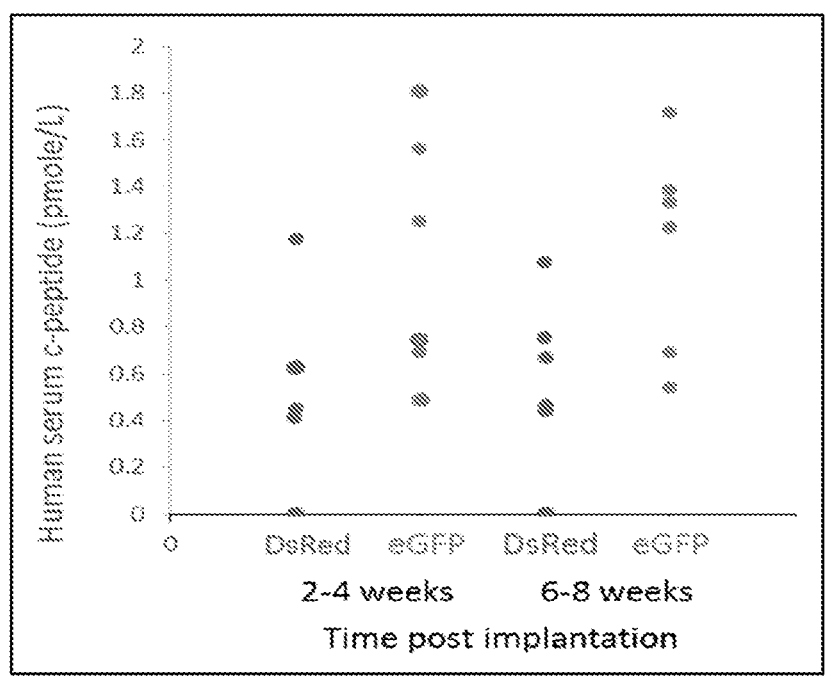
FIGS. 17A-17B show long-lasting functional superiority of transdifferentiated eGFP+ cells over transdifferentiated DsRed+ cells upon in vivo implantation in immune deficient mice.

Results:

Blood analysis performed 2-8 weeks following implantation showed that mice implanted with transdifferentiated eGFP+ (TD-eGFP+) cells consistently had more processed human insulin (C-peptide) secreted into the blood stream than mice implanted with transdifferentiated Red+(TD-DsRed+) cells (FIG. 17A).

Figure 17B:
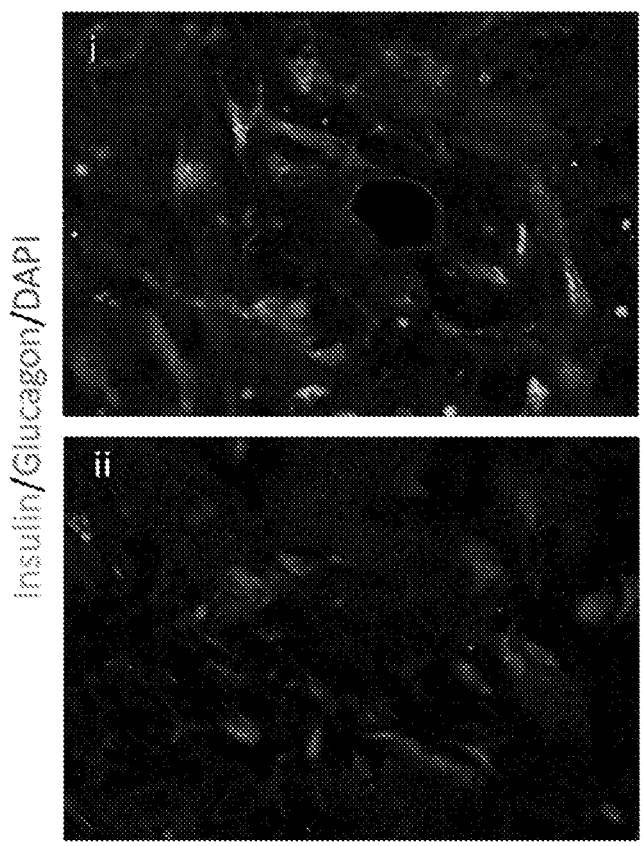

Implants were excised from mice 2 weeks after implantation. Analysis of the implants suggested increased hormone production in eGFP+ cells compared to DsRed+ cells. Implants of eGFP+ cells contained many more insulin producing cells (green), glucagon producing cells (red), and bi-hormonal containing cells (orange) than DsRed+ explants (FIG. 17B). The bi-hormonal cells may suggest the potential immaturity of some of the implanted cells.

Figure 18:
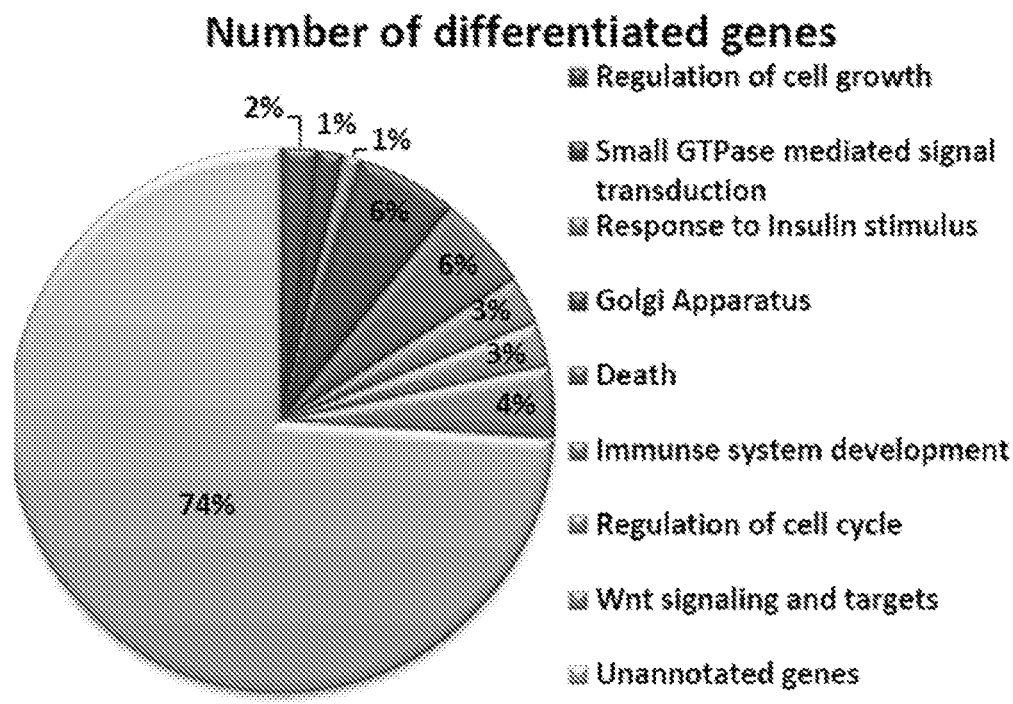
FIG. 18 shows differential gene expression profiles of eGFP+ and DsRed2+ cells performed by microarray analyses and analyzed according to DAVID Bioinformatics Resources 6.7. Four Percent of the differential genes belong to the Wnt signaling pathway.

Example 10: Characterization of Cells With Predisposition For Transdifferentiation To identify the factors that could potentially affect the distinct transdifferentiation efficiencies of the human liver cells, the global gene expression profile of the two separated populations was compared using microarray chip analyses. Human liver cell cultures derived from 3 different donors and separated into eGFP+ and DsRed2+ cells were propagated for 4 passages. The extracted RNA was converted into cDNA and subjected to microarray chip analysis using the General Human Array (GeneChip Human Genome U133A 2.0 Array, Affymetrix). While most of the genes were expressed at comparable levels in the separated groups, the expression of about 800 probes was significantly different (FIG. 18). According to microarray chip analyses, about 100 genes coding for membrane proteins are differentially expressed between the transdifferentiation-prone (eGFP+) and non-responding (DsRed2+) cells. Several of these markers are presented in Table 2A and 2B.

TABLE 2A

Membrane antigens that are differentially expressed in eGFP+ and DsRed2+ cells.

| Antigene | High expression | Fold (Log2) | p-value | commercial antibody |
|---|---|---|---|---|
| ABCB1 | DsRed2 | −6.363 | 1.52E−02 | BD Biosciences (#557002) |
| ITGA4 | DsRed2 | −1.979 | 2.69E−02 | R&D system (FAB1354G) |
| ABCB4 | DsRed2 | −4.42 | 4.62E−02 | Abcam (ab24108) |
| PRNP | DsRed2 | −1.35 | 4.20E−02 | eBioscience (12-9230-73) |
| HOMER1 | eGFP | 1.41 | 3.25E−04 | Biorbyt(orb37754) |
| LAMP3 | eGFP | 1.285 | 1.81E−02 | BD Biosciences (#558126) |
| BMPR2 | eGFP | 1.236 | 3.50E−02 | R&D system (AF811) |

TABLE 2B

Cell-surface coding transcripts differentially expressed in eGFP+ vs. DsRed2+ cells

| Gene symbol | Gene name | Fold change EGFP+/DsRed2+ cells | ΔCt (gene-actin) eGFP+ cells |
|---|---|---|---|
| ITGA6 | INTEGRIN ALPHA-6 | 2.82759 | 8.6 |
| DCBLD2 | DISCOIDIN, CUB AND LCCL DOMAIN-CONTAINING PROTEIN 2 | 2.4747 | 12.3 |
| THBS1 | THROMBOSPONDIN-1 | 2.29441 | 1.5 |
| VAMP4 | VESICLE-ASSOCIATED MEMBRANE PROTEIN 4 | 1.97484 | 18.3 |

Figure 19:
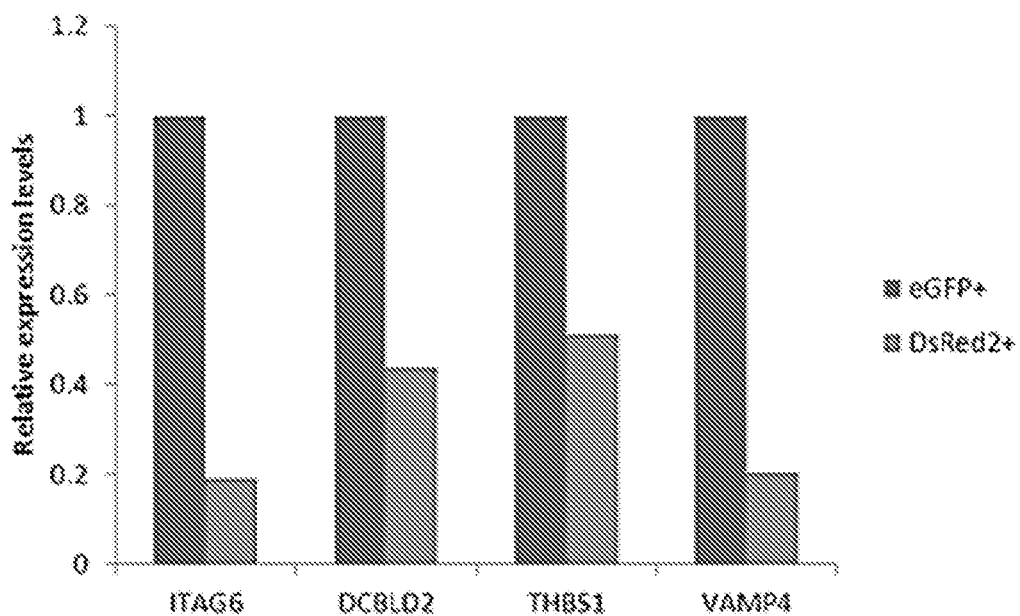
FIG. 19 shows a bar graph of the relative expression levels of cell-surface molecules in eGFP+ and DsRed2+ cells, listed in Table 2B of Example 17.

FIG. 19 shows the relative expression of the cells surface molecules presented in Table 2B. Expression levels of specified molecules were tested by Real Time PCR and normalized to beta-actin expression. Microarray data suggested numerous membrane proteins that are differential expression between the eGFP+ and the DsRed2+ cells (Fold=eGFP+ differential expression compared to the DsRed2+(log 2). All the presented antigens have commercially available antibodies.

Example 11: WNT Signaling is Active in Cells Predisposed for Transdifferentiation Liver zonation has been suggested to be controlled by a gradient of activated β-catenin levels; while most cells in the liver contain very low β-catenin activity, the pericentral liver cells express high β-catenin activity associated with active Wnt signaling. Since Wnt signaling is obligatory for competent β cell activity, the pTFs-induced pancreatic lineage activation in the liver is restricted to cells that a priori display active Wnt signaling.

GSRE utilized a TCF regulatory element isolated from the 5' enhancer of GS. If Pdx-1-induced liver to pancreas transdifferentiation is mediated in part by the intracellular Wnt signaling pathway, factors that modulate the Wnt signaling pathway can also affect transdifferentiation efficiency (FIG. 11).

Figure 11:
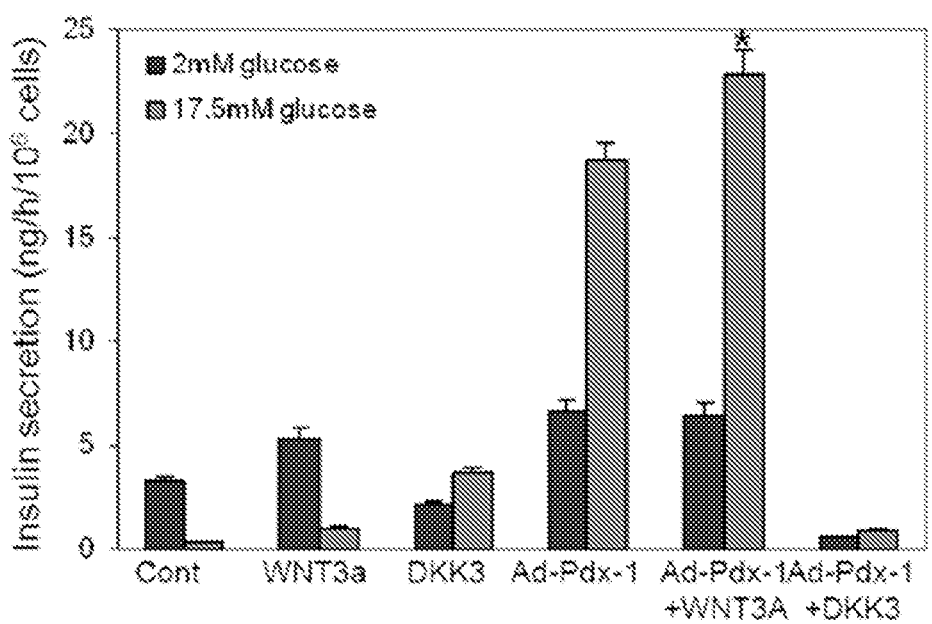
FIG. 11 shows that active Wnt signaling promotes liver to pancreas transdifferentiation. Adult human liver cells were treated with Ad-CMV-Pdx-1 and soluble factors, as previously reported, supplemented with Wnt3A (50 ng/ml R&D or DKK3 (3 µg/ml R&D). After 5 days, insulin secretion was analyzed by static incubations at low followed by high glucose concentrations (2 mM and 17.5 mM glucose in KRB, respectively). Insulin secretion is measured using the human insulin radioimmunoassay kit (DPC; n≥8 from 3 different experiments) and compared to untreated cells (Cont). *p<0.01 compared to Ad-CMV-Pdx-1 alone, using Student's t-test analysis.
Figure 20:
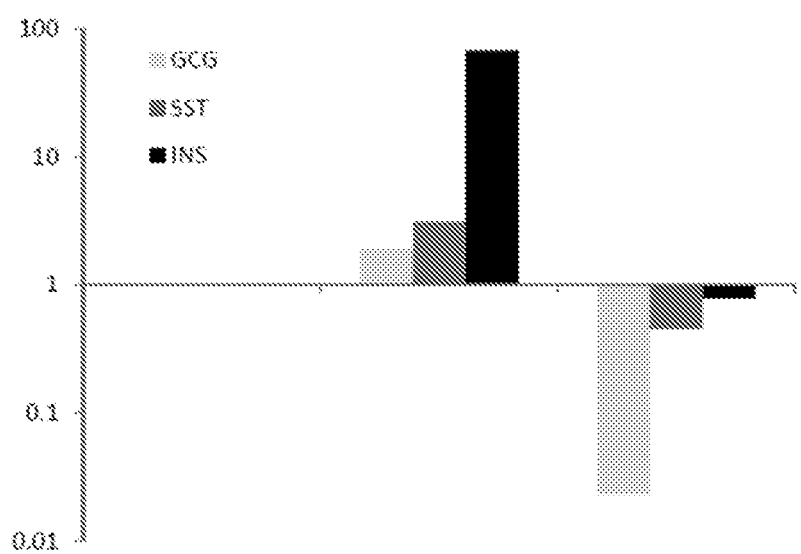
FIG. 20 shows that blocking the Wnt signaling pathway abolishes the transdifferentiation of eGFP+ cells. eGFP cells were Ad-CMV-Pdx-1 or a control virus (Ad-CMV-β-gal) for 5 days supplemented with DKK3 (Dickkopf-related protein 3) (0.5 µg/ml R&D). Pancreatic hormones gene expression was studied by Quantitative real-time RT-PCR compared to the control-treated cells.

This data in adult human liver cells suggest that increasing concentrations of Wnt3a increased Pdx-1-induced glucose-regulated insulin secretion, while DKK3 (an inhibitor of the Wnt signaling pathway) completely abolished the effect of Pdx-1 on the process (FIG. 11). DKK3 also totally abolished the transdifferentiation capacity of the eGFP cells isolated according to their ability to activate GSRE (FIG. 20).

Characterization of Wnt signaling pathway activity in the eGFP+ and DsRed+ cell populations was performed. The APC expression, which participates in β-catenin destabilization, thus diminishing Wnt signaling, was 700% higher in DsRed2+ cells than in the eGFP+ cells (FIG. 21A, in relative agreement with the zonation displayed in vivo). The eGFP+ population has increased activated β-catenin levels (40%) compared to the levels analyzed in DsRed2+ cells (FIGS. 21B and 21C). These data demonstrate that Wnt signaling is active in cells that are competent for GSRE activation and have predisposition for transdifferentiation.

Example 12: Determining the Optimal Protocol for the Transdifferentiation Process Aim The aim of this study was to compare the transdifferentiation efficiency of the full hierarchy (1+1+1 protocol), with the 2+1 protocol, and with simultaneous infection with all three adenoviruses.

The Test System

The different transdifferentiation protocols were examined on three primary cultures of human liver cells, Leon, Muhammad, and Pedro grown in DMEM 1 g/L glucose. After viral infection cells were grown in DMEM 1 g/L glucose media supplemented with 5 nM Exendin-4, 20 ng/ml EGF and 10 mM Nicotinamide.

Experimental Design

The different transdifferentiation (TD) protocols were examined according to the Table 3 below. Briefly, on the first day of the experiment 300,000 cells were seeded after viral infection on 100 mm Falcon dish according to Table 3 below for protocols A (Null), B (2+1) and E (Hierarchy 1+1+1). On the second day of the experiment 100,000 cells were seeded on 6 wells dish for protocol C (3 factors simultaneously) and 70,000 cells were seeded on 6 wells dish for protocol D (3 factors simultaneously). On the third day of the experiment, cells were counted and treated by Ad-MafA (protocols B and E) and seeded on 3 wells of a 6 wells dish to a final concentration of 100,000 cells/well.

TABLE 3

| | Day 1 | Day 2 | Day 3 | Day 6 |
|---|---|---|---|---|
| A | Null (1300moi) | | | GSIS* |
| B | PDX1 1000moi + NeuroD1 250moi | | MafA 50moi | GSIS |
| C | | PDX1 1000moi + NeuroD1 250moi + MafA 50moi | | GSIS |
| D | | PDX1 1000moi + NeuroD1 250moi + MafA 50moi | | GSIS |
| E | PDX1 (E4)1000moi | NeuroD1 250moi | MafA 50moi | GSIS |

*GSIS—Glucose stimulated insulin secretion

Figure 22B:
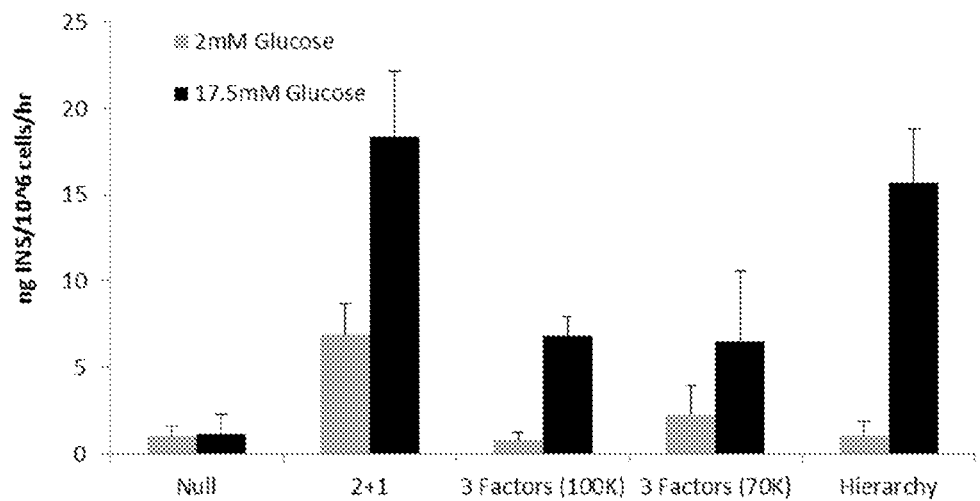
Figure 22C:
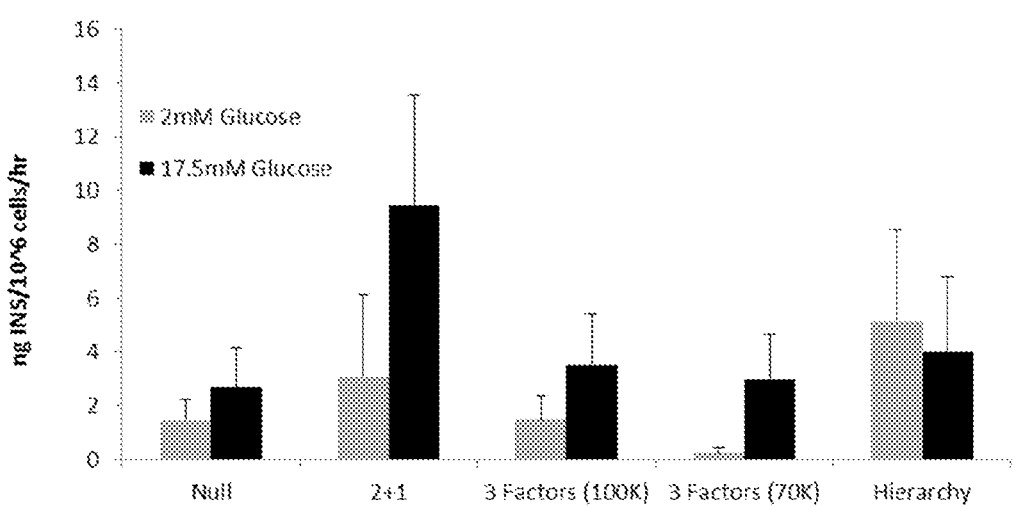

On the sixth day of the experiment, cells underwent secretion analysis in the presence of 2 mM glucose (low) or 17.5 mM glucose (high) (FIGS. 22A-22C). Insulin secretion was measured following incubation of cells for 15 minutes with 2 mM glucose or 17.5 mM glucose in KRB.

Results and Analysis

The present study sought to determine the optimal protocol for the transdifferentiation process. In the traditional hierarchy protocol (1+1+1), cells are treated sequentially with three transcription factors: PDX1 on day 1, NeuroD1 on day 2 and MafA on day 3. In an effort to develop an efficient and easier protocol, the transdifferentiation efficiency of the traditional protocol, was compared with the 2+1 protocol and simultaneous treatment with all three transcription factors present.

The read out assay for this examination was insulin secretion. According to knowledge in the field, all treatments should have presented similar levels of insulin secretion, as differences in efficiency should be presented only in the maturation of the cells, for example as measured by C-peptide secretion. However, in the present experiments there were unexpected differences in transdifferentiation efficiency as clearly seen by the insulin secretion measurements (FIGS. 22A-22C). The best results were obtained in the 2+1 protocol. These results were statistically significant, as shown in Table 4 below.

TABLE 4 p-value (t-Test) for the comparison of the different transdifferentiation protocols presented in Table 4 above.

| 1 | Hierarchy | 3 factors (70K cells - in 6W dish) | 3 factors (100K, 100,000 cells in 6W dish) | 2 + 1 |
|---|---|---|---|---|
| 2 + 1 | 0.06691407 | 0.04561124 | 0.017915142 | |
| 3 factors (100K) | 0.223713506 | 0.35910095 | | 0.017915142 |
| 3 factors (70K) | 0.376772188 | | 0.35910095 | 0.04561124 |
| Hierarchy | | 0.376772188 | 0.223713506 | 0.06691407 |

The p-value of the 2+1 protocol and the hierarchy protocol is significant but relatively high. The simultaneous treatment with all three factors presented the lowest results even though two seeding densities were examined (not significant in comparison to the hierarchy protocol).

Example 13: Protocol for Producing Autologous Insulin Producing (AIP) Cells for the Treatment of Diabetes Aim The aim of this study was developing an industrial scale protocol for producing autologous insulin producing (AIP) cells from non-β pancreatic cells for the treatment of diabetes. By correcting functionally for malfunctioning pancreatic insulin producing β-cells with new functional tissues generated from the patient's own existing organs, a cell-based autologous therapy could successfully target diabetes in a subject.

Figure 23:
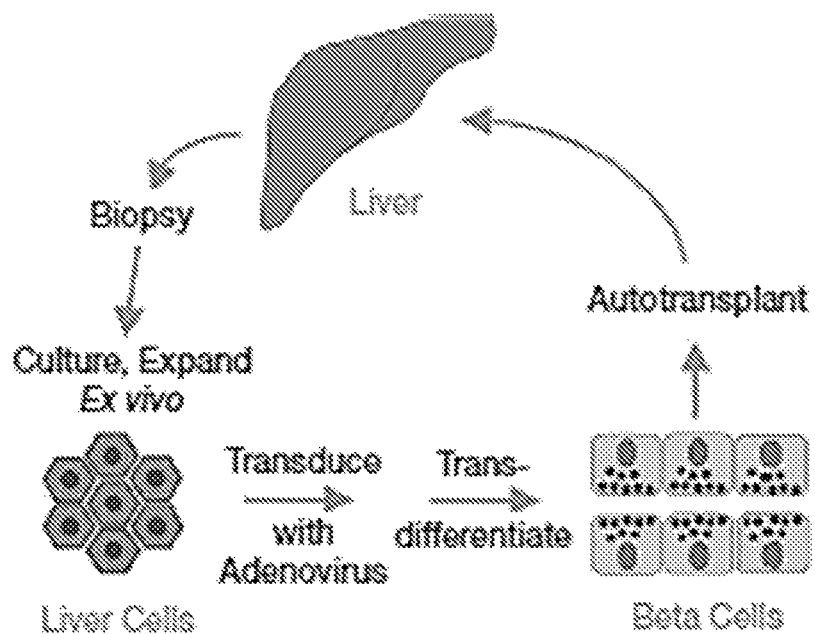
FIG. 23 shows a liver cell-based autologous cell therapy schema, adapted from Cozar-Castellan and Stewart (2005) Proc Nat Acad Sci USA 102(22): 7781-7782.

The protocol presented herein employs a molecular and cellular approach directed at converting human liver derived cells into functional insulin-producing cells by transcription factors induced transdifferentiation (FIG. 23). This therapeutic approach generates Autologous Insulin Producing (AIP) cells on an industrial scale, overcoming the shortage in tissue availability from donors.

Overview of the Protocol

FIG. 24 provides an overview of the protocol provided here, demonstrating an approximate time from biopsy to finished product of 6-weeks, along with approximate cell numbers at each step. FIG. 25 presents a flowchart of the human insulin producing cell product cell product manufacturing process, which may in one embodiment be autologous or allogeneic insulin producing cells (AIP). Details are provided below.

Obtaining Liver Tissue Step 1 of FIG. 25

Liver tissue was obtained from adult human subjects. All liver tissue obtained were received under approval of the Helsinki Committee of the Medical Facility. Accordingly, all liver tissue donors signed an informed consent and Donor Screening and Donor Testing was performed to ensure that biopsies from donors with clinical or physical evidence of or risk factors for infectious or malignant diseases were excluded from manufacturing of human insulin producing cells.

Liver biopsies were obtained in an operating theatre by qualified and trained surgeons. A biopsy of the size of about 2-4 g of liver tissue was taken from eligible patients and transported at 2-8° C. in University of Wisconsin (UW) solution in a sterile bag to the GMP facility.

In vitro culture/Steps 2 and 3 of FIG. 25

At the manufacturing site, liver biopsies were processed as for adherent cells. Briefly, biopsy tissue was cut into thin slices and digested by collagenase type I for 20 min at 37° C. Subsequently, cells were repeatedly digested with trypsin in order to obtain isolated single cells; initial experiments had shown that approx. $0.5 \times 10^6$ cells can be isolated per gram biopsy.

Cells were then expanded ex vivo in cells medium supplemented with 10% FCS, Exendin-4 and a mix of antibiotics (Penicillin, Streptomycin and Amphotericin B). Cells were passaged at 37° C. in a humidified atmosphere of 5% $CO_2$/95% air (up to 20 passages) using pre-treated Fibronectin-coated tissue culture dishes. Medium was changed daily during the first three days post biopsy plating to remove non-adherent cells followed by twice a week, after the first cell passage. At the time of the first cell passage at least one aliquot of cells was cryopreserved (see below; Optional Step of FIG. 25).

Cells were passaged 1:3 using trypsin until the desired number of cells was generated (about 1-3 billion cells, within about 4 to 7 weeks). Expansion of cells included use of Multi-plate systems as described in US Patent Application Publication No. 2016/0220616, incorporated herein in full, and shown in FIG. 23 at approximately week 4 through weeks 7. (Step 3 of FIG. 25)

Human liver cells that adhered to the tissue culture plates underwent epithelial to mesenchymal transition (EMT) and efficiently proliferated. Close to 100% of these EMT-like cells displayed the known mesenchymal characteristics (CD29, CD105, CD90 and CD73) but also expressed adult hepatic markers such as albumin and AAT. The cells neither express hepatoblast nor "stemness" markers. Table 5 below shows the results of analysis of these EMT-like cultured liver cells for the presence of mesenchymal, hematopoietic, and hepatic markers on the cultured liver cells prior to transdifferentiation (TD).

TABLE 5

| Before Transdifferentiation | Specification |
|---|---|
| Mesenchymal markers | |
| CD105, CD73, CD90, CD44 | >95% |
| Haemapoeitic markers | <2% |
| Hepatic markers | |
| Albumin | >80% |
| AAT | >60% |

The percentages shown in Table 5 are at low passage number.

Cryopreservation of Passage 1 Cells (FIG. 25)

Briefly, Passage 1 cells were cryopreserved in DMEM supplemented with 10% FBS and 10% DMSO in 2 ml cryovials (minimum of $0.5 \times 10^6$ cells). It is recommended to cryopreserve cells at the earliest passage possible. Frozen cells were first stored at −70° C. for 24-48 hours and then transferred to liquid $N_2$ for long term storage.

Thawing of Cryopreserved Cells (FIG. 25)

Cryopreserved cells were thawed using well-known methods in the art. Briefly, vials were removed from liquid $N_2$ and allowed to slowly thaw until sides were thawed but center was still frozen. Cells were gently transferred to tissue culture plates. Once cells have attached to the plate, in vitro processing (Steps 2 and 3 of FIG. 25) to expand the cell culture was performed.

Select Predisposed Liver Cells (FIG. 25)

An option at Step 3 of FIG. 25 is to sort the Primary Liver Cells in order to enrich for cells predisposed to transdifferentiation. For example, cells could be sorted for glutamine synthetase response element (GSRE) activation (GS enriched cells), as described herein in Examples 3-8. Alternatively, cells could be enriched for having an active Wnt signaling pathway, wherein they are predisposed to respond to Wnt signaling, as described herein in Example 11. In addition, cells could be enriched by monitoring increases or decreases of expression of certain genes, for example decrease in expression of ABCB1, 1TGA4, ABCB4, or PRNP, or any combination thereof, or increases in expression of HOMER1, LAMP3, BMPR2, ITGA6, DCBLD2, THBS1, or VAMP4, or any combination thereof, as described herein in Example 9. The cell population could be treated with lithium, as described in Example 13, in order to enhance the predisposition of cells to transdifferentiation. Following enrichment for predisposition to transdifferentiation, cells are used at Step 4 of FIG. 25.

Trans-Differentiation (Step 4 of FIG. 25)

For trans-differentiation cells were grown in trans-differentiation medium for an additional 5 days. Trans-differentiation medium is Dulbecco's minimal essential medium (1 g/l of glucose) supplemented with 10% FCS, Exendin-4, Nicotinamide, EGF and a mix of antibiotics (Penicillin, Streptomycin and Amphotericin B).

Two different protocols were used for transdifferentiation of cells. Cells were transdifferentiated using the Hierarchy (1+1+1) sequential protocol or using the 2+1 protocol. Examples of each method are provided below.

Hierarchy (1+1+1) Sequential Protocol

Ex vivo expanded liver cells were then sequentially infected with 3 serotype-5 recombinant replication-deficient adenovirus vectors, each carrying the human gene for one of the pancreatic Transcription Factors (pTFs), PDX-1, Neuro-D or MafA, under the control of the cytomegalovirus (CMV) promoter. The 3 human pTF genes had been inserted into the same backbone of FGAD vectors under the control of the CMV promoter. The CMV promoter is a heterologous promoter that is usually turned off within 3-4 weeks after infection. Nevertheless the short-term expression of the ectopic pTF genes was sufficient to induce the endogenous human homologs.

FGAD vectors were selected as an optimal gene delivery tool for inducing developmental redirection. Examples above demonstrated that introduction of these ectopic genes into primary adult human liver cells acts as short term triggers for an irreversible process of reprogramming of adult cells. On the other hand, the recombinant adenoviruses were relatively safe as they do not integrate into the host genome and therefore do not disrupt the host sequence of genetic information. PDX-1 induces epigenetic alterations in the chromatin structure, thus allowing the activation of otherwise silent genetic information, while turning off the host repertoire of expressed genes (compare the results of Tables 5 and 6).

The transdifferentiation process was performed using a closed automatic Xpansion bioreactor system (Pall Life Sciences), following the flow of steps presented in FIG. 24. The bioreactor system was used for cultivation of cell cultures, under conditions suitable for high cell concentrations. The bioreactor system was constructed of two main systems, a control system and a bioreactor itself (vessel and accessories).

The parameters of the process were monitored and controlled by the control console which included connectors for probes, motor and pumps, control loops for Dissolved Oxygen (DO), pH, a gases control system and place in the incubator for temperature control. The controlled process parameters (such as temperature, pH, DO etc.) could be displayed on the operator interface and monitored by a designated controller.

Cell Culture Growth Procedure in the Bioreactors $250 \pm 50 \times 10^6$ cells were seeded in a sterile XP-200 bioreactor. The growth medium in the bioreactor was kept at the following conditions: 37° C., 70% Dissolved Oxygen (DO) and pH 7.3. Filtered gases (Air, $CO_2$, $N_2$ and $O_2$) were supplied as determined by the control system in order to keep the DO value at 70% and the pH value at 7.3. Growth media was changed when the medium glucose concentration decreased below 500 mg/liter. The medium was pumped from the feeding container to the bioreactor using sterile silicone tubing. All tubing connections were performed with a tube welder providing sterile connectors. A sample of the growth medium was taken every 1-2 days for glucose, lactate, glutamine, glutamate and ammonium concentration determination. The glucose consumption rate and the lactate formation rate of the cell culture enabled to measure cell growth rate. These parameters were used to determine the harvest time based on accumulated experimental data.

Harvest of the Cells from the Bioreactor

The cell harvest process started at the end of the growth phase (8-16 days). The culture was harvested in the Class-100 laminar area as follows:

The bioreactor vessel was emptied using gravitation via tubing to a waste container. The bioreactor vessel was then refilled with 22 L pre-warmed PBS (37° C.). The PBS was drained via tubing by pressure or gravity to the waste bottle. The washing procedure was repeated twice.

In order to release the cells from the surface, 22 L pre-warmed to 37° C. of Trypsin-EDTA (Trypsin 0.25%, EDTA 1 mM) was added to the bioreactor vessel. 500 ml FBS was added to the bioreactor vessel and the cell suspension was collected to a sterile container. Cell suspension was centrifuged (600 RPM, 10 min, 4° C.) and re-suspended in culture media.

Hierarchy (1+1+1) Viral Infection Steps

The ectopic transgenes were sequentially administered by recombinant adenoviruses on three successive days. Sequential administration of the ectopic genes has been documented to both increase the trans-differentiation efficiency and to increase the maturation of the cells, specifically along the β cell lineage and function.

The trans-differentiation procedure took approx. 7 days, at the end of which cells are washed to remove the un-incorporated recombinant adenoviruses. Briefly:

On day 1, resuspended cells were infected with the PDX-1 adenoviral vector using an MOI of 1,000. Cells were then seeded onto culture dishes are incubated overnight in in a humidified 37° C. incubator supplied with 5% $CO_2$.

On day 2, cells were detached from culture dishes using trypsin and resuspended. Resuspended cells were infected with the NeuroD1 adenoviral vector using an MOI of 250. Cells were then seeded onto culture dishes are incubated overnight in in a humidified 37° C. incubator supplied with 5% $CO_2$.

On day 3, cells were detached from culture dishes using trypsin and resuspended. Resuspended cells were infected with the MafA adenoviral vector using an MOI of 50. Cells were then seeded onto culture dishes are incubated for three days in a humidified 37° C. incubator supplied with 5% $CO_2$.

Cells were then recovered and analyzed for markers and glucose regulated processed insulin secretion. Control cells included those propagated and incubated following the same protocol but without addition of adenovirus.

Materials and Experimental Methods

FACS analysis of membrane markers-cells were stained with monoclonal antibodies as follows: 400,000-600,000 cells were suspended in 0.1 ml flow cytometer buffer in a 5 ml test tube and incubated for 15 minutes at room temperature (RT), in the dark, with each of the following monoclonal antibodies (MAbs):

Harvesting AIP cells (Step 5 of FIG. 25) Cells were then washed twice with flow cytometry buffer, resuspended and analyzed by flow cytometry using an FC-500 flow Cytometer (Beckman Coulter). Negative controls were prepared with relevant isotype fluorescence molecules.

Packaging and Release

At the end of manufacturing, AIP cells will be packed for shipment and released at the manufacturing site. It is planned to ship AIP cells at 2-8° C. to the hospitals.

Results of Hierarchy (1+1+1) Protocol

The adenoviral infection of the cells resulted in transient expression of the transgenes, which triggers permanent induction of endogenous genes, resulting in stable transdifferentiation to AIP cells (data not shown). As a result, there was no modification or insertions of viral DNA in the final product.

Analysis of harvested AIP cells (Step 6 of FIG. 25)

An analysis of the transdifferentiated liver cells (AIP cells) for the presence of mesenchymal, hematopoietic, and hepatic markers is presented in Table 7. Negative markers include hematopoietic markers.

TABLE 6

| % CD105 | % CD73 | % CD90 | % CD44 | % Negative markers |
|---|---|---|---|---|
| 99.32 | 99.85 | 99.55 | 99.77 | 0.93 |
| 98.75 | 99.71 | 99.67 | 99.70 | 0.73 |
| 97.89 | 98.71 | 99.80 | 99.77 | 0.94 |
| 96.77 | 98.60 | 99.50 | 99.64 | 0.58 |

While variability was noted across different patient samples in Xpansion bioreactors, in all cased cell density of harvested cells was greatly increase as compared with the starting culture (FIG. 26).

The harvested AIP cell product was analyze to identify expression of numerous markers. Identity was by RT-PCR and FACS. The results presented in Tables 7 and 8 below show the fold increase of endogenous expression of β-cell pancreatic marker genes including PDX-1, NeuroD, MafA, Pax4, Nkx6.1 and insulin.

TABLE 7

| RT-PCR | Fold increase (over control) |
|---|---|
| Pdxl | $>10^5$ |
| NeuroD | $>10^4$ |

| Ab | Antibody foil name | Company | Cat. No. |
|---|---|---|---|
| PDX1 | BD Pharmingen ™ PE Mouse anti-PDX-1 | BD | 562161 |
|  | Human/Mouse PDX-1/IPF1 Phycoerythrin MAb | R&D Systems | IC2419P |
|  | Human/Mouse PDX-1/IPF1 Allophycocyanin Mab | R&D Systems | IC2419A |
| NEUROD1 | BD Pharmingen ™ PE Mouse Anti-NeuroD1 | BD | 563001 |
|  | BD Pharmigen ™ Alexa Fluor ® 647 Mouse anti-NeuroD1 | BD | 563566 |
| MAFA | Anti-KLRG1 (MAFA-)-PE-Vio770, human (clone: REA262) | Miltenyi Biotec | 130-103-641 |
|  | Anti-KLRG1 (MAFA)-APC-Vio770, human (clone: REA261) | Miltenyi Biotec | 130-103-642 |
| Vimenten | BD Pharmingen ™ PE Mouse Anti-Human Vimentin | BD | 562337 |
|  | BD Pharmingon ™ Alexa Fluor ® 488 Mouse Anti-Human Vimentin | BD | 562338 |
| E-Cadherin | BD Horizon ™ BV421 Mouse Anti-E-Cadherin | BD | 564186 |
|  | BD Pharmingen ™ PE Mouse anti-E-Cadherin | BD | 562526 |
|  | BD Pharmingen ™ Alexa Fluor ® 488 Mouse Anti-Human CD324 (E-Cadherin) | BD | 563570 |
|  | BD Pharmingen ™ PerCP-Cy ™5.5 Mouse Anti-Human CD324 (E-Cadherin) | BD | 563573 |
|  | BD Pharmingen ™ Alexa Fluor ® 647 Mouse Anti-Human CD324 (E-Cadherin) | BD | 563571 |
|  | BD Pharmingen ™ PE Mouse Anti-Human CD324 (E-Cadherin) | BD | 562870 |
|  | BD Horizon ™ PE-CF594 Mouse Anti-Human CD324 (E-Cadherin) | BD | 563572 |

TABLE 7-continued

| RT-PCR | Fold increase (over control) |
|---|---|
| MafA | >10$^3$ |
| Insulin | >10$^1$ |

TABLE 8

| RT-PCR | Fold increase (over control) |
|---|---|
| Glucagon | >10$^2$ |
| Somatostatin | >10$^1$ |
| Nkx6.1 | >10$^1$ |
| Pax4 | >10$^1$ |

Figure 27A:
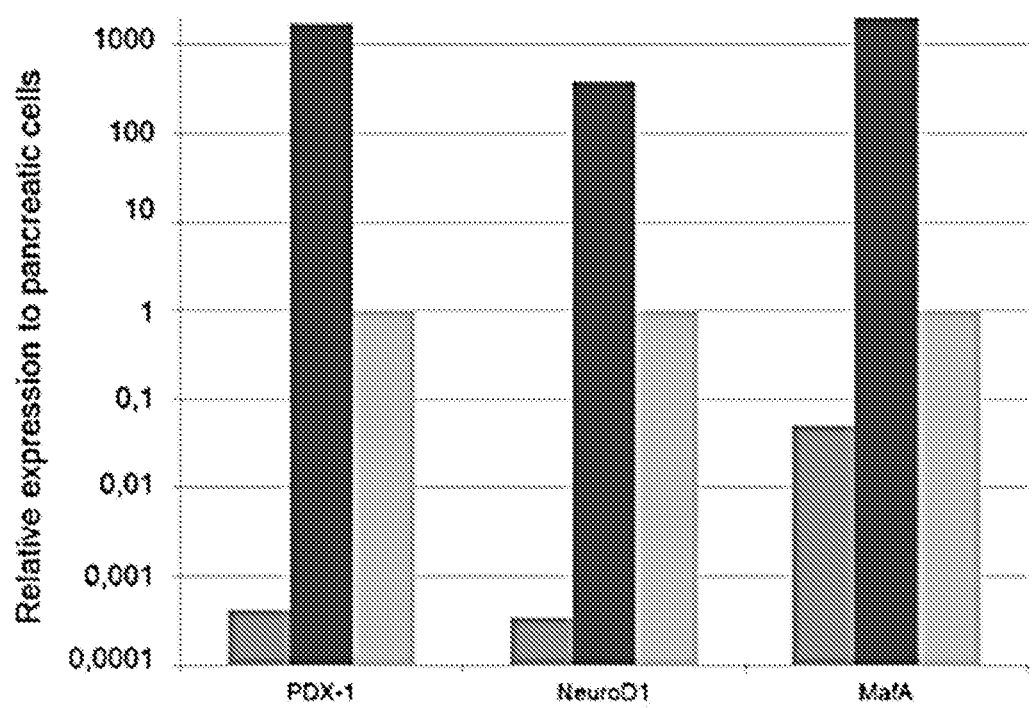
FIGS. 27A-27B show bar graphs displaying typical results of endogenous gene expression from populations of transdifferentiated human primary liver cells, the results showing an increase in endogenous of pancreatic cell markers (PDX-1, NeuroD1, MafA, glucagon, and somatostatin) compared with control untreated (non-transdifferentiated) cells.
Figure 27B:
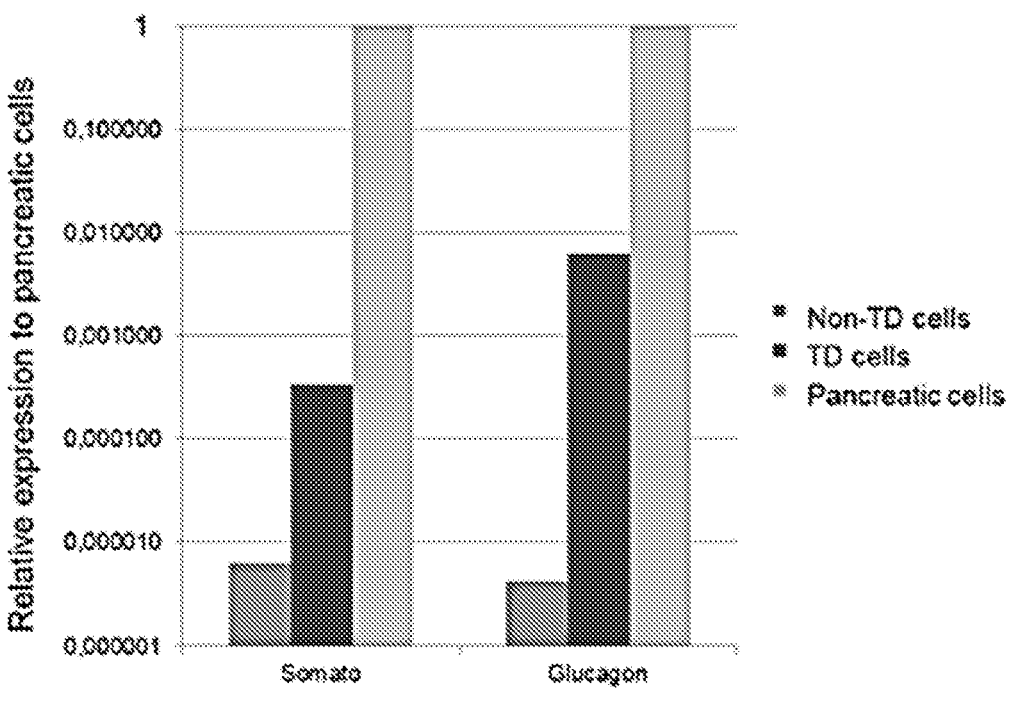

The bar graphs presented in FIGS. 27A and 27B show the typical results obtained following use of the hierarchy protocol. A comparison of transdifferentiated liver cells (AIP cells) with pancreatic cells and the control population of non-transdifferentiated liver cells is presented wherein it can be seen the AIP cells show a significant increase in pancreatic cell markers compared with control.

The result of further characterization of the cells for hepatic versus pancreatic phenotype of function of the AIP cells is presented in Table 9 below. The significant decrease of hepatic markers in PDX-1 cells combined with the increase of pancreatic cell markers indicates successful transformation of liver cells to cells having phenotype and function of pancreatic β-cells.

TABLE 9

| AIP cells product specification, as identified by FACS | |
|---|---|
| After Trans-differentiation | Specifications |
| Hepatic markers in Pdx-1 + positive cells | <1% |
| Each ectopic pTF | >80% |
| Insulin/c-peptide | >10% |
| NKX6.1 | >10% |
| Glucagon | >10% |

Analysis for dead cells within the population of harvested AIP cells showed that less than 20% of the cells were dead (data not shown).

Figure 28:
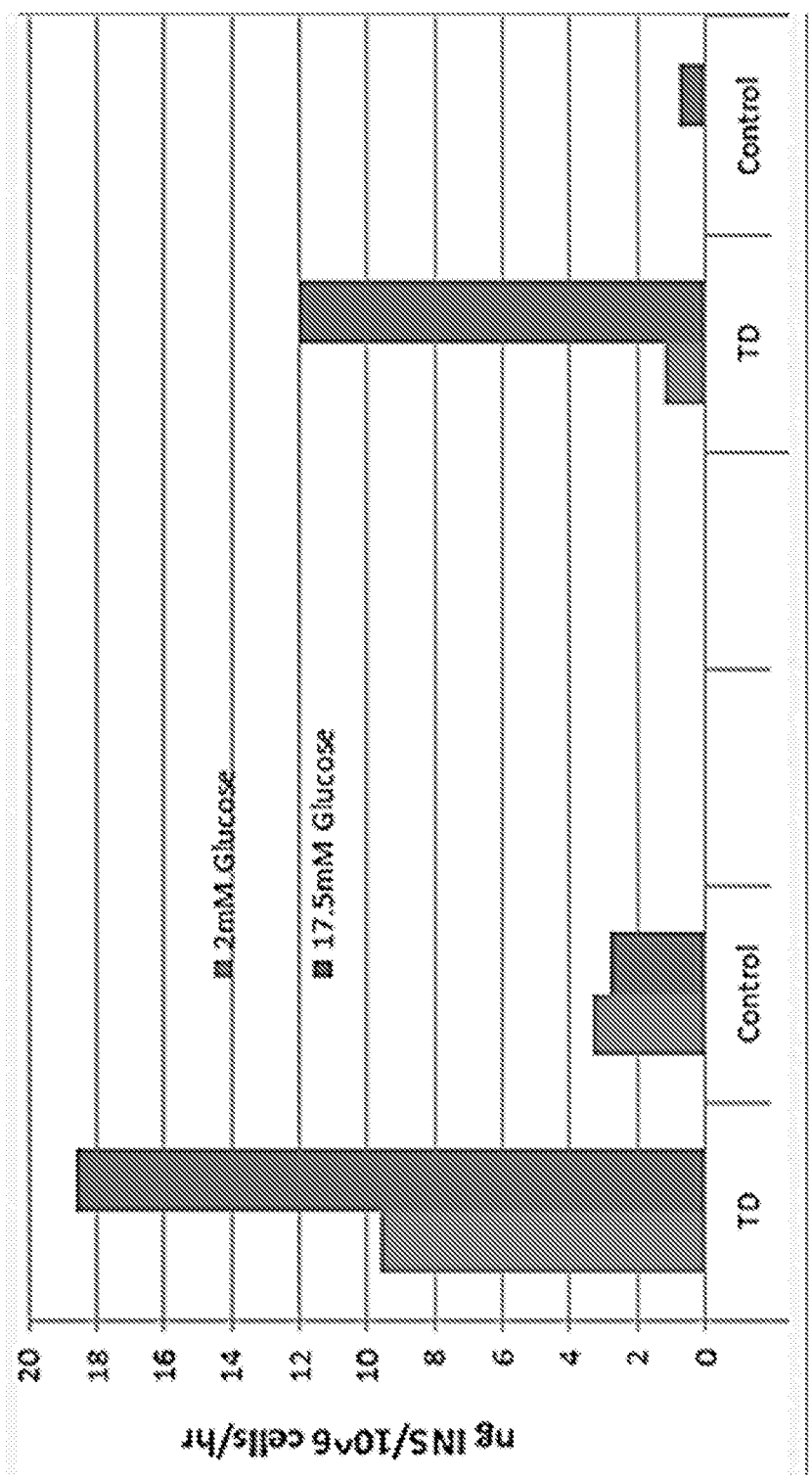
FIG. 28 shows the results of testing for AIP cell product Potency (glucose regulated insulin secretion, assayed by ELISA).

The harvested AIP cell product was also analyze for function secretion of insulin. FIG. 28 shows AIP cell product Potency (glucose regulated secretion of insulin as measured using ELISA). The AIP cell product tested represents a transdifferentiated population of cells that had been expanded in an XP-200 bioreactor. Insulin secretion was measured by GSIS (glucose stimulated insulin secretion at low (2 mM) and high (17.5 mM) glucose concentrations with KRB+0.1% BSA RIA-grade, or recombinant BSA). Results are presented as ng insulin per million cells per hour and show the significant increase of response of AIP cells.

2+1 Transdifferentiation (TD) Protocol

Figure 29:
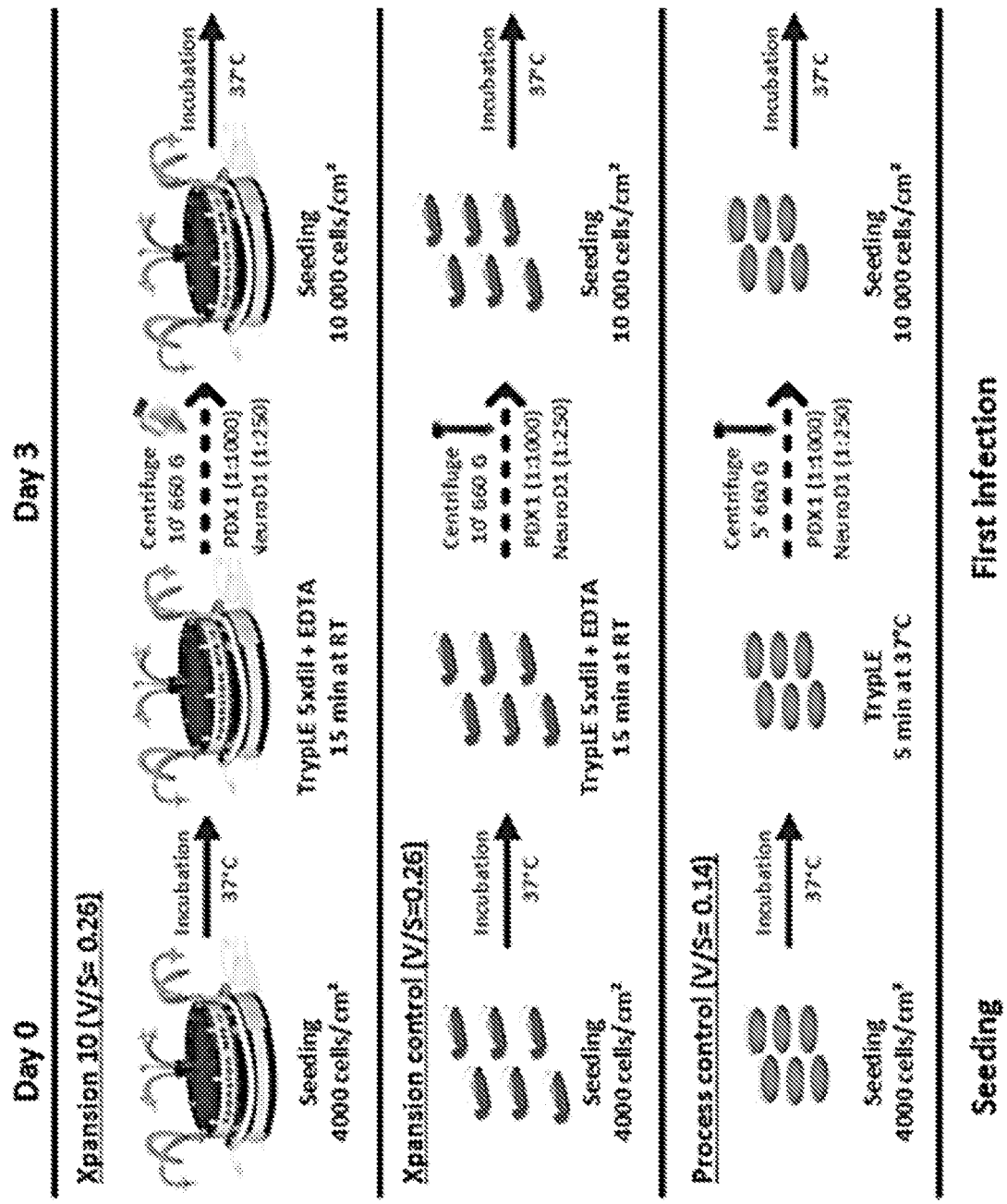
FIG. 29 shows a flowchart showing three different "2+1" transdifferentiation protocols, including protocols using multi-system bioreactors, for the production of human insulin producing cells from non-pancreatic cells, as shown here starting from liver cells. The flowchart indicates target cell densities at seeding and plating post infection, as well as the first infection comprising infecting with adenoviral vectors comprising DNA encoding PDX-1 and NeuroD1 polypeptides, and the second infection comprising infecting with an adenoviral vector comprising DNA encoding MafA. In all, seeding to harvest occurs in about 8 days.
Figure 29:
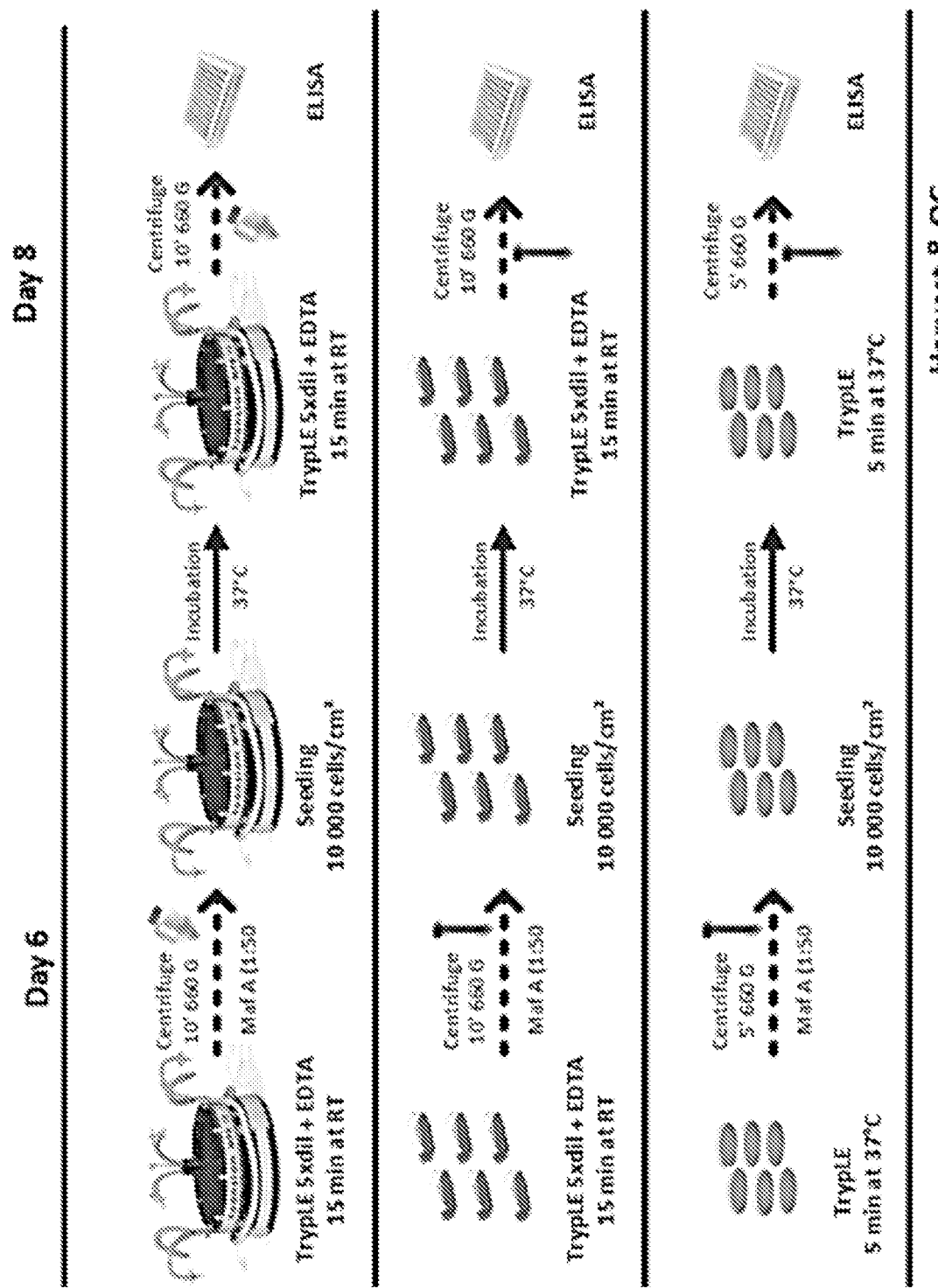

FIG. 29 presents "2+1" TD protocols using Xpansion bioreactor systems as well as a process control. The results of using the "2+1" TD protocol in combination with a multi-system bioreactor demonstrated the feasibility of this protocol, which efficiently produced AIP product cells. The first infection was performed at day 3 using either an adenoviral vector comprising a nucleic acid that encoded PDX-1 and NeuroD1 polypeptides on two adenoviral vectors—one comprising a nucleic acid encoding PDX-1 and the other comprising a nucleic acid encoding NeuroD1. The MOI for PDX-1 as 1:1,000 and for NeuroD1 was 1:250. Cells were then incubated for 3 days and a second infection was performed on day 6 using an adenoviral vector comprising a nucleic acid encoding MafA (1:50 MOI). The cells were harvested two days later at day 8 and screened for quality control markers, similar to that described above when the hierarchy (1+1+1) protocol was used.

Observation of cell cultures at the time of the second infection (day 6) showed similar confluences independent of the conditions used (FIGS. 30A-30D and 31A-31B). At the time of final harvest cells processed under CTL (control) conditions presented slightly higher cell confluence than other conditions (FIGS. 32A-32D). Differences in cell densities were due mainly to different seeding densities, and cell recovery yields and mortality on days following infection.

The insulin content of harvested cells was assayed and the results presented in FIGS. 33A-33B demonstrates increased insulin content (micro International Units/million cells) for cells transdifferentiated under all three 2+1 protocols tested, as compared with controls that were untreated (not infected with viral vectors comprising nucleic acids encoding PDX-1, NeuroD1, and MafA). The process CTL condition presented expected trend yielding significantly higher insulin content than untreated cells (~2.5× higher). The Xpansion CTL condition also presented expected trend wherein treated cells presented significantly higher insulin content than untreated cells (~1.7× higher). Cells transdifferentiated in the Xpansion 10 system presented similar insulin content than treated cells of the Xpansion CTL condition (~1.7× higher than untreated control)

Use of the "2+1" transdifferentiation protocol was efficient (reduced step number and opportunities for cell lose) in producing AIP cell product with significantly higher insulin content than untreated liver cells.

Purity Assays

Purity assays were developed to ensure that more than 90% of the cells during the expansion and transdifferentiation steps have a mesenchymal stem cell (MSC)-like phenotype (See above in Methods). These purity assays were used independent of the protocol used for transdifferentiation. Cultivated MSCs should stain positive for CD73, CD90, CD105, and CD44. In addition, MSCs should be negative for CD45, CD34, CD14 or CD11b, CD19 or CD79 #, and HLA-DR surface molecules. Previous results (FIGS. 34A and 34B) demonstrated that MSC markers were stable over time and during transdifferentiation of liver cells. Results showing the MSC-like phenotype of AIP cells are presented in Tables 3 and 4. Both flow cytometry and immunofluorescence assays were used to examine these parameters.

Example 14: Wnt Treatment Prior To Transdifferentiation Improves Transdifferentiation Competence Objective The objective of this study was to improve transdifferentiation competence within a cell population.

As described above at Example 10, active WNT signaling characterized the eGFP+ predisposed population. While the experiment described above demonstrated that induction of WNT signaling improved transdifferentiation efficiency when applied together with the transdifferentiation transcription factors, it did not show whether the pre-existing WNT signaling in eGFP+ is associated with their increased competence to redirect their differentiation fate.

Methods

In order to test whether WNT signaling endows the cells with competence for transdifferentiation, eGFP+ cells were treated with 10 mM lithium (Li) for 48 hours prior to the addition of the transdifferentiation factors. The lithium was then removed from the media when the pancreatic transcription factors were added.

Results

Figure 35B:
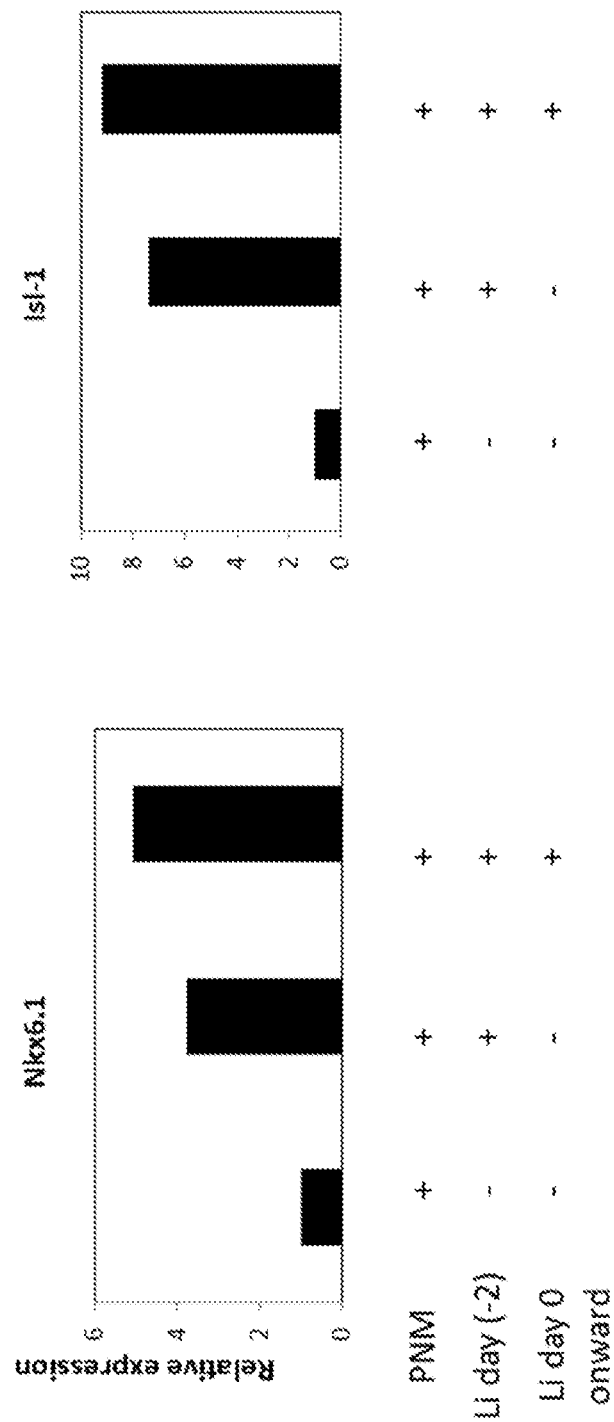
Figure 35C:
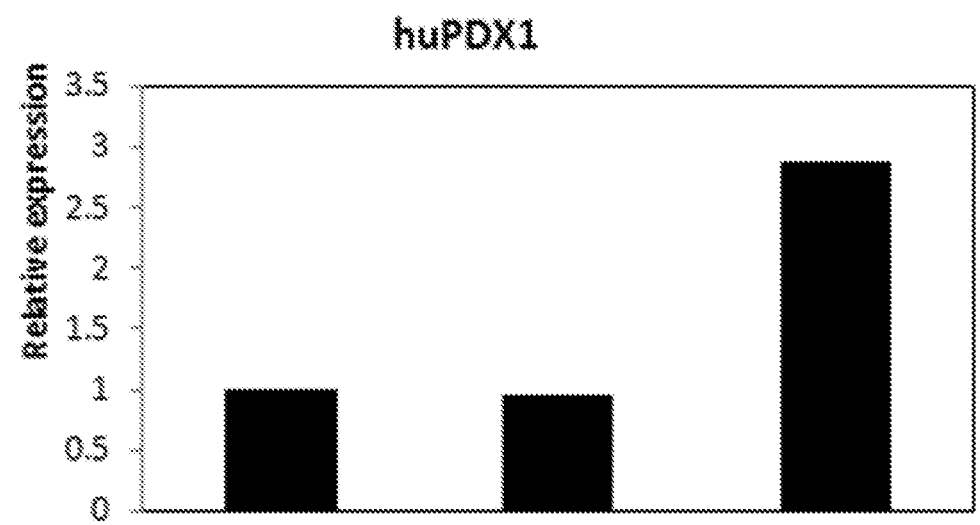

Upon transdifferentiation, cells that were pre-treated with Li demonstrated an increase in insulin secretion (FIG. 35A), as well as expression of pancreatic genes (FIG. 35B) indicating that WNT signaling is a "built-in" signal pathway enabling the cells to undergo efficient transdifferentiation. Interestingly, endogenous PDX-1 expression levels were not upregulated with Li pre-treatment (FIG. 35C), suggesting that late WNT signal is necessary for stable pancreatic repertoire.

General Methods for Examples 15-21

Human Liver Tissues and Cultures:

Liver tissues were used with the approval of the Sheba Medical Center Committee on Clinical Investigations (the institutional review board). All liver specimen donors or guardians on behalf of minors provided written informed consent for the collection of all samples and subsequent analyses. Tissue processing, isolation and maintenance of cell cultures were described previously (Berneman-Zeitouni D, Molakandov K, Elgart M, Mor E, Fornoni A, Dominguez M R, Kerr-Conte J, et al. The temporal and hierarchical control of transcription factors-induced liver to pancreas transdifferentiation. PLoS One 2014; 9:e87812)

Induction of TD In-Vitro:

100,000 cells/well were seeded in a 6-wells plate in a low glucose DMEM media supplemented with 2 mM L-glutamine, 10% serum, antibiotics, 10 mM Nicotinamide, 20 ng/ml EGF, and 5 nM exendin4. The cells were infected with 1000MOI Ad-STF (rat Pdx-1) and 250MOI Ad-NeuroD1. After 48 hours the cells were harvested, counted, and 100,000 cells were infected with 50MOI of Ad-MafA and re-plated as above. 72 hours later the cells were analyzed for gene expression and insulin secretion, as detailed below. In separated cultures, TD was induced at similar passages of eGFP+ and DsRed+ cultures.

Mice:

Balb/c mice (8-9 weeks old, 18-19 g) were housed in an air-conditioned environment, under a 12-h light/dark cycle, and handled according to institutional animal welfare regulations. Treatment with Pdx-1 recombinant adenoviruses was described previously (Ber I, Shternhall K, Perl S, Ohanuna Z, Goldberg I, Barshack I, Benvenisti-Zarum L, et al. Functional, persistent, and extended liver to pancreas transdifferentiation. J Biol Chem 2003; 278:31950-31957.). Immunohistochemistry Analyses of insulin and GS positive cells on day 5th post treatment was performed as described (Ber et al., ibid) and using anti GLUL monoclonal antibody (BD Bioscience, 1; 1000), respectively.

Soluble Factors:

WNT3A protein (R&D) was added at concentrations of 100 ng/ml. DKK (R&D) concentrations are indicated in the text. Sodium butyrate (sigma) was added at concentration of 5 mM.

Viruses:

Lineage tracing lentiviruses: CMV-loxP-DsRed-loxP-eGFP was described previously (Mauda-Havakuk M, Litichever N, Chernichovski E, Nakar O, Winkler E, Mazkereth R, Orenstein A, et al. Ectopic PDX-1 expression directly reprograms human keratinocytes along pancreatic insulin-producing cells fate. PLoS One 2011; 6:e26298.). A vector containing GS-regulatory element (GSRE) upstream of minimal Thymidine Kinase promoter (TKp) has been described (Werth M, Gebhardt R, Gaunitz F. Hepatic expression of glutamine synthetase in rats is controlled by STAT5 and TCF transcription factors. Hepatology 2006; 44:967-975.). The GSRE/TKp element was subsequently cloned into an EcoRI/AvaI site upstream of a Cre-recombinase in a pTrip lentiviral expression clone. In one embodiment, the nucleotide sequence of the GSRE-Cre element comprises a GS Intron1, a GS 5' enhancer, and a Tk partial promoter. In one embodiment, the nucleotide sequence of the GSRE-CRE element comprises (SEQ ID NO: 10)
CAAGCTCAGATCCAAGCTGGGCTGCAGGAATTCTCTACAAGCCCTCTCTG

TCCTGGTACTCATTATGAAGACCAAGATTTCCTGAAATCAGACAATCTAC

CGGTCTCCTGAGAACTGGGATTAAAGGTATTCCCCTCTACACCAGGCCTC

AATGGCTGACTTCATTACTGGGATGAAAAGTCCTTCCTCCAGAGACAGAT

TTCAATGCGAAAATTACAGTATTTGAGAAGATCCCACCAGATGATATTTT

CTGGTGAGTAGAAAAAAATCCCACCTCTAATAAAGACCCCAGCTTCTTGT

TTACCCCTGAAAGTCAGTGGTCACATGAGATGTTCCTGGTCACATGGAAG

GATCAAAGCAAGCCTGCTTCTATTCTTGGAAACAGAGCAAATGTTCTCTT

GATGCTGCCGCTGTTTCTGTGTGGTCAATTTGTGTTTATCGAACACTCAG

TCTGGAAACTGTTTGGGGGCGGGGTGGGGTATAGGAGAATAAGCAGCAAA

AGAGGTTAACGTGTCTAGGAAGGGAAGCCAGCACTCCCGTGGCGGAAATG

CAAGAAACCCAGGAAAAACAACACATTTGCTCAGGGTTTTCACCTTTTCT

ACTGAGATTCCCCTGGCCTCATTCTGGACCCTGGTGAAGACTGCTGAAGG

CTACTCTGTTTGATGGGTACCGAGCTCGAGATCCGGCGAATTCGAACACG

CAGATGCAGTCGGGGCGGCGCGGTCCGAGGTCCACTTCGCATATTAAGGT

GACGCGTGTGGCCTCGAACACCGAGC

In one embodiment, the nucleotide sequence of the GS Intron1 comprises: CAAGCTCAGATCCAAGCTGGGCTGCAGGAATTCTCTA-CAAGCCCTCTCTGTCCTGGTA CTCATTATGAAGAC-CAAGATTTCCTGAAATCAGACAATCTACCGGTCT-CCTGAGAACT GGGATTAAAGGTATTCCCCTCTA-CACCAGGCCTCAATGGCTGACTTCATTACTGGGAT GAAAAGTCCTTCCTCCAGAGACAGATTT-CAATGCGAAAATTACAGTATTTGAGAAGAT CCCACCAGATGATATTTTCTGGTGA (SEQ ID NO: 11). In one embodiment, the nucleotide sequence of the GS 5' enhancer comprises: GTAGAAAAAAATCC-CACCTCTAATAAAGACCCCAGCTTCTTGTT-TACCCCTGAAAGTC AGTGGTCACAT-GAGATGTTCCTGGTCACATGGAAGGATCAAAGC-AAGCCTGCTTCTAT TCTTG-GAAACAGAGCAAATGTTCTCTT-GATGCTGCCGCTGTTTCTGTGTGGTCAATTTG TGTTTATCGAACACTCAGTCTG-GAAACTGTTTGGGGGCGGGGTGGGGTATAG-GAGAAT AAGCAGCAAAAGAGGTTAACGTGTCTAG- GAAGGGAAGCCAGCACTCCCGTGGCGGA AATGCAAGAAACCCAGGAAAAACAACACAT-TTGCTCAGGGTTTTCACCTTTTCTACTG AGAT-TCCCCTGGCCTCA (SEQ ID NO: 12). In one embodiment, the nucleotide sequence of the Tk partial promoter comprises: GCTGAAGGCTACTCTGTTT-GATGGGTACCGAGCTCGAGATCCGGCGAATTC GAACACGCA-GATGCAGTCGGGGCGGCGCGGTCCGAGGTC-CACTTCGCATATTAAGGT GACGCGTGTGGCCTCGAACACCGAGC (SEQ ID NO: 13).

Recombinant adenoviruses: Ad-CMV-pdx1, Ad-CMV-mafA, Ad-CMV-β-Gal were described previously (Berneman-Zeitouni D. ibid) and in the Examples above. Ad-CMV-NeuroD1 contains human NEUROD1 cDNA sequence. Ad-β-catenin-S37A (S37A) is described in Young C S, Masckauchan T N H, Kitajewski J. β-catenin/Tcf activation partially mimics the transforming activity of Wnt-1 in Rat-1 fibroblasts. Differentiation 2003; 71:477-485, and was used to infect liver cells at 10 MOI.

In vitro lineage tracing was performed by a modified dual lentivirus system as in Meivar-Levy I, Sapir T, Berneman D, Weissbach T, Polak-Charcon S, Ravassard P, Tzakis A G, et al. Human liver cells expressing albumin and mesenchymal characteristics give rise to insulin-producing cells. J Transplant 2011; 2011:252387. Cells derived from >20 different donors (ages 3-60) were treated by both lentiviruses. Five to fifteen percent of the cells became eGFP+ within 10 days at most (Data not shown), and sorted by FACSAria, followed by separate propagation.

Insulin Secretion:

Glucose regulated insulin secretion (FIGS. 38D and 38F, and 41A) was measured by radioimmunoassay kit (DPC, Los-Angeles, Calif.) as described previously (Berneman-Zeitouni D et al., ibid). Secretion under high glucose concentration (17.5 mM, FIGS. 41C and 41F) was measured by Ultrasensitive Insulin ELISA kit (Alpco, Salem, N.H.) according to manufacturer's protocol.

Antibodies:

IHC was performed as described previously (Berneman-Zeitouni D et al., ibid). Polyclonal Guinea pig anti-Insulin antibody (Dako, cat #A0564) was used at 1:1000 dilution. GS/Glul expression was detected by monoclonal antibody (BD Bioscience, 1:1000). Western blot was performed as described previously (Aviv V et al., ibid). Monoclonal anti-active-β-catenin antibody (Millipore, clone 8E7) was used at a 1:2000 dilution.

Gene Expression:

RNA was prepared from cells and reverse-transcribed. Relative expression of indicated genes was measured by StepOne Real-Time PCR System using Fast SYBR Green Master Mix (Applied Biosystems), with β-actin as reference. Amplification primers are detailed in table 10.

TABLE 10

Real Time PCR primers for endogenous human genes

| Gene | Forward primer | SEQ ID NO: | Reverse primer | SEQ ID NO: |
| --- | --- | --- | --- | --- |
| Ins | 5' GAAGCGTGGCATTGTGGAAC 3' | 14 | 5' GCTGCGTCTAGTTGCAGTAGT 3' | 15 |
| GCG | 5' CCAAGATTTTGTGCAGTGGT 3' | 16 | 5' GGTAAAGGTCCCTTCAGCAT 3' | 17 |
| SST | 5' ATGATGCCCTGGAACCTGAAG 3' | 18 | 5' GCCGGGTTTGAGTTAGCAGAT 3' | 19 |
| NKX6-1 | 5' GGGCTCGTTTGGCCTATTCG 3' | 20 | 5' GTGCTTCTTCCTCCACTTGGT 3' | 21 |
| PAX6 | 5' CCAGTATAAGCGGGAGTGCC 3' | 22 | 5' GCTTTTCGCTAGCCAGGTTG 3' | 23 |
| ISL1 | 5' TGGGCTGTTCACCAACTGTA 3' | 24 | 5' CGCAACCAACACATAGGGAA 3' | 25 |
| PDX1 | 5' AAGTCTACCAAAGCTCACGCG 3' | 26 | 5' GTAGGCGCCGCCTGC 3' | 27 |
| WNT1 | 5' CAACCGAGGCTGTCGAGAAA 3' | 28 | 5' TCACACGTGCAGGATTCGAT 3' | 29 |
| FZD4 | 5' CACACCGCTCATCCAGTACG 3' | 30 | 5' TTCCTTCAGGACGGGTTCAC 3' | 31 |
| ROR2 | 5' GCTCTCAGTGTCCCGGACTT 3' | 32 | 5' GCCCATCAAGGGGTCCTAAA 3' | 33 |
| LRP5 | 5' CCATCCATGCCTGCAACAAG 3' | 34 | 5' GCGAGTGTGGAAGAAAGGCT 3' | 35 |
| beta-actin | 5' CCTGGACTTCGAGCAAGAGA 3' | 36 | 5' CAGCGGAACCGCTCATTGCCAATGG 3' | 37 |

Global Gene Expression Analysis:

cDNA was synthesized, labeled and hybridized to HG-U133A-2 array (Affymetrix, Inc., Santa Clara, Calif.) containing 22,215 gene-transcripts (corresponded to 14500 well characterized human genes), washed and scanned (Hewlett Packard, GeneArray™ scanner G2500A) according to manufacturer's protocol. Data analysis was performed using the Partek Genomics Solution software (www.partek-.com). For the raw data normalization the Robust Multichip Average (RMA) method was applied. Biological processes enrichment was analyzed through Panther tool (http://pantherdb.org/).

Statistical Analyses:

Statistical analyses were performed using Two-Sample Student's t-test assuming equal variances.

Example 15: Primary Cultures of Human Liver Cells are Consistently Separated into 2 Discrete Groups with Regard to Wnt Signaling In-Vitro It was previously demonstrated that a combination of pTFs and soluble factors activates the pancreatic lineage in about 10-15% of the treated liver cells (See Examples 4, 5, 6, and 7 above). In pTFs-treated mouse livers, despite uniform distribution of ectopic PDX1 expression, induced insulin producing cells (IPCs) were primarily localized in the vicinity of the central vein (FIGS. 8A-D), possibly suggesting that pericentral hepatic cells may have a predisposition for transdifferentiation into pancreatic-like cells. This led to an examination for a possible association between transdifferentiation-competence and cells' lineage in human livers as well.

Figure 36:
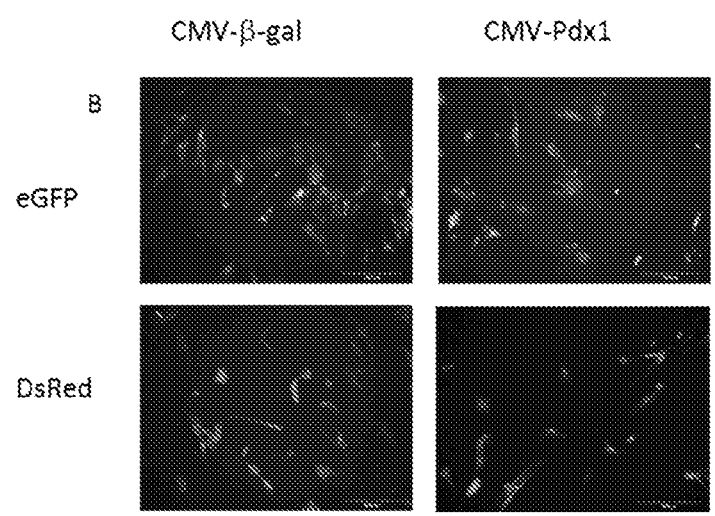
FIG. 36 shows eGFP (top) and DsRed cells (bottom) were stained for PDX1 expression (blue) following infection with CMV-Pdx1 virus (right panels). In both cultures 78.5±9% of the cells stained positive for PDX1. Left panels: control (CMV-b-gal) infection. Similar levels of PDX1 transcripts were verified by RT-qReal-time PCR. Ct for rat pdx 1 transcript is typically 19-20 in both eGFP and DsRed cells; (Ct forbeta-actin is 17-19.)
Figure 37A:
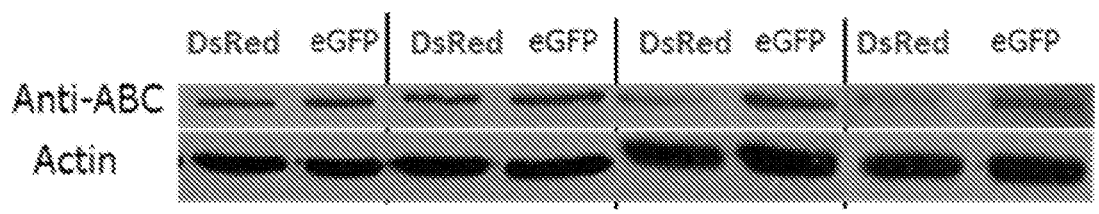
FIGS. 37A-37D show separation of human liver cells based on the Glutamine Synthetase regulatory element. Differential expression of wnt pathway molecules in eGFP and DsRed, cells: Levels of activated β-catenin (FIG. 37A-37C) were measured by Western blot in DsRed and eGFP cells originating from four liver donors (FIG. 37A), and quantified (relative to beta-actin) by ImageJ (FIG. 37B). Relative transcript levels of wnt signaling downstream transcription factors; PITX2 (FIG. 37C) and wnt signaling inhibiting gene APC (FIG. 37D), were measured in DsRed and eGFP cells by RT-qReal Time PCR, and normalized to β-actin levels. Results are average and SE of seven independent donors. * P-value<0.05; ***P-value=0.0006.
Figure 37B:
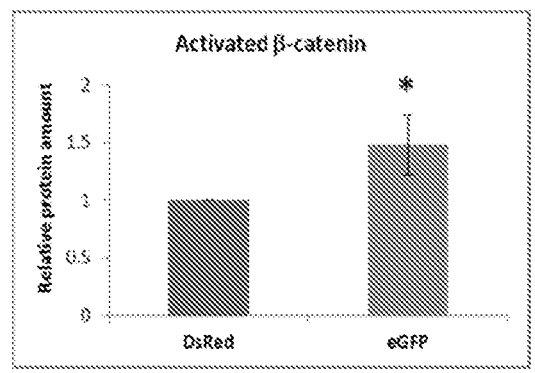
Figure 37C:
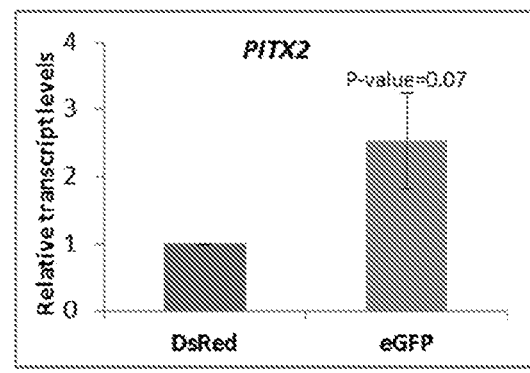
Figure 37D:
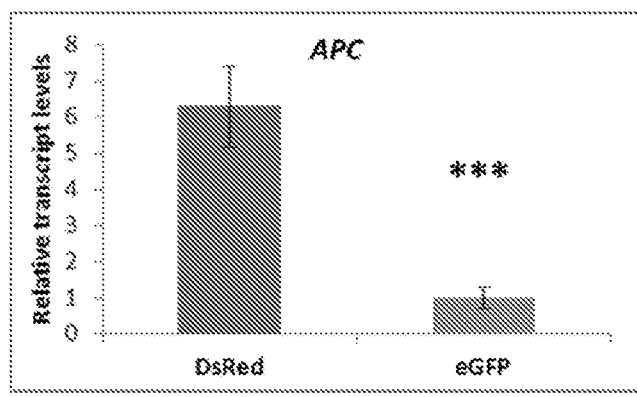

Lineage tracing was used to isolate human pericentral liver cells in vitro. The system is based on a CMV-loxP-DsRed-loxP-eGFP (R/G) reporter and Cre-recombinase under the control of the pericentral specific glutamine synthetase response element (GSRE), which contains a wnt response element (WRE) (FIG. 14). In experiments similar to those performed in Example 4, primary cultures derived from 20 different human donors, typically 5-15% of the cells were GS/eGFP-positive, while most of the cells retained DsRed expression (FIGS. 10A, 10B, 10D, and 10E). Both populations had similar rate of proliferation after separation (FIG. 14). Differential expression of wnt pathway genes was preserved, as confirmed by higher levels of active β-catenin protein and the wnt-regulator Pituitary homeobox-2 (PITX2) expression in eGFP+ cells (FIG. 37A-36D) while expression of the wnt inhibitor gene APC was six fold higher in DsRed+, cells (FIG. 37D).

These characteristics were maintained with increase in culture passage and after cryopreservation, suggesting that surprisingly, primary liver cells in culture maintain their unique wnt-signaling patterns, and can be separated into two sub-populations of cells with consistent characteristics.

Figure 38A:
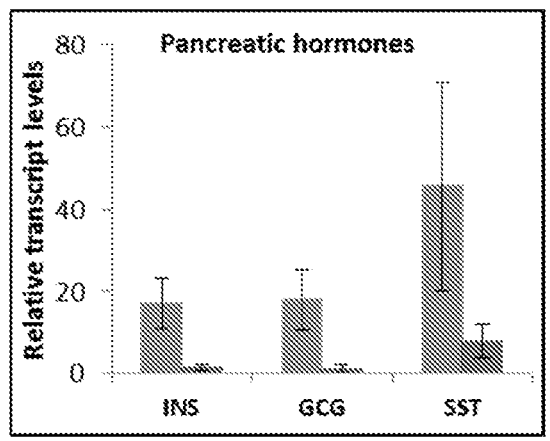
Figure 38B:
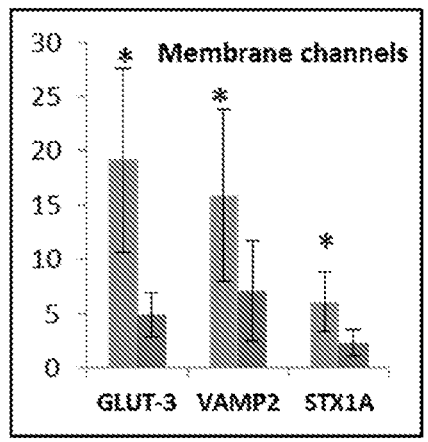
Figure 38C:
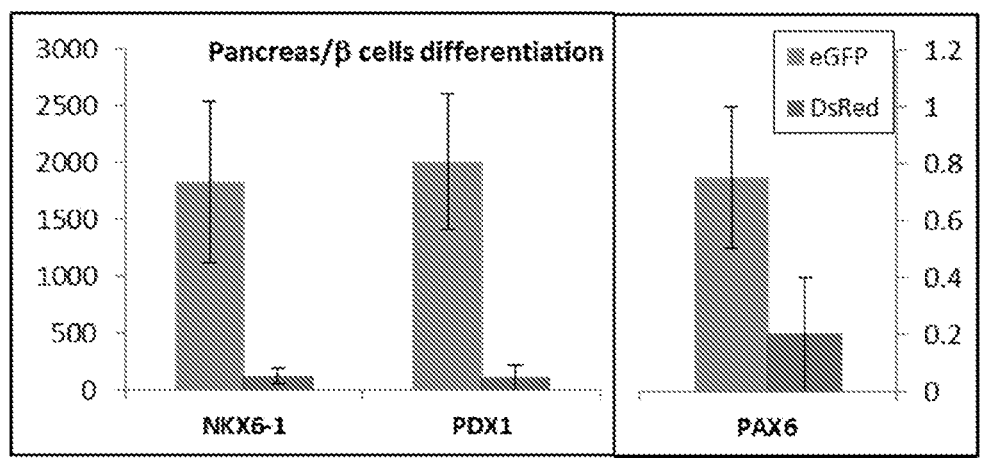
Figure 38D:
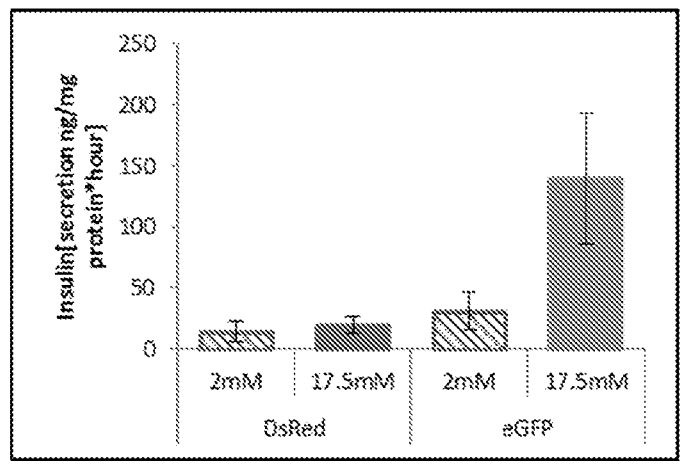

Example 16: Cells Originating from Human Pericentral Populations Possess an Innate Propensity for Reprogramming into Endocrine Pancreas Upon Ectopic pTFs Expression Both eGFP+ and DsRed+ cultures were similarly treated by pTFs according to the TD protocol and analyzed for the activation of the pancreatic lineage at molecular, cellular and functional levels. eGFP+ cells displayed higher levels of endogenous pancreatic gene expression pattern (FIGS. 38A-38C) and glucose-dependent insulin secretion (FIG. 38D), despite equivalent expression of ectopic rat-PDX1 and similar rate of cell proliferation (FIG. 36). FIG. 38A shows increase in pancreatic hormones insulin (INS), glucagon (GCG), and somatostatin (SST). FIG. 38B shows increase in membrane channel proteins GLUT-3 (Solute carrier family 2, facilitated glucose transporter member 3), VAMP2 (Vesicle-associated membrane protein 2), and Stx1a (Syntaxin-1A).

IHC revealed that 64.1±7.9% of the cells stained positive for insulin (FIG. 38E), as opposed to up to 10-14% of cells in unseparated culture. Unexpectedly, the difference in the efficiency of reprogramming was heritable and maintained following extended cell propagation in culture (FIG. 38F). Comparable expression of liver progenitor genes SOX9 and FOX11 (FIGS. 39C-39D), suggest that their expression is elevated in dsRed+ cells compared to the eGFP+ cells. Neither EpCam; nor LGR5, could be detected in both groups (data not shown)

These data demonstrate that transdifferentiation propensity consistently correlates with a small specific population of cells in the human liver.

Example 17: eGFP+ and DsRed+ Cells Undergo Equivalent Hepatic Dedifferentiation in Response to Ectopic pTFs Expression Transdifferentiation is characterized by two distinct developmental processes, both induced by the expression of the ectopic pTFs. The first is the repression of the hepatic repertoire of genes, and the second is the activation of the alternate pancreatic set of genes. While the former occurs in each of the ectopic transcription factors expressing cells, the latter is restricted to a small proportion of the liver cells both in vivo and in vitro. Hepatic dedifferentiation has been suggested obligatory but insufficient for the activation of the alternate pancreatic function by ectopic pTFs.

The contrast between the uniform dedifferentiation and the limited pancreatic differentiation, led to the hypothesis that TD predisposition lies in the capacity to activate the pancreatic lineage, rather than the loss of hepatic terminal fate.

Supporting this hypothesis, following TD both eGFP+ and DsRed+ cells exhibited hepatic dedifferentiation as manifested by decreased expression of the key hepatic genes ADH and CEBPb (FIGS. 39A-39B).

These data suggest that the discriminating factor between the two populations of cells lies in their differential capacity to activate the pancreatic repertoire.

Figure 40C:
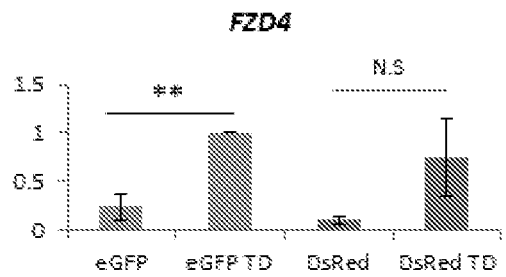
Figure 40D:
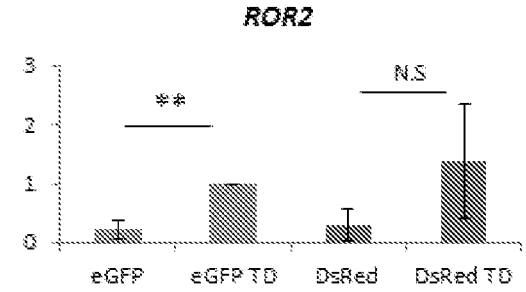

Example 18: Predisposition to Transdifferentiation is Associated with Distinct Signaling Pathways Alterations Upon Reprogramming In order to test whether inherent molecular characteristics are associated with the ability to transdifferentiate, the global gene expression profiles of both populations was examined by microarrays. 394 genes were differentially expressed between the two populations (p-value<0.05), of which, as expected, a large portion is associated with metabolic processes and responses to stimuli, as well as developmental processes (FIG. 40A).

Following reprogramming, 1737 genes were altered in eGFP+ cells and 2775—in DsRed+ cells (p-value ≤0.05). Of these, only 564 genes were common. In order to analyze the biological significance, published over-representation analysis was used and found that distinct biological functions are enriched by genes that are altered upon reprogramming in each population. Changes in differentiation and developmental processes are unique to the predisposed population. By contrast, genes that were altered in DsRed+ cells did not enrich any biological processes that we could associate with differentiation or reprogramming (FIGS. 40B-40F). These results suggest that the ability of pericentral cells to turn on specific developmental pathways may govern their predisposition to transdifferentiate into IPCs.

During normal development, expression of mutually exclusive wnt pathway genes specifies liver/pancreas development from common progenitors. Since microarray analyses indicated that most of the genetic alterations upon pTFs treatment are population-specific, it was tested if the same applies to wnt pathway components.

Figure 40E:
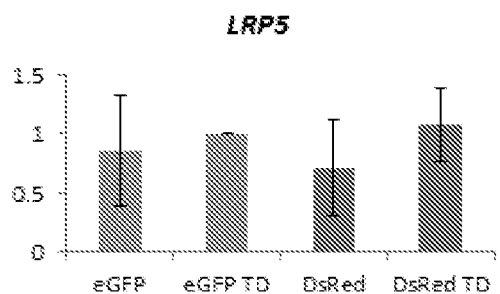
Figure 40F:
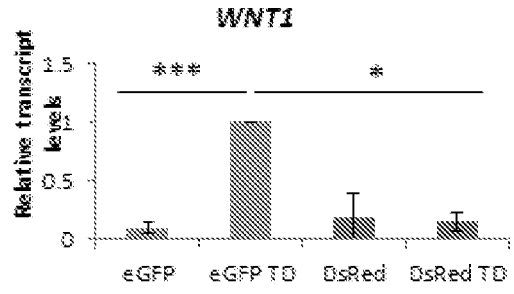

WNT receptors ROR2, FZD4 and LRP5 specify pancreatic (ROR2 and FZD4) or hepatic (LRP5) cell fate, respectively, from common endoderm progenitor. An increase in ROR2 and FZD4 transcripts was exclusive to eGFP+ cells (FIGS. 40C and 40D respectively), while increase in transcript levels of the hepatic lineage-specifying LRP5 was ubiquitous (FIG. 40E). Consistently, expression of the WNT1 gene, which has been associated with pancreas development, increased significantly only in eGFP+ cells (FIG. 40F).

Thus, activation of pancreas-specifying wnt signals is correlated with pericentral cells' predisposition for transdifferentiation.

Figure 41A:
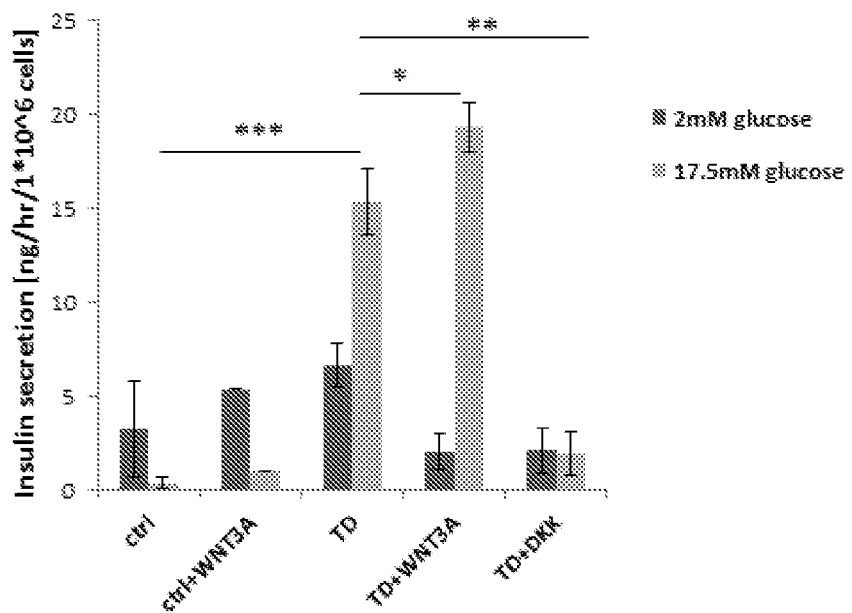
FIGS. 41A-41G show active WNT signaling controls the activation of the pancreatic lineage in liver.

Example 19: Active Wnt Signaling is Obligatory for the Activation of the Pancreatic Lineage, and it Further Promotes Reprogramming Efficiency Only in the Predisposed Human Liver Cells Based on the major role of wnt pathway in liver/pancreas cell fate acquisition, and the presence of WRE in the lineage tracing system, it was tested whether liver to pancreas transdifferentiation is controlled by wnt pathway. In human livers, addition of exogenous WNT3A protein during TD resulted in a marked increase in glucose-regulated insulin secretion, while insulin secretion was abolished by addition of the competitive WNT signaling inhibitor Dickkopf (DKK) (FIG. 41A). These observations suggest that wnt signaling plays an obligatory role in pTFs-induced liver cells reprogramming.

Next it was asked whether DsRed+ cells can be induced to transdifferentiate by activation of wnt. The wnt pathway was activated 48 hours before induction of reprogramming at two points along its pathway, separately: (1) Stabilizing endogenous β-catenin by Lithium (Li); and (2) Replenishing active β-catenin by ectopic expression of S37A, a constitutively active β-catenin mutant.

Figure 41B:
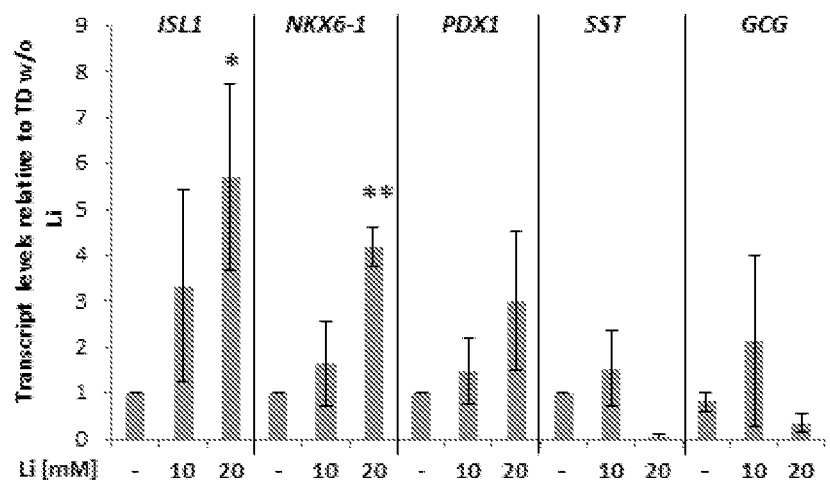
Figure 41C:
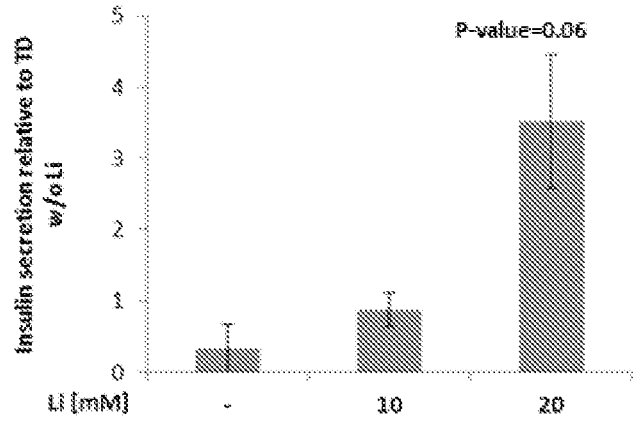
Figure 41D:
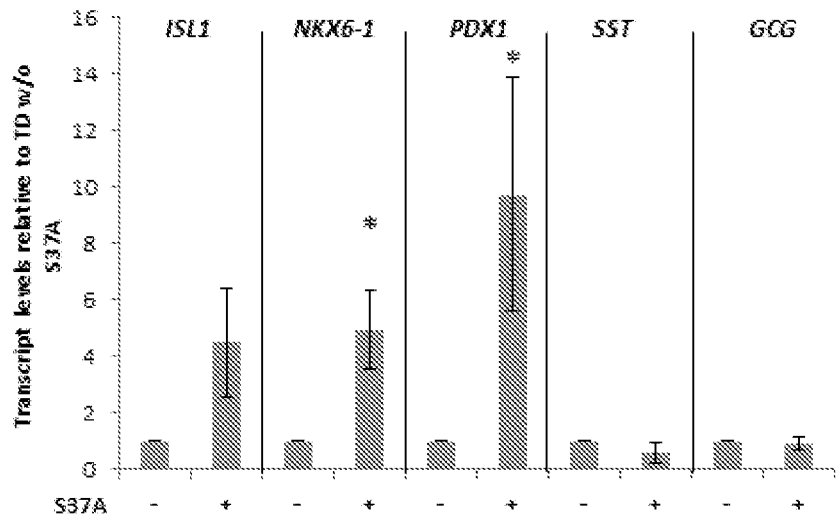
Figure 41E:
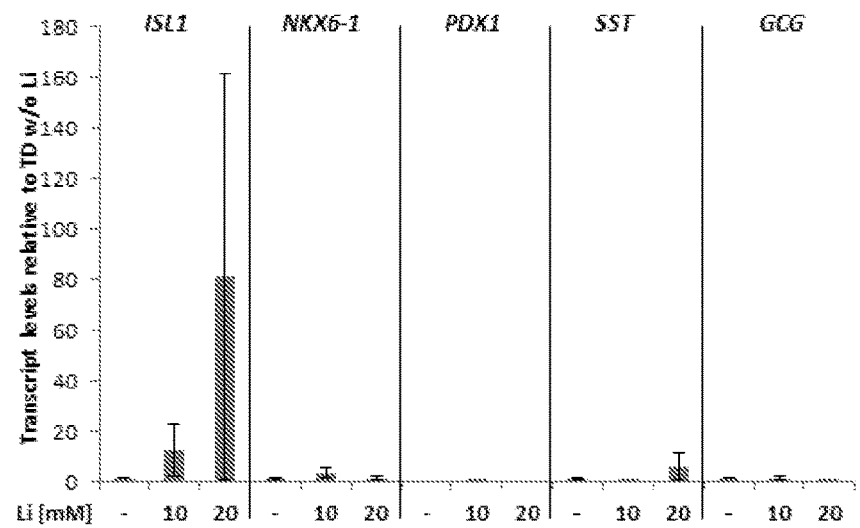
Figure 41F:
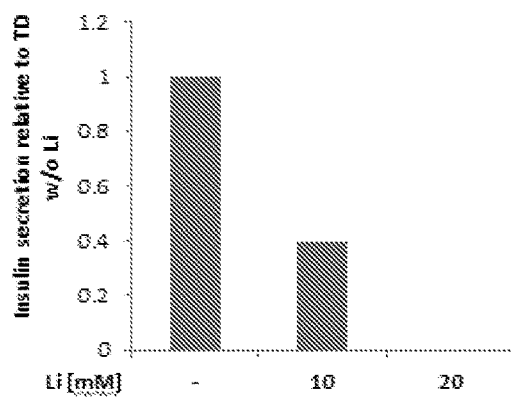
Figure 41G:
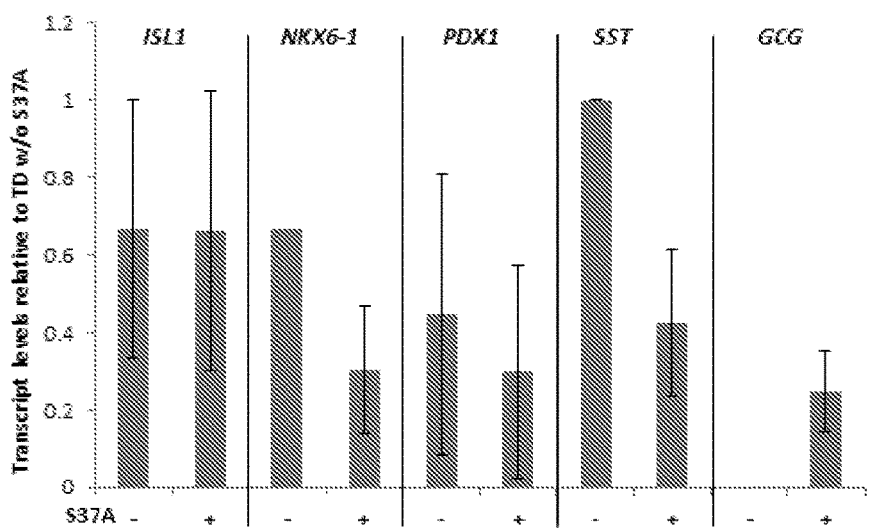
Figure 42:
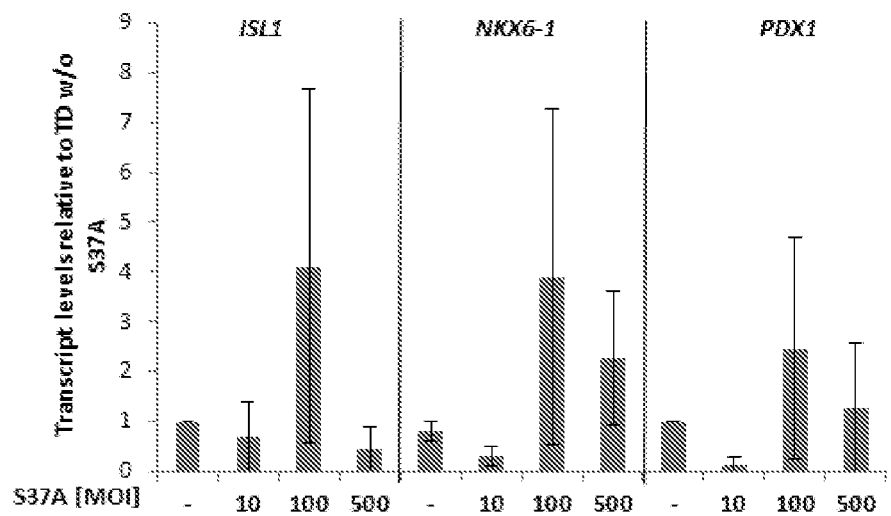
FIG. 42 shows up to 50 fold increase in S37A does not rescue TD in DsRed cells. DsRed cells were treated with pTFs and S37A at concentrations indicated in the graph. Transcript levels of pancreatic genes were measured by RT-q Real time PCR relative to treatment with pTFs alone and normalized to beta-actin.

Consistent with the induction of reprogramming in unseparated cultures by WNT3A, both treatments increased the efficiency of TD in eGFP+ cells (FIGS. 41B-41D). The increase in pancreatic cell-fate acquisition appears to be specific towards β-like cells, while SST and GCG levels (delta (δ) and alpha (a) cells, respectively) remained unaffected. By contrast, DsRed+ cells were unaffected by wnt activation (FIGS. 41E-41G). Moreover, while the effect of S37A on eGFP+ peaked at 10MOI, increasing the viral load up to 50 fold did not have a significant effect on DsRed+ cells (FIG. 42). Thus, not only lower levels of β-catenin, but innate molecular characteristics of the DsRed+ population dictate its inability to undergo efficient reprogramming.

Example 20: Innate Wnt Signaling is a Prerequisite for Reprogramming Propensity

The Examples presented above demonstrate that activating wnt signaling increased the efficiency of reprogramming only in the predisposed liver cells, without affecting the TD-resistant DsRed+ population. The next question asked was if pre-existing active wnt signaling pathway is a necessary prerequisite for reprogramming predisposition.

Figure 43A:
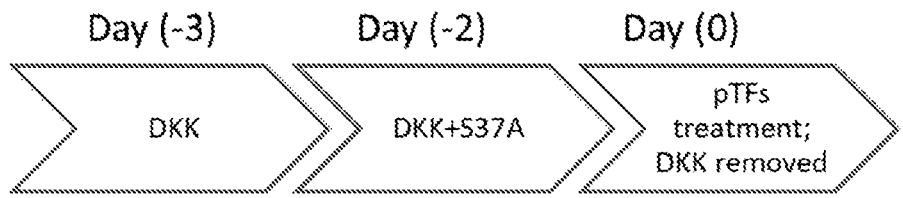
FIGS. 43A-43B show Blocking WNT receptor prior to pTFs treatment irreversibly abolishes predisposition for reprogramming.

To test that, the cell-surface WNT receptor was blocked in the eGFP+ cells by DKK for 48 hours prior to TD. The DKK was then removed, and TD treatment with pTFs was carried out in the presence of S37A, which acts downstream of the WNT receptor (see schematic illustration in FIG. 43A). S37A should thus be able to rescue wnt-dependent reprogramming if preliminary wnt signaling is not required for predisposition.

Figure 43B:
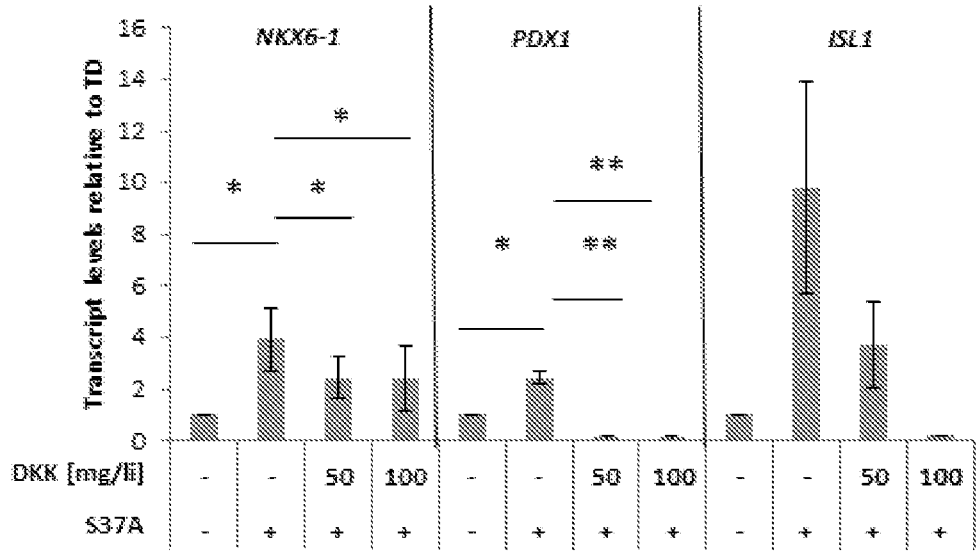

As was observed earlier, S37A increased the efficiency of reprogramming in the eGFP+ population. However, when preceded by wnt signaling inhibition, S37A was unable to enhance the process (FIG. 43B), turning the eGFP+ cells into "DsRed-like" cells by abrogating the predisposition for efficient reprogramming.

These data suggest that even a short term disruption of the innate wnt signaling induces intra-cellular alteration that cannot be overcome by β-catenin replenishment.

Example 21: Opening Chromatin Enables DsRed Cells to Respond to pTFs Induced Reprogramming and to Wnt Activation β-catenin and its downstream DNA-binding proteins recruit chromatin modifying enzymes, such as histone acetyl transferases (HAT) and histone deacetylases (HDAC) to facilitiate or hinder gene transcription, respectively. It is possible that condensed chromatin is formed in the absence of Wnt signaling, preventing activation of pancreatic genes in DsRed+ cells and in DKK-treated eGFP+ cells. Therefore, it was tested if "chromatin-opening" by HDAC inhibitors (HDACi) would enable induction of reprogramming.

Figure 44A:
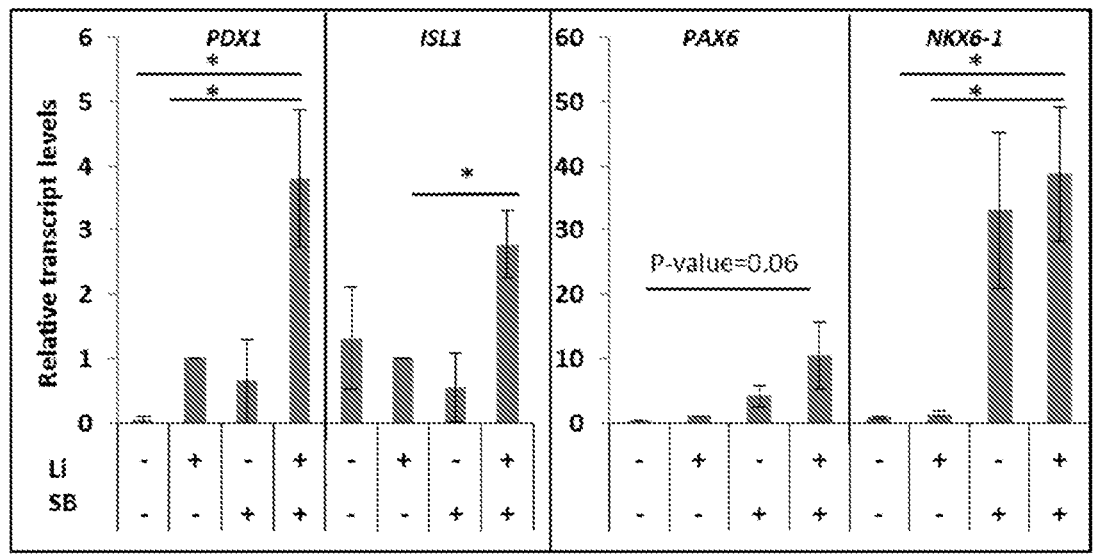
FIGS. 44A-44B The DsRed cells population shows that resistance to transdifferentiation is overcome by combining WNT activation with HDACi. Wnt-pathway activation was induced by supplementing cell medium with 10 mM Li for 48 hours. Subsequently, cells were transdifferentiated by pancreatic transcription factors (pTFs) in the presence of 5 mM sodium butyrate (SB) (FIG. 44A) or 1 µM suberanilohydroxamic acid (SAHA) (FIG. 44B). In the GFP+ cell population, a similar effect was observed when Wnt-pathway was inhibited by supplementing serum-based medium with 3 µg/ml Dickkopf (DKK) for 48 hours followed by the transdifferentiation of cells by pTFs in the presence of 5 mM sodium butyrate (SB) (FIG. 44C). Bars show ratios of transcript levels of cells treated with HDACi and pTFs compared with cells treated with pTFs alone. Transcript levels were normalized to β-actin transcript levels. N=4 independent experiments with cells from two donors. * P-value<0.05.
Figure 44B:
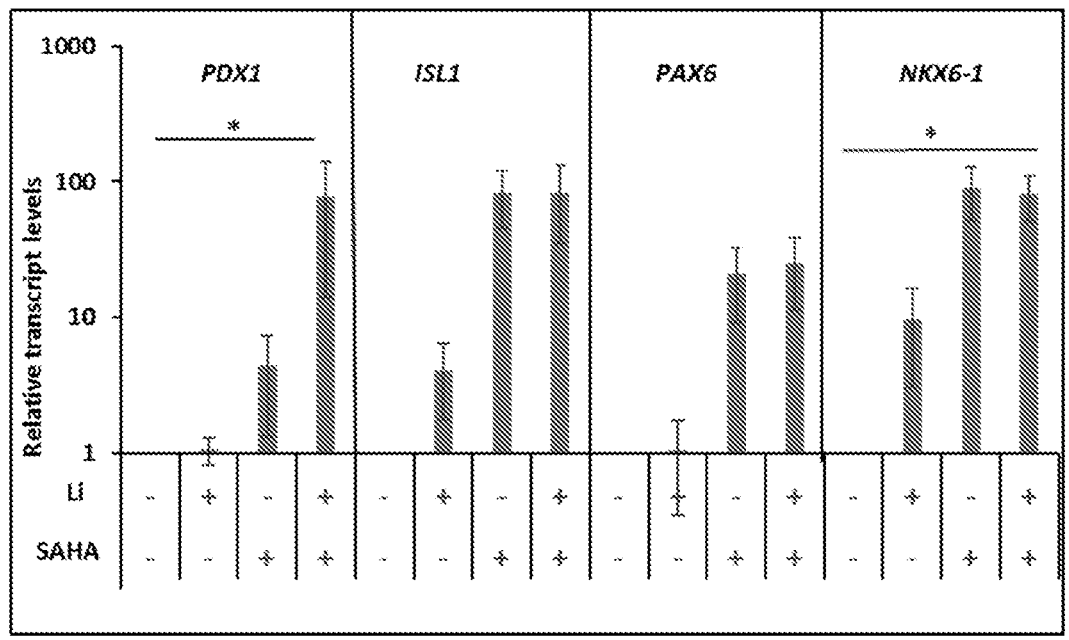

Representative HDACi sodium-butyrate (SB) and suberanilohydroxamic acid (SAHA) were used to induce histone hyperacetylation, which is associated with permissive chromatin structure. Methods: Primary liver cells were incubated with 10 mM lithium (Li) for 48 hours to activate Wnt signaling. Subsequently, cells were contacted with pancreatic transcription factors according to the "2+1" transdifferentiation protocol described in Example 12 in the presence of 5 mM SB (Na-Butyrate) or 1 μM SAHA. Results: FIGS. 44A and 44B show that cells were incubate in the absence of of Li, SB (Na-Butyrate), or SAHA; in the presence of one of Li, SB, or SAHA; or in a combination of Li with SB (Na-Butyrate) or SAHA. Surprisingly, increased reprogramming of DsRed+ cells resulted from the combination of Li with SB Na-Butyrate (FIG. 44A) or SAHA (FIG. 44B), as indicated by increased expression of pancreatic specific transcription factors PDX-1, Isl-1, Pax-4, and Nkx6.1 in these cells.

Figure 44C:
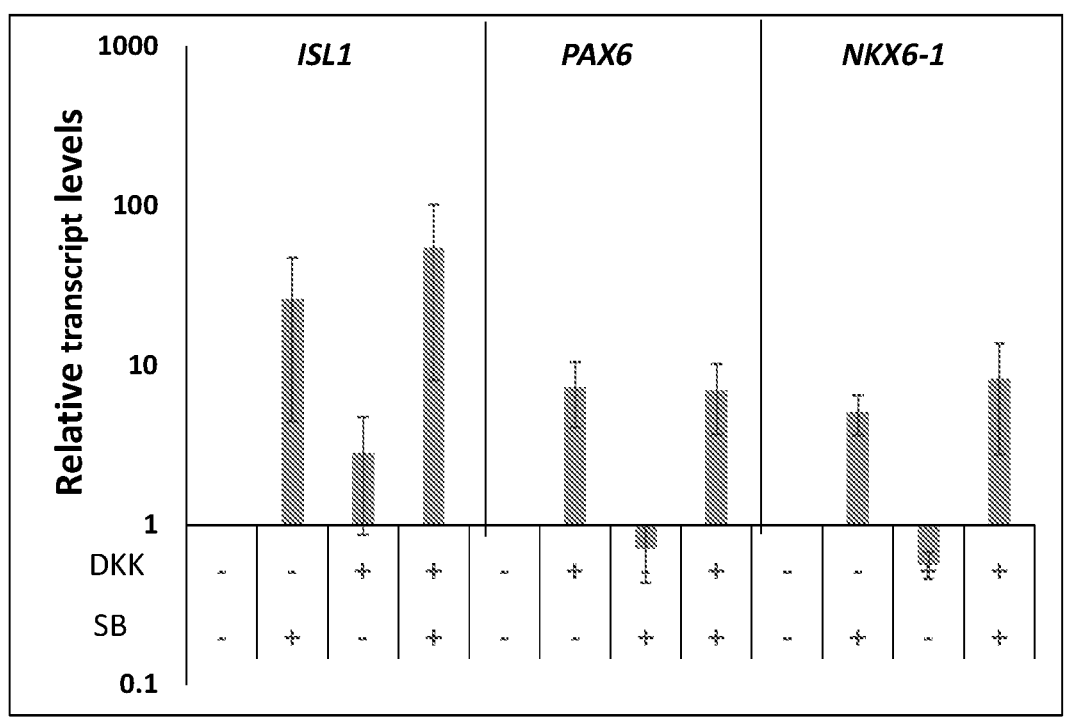

Similarly, SB (HDAC inhibitor) treatment alleviated the effect of Wnt signaling inhibition of eGFP+ cells (FIG. 44C).

Example 22: Soluble Factors that Promote pTFs Induced Liver to Pancreas Transdifferentiation Objective:

To analyze if soluble factors promote pTFs induced pancreatic transdifferentiation by inducing epigenetic modifications (such as 5-AZA for inhibiting DNA methylation and SAHA for inhibiting Histone deacetylation), by altering signaling pathways (such as TGFβ signaling or Rho signaling) and more, as elaborated in Table 11 below. Transdifferentiation of adult human liver cells (primary culture) was induced by the addition of ectopic pancreatic transcription factors (pTFs), using the "2+1" method described herein. The addition of ectopic pTFs was further supplemented with different soluble factors and a WNT pathway activator (LiCl) (as detailed in Table 11).

TABLE 11

Soluble Factors Used for the Transdifferentiation Process.

| Reagent/material | Type | Mechanism/Pathway influenced | Concentration | Timing of addition |
|---|---|---|---|---|
| 5-Aza-2-deoxycytidine (5-AZA) | Reagent | inhibitor of DNA methylation | 0.5 µM | Pre-TD |
| SAHA | Reagent | Inhibitor of Histone deacetylation | 0.5 µM | Pre-TD |
| SB431542 (SB) | Reagent | TGFβ inhibitor, promoting MET | 10 µM | Pre-TD |
| Y27632 (y2) | Reagent | Rho kinase inhibitor (ROCK) | 2 µM | Pre-TD |
| LiCl | Reagent | WNT pathway activator | 10 µM | Pre-TD |
| Triodothyronine (T3) | Reagent | Thyroid hormone | 1 µM | with TD |
| Alk5i II | Reagent | TGFβ/Activin inhibitor | 10 µM | with TD |
| GABA | Reagent | Conversion of α-cells to β-cells | 0.5 µM | with TD |

Soluble factors promote pancreatic differentiation and reprogramming by inducing epigenetic modifications (such as 5-AZA and SAHA, DNMT1 inhibition) or altering signaling pathways (such as TGFβ signaling or Rho signaling) and more, as set forth in the table above and described elsewhere herein.

Methods

Primary cultures of adult human liver cells were induced to transdifferentiation by ectopic expression of pancreatic transcription factors using the "2+1" method described herein and were supplemented by the soluble factors and Lithium (to activate the WNT pathway) as indicated in the table above.

Briefly, adult human liver cells were pre-treated with Lithium (LiCl) 72h prior to the first infection with Ad-PDX-1 and Ad-NeuroD1 in TD medium (DMEM 1 g/L glucose supplemented with 10% FCS, 10 mM Nicotinamide, 20 ng/ml EGF, and 5 nM exendin4), which was followed by a second infection with Ad-MAFA 48h later.

Different soluble factors were added either individually or in combinations at different timepoints in order to promote the transdifferentiation process efficiency: 5-AZA, SAHA, SB and Y2 were added 72h before the first infection, T3, GABA and Alk5i II were supplemented with the Ad-MAFA infection. Twenty-four hours following infection with Ad-MAFA, the medium was replaced with serum-free medium (SFM) (DMEM 1 g/L glucose supplemented with ITS and 10 mM Nicotinamide, 20 ng/ml EGF, and 5 nM exendin4) for additional 21 days until collecting the cells for analyses.

In addition to analyzing the effect of different soluble factors on transdifferentiation efficiency, another treatment being analyzed included infection with Ad-PAX4 (250 moi) pancreatic transcription factor, which was performed at the same time as the first infection with Ad-PDX-1 and Ad-NeuroD. Thus, the cells were introduced to three pTFs simultaneously during the first infection in the process (PDX-1, NeuroD1, and PAX4) and to a total of four pTFs after the second infection with Ad-MAFA 48h later. (See also Example 23 below).

Transdifferentiation followed a modified "2+1" protocol as described herein, wherein the modification comprises the addition of soluble factors or another pTF. Accordingly, 72 hours prior to the first transdifferentiation step, Lithium (LiCl) and soluble factors 5-AZA, SAHA, SB, and Y2 were individually added to the cells; each soluble factor was added to a parallel population of cells. At the first transdifferentiation step, the cells were infected by two pTFs, namely Ad-PDX-1 and Ad-NeuroD1. After 48 hours, the cells were infected by the pTF Ad-MAFA. Soluble factors T3, GABA and ALK5i II were added with the Ad-MAFA infection to parallel populations. Infection with the pTF Ad-PAX4 was added as a treatment (as a fourth pancreatic transcription factor), as it was previously reported to significantly improve the transdifferentiation process. The control population underwent the TD process using the 2+1 protocol, without an addition of any of the soluble factors as listed in Table 11, and without the addition of the Li.

In certain cases, multiple soluble factors were added to the cell transdifferentiation population, using the timing as described above. For example, 5-AZA, SAHA, SB, and Y2 were all added to a single TD population 72h before the first infection using the protocol described herein and NKX6.1 gene expression measured. Additionally, T3, ALK5i II, and GABA were all added to a single TD population, wherein GABA, T3 and ALK5i II were added at the same time as the second infection with Ad-MafA using the protocol described herein and NKX6.1 gene expression measured.

Results

Figure 46:
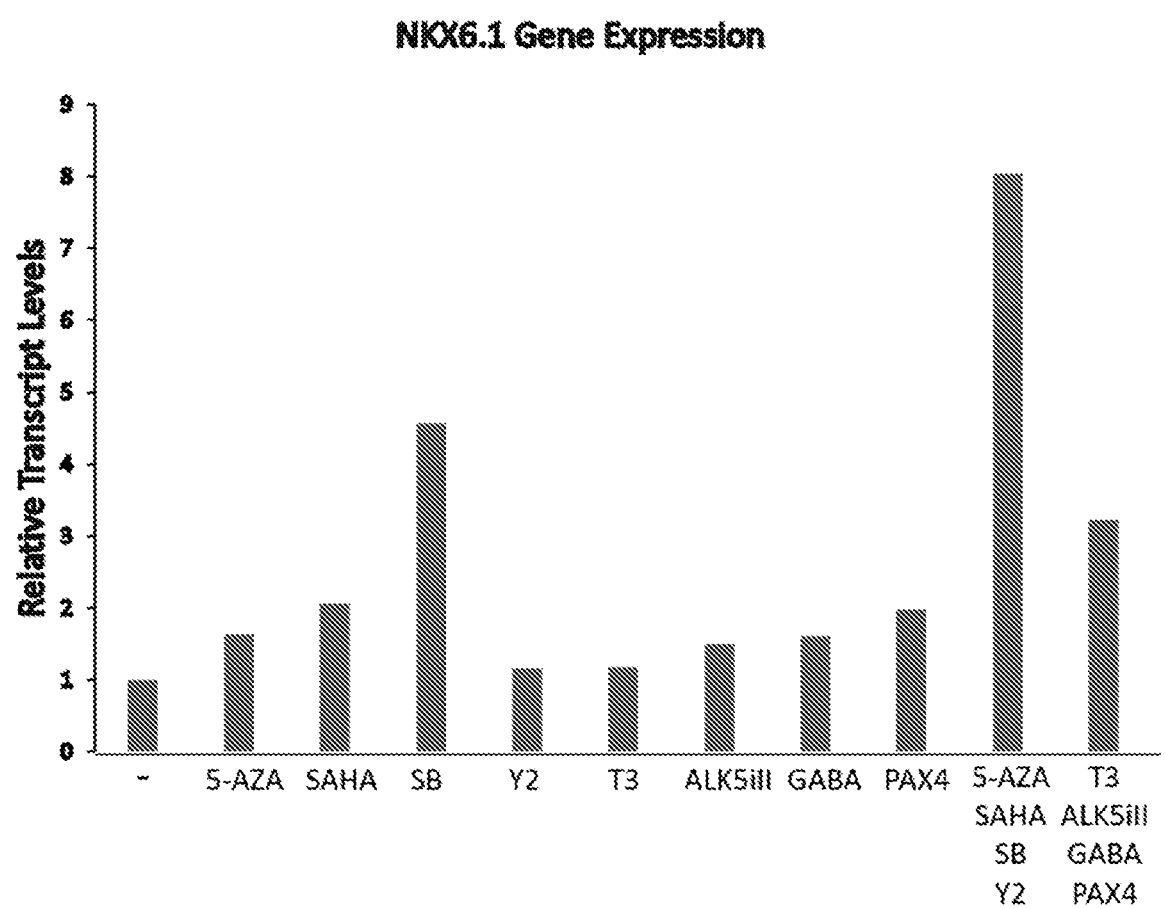
FIG. 46 provides a Comparison of the NKX6.1 Gene Expression Levels by Transdifferentiated Cells Treated with Different Soluble Factors or Combinations Thereof. The promoting effects of the individual soluble factors (as appear in Table 11) or their combinations were analyzed by qRT-PCR of NKX6.1 gene expression. The presented transcript levels are normalized to the expression in cells that were treated with pTFs alone (marked as "-" in the histogram), i.e. the basic protocol of infection with Ad-PDX-1 and Ad-NeuroD1 in TD medium (DMEM 1 g/L glucose supplemented with 10% FCS, 10 mM Nicotinamide, 20 ng/ml EGF, and 5 nM exendin4), followed by an infection with Ad-MAFA 48h later).
Figure 48B:
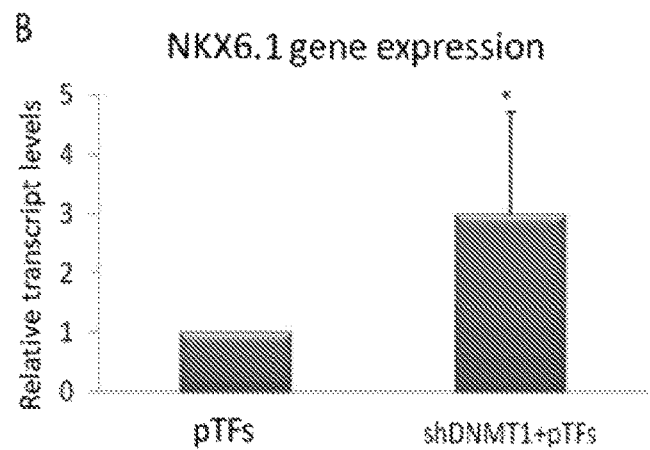
Figure 48C:
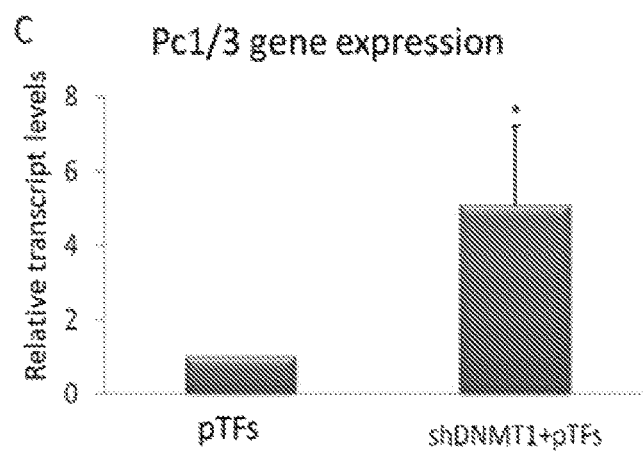
Figure 48D:
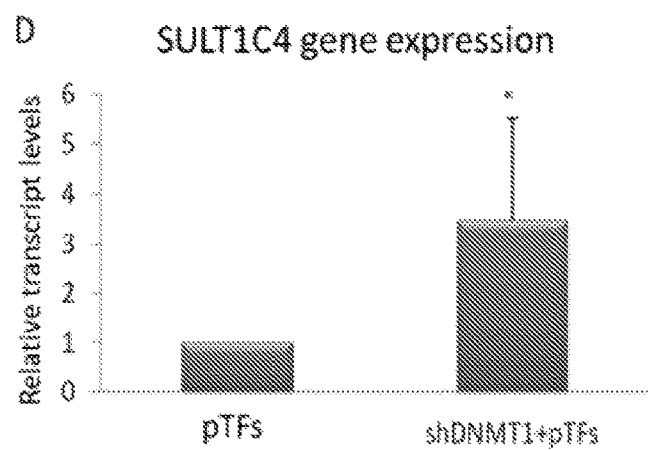

The promoting effects of the individual soluble factors or combined actions of the factors were analyzed by qRT-PCR of NKX6.1 gene expression as demonstrated in the bar graph in FIG. 46. NKX6.1 expression is increased during pancreas development and is used as a β-cell differentiation "readout", and a marker for successful induction of β-cell repertoire. The levels presented are normalized to the expression in cells treated with pTFs alone.

Example 23: Promoting the Activation of the Pancreatic Lineage in Liver Cells by Addition of a Fourth Pancreatic Transcription Factor, Ad-PAX4

Objective:

To analyze a fourth pancreatic transcription factor addition (at different timepoints) on promoting pancreatic differentiation and reprogramming Methods:

The basic transdifferentiation (TD) protocol involving infection with Ad-PDX-1 and Ad-NeuroD1 in TD medium (DMEM 1 g/L glucose supplemented with 10% FCS, 10 mM Nicotinamide, 20 ng/ml EGF, and 5 nM exendin4), followed by an infection with Ad-MAFA 48h later, was revised to include an introduction of a fourth pancreatic transcription factor, Pax-4, to the cells. Ad-Pax-4 has been added to the cells either with Ad-Pdx-1 and Ad-NeuroD1, or one day later (about 24 hours), or with MafA (about 48 hours after the Ad-PDX-1 and Ad-NeuroD1 infection.

Results:

Using the method described herein, there was an increased level of pancreatic beta cells markers. (Partial data presented in FIG. 46).

Example 24: The Effect of DNA Demethylation Using DNMT1 Inhibitor on the Transdifferentiation Process Objective:

To analyze the effect of DNA de-methylation on the Transdifferentiation process.

One of the factors that could potentially affect the capacity of cells to undergo transdifferentiation was identified to relate to their epigenetic characteristics, namely the level of DNA methylation, with less methylation generally associated with improved capacity for TD. To investigate the role of de-methylation in the TD process and the activation of the alternate pancreatic repertoire, a DNA (cytosine-5)-methyltransferase 1 (DNMT1), was knocked down (KD) using a specific short hairpin DNMT1 (in lentivirus).

Methods:

DNMT1 ShRNA

An anti-DNMT1 construct for lentivirus infection was generously provided by Moshe Szyf, McGill University, Montreal [siDNMT1 5'-GGAAGAAGAGUUACUAUAA-3']. eGFP+ and DsRed+ cells, as well as non-separated liver cultures were infected with lentivirus along with 8 ng/ml polybrene (Sigma) over-night. Once cells were more than 90% confluent, they were detached with trypsin-EDTA (0.25%) and re-plated at a 1:2 dilution. The infected cells were kept under puromycin selection pressure for two weeks, and the infection efficiency were measured by GFP content, and DNMT1 RNA and protein levels.

Protein Purification from Cells Treated by Sh DNMT1 Lentivirus and Selected for Puromycin Resistance for 2 Weeks Total protein harvesting was performed by incubating the cells in Lysis Buffer (50 mM Tris pH 7.5; 1% NP40; 150 mM NaCl; 0.25% Deoxycholic acid and InM EGTA, supplemented with protease inhibitor cocktail (1:1000, Sigma)) for 15 minutes on ice. Supernatant containing proteins was collected after centrifugation for 30 minutes at 13,000 g. Protein concentrations were measured by the Bradford protein assay (Bio-Rad, USA).

Western-Blot

A total of 50 µg protein extracts were separated on 10% SDS-polyacrylamide gel, for 2 hours in 150V and electro-blotted onto nitrocellulose membrane (Schleicher & Schuell Bioscience GmbH, USA), 250 mA, for 1.5 hour. The membrane was blocked with 5% milk in PBS, for 1 hour in room temperature, followed by over-night incubation of the primary antibody at 4° C. Following 3 washes in TBS-T buffer, the membrane was incubated with a horseradish-peroxidase-conjugated (HRP) secondary antibody for 1 hour, and after 3 washes, the electrochemiluminescence (ECL) reagents (Sigma) were incubated with the membrane for 2 minutes. The membrane was dried and placed on light sensitive film. The intensities of protein bands were quantified using ImageJ software.

Gene Expression

An analysis of expression of four genes was carried out on both DNMT1 KD cells (treated with both shDNMT1 and pTFs) and control TD cells (treated with pTFs alone) for comparison.

Liver cells derived from four different donors pre-treated for DNMT1 knock-down (KD) as described above and their similar donor and passage counterparts (not pre-treated for DNMT1 KD) were transdifferentiated by infection with Ad-PDX-1 and Ad-NeuroD1, and two days later by infection with Ad-MafA. Three days later, RNA was extracted and the gene expression as well as protein levels of glucagon (GCG), NKx6.1, proprotein convertase 1 (PC1/3), and sulfotransferase 1C4 (SULTIC4) were analyzed. The cell infections with pTFs were carried out following the basic protocol (Pdx-1+NeuroD on the first day and MafA 2 days later, 2+1) as described above, and on day 6 the cells were transferred to serum-free medium supplemented with ITS (Insulin-Transferrin-Selenium). Gene expression levels were analyzed 28 days post pTFs infection.

Results:

The resulting DNMT1 KD cells exhibited and maintained more than 50% reduction in DNMT1 protein levels with increasing passages compared to cells treated with pTFs alone, as can be seen in FIGS. 47A and 47B.

The results of analysis of the four test gene expressions can be seen in FIGS. 48A-48D. The expression levels of the pancreatic genes GCG (FIG. 48A), Nkx6.1 (FIG. 48B), and PC1/3 (FIG. 48C), as well as SULT1C4 (FIG. 48D) remained higher in the DNMT1 KD cells infected with pTFs, compared to the control group that was infected with pTFs alone. These results indicate that while DNMT1 expression remains low, the new acquired pancreatic phenotype stably persists even 28 days post infection.

While certain features disclosed here have been illustrated and described herein, many modifications, substitutions, changes, and equivalents will now occur to those of ordinary skill in the art. It is, therefore, to be understood that the appended claims are intended to cover all such modifications and changes as fall within the true spirit disclosed here.

What is claimed is:

1. A method of manufacturing a population of transdifferentiated human insulin producing cells, the method comprising the steps of:
    (a) obtaining a population of primary liver cells;
    (b) propagating and expanding the primary cells of step (a);
    (c) pre-incubating the expanded cells of step (b) with a Wnt-pathway agonist,
    (d) transdifferentiating said pre-incubated cells of step (c) by a method comprising:
        (i) contacting said pre-incubated cells with a PDX-1 polypeptide or a nucleic acid encoding a PDX-1 polypeptide, and a NeuroD1 polypeptide or nucleic acid encoding a NeuroD1 polypeptide; and
        (ii) contacting the cells of step (i) with a MafA polypeptide or a nucleic acid encoding a MafA polypeptide; and
    (e) harvesting said transdifferentiated cells;
    wherein said method further comprises a step of incubating the cells with an epigenetic modifier, either prior to step (c), or prior, concurrent, or after step (d);
    thereby manufacturing a population of transdifferentiated human insulin producing cells.

2. The method of claim 1, further comprising incubating the cells with a thyroid hormone, a TGFβ/Activin inhibitor, or a reagent that converts α-pancreatic cells to β-pancreatic cells, or any combination thereof.

3. The method of claim 2, wherein said thyroid hormone comprises T3, said TGFβ/activin inhibitor comprises Alk5i II, and said reagent that converts α-pancreatic cells to β-pancreatic cells comprises GABA.

4. The method of claim 1, wherein said epigenetic modifier comprises a histone deacetylase inhibitor (HDACi), an inhibitor of DNA methylation, a TGF0 inhibitor, or any combination thereof.

5. The method of claim 4, wherein said HDACi comprises suberanilohydroxamic acid (SAHA), sodium butyrate, romidepsin, chidamide, panobinostat, or belinostat, or any combination thereof; and wherein said TGFβ inhibitor comprises SB431542, and said inhibitor of DNA methylation comprises 5-Aza-2-deoxycitidine (5-AZA).

6. The method of claim 4, wherein said epigenetic modifier comprises a histone deacetylase inhibitor (HDACi), an inhibitor of DNA methylation, and a TGFβ inhibitor, wherein said Wnt-pathway agonist comprises a Rho kinase inhibitor, and wherein said epigenetic modifier and said Wnt-pathway agonist are added prior to step (d).

7. The method of claim 1, wherein said Wnt-pathway agonist comprises lithium (Li), Wnt9, Wnt3A, a GSK3b antagonist, a Rho Kinase inhibitor, Y27632 (Y2), or any combination thereof.

8. The method of claim 1, wherein said Wnt-pathway agonist pre-incubation occurs 24, 48, or 72 hours prior to step (d), wherein said addition of the epigenetic modifier occurs 24, 48, or 72 hours prior to the transdifferentiation step (d), or wherein said addition of the epigenetic modifier and said pre-incubation with Wnt-pathway agonist are concurrent, or any combination thereof.

9. The method of claim 1, wherein said method further comprises
    contacting said pre-incubated cells with an additional pancreatic transcription factor at step (i); or
    contacting said pre-incubated cells with an additional pancreatic transcription factor at step (ii); or
    contacting said pre-incubated cells with an additional pancreatic transcription factor at both step (i) and step (ii).

10. The method of claim 9, wherein said additional pancreatic transcription factor comprises PAX4, PAX6, ILS-1, NGN3, NKX6.1, RFX6, or FOXA2.

11. The method of claim 1, further comprising incubating the cells with nicotine amide, epidermal growth factor (EGF), exendin-4, or any combination thereof, during step (d).

12. A method for enriching a population of primary liver cells comprising enriched capacity for transcription factor-induced transdifferentiation into a pancreatic β-cell like phenotype and function, said method comprising the steps of:
  (a) obtaining a population of primary human liver cells;
  (b) identifying cells within the population of (a) having increased expression of at least one gene of the group comprising a solute carrier family 2, facilitated glucose transporter member 3 (GLUT-3); a vesicle-associated membrane protein 2 (VAMP2); a syntaxin-1A (Stx1a); a tyrosine-protein kinase transmembrane receptor ROR2 (ROR2); Frizzled-4 (FZD4); a pituitary homeobox 2 (PITX2); and
  a Proto-oncogene Wnt-1 (WNT1); or any combination thereof, wherein said increased expression is compared within the non-pancreatic β-cell population; and
  (c) selecting said liver cells having increased expression of at least one gene recited in (b);
  wherein said selected cells comprise an enriched capacity for transcription factor induced transdifferentiation to a pancreatic β-cell like phenotype and function.

13. The method of claim 12, wherein said identifying further comprises identifying cells with increased expression of at least one gene selected from the group comprising vesicle-associated membrane protein 4 (VAMP4); thrombospondin-1; discoidin, CUB and LCCL domain-containing protein 2 (THBS1); integrin alpha-6 (ITGA6); homer protein homolog 1 (HOMER1); lysosome-associated membrane glycoprotein 3 (LAMP3); bone morphogenetic protein receptor type-2(BMPR2); or with decreased expression of at least one gene selected from the group comprising multidrug resistance protein 1 (ABCB1), integrin alpha-4 (ITGA4), and phosphatidylcholine translocator ABCB4 ABCB4), or any combination thereof.

14. The method of claim 12, said method further comprising steps of
  (a) propagating and expanding said enriched primary liver cells;
  (b) pre-incubating the expanded cells of step (a) with a Wnt-pathway agonist;
  (c) incubating said pre-incubated cells with at least one epigenetic modifier; and
  (d) collecting said cells.

15. The method of claim 14, wherein said epigenetic modifier comprises a histone deacetylase inhibitor (HDACi), an inhibitor of DNA methylation, a TGFβ inhibitor, suberanilohydroxamic acid (SAHA), sodium butyrate, romidepsin, chidamide, panobinostat, belinostat, SB431542, 5-Aza-2-deoxycitidine (5-AZA), or said Wnt-pathway agonist comprises lithium (Li), Wnt9, Wnt3, a GSK3b antagonist, a Rho Kinase inhibitor comprises Y27632 (Y2), or any combination thereof.

16. The method of claim 14, wherein said incubating with said epigenetic modifier occurs before said pre-incubation, at the same time as said pre-incubation, following said pre-incubation and at the same time than a transdifferentiation step, or following a transdifferentiation step.

17. The method of claim 14, wherein said Wnt-pathway agonist pre-incubation occurs 24, 48, or 72 hours prior to a transdifferentiation step.

18. The method of claim 14, wherein said identifying comprises incubating cells with a labeled antibody or ligand that binds the protein product of said at least one gene and wherein said selecting comprises selecting cells bound to said labeled antibody or ligand.

19. The method of claim 12, wherein following transcription factor induced transdifferentiation of said selected cells, said transdifferentiated selected cell population expresses increased endogenous Nkx6.1, increased insulin content, increased glucagon content, or increased glucose-regulated insulin secretion and C-peptide secretion, or any combination thereof, compared with a control transdifferentiated non-selected population of cells.

* * * * *

SEQUENCE LISTING

```
<160> NUMBER OF SEQ ID NOS: 37

<210> SEQ ID NO 1
<211> LENGTH: 51
<212> TYPE: DNA
<213> ORGANISM: Rattus rattus

<400> SEQUENCE: 1
tcacatggaa ggatcaaagc aagcctgctt ctattcttgg aaacagagca a          51

<210> SEQ ID NO 2
<211> LENGTH: 51
<212> TYPE: DNA
```

<213> ORGANISM: Mus musculus

<400> SEQUENCE: 2
tcacatgaaa ggatcaaagc aaatccgctt ctattcttgg aaacagagca a        51

<210> SEQ ID NO 3
<211> LENGTH: 51
<212> TYPE: DNA
<213> ORGANISM: Homo sapiens

<400> SEQUENCE: 3
tcacatgaat ggatcaaagc aaatccattt ccattcttgg aaaagcagct c        51

<210> SEQ ID NO 4
<211> LENGTH: 283
<212> TYPE: PRT
<213> ORGANISM: Homo sapiens

<400> SEQUENCE: 4

Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
            20                  25                  30

Pro Ala Cys Leu Tyr Met Gly Arg Gln Pro Pro Pro Pro Pro His
        35                  40                  45

Pro Phe Pro Gly Ala Leu Gly Ala Leu Glu Gln Gly Ser Pro Pro Asp
    50                  55                  60

Ile Ser Pro Tyr Glu Val Pro Pro Leu Ala Asp Asp Pro Ala Val Ala
65                  70                  75                  80

His Leu His His His Leu Pro Ala Gln Leu Ala Leu Pro His Pro Pro
                85                  90                  95

Ala Gly Pro Phe Pro Glu Gly Ala Glu Pro Gly Val Leu Glu Glu Pro
            100                 105                 110

Asn Arg Val Gln Leu Pro Phe Pro Trp Met Lys Ser Thr Lys Ala His
        115                 120                 125

Ala Trp Lys Gly Gln Trp Ala Gly Gly Ala Tyr Ala Ala Glu Pro Glu
    130                 135                 140

Glu Asn Lys Arg Thr Arg Thr Ala Tyr Thr Arg Ala Gln Leu Leu Glu
145                 150                 155                 160

Leu Glu Lys Glu Phe Leu Phe Asn Lys Tyr Ile Ser Arg Pro Arg Arg
                165                 170                 175

Val Glu Leu Ala Val Met Leu Asn Leu Thr Glu Arg His Ile Lys Ile
            180                 185                 190

Trp Phe Gln Asn Arg Arg Met Lys Trp Lys Lys Glu Glu Asp Lys Lys
        195                 200                 205

Arg Gly Gly Gly Thr Ala Val Gly Gly Gly Val Ala Glu Pro Glu
    210                 215                 220

Gln Asp Cys Ala Val Thr Ser Gly Glu Glu Leu Leu Ala Leu Pro Pro
225                 230                 235                 240

Pro Pro Pro Pro Gly Gly Ala Val Pro Ala Ala Pro Val Ala Ala
                245                 250                 255

Arg Glu Gly Arg Leu Pro Pro Gly Leu Ser Ala Ser Pro Gln Pro Ser
            260                 265                 270

Ser Val Ala Pro Arg Arg Pro Gln Glu Pro Arg
        275                 280

-continued

```
<210> SEQ ID NO 5
<211> LENGTH: 852
<212> TYPE: DNA
<213> ORGANISM: Homo sapiens

<400> SEQUENCE: 5
atgaacggcg aggagcagta ctacgcggcc acgcagcttt acaaggaccc atgcgcgttc      60
cagcgaggcc cggcgccgga gttcagcgcc agccccctg cgtgcctgta catgggccgc     120
cagcccccgc cgccgccgcc gcacccgttc cctggcgccc tgggcgcgct ggagcagggc     180
agccccccgg acatctcccc gtacgaggtg ccccccctcg ccgacgaccc cgcggtggcg     240
caccttcacc accacctccc ggctcagctc gcgctccccc acccgcccgc cgggcccttc     300
ccggagggag ccgagccggg cgtcctggag gagcccaacc gcgtccagct gccttttccca    360 tggatgaagt ctaccaaagc tcacgcgtgg aaaggccagt gggcaggcgg cgcctacgct     420
gcggagccgg aggagaacaa gcggacgcgc acggcctaca cgcgcgcaca gctgctagag     480
ctggagaagg agttcctatt caacaagtac atctcacggc cgcgccgggt ggagctggct     540
gtcatgttga acttgaccga gagacacatc aagatctggt tccaaaaccg ccgcatgaag     600
tggaaaaagg aggaggacaa gaagcgcggc ggcgggacag ctgtcggggg tggcggggtc     660
gcggagcctg agcaggactg cgccgtgacc tccggcgagg agcttctggc gctgccgccg     720
ccgccgcccc ccggaggtgc tgtgccgccc gctgccccccg ttgccgcccg agagggccgc    780
ctgccgcctg gccttagcgc gtcgccacag ccctccagcg tcgcgcctcg gcggccgcag     840
gaaccacgat ga                                                          852

<210> SEQ ID NO 6
<211> LENGTH: 356
<212> TYPE: PRT
<213> ORGANISM: Homo sapiens

<400> SEQUENCE: 6

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Thr Met Asn Ala
        35                  40                  45

Glu Glu Asp Ser Leu Arg Asn Gly Gly Glu Glu Asp Glu Asp
    50                  55                  60

Asp Leu Glu Glu Glu Glu Glu Glu Glu Asp Asp Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
```

|  |  | 180 |  |  | 185 |  |  | 190 |  |

Arg Thr Phe Leu Pro Glu Gln Asn Gln Asp Met Pro Pro His Leu Pro
                195                 200                 205

Thr Ala Ser Ala Ser Phe Pro Val His Pro Tyr Ser Tyr Gln Ser Pro
        210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
        260                 265                 270

Leu Ser Pro Pro Leu Ser Ile Asn Gly Asn Phe Ser Phe Lys His Glu
    275                 280                 285

Pro Ser Ala Glu Phe Glu Lys Asn Tyr Ala Phe Thr Met His Tyr Pro
        290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
        340                 345                 350

Ile Phe His Asp
        355

<210> SEQ ID NO 7
<211> LENGTH: 1071
<212> TYPE: DNA
<213> ORGANISM: Homo sapiens

<400> SEQUENCE: 7

| atgaccaaat cgtacagcga gagtgggctg atgggcgagc ctcagcccca aggtcctcca | 60 |
| agctggacag acgagtgtct cagttctcag gacgaggagc acgaggcaga caagaaggag | 120 |
| gacgacctcg aagccatgaa cgcagaggag gactcactga ggaacggggg agaggaggag | 180 |
| gacgaagatg aggacctgga gaggaggaa gaagaggaag aggaggatga cgatcaaaag | 240 |
| cccaagagac gcggccccaa aaagaagaag atgactaagg ctcgcctgga gcgttttaaa | 300 |
| ttgacgcgca tgaaggctaa cgcccgggag cggaaccgca tgcacggact gaacgcggcg | 360 |
| ctagacaacc tgcgcaaggt ggtgccttgc tattctaaga cgcagaagct gtccaaaatc | 420 |
| gagactctgc gcttggccaa gaactacatc tgggctctgt cggagatctc cgctcaggc | 480 |
| aaaagcccag acctggtctc cttcgttcag acgctttgca agggcttatc ccaacccacc | 540 |
| accaacctgt tgcgggctg cctgcaactc aatcctcgga cttttctgcc tgagcagaac | 600 |
| caggacatgc ccccgcacct gccgacggcc agcgcttcct tccctgtaca cccctactcc | 660 |
| taccagtcgc ctgggctgcc cagtccgcct acggtacca tggacagctc ccatgtcttc | 720 |
| cacgttaagc ctccgccgca cgcctacagc gcagcgctgg agcccttctt tgaaagccct | 780 |
| ctgactgatt gcaccagccc ttcctttgat ggacccctca gccgccgct cagcatcaat | 840 |
| ggcaacttct ctttcaaaca cgaaccgtcc gccgagtttg agaaaaatta tgcctttacc | 900 |
| atgcactatc ctgcagcgac actggcaggg gcccaaagcc acggatcaat cttctcaggc | 960 |
| accgctgccc ctcgctgcga gatccccata gacaatatta tgtccttcga tagccattca | 1020 |
| catcatgagc gagtcatgag tgcccagctc aatgccat ttcatgatta g | 1071 |

<210> SEQ ID NO 8
<211> LENGTH: 353
<212> TYPE: PRT
<213> ORGANISM: Homo sapiens

<400> SEQUENCE: 8

```
Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
            20                  25                  30

Lys Glu Pro Pro Glu Ala Glu Arg Phe Cys His Arg Leu Pro Pro Gly
        35                  40                  45

Ser Leu Ser Ser Thr Pro Leu Ser Thr Pro Cys Ser Ser Val Pro Ser
50                  55                  60

Ser Pro Ser Phe Cys Ala Pro Ser Pro Gly Thr Gly Gly Gly Gly
65                  70                  75                  80

Ala Gly Gly Gly Gly Ser Ser Gln Ala Gly Gly Ala Pro Gly Pro
                85                  90                  95

Pro Ser Gly Gly Pro Gly Ala Val Gly Gly Thr Ser Gly Lys Pro Ala
            100                 105                 110

Leu Glu Asp Leu Tyr Trp Met Ser Gly Tyr Gln His His Leu Asn Pro
        115                 120                 125

Glu Ala Leu Asn Leu Thr Pro Glu Asp Ala Val Glu Ala Leu Ile Gly
130                 135                 140

Ser Gly His His Gly Ala His His Gly Ala His His Pro Ala Ala Ala
145                 150                 155                 160

Ala Ala Tyr Glu Ala Phe Arg Gly Pro Gly Phe Ala Gly Gly Gly Gly
                165                 170                 175

Ala Asp Asp Met Gly Ala Gly His His His Gly Ala His His Ala Ala
            180                 185                 190

His His His His Ala Ala His His His His His His His His His His
        195                 200                 205

Gly Gly Ala Gly His Gly Gly Ala Gly His His Val Arg Leu Glu
210                 215                 220

Glu Arg Phe Ser Asp Asp Gln Leu Val Ser Met Ser Val Arg Glu Leu
225                 230                 235                 240

Asn Arg Gln Leu Arg Gly Phe Ser Lys Glu Glu Val Ile Arg Leu Lys
                245                 250                 255

Gln Lys Arg Arg Thr Leu Lys Asn Arg Gly Tyr Ala Gln Ser Cys Arg
            260                 265                 270

Phe Lys Arg Val Gln Gln Arg His Ile Leu Glu Ser Glu Lys Cys Gln
        275                 280                 285

Leu Gln Ser Gln Val Glu Gln Leu Lys Leu Glu Val Gly Arg Leu Ala
290                 295                 300

Lys Glu Arg Asp Leu Tyr Lys Glu Lys Tyr Glu Lys Leu Ala Gly Arg
305                 310                 315                 320

Gly Gly Pro Gly Ser Ala Gly Gly Ala Gly Phe Pro Arg Glu Pro Ser
                325                 330                 335

Pro Pro Gln Ala Gly Pro Gly Gly Ala Lys Gly Thr Ala Asp Phe Phe
            340                 345                 350

Leu
```

<210> SEQ ID NO 9
<211> LENGTH: 1059

```
<212> TYPE: DNA
<213> ORGANISM: Homo sapiens

<400> SEQUENCE: 9
atggccgcgg agctggcgat gggcgccgag ctgcccagca gcccgctggc catcgagtac      60
gtcaacgact tcgacctgat gaagttcgag gtgaagaagg agcctcccga ggccgagcgc     120
ttctgccacc gctgccgcc aggctcgctg tcctcgacgc cgctcagcac gccctgctcc      180
tccgtgccct cctcgcccag cttctgcgcg cccagcccgg caccggcgg cggcggcggc     240
gcggggggcg gcggcggctc gtctcaggcc gggggcgccc ccgggccgcc gagcggggc      300
cccggcgccg tcgggggcac ctcggggaag ccggcgctgg aggatctgta ctggatgagc    360
ggctaccagc atcacctcaa ccccgaggcg ctcaacctga cgcccgagga cgcggtggag    420
gcgctcatcg gcagcggcca ccacggcgcg caccacggcg cgcaccaccc ggcggccgcc    480
gcagcctacg aggctttccg cggcccgggc ttcgcgggcg gcggcggagc ggacgacatg    540
ggcgccggcc accaccacgg cgcgcaccac gccgcccacc accaccacgc cgcccaccac    600
caccaccacc accaccacca tggcggcgcg ggacacggcg gtggcgcggg ccaccacgtg    660
cgcctggagg agcgcttctc cgacgaccag ctggtgtcca tgtcggtgcg cgagctgaac    720
cggcagctcc gcggcttcag caaggaggag gtcatccggc tcaagcagaa gcggcgcacg    780
ctcaagaacc gcggctacgc gcagtcctgc cgcttcaagc gggtgcagca gcggcacatt    840
ctggagagcg agaagtgcca actccagagc caggtggagc agctgaagct ggaggtgggg    900
cgcctggcca agagcgggga cctgtacaag gagaaatacg agaagctggc gggccggggc    960
ggccccggga gcgcgggcgg ggccggtttc ccgcgggagc cttcgccgcc gcaggccggt   1020
cccggcgggg ccaagggcac ggccgacttc ttcctgtag                           1059

<210> SEQ ID NO 10
<211> LENGTH: 776
<212> TYPE: DNA
<213> ORGANISM: Artificial Sequence
<220> FEATURE:
<223> OTHER INFORMATION: GSRE-CRE element

<400> SEQUENCE: 10
caagctcaga tccaagctgg gctgcaggaa ttctctacaa gccctctctg tcctggtact      60
cattatgaag accaagattt cctgaaatca gacaatctac cggtctcctg agaactggga     120
ttaaaggtat tccctctac accaggcctc aatggctgac ttcattactg ggatgaaaag      180
tccttcctcc agagacagat ttcaatgcga aaattacagt atttgagaag atcccaccag    240
atgatatttt ctggtgagta gaaaaaaatc ccacctctaa taaagacccc agcttcttgt    300
ttaccccctga aagtcagtgg tcacatgaga tgttcctggt cacatggaag gatcaaagca    360
agcctgcttc tattcttgga aacagagcaa atgttctctt gatgctgccg ctgtttctgt    420
gtggtcaatt tgtgtttatc gaacactcag tctggaaact gttttggggc ggggtggggt    480
ataggagaat aagcagcaaa agaggttaac gtgtctagga agggaagcca gcactcccgt   540
ggcggaaatg caagaaaccc aggaaaaaaca acacatttgc tcagggtttt caccttttct    600
actgagattc ccctggcctc attctggacc ctggtgaaga ctgctgaagg ctactctgtt    660
tgatgggtac cgagctcgag atccggcgaa ttcgaacacg cagatgcagt cggggcggcg   720
cggtccgagg tccacttcgc atattaaggt gacgcgtgtg gcctcgaaca ccgagc         776

<210> SEQ ID NO 11
```

```
<211> LENGTH: 257
<212> TYPE: DNA
<213> ORGANISM: Artificial Sequence
<220> FEATURE:
<223> OTHER INFORMATION: GS Intron1

<400> SEQUENCE: 11
caagctcaga tccaagctgg gctgcaggaa ttctctacaa gccctctctg tcctggtact    60
cattatgaag accaagattt cctgaaatca gacaatctac cggtctcctg agaactggga   120
ttaaaggtat tcccctctac accaggcctc aatggctgac ttcattactg ggatgaaaag   180
tccttcctcc agagacagat ttcaatgcga aaattacagt atttgagaag atcccaccag   240
atgatatttt ctggtga                                                  257

<210> SEQ ID NO 12
<211> LENGTH: 364
<212> TYPE: DNA
<213> ORGANISM: Artificial Sequence
<220> FEATURE:
<223> OTHER INFORMATION: GS 5' enhancer

<400> SEQUENCE: 12
gtagaaaaaa atcccacctc taataaagac cccagcttct tgtttacccc tgaaagtcag    60
tggtcacatg agatgttcct ggtcacatgg aaggatcaaa gcaagcctgc ttctattctt   120
ggaaacagag caaatgttct cttgatgctg ccgctgtttc tgtgtggtca atttgtgttt   180
atcgaacact cagtctggaa actgtttggg ggcggggtgg ggtataggag aataagcagc   240
aaaagaggtt aacgtgtcta ggaagggaag ccagcactcc cgtggcggaa atgcaagaaa   300
cccaggaaaa acaacacatt tgctcagggt tttcaccttt tctactgaga ttcccctggc   360
ctca                                                                364

<210> SEQ ID NO 13
<211> LENGTH: 134
<212> TYPE: DNA
<213> ORGANISM: Artificial Sequence
<220> FEATURE:
<223> OTHER INFORMATION: Tk partial promoter

<400> SEQUENCE: 13
gctgaaggct actctgtttg atgggtaccg agctcgagat ccggcgaatt cgaacacgca    60
gatgcagtcg gggcggcgcg gtccgaggtc cacttcgcat attaaggtga cgcgtgtggc   120
ctcgaacacc gagc                                                     134

<210> SEQ ID NO 14
<211> LENGTH: 20
<212> TYPE: DNA
<213> ORGANISM: Artificial Sequence
<220> FEATURE:
<223> OTHER INFORMATION: Forward primer - Ins

<400> SEQUENCE: 14
gaagcgtggc attgtggaac                                                20

<210> SEQ ID NO 15
<211> LENGTH: 21
<212> TYPE: DNA
<213> ORGANISM: Artificial Sequence
<220> FEATURE:
<223> OTHER INFORMATION: Reverse primer - Ins

<400> SEQUENCE: 15
```

```
gctgcgtcta gttgcagtag t                                              21

<210> SEQ ID NO 16
<211> LENGTH: 20
<212> TYPE: DNA
<213> ORGANISM: Artificial Sequence
<220> FEATURE:
<223> OTHER INFORMATION: Forward primer - GCG

<400> SEQUENCE: 16
ccaagatttt gtgcagtggt                                                20

<210> SEQ ID NO 17
<211> LENGTH: 20
<212> TYPE: DNA
<213> ORGANISM: Artificial Sequence
<220> FEATURE:
<223> OTHER INFORMATION: Reverse primer - GCG

<400> SEQUENCE: 17
ggtaaaggtc ccttcagcat                                                20

<210> SEQ ID NO 18
<211> LENGTH: 21
<212> TYPE: DNA
<213> ORGANISM: Artificial Sequence
<220> FEATURE:
<223> OTHER INFORMATION: Forward primer - SST

<400> SEQUENCE: 18
atgatgccct ggaacctgaa g                                              21

<210> SEQ ID NO 19
<211> LENGTH: 21
<212> TYPE: DNA
<213> ORGANISM: Artificial Sequence
<220> FEATURE:
<223> OTHER INFORMATION: Reverse primer - SST

<400> SEQUENCE: 19
gccgggtttg agttagcaga t                                              21

<210> SEQ ID NO 20
<211> LENGTH: 20
<212> TYPE: DNA
<213> ORGANISM: Artificial Sequence
<220> FEATURE:
<223> OTHER INFORMATION: Forward primer - NKX6-1

<400> SEQUENCE: 20
gggctcgttt ggcctattcg                                                20

<210> SEQ ID NO 21
<211> LENGTH: 21
<212> TYPE: DNA
<213> ORGANISM: Artificial Sequence
<220> FEATURE:
<223> OTHER INFORMATION: Reverse primer - NKX6-1

<400> SEQUENCE: 21
gtgcttcttc ctccacttgg t                                              21

<210> SEQ ID NO 22
<211> LENGTH: 20
<212> TYPE: DNA
```

```
<213> ORGANISM: Artificial Sequence
<220> FEATURE:
<223> OTHER INFORMATION: Forward primer - PAX6

<400> SEQUENCE: 22
ccagtataag cgggagtgcc                                               20

<210> SEQ ID NO 23
<211> LENGTH: 20
<212> TYPE: DNA
<213> ORGANISM: Artificial Sequence
<220> FEATURE:
<223> OTHER INFORMATION: Reverse primer - PAX6

<400> SEQUENCE: 23
gcttttcgct agccaggttg                                               20

<210> SEQ ID NO 24
<211> LENGTH: 20
<212> TYPE: DNA
<213> ORGANISM: Artificial Sequence
<220> FEATURE:
<223> OTHER INFORMATION: Forward primer - ISL1

<400> SEQUENCE: 24
tgggctgttc accaactgta                                               20

<210> SEQ ID NO 25
<211> LENGTH: 20
<212> TYPE: DNA
<213> ORGANISM: Artificial Sequence
<220> FEATURE:
<223> OTHER INFORMATION: Reverse primer - ISL1

<400> SEQUENCE: 25
cgcaaccaac acatagggaa                                               20

<210> SEQ ID NO 26
<211> LENGTH: 21
<212> TYPE: DNA
<213> ORGANISM: Artificial Sequence
<220> FEATURE:
<223> OTHER INFORMATION: Forward primer - PDX1

<400> SEQUENCE: 26
aagtctacca aagctcacgc g                                             21

<210> SEQ ID NO 27
<211> LENGTH: 15
<212> TYPE: DNA
<213> ORGANISM: Artificial Sequence
<220> FEATURE:
<223> OTHER INFORMATION: Reverse primer - PDX1

<400> SEQUENCE: 27
gtaggcgccg cctgc                                                    15

<210> SEQ ID NO 28
<211> LENGTH: 20
<212> TYPE: DNA
<213> ORGANISM: Artificial Sequence
<220> FEATURE:
<223> OTHER INFORMATION: Forward primer - WNT1

<400> SEQUENCE: 28
caaccgaggc tgtcgagaaa                                               20
```

```
<210> SEQ ID NO 29
<211> LENGTH: 20
<212> TYPE: DNA
<213> ORGANISM: Artificial Sequence
<220> FEATURE:
<223> OTHER INFORMATION: Reverse primer - WNT1

<400> SEQUENCE: 29
tcacacgtgc aggattcgat                                              20

<210> SEQ ID NO 30
<211> LENGTH: 20
<212> TYPE: DNA
<213> ORGANISM: Artificial Sequence
<220> FEATURE:
<223> OTHER INFORMATION: Forward primer - FZD4

<400> SEQUENCE: 30
cacaccgctc atccagtacg                                              20

<210> SEQ ID NO 31
<211> LENGTH: 20
<212> TYPE: DNA
<213> ORGANISM: Artificial Sequence
<220> FEATURE:
<223> OTHER INFORMATION: Reverse primer - FZD4

<400> SEQUENCE: 31
ttccttcagg acgggttcac                                              20

<210> SEQ ID NO 32
<211> LENGTH: 20
<212> TYPE: DNA
<213> ORGANISM: Artificial Sequence
<220> FEATURE:
<223> OTHER INFORMATION: Forward primer - ROR2

<400> SEQUENCE: 32
gctctcagtg tcccggactt                                              20

<210> SEQ ID NO 33
<211> LENGTH: 20
<212> TYPE: DNA
<213> ORGANISM: Artificial Sequence
<220> FEATURE:
<223> OTHER INFORMATION: Reverse primer - ROR2

<400> SEQUENCE: 33
gcccatcaag gggtcctaaa                                              20

<210> SEQ ID NO 34
<211> LENGTH: 20
<212> TYPE: DNA
<213> ORGANISM: Artificial Sequence
<220> FEATURE:
<223> OTHER INFORMATION: Forward primer - LRP5

<400> SEQUENCE: 34
ccatccatgc ctgcaacaag                                              20

<210> SEQ ID NO 35
<211> LENGTH: 20
<212> TYPE: DNA
<213> ORGANISM: Artificial Sequence
<220> FEATURE:
```

```
<223> OTHER INFORMATION: Reverse primer - LRP5

<400> SEQUENCE: 35
gcgagtgtgg aagaaaggct                                              20

<210> SEQ ID NO 36
<211> LENGTH: 20
<212> TYPE: DNA
<213> ORGANISM: Artificial Sequence
<220> FEATURE:
<223> OTHER INFORMATION: Forward primer - Beta-actin

<400> SEQUENCE: 36
cctggacttc gagcaagaga                                              20

<210> SEQ ID NO 37
<211> LENGTH: 25
<212> TYPE: DNA
<213> ORGANISM: Artificial Sequence
<220> FEATURE:
<223> OTHER INFORMATION: Reverse primer - Beta-actin

<400> SEQUENCE: 37
cagcggaacc gctcattgcc aatgg                                        25
```